US011820994B2

(12) United States Patent
Carman et al.

(10) Patent No.: US 11,820,994 B2
(45) Date of Patent: Nov. 21, 2023

(54) METHODS OF INDUCING APOMICTIC OR SEXUAL REPRODUCTION

(71) Applicant: UTAH STATE UNIVERSITY, Logan, UT (US)

(72) Inventors: John G. Carman, Smithfield, UT (US); David Sherwood, Wellsville, UT (US); Lei Gao, Logan, UT (US)

(73) Assignee: Utah State University, North Logan, UT (US)

( * ) Notice: Subject to any disclaimer, the term of this patent is extended or adjusted under 35 U.S.C. 154(b) by 88 days.

(21) Appl. No.: 16/273,132

(22) Filed: Feb. 11, 2019

(65) Prior Publication Data

US 2020/0109414 A1      Apr. 9, 2020

Related U.S. Application Data

(60) Provisional application No. 62/628,743, filed on Feb. 9, 2018.

(51) Int. Cl.
*C12N 15/82* (2006.01)
*A01H 3/04* (2006.01)

(52) U.S. Cl.
CPC .......... *C12N 15/8287* (2013.01); *A01H 3/04* (2013.01); *C12N 15/8218* (2013.01); *C12N 15/8238* (2013.01)

(58) Field of Classification Search
None
See application file for complete search history.

(56) References Cited

U.S. PATENT DOCUMENTS 9,426,953 B1 *  8/2016  Kubik ................... A01H 5/10

FOREIGN PATENT DOCUMENTS

WO     WO-2017039452 A1 *  3/2017  ........... C12N 15/625

OTHER PUBLICATIONS

Fu et al. Journal of Experimental Botany 59(9): 2299-2308 (2008).*
Carman et al. Utah Science 46(3): 90-94.*
Zacarias et al. Physiologia Plantarum 95: 613-619 (1995).*
Shah, Depletion of Key Meiotic Genes and Transcriptome-Wide Abiotic Stress Reprogramming Mark Early Preparatory Events Ahead of Apomeiotic Transition, Frontiers in Plant Science, Oct. 26, 2016 (Year: 2016).*
Hasanuzzaman, Glutathione in plants: biosynthesis and physiological role in environmental stress tolerance, Physiology and Molecular Biology of Plants, Mar. 10, 2017, pp. 249-268 (Year: 2017).*
Lukesh, A Potent, Versatile Disulfide-Reducing Agent from Aspartic Acid, Journal of the American Chemical Society, Feb. 21, 2012 (Year: 2012).*
Hu, Chemical induction of apomictic seed formation in maize, Euphytica 56: 97-105, 1991 (Year: 1991).*
Zhu, Glucose-Induced Delay of Seed Germination in Rice is Mediated by the Suppression of ABA CatabolismoRather Than an Enhancement of ABA Biosynthesis, Plant and Cell Physiology, 2009, 50(3) pp. 644-651 (Year: 2009).*
Chae, Fluridone and norflurazon, carotenoid-biosynthesis inhibitors, promote seed conditioning and germination of the holoparasite Orobanche minor, Physiologia Plantarum 120: pp. 328-337, 2004 (Year: 2004).*
Williams, Joseph H. "Novelties of the flowering plant pollen tube underlie diversification of a key life history stage." Proceedings of the National Academy of Sciences 105.32 (2008): 11259-11263. (Year: 2008).*
Salinas-Gamboa, Rigel, et al. "New observations on gametogenic development and reproductive experimental tools to support seed yield improvement in cowpea [*Vigna unguiculata* (L.) Walp.]." Plant reproduction 29.1 (2016): 165-177. (Year: 2016).*
Sanna, Gavino, et al. "Genetic variation for the duration of pre-anthesis development in durum wheat and its interaction with vernalization treatment and photoperiod." Journal of Experimental Botany 65.12 (2014): 3177-3188. (Year: 2014).*
Bajon, C., et al. "Megasporogenesis in *Arabidopsis thaliana* L.: an ultrastructural study." Sexual Plant Reproduction 12.2 (1999): 99-109. (Year: 1999).*
Pal, Ram, et al. "Cymbidium: botany, production, and uses." Orchids phytochemistry, biology and horticulture: fundamentals and applications (2019): 1-37. (Year: 2019).*
Rost, Rice Anatomy Flowers Fertilization, Section of Plant biology Division of Biological Sciences, University of California Davis, 1997 (Year: 1997).*
Arve, Louise E. et al., "Growth in continuous high air humidity increases the expression of CYP707A-genes and inhibits stomatal closure", Environmental and Experimental Botany, 115:11-19 (2015).
Barcaccia, Gianni et al., "Apoximis in plant reproduction: a novel perspective on an old dilemma", Plant Reprod, 26:159-179 (2013).
Barke, Birthe H. et al., "Establishing of Apomixis in Diploid F2 Hybrids and Inheritance of Apospory From F1 to F2 Hybrids of the Ranunculus auricomus Complex", Frontiers in Plant Science, 9:1-12 (Aug. 2018).
Bertero, Thomas et al., "Impact of MicroRNAs in the Cellular Response to Hypoxia", International Review of Cell and Molecular Biology, 333:91-158 (2017).
Broeckx, Tom et al., "The plant energy sensor: evolutionary conservation and divergence of SnRK1 structure, regulation, and function", Journal of Experimental Botany, 67(22):6215-6252 (2016).
Brukhin, Vladimir, "Molecular and Genetic Regulation of Apomixis", Russian Journal of Genetics, 53(9):943-964 (2017).
Carman, John G., "The Evolution of Gametophytic Apomixis (Lab Version)", Embryology of Flowering Plants, vol. 3: The Systems of Reproduction pp. 218-245 (2000).

(Continued)

*Primary Examiner* — Weihua Fan
*Assistant Examiner* — Brian James Sullivan
(74) *Attorney, Agent, or Firm* — Rodney J. Fuller; BOOTH UDALL FULLER, PLC

(57) ABSTRACT

This invention is directed to methods of switching from sexual reproduction to apomixis or from apomixis to sexual reproduction in a eukaryote. More particularly, this invention provides methods of switching from meiosis to apomeiosis and from syngamy to parthenogenesis in a plant. The invention also provides methods of producing an apomictic eukaryote from a sexual eukaryote and a sexual eukaryote from an apomictic eukaryote.

20 Claims, 74 Drawing Sheets

Specification includes a Sequence Listing.

(56) References Cited

OTHER PUBLICATIONS

Carman, John G. et al., "Apospory appears to accelerate onset of meiosis and sexual embryo sac formation in sorghum ovules", BMC Plant Biology, 11:1-13 (2011).

Carman, John G., "Do duplicate genes cause apomixis?", Apomixis: Evolution, Mechanisms and Perspectives, pp. 63-91 (2007).

Carvalho, Raquel F. et al., "The *Arabidopsis* SR45 Splicing Factor, a Negative Regulator of Sugar Signaling, Modulates SNF1-Related Protein Kinase 1 Stability", The Plant Cell, 28(8):1910-1925 (Aug. 2016).

Dong, Yihan et al., "Sulfur availability regulates plant growth via glucose-TOR signaling", Nat Commun 8(1):1174 (2017).

Downs, Jessica A., et al., "Suppression of homologous recombination by the *Saccharomyces cerevisiae* linker histone", Molecular Cell, 11:1685-1692 (2003).

Gao, Lei, "Pharmacologically Induced Meiosis Apomeiosis Interconversions in Boechera, *Arabidopsis* and Vigna", (Utah State University, https://digitalcommons.usu.edu/etd/7222) (2018).

Grimanelli, Daniel, "Epigenetic regulation of reproductive development and the emergence of apomixis in angiosperms" Curr Opin Plant Biol, 15(1):57-62 (2012).

Hand, Melanie L. et al., "The genetic control of apomixis: asexual seed formation", Genetics 197(2):441-450 (2014).

Hojsgaard, Diego et al., "Emergence of apospory and bypass of meiosis via apomixis after sexual hybridisation and polyploidisation", New Phytol 204(4):1000-1012 (2014).

Hojsgaard, Diego et al., "Taxonomy and Biogeography of Apomixis in Angiosperms and Associated Biodiversity Characteristics", Critical Reviews in Plant Sciences, 33(5):414-427 (2014).

Iordachescu, Mihaela et al., "Trehalose and abiotic stress in biological systems", Abiotic Stress in Plants—Mechanisms and Adaptations, pp. 215-234 (2011).

Jamsheer, KM, et al., "FCS-like zinc finger 6 and 10 repress SnRK1 signalling in *Arabidopsis*", Plant J, 94 (2):232-245 (2018).

Khanday, Imtiyaz et al., "A male-expressed rice embryogenic trigger redirected for asexual propagation through seeds", Nature, 565 (Jan. 3, 2019).

Kirk, Heather et al., "Comparing metabolomes: the chemical consequences of hybridization in plants", New Phytol, 167(2):613-622 (2005).

Li, Fay-Wei et al., "Boechera microsatellite webiste: an online portal for species identification and determination of hybrid percentage", Database, 1-11 (2017).

Li, Xiaojuan et al., "Differential TOR activation and cell proliferation in Arabidopsis root and shoot apexes", Proc Natl Acad Sci U S A, 114(10):2765-2770 (2017).

Li, Qian-Feng et al., "The brassinosteroid-regulated transcription factors BZR1/BES1 function as a coordinator in multisignal-regulated plant growth", Biochim Biophys Acta Gene Regul Mech, 1861(6):561-571 (2018).

Liu, Yidong et al., "Phosphorylation of 1-aminocyclopropane-1-carboxylic acid synthase by MPK6, a stress-responsive mitogen-activated protein kinase, induces ethylene biosynthesis in *Arabidopsis*", The Plant Cell, 16(12):3386-3399 (Dec. 2004).

Liu, Yanan et al., "Loss of-function of *Arabidopsis* receptor-like kinase BIR1 activates cell death and defense responses mediated by BAK1 and SOBIR1", New Phytol 212(3):637-645 (2016).

Luna, Estrella et al., "Callose Deposition: A Multifacted Plant Defense Response", Mol Plant Microbe Interact, 24 (2):183-193 (2011).

Mateo de Arias, Mayelyn, "Effects of Plant Stress on Facultative Apomixis in Boechera (Brassicaceae)", PhD Dissertation (Utah State University, Logan, UT, USA) (2015).

Mau, Martin et al., "Hybrid apomicts trapped in the ecological niches of their sexual ancestors", Proc Natl Acad Sci U S A, 112(18):E2357-2365 (Apr. 20, 2015).

Metallo, Christian M. et al., "Understanding metabolic regulation and its influence on cell physiology", Mol Cell., 49 (3):388-398 (Feb. 7, 2013).

Michelakis, Evangelos D. et al., "Diversity in mitochondrial function explains differences in vascular oxygen sensing", Circ Res, 90(12):1307-1315 (2002).

Mittler, Ron et al., "The Roles of ROS and ABA in Systemic Acquired Acclimation", The Plant Cell, 27:64-70 (Jan. 2015).

Mittler, Ron, "ROS Are Good", Trends Plant Sci 22(1):11-19 (2017).

Muller, Maren et al., "Ethylene Response Factors: A Key Regulatory Hub in Hormone and Stress Signaling", Plant Physiol 169(1):32-41 (2015).

Musial Krystyna et al., "Pattern of callose deposition during the course of meiotic diplospory in *Chondrilla juncea* (Asteraceae, Cichorioideae)", Protoplasma 254(4):1499-1505 (2017).

Narula, Jatin et al., "Functional requirements of cellular differentiation: lessons from Bacillus subtilis", Curr Opin Microbiol, 34:38-46 (2016).

Neiman, M. et al., "Genetic causes of transitions from sexual reproduction to asexuality in plants and animals", J Evol Biol, 27(7):1346-1359 (2014).

Nukarinen, Ella et al., "Quantitative phosphoproteomics reveals the role of the AMPK plant ortholog SnRK1 as a metabolic master regulator under energy deprivation", Sci Rep 6:31697 (2016).

Paul, Matthew J. et al., "Increasing crop yield and resilience with trehalose 6-phosphate: targeting a feast-famine mechanism in cereals for better source-sink optimization", J Exp Bot, 68(16):4455-4462 (2017).

Peel, Michael D. et al., "Megasporocyte callose in *Apomictic buffelgrass*, Kentucky bluegrass, Pennisetum squamulatum Fresen, *Tripsacum* L. and weeping lovegrass", Crop Science 37:724-732 (1997).

Projecto Garcia, Joana et al., "Decoding the architecture and origins of mechanisms for developmental polyphenism", Curr Opin Genet Dev, 47:1-8 (2017).

Rahikainen, Moona et al., "PP2A Phosphatase as a Regulator of ROS Signaling in Plants", Antioxidants, 5, pp. 1-11 (2016).

Rosenberger, Christina L. et al., "To Grow or Not to Grow: TOR and SnRK2 Coordinate Growth and Stress Response in *Arabidopsis*", Mol Cell, 69(1):3-4 (2018).

Sailer, Christian et al., "Apomixis Allows the Transgenerational Fixation of Phenotypes in Hybrid Plants", Curr Biol, 26(3):331-337 (2016).

Schmidt, Anja et al., "Apomictic and sexual germline development differ with respect to cell cycle, transcriptional, hormonal and epigenetic regulation", PLOS Genet, 10(7):e1004476 (2014).

Sessa, Guido et al., "PK12, a plant dual-specificity protein kinase of the LAMMER family, is regulated by the hormone ethylene", The Plant Cell, 8:2223-2234 (1996).

Sharbel, Timothy F. et al., "Apomictic and sexual ovules of Boechera display heterochronic global gene expression patterns", Plant Cell, 22(3):655-671 (2010).

Sheen, Jen, "Master Regulators in Plant Glucose Signaling Networks", Journal of Plant Biology, 57(2):67-79 (2014).

Sherwood, David Alan, "A simple metabolic switch may activate apomixis in *Arabidopsis thaliana*", Utah State University, Logan, Utah (2018).

Shilling, Martin Peter, "Hybridization, population genetic structure and gene expression in the genus *Boechera*", Utah State University, All Graduate Theses and Dissertations. 5192 (2016).

Simon, Jean-Christophe et al., "Phylogenetic relationships between parthenogens and their sexual relatives: the possible routes to parthenogenesis in animals", Biological Journal of the Linnean Society, 79:151-163 (2003).

Siqueira Joao Antonio et al., "Unraveling Interfaces between Energy Metabolism and Cell Cycle in Plants", Trends Plant Sci, 23(8):731-747 (2018).

(56) References Cited

OTHER PUBLICATIONS

Soto-Burgos, Junmarie et al., "SnRK1 activates autophagy via the TOR signaling pathway in *Arabidopsis thaliana*", PLOS One, 12(8):e0182591 (2017).
Stresemann, Carlo et al., "Modes of action of the DNA methyltransferase inhibitors azacytidine and decitabine", Int J Cancer, 123(1):8-13 (2008).
Tian, Yanchen et al., "Hydrogen peroxide positively regulates brassinosteroid signaling through oxidation of the BRASSINAZOLE-RESISTANT1 transcription factor", Nat Commun, 9(1):1063 (2018).
Tsai, Allen Y.-L .et al., "Trehalose-6-phosphate and SnRK1 kinases in plant development and signaling: the emerging picture", Front Plant Sci, 5:119 pp. 1-11 (2014).
Walker, James et al., "Sexual-lineage-specific DNA methylation regulates meiosis in *Arabidopsis*", Nat Genet, 50 (1):130-137 (2018).
Wang, Pengcheng et al., "Reciprocal Regulation of the TOR Kinase and ABA Receptor Balances Plant Growth and Stress Response", Mol Cell, 69(1):100-112 e106 (2018).
Wang, Lian-Chin et al., "*Arabidopsis* HIT4, a regulator involved in heat-triggered reorganization of chromatin and release of transcriptional gene silencing, relocates from chromocenters to the nucleolus in response to heat stress", New Phytol, 205(2):544-554 (2015).
Xing, Denghui et al., "Transcriptome-Wide Identification of RNA Targets of *Arabidopsis* SERINE/ARGININE-RICH45 Uncovers the Unexpected Roles of This RNA Binding Protein in RNA Processing", Plant Cell, 27(12):3294-3308 (2015).
Xiong, Yan et al., "Novel links in the plant TOR kinase signaling network", Curr Opin Plant Biol, 28:83-91 (2015).
Xiong, Yan et al., "Glucose-TOR signalling reprograms the transcriptome and activates meristems", Nature, 496 (7444):181-186 (2013).
Yan, Haojie et al., "Brassinosteroid-Signaling KINASE1 Phosphorylates MAPKKK5 to Regulate Immunity in Arabidopsis", Plant Physiol, 176(4):2991-3002 (2018).
Yao, Yuan et al., "Ethylene Response Factor 74 (ERF74) plays an essential role in controlling a respiratory burst oxidase homolog D (RbohD)-dependent mechanism in response to different stresses in *Arabidopsis*", New Phytol, 213(4):1667-1681 (2017).
Youn, Ji-Hyun et al., "Functional insights of plant GSK3-like kinases: multi-taskers in diverse cellular signal transduction pathways", Mol Plant, 8(4):552-565 (2015).
Zhang, Zhenzhen et al., "TOR Signaling Promotes Accumulation of BZR1 to Balance Growth with Carbon Availability in *Arabidopsis*", Curr Biol, 26(14):1854-1860 (2016).

\* cited by examiner

FIG. 4

Accession numbers, herbarium voucher numbers, collection location information, and *Boechera* Microsatellite Database (BMD) numbers for *Boechera* species and hybrids evaluated cytologically for mode of reproduction. Collection numbers are those of J. G. Carman (JC) and M. D. Windham (MW).

| *Boechera* taxon | Collection & voucher no. | Collection location | GPS |
|---|---|---|---|
| caeruleamontana (CAE) | MW4372 | | |
| crandallii x (CR1) | MW4026 | | |
| crandallii (CR2) | MW4032 | | |
| crandallii x gracilipes (CxG) | MW4207 | | |
| cusickii x sparsiflora (CxS) | MW99-224 | NV, Elko Co., above Gance Creek, Ca. 4.25 km SE of Spaghetti Spring. | 41.3242 -115.9678 |
| duchesnensis (DU1) | JC UT05002, UTC???? | UT, Duchesne Co., Bluffs overlooking Duchesne River, s of HW 40 | 40.1694 -110.3281 |
| duchesnensis (DU2) | MW3003 | UT, Duchesne Co., Bluffs overlooking Duchesne River | 40.1694 -110.3281 |
| exilis (EX1) | JC UT10011, UTC00276071 | UT, Summit Co., Rockport Lake, East of Highway 32 | 40.7753 -111.4078 |
| exilis (EX2) | JC NE14003, UTC00276512 | NE, Elko Co., 0.7 km W of I-80 Moor exit, by Moor summit | 41.1150 -114.8141 |
| exilis (EX3) | MW3987, DUKE????? | | |
| exilis x retrofracta (ExR1) | JC UT11004, UTC00275882 | UT, Utah Co., Right Fork, Hobble Creek Canyon | 40.0128 -109.2219 |
| exilis x retrofracta (ExR2) | MW2x-3691, DUKE???? | ID, Bingham Co., SW of Idaho Falls, Hells Lava flow | 43.3059 -112.2714 |
| exilis x retrofracta (ExR3) | MW4378 | | |
| falcatoria 3x A (FA) | MW, not listed | | |
| fendleri x stricta (FxS1) | MW4182 | | |
| fendleri x stricta (FxS2) | MW3600 | UT, Kane Co., Along Strawberry Creek near UT 14, ca. 0.78 km WSW of Cold Spring | 37.5081 -112.6217 |
| fernaldiana (FE) | MW3910 | NV, Churchill Co., above War Canyon road NW of Edwards Creek Valley road | 39.5736 -117.8560 |
| formosa (FO1) | MW99-051 | UT, Grand Co., along UT 128 ca. 5.07 km NNE of Parrott Mesa summit | 38.7042 -109.3869 |
| formosa (FO2) | JC UT05003 | UT, Duchesne Co., Bluffs overlooking Duchesne River, S of HW 40 | 40.1694 -110.3281 |

FIG. 4 (cont.)

| | | | | |
|---|---|---|---|---|
| *formosa* (FO3) | UT10006 | UT | | |
| *gracilipes* (GR) | MW3593 | AZ, Coconino Co., NE of Flagstaff on ridge above Switzer Canyon | 35.2036 -111.6414 | JB124 |
| *gracilipes x pendulina* GXPEN) | MW3592 | AZ, Coconino Co., W of Flagstaff along Observatory Mesa trail | 35.2017 -111.6675 | JB223 |
| *gracilipes x perennans* (GxPER) | MW3578a | UT, Beaver Co., Tushar Mtns. along Beaver River | 38.2547 -112.5289 | JB225 |
| *gracilipes x retrofracta* (GxR) | MW3382 | CO, Archuleta Co., WNW of Pagosa Springs on ridge above Sullenburger Reservoir | 37.2869 -107.0822 | JB299 |
| *gracilipes x thompsonii* (GcT) | MW3989 | | | |
| *c.f. gunnisoniana* 3x (GUcf) | JC CO11005, UTC00275883 | CO, Gunnison Co., North of Highway 50 | 38.5274 -106.8144 | |
| *hastate* 3x A (HA) | WP #95 A3x | 2n=3x=21 | | |
| *imnahaensis* (IM) | JC OR12002, UTC00276189 | OR, Wallowa Co., confluence of Snake & Imnaha rivers | 45.8160 -116.7654 | |
| *juniperina* (JU) | MW3425 | CA, San Bernardino Co., hill overlooking Baldwin Lake ca. 2.61 km W of Granite Spring | 34.2722 -116.7806 | JB107 |
| *kelseyana* (KE) | MW et al. 3950a, DUKE 404122 | NM, Sandoval Co., ca. 3.00 km SSE of Escrito Spring | | |
| *kelseyana* hybrid (KEx) | MW2320 | AZ, Apache Co., SE of Nazlini along Navajo Route 27 on bench of Red Mesa | 35.8806 -109.4333 | JB1409 |
| *laevigata* (LA1) | MW4087 | MO | | |
| *laevigata* (LA2) | MW3449 | MO, McDonald Co., NW of Noel on bluff overlooking Elk River | 36.6317 -94.5903 | JB234 |
| *laevigata x stricta* (*inexpectata*) (LxS) | MW4089 | | | |
| *lemmonii* (LE) | MW2483 | CA, Mono Co., E of Lobdell Lake near trail to Mt. Patterson, Sweetwater Mts. | 38.44 -119.3242 | JB318 |
| *lemmonii x mitchell-oldsiana* (LM) | MW4130 | | | |
| *lignifera* (*exilis x thompsonii*) (LI1) | MW3916 | UT, Tooele Co., NE of Ibapah on slope above Pony Express Wash along Lower Gold Hill Road | 40.099 -113.9243 | JB1305 |

FIG. 4 (cont.)

| Taxon | Accession | Locality | Lat | Lon | Collector |
|---|---|---|---|---|---|
| *formosa* (FO3) | UT10006 | UT | | | |
| *gracilipes* (GR) | MW3593 | AZ, Coconino Co., NE of Flagstaff on ridge above Switzer Canyon | 35.2036 | -111.6414 | JB124 |
| *gracilipes x pendulina* (GXPEN) | MW3592 | AZ, Coconino Co., W of Flagstaff along Observatory Mesa trail | 35.2017 | -111.6675 | JB223 |
| *gracilipes x perennans* (GxPER) | MW3578a | UT, Beaver Co., Tushar Mtns. along Beaver River | 38.2547 | -112.5289 | JB225 |
| *gracilipes x retrofracta* (GxR) | MW3382 | CO, Archuleta Co., WNW of Pagosa Springs on ridge above Sullenburger Reservoir | 37.2869 | -107.0822 | JB299 |
| *gracilipes x thompsonii* (GcT) | MW3989 | | | | |
| *c.f. gunnisoniana* 3x (GUcf) | JC CO11005, UTC00275883 | CO, Gunnison Co., North of Highway 50 | 38.5274 | -106.8144 | |
| *hastate* 3x A (HA) | WP #95 A3x | 2n=3x=21 | | | |
| *imnahaensis* (IM) | JC OR12002, UTC00276189 | OR, Wallowa Co., confluence of Snake & Imnaha rivers | 45.8160 | -116.7654 | |
| *juniperina* (JU) | MW3425 | CA, San Bernardino Co., hill overlooking Baldwin Lake ca. 2.61 km W of Granite Spring | 34.2722 | -116.7806 | JB107 |
| *kelseyana* (KE) | MW et al. 3950a, DUKE 404122 | NM, Sandoval Co., ca. 3.00 km SSE of Escrito Spring | | | |
| *kelseyana* hybrid (KEx) | MW2320 | AZ, Apache Co., SE of Nazlini along Navajo Route 27 on bench of Red Mesa | 35.8806 | -109.4333 | JB1409 |
| *laevigata* (LA1) | MW4087 | MO | | | |
| *laevigata* (LA2) | MW3449 | MO, McDonald Co., NW of Noel on bluff overlooking Elk River | 36.6317 | -94.5903 | JB234 |
| *laevigata x stricta* (*inexpectata*) (LxS) | MW4089 | | | | |
| *lemmonii* (LE) | MW2483 | CA, Mono Co., E of Lobdell Lake near trail to Mt. Patterson, Sweetwater Mts. | 38.44 | -119.3242 | JB318 |
| *lemmonii x mitchell-oldsiana* (LM) | MW4130 | | | | |
| *lignifera* (*exilis x thompsonii*) (LI1) | MW3916 | UT, Tooele Co., NE of Ibapah on slope above Pony Express Wash along Lower Gold Hill Road | 40.099 | -113.9243 | JB1305 |

FIG. 4 (cont.)

| | | | | |
|---|---|---|---|---|
| lignifera (LI2) | MW3876 | UT | | |
| lignifera (LI3) | JC WY05001, UTC00276008 | WY, Sweetwater Co., South of Green River | 41.5517 -109.5253 | |
| lignifera (LI4) | MW3876, DUKE 401957 | UT, Uintah Co., Miners Draw Road, 0.8 km ENE of Rt. 40 | 40.2903 -109.13315 | JB1270 |
| lignifera (LI5) | MW3914, DUKE????? | NE, Eureka Co., Near Devils Gate along U.S. Rt. 50 | 39.5727 -116.0772 | JB1303 |
| microphylla (MI1) | JC UT05001, UTC00276225 | UT, Cache County, Logan Canyon, above Wood Camp Campground | 41.7952 -111.6470 | |
| microphylla (MI2) | JC UT10003, UTC00275885 | UT, Millard Co., Oak Creek Canyon | 39.3500 -112.2642 | |
| mitchell-oldsiana (MO) | MW WP #95 n=7 | 2n=2x=14 | | |
| mitchell-oldsiana x retrofracta 2:1 (MOxR1) | MW4126 | 2n=3x hast emb/morph | | |
| mitchell-oldsiana x retrofracta 2x (MOxR2) | MW WP #97 | 2n=2x+1=15 (1 B cs) | | |
| oxylobula (OX) | MW3052, DUKE????? | CO, Montrose Co., NNE of Cimarron by Gunnison River below Morrow Point Dam | 38.4558 -107.5456 | JB141 |
| pallidifolia (PA) | MW4029 | | | |
| pendulina (PE) | MW2025 | CA, San Bernardino Co., San Bernardino Mtns, Furnace Canyon, Specialty Minerals Quarry | 34.35 -116.9167 | FW9 |
| pendulina x thompsonii (PxT) | MW3364 | UT, Carbon Co., E of Wellington along U.S. Route 6 in Cat Canyon | 39.5475 -110.6483 | JB338 |
| pendulina x wyomingensis (PxW) | MW2078 | WY, Sweetwater Co., NE of Dutch John along U.S. 191 on S slope of Little Mtn. | 41.0678 -109.2792 | JB255 |
| puberula (PUB1) | JC NV10004 | NV | | |
| puberula (PUB2) | JC NV10003 | NV | | |
| pulchra (PUL) | MW3435 | CA, Kern Co., SE of Lake Isabella along Erskine Creek road in the Piute Mts. | 35.5808 -118.4244 | JB270 |
| retrofracta (RE) | MW 2x-4103, DUKE?? | | | |
| retrofracta x stricta (RxS) | JC CO11010, UTC00276007 | CO, Rio Blanco Co., Cow Creek Access Road | 39.7029 -107.9986 | |
| schistacea (SC) | MW99-284 | NV, Nye Co., near Ophir Pass road on ridge S of Crane Canyon | 38.9522 -117.3378 | JB365 |

FIG. 4 (cont.).

| | | | | |
|---|---|---|---|---|
| *selbyi* (SE) | MW4023 | | | |
| *sparsiflora* (SPA) | MW3647 | OR, Malheur Co., NNW of Ontario on bluff above Snake River along State Route 201 | 44.2275 -117.0500 | JB280 |
| species *n*=7 (SPE1) | MW3682 | Devils Gap, WA | | |
| species 3x A (SPE2) | MW WP #96 | 2n=3x+1=22 (1 B cs) | | |
| *stricta* (ST1) | MW2128 | UT, Piute Co., NE of Kingston along Pole Creek on the Sevier Plateau | 38.29 -112.0622 | JB1124 |
| *stricta* (ST2) | JC UT10007, UTC00275884 | UT, Duchesne Co., North Fork of Duchesne River, NW side of river | 40.5559 -110.8918 | |
| *thompsonii* (TH1) | MW 3080, DUKE????? | UT, San Juan Co., S of Beef Basin near head of South Canyon at Moki Spring | 37.9181 -109.9453 | JB335 |
| *thompsonii* (TH2) | MW 2313, DUKE????? | | | |
| *thompsonii* (TH3) | MW3923 | | | |
| *thompsonii* (TH4) | MW3931 | | | |
| *thompsonii* (TH5) | MW3083 | | | |
| *thompsonii* (TH6) | MW3925 | | | |
| *yellowstonensis* (YE) | JC WY12003, UTC00276188 | WY, Park Co., mat-forming, within 1 m of the base of Flag Peak cliff | 44.4559 -109.5285 | |

FIG. 5

Primers used to test microarray accuracy by qPCR.

| Gene | Name | Dir. | Primer | Tm |
|---|---|---|---|---|
| AT1G32640 | MYC2 | F | CGACGACAACGCTTCTATGA | 60.4 |
| | | R | CCAACCTTCGTGTGTTCCTT | 62.4 |
| AT5G20240 | PI | F | CTTCCATGGATCTTGGTGCT | 60.4 |
| | | R | ATCTCCATCTGGTGGTCTCG | 60.4 |
| AT1G69120 | AP1 | F | GCAAGCAATGAGCCCTAAAG | 60.4 |
| | | R | ACTGCTCCTGTTGAGCCCTA | 62.4 |
| AT5G53250 | AGP22 | F | CCTGAAATTCCGTTGGAGA | 58.4 |
| | | R | GCCAAAGCCACCATCATTAG | 60.4 |
| AT4G09960 | STK | F | TGCCGCGTACTATCAACAAG | 60.4 |
| | | R | TGCTTCTTGGACCTGATCCT | 60.4 |
| AT1G20930 | CDKB2 | F | ATCTTTGCGGGAGACTCTGA | 60.4 |
| | | R | GTTTTGCTGGCTCGTACTCC | 62.4 |
| AT5G51230 | EMF2 | F | CGTTTCTCCTAAGCCTGTCG | 62.4 |
| | | R | GATCCTGATTTTGCCTCCAA | 58.4 |
| AT3G52940 | FK | F | TGTTACTGGGCGAAGTTCCT | 60.4 |
| | | R | GGAACCATCCTGCACACTTT | 60.4 |
| AT3G13160 | PPR | F | GTTCAAGAAAGCCTGCCAAG | 60.4 |
| | | R | GGCATTTCGTCGAACACTTT | 58.4 |
| AT5G61380 | TOC1 | F | GATCTCCCAATGGCTAAGG | 60.4 |
| | | R | CATGCGTCTTCTTCTCCACA | 60.4 |
| AT4G30270 | MERI5B | F | CAACGGCCAGCTTCTTACTC | 62.4 |
| | | R | TCATCCCAAGTGGATCCTTC | 60.4 |
| AT4G25100 | FSD1 | F | TGGAGGAAAACCATCAGGAG | 60.4 |
| | | R | GGATTCACAGCATTGGGAGT | 60.4 |
| AT3G13580 | RPL7D | F | TCATCTGCGTTGAGGATCTG | 60.4 |
| | | R | GATGAAGTTCTCGCGGTTTC | 60.4 |
| AT2G35940 | BLH1 | F | AACATGGGATCCATGGAAAA | 56.3 |
| | | R | ATTGTCTCGTCGCTGGTTCT | 60.4 |

FIG. 7A
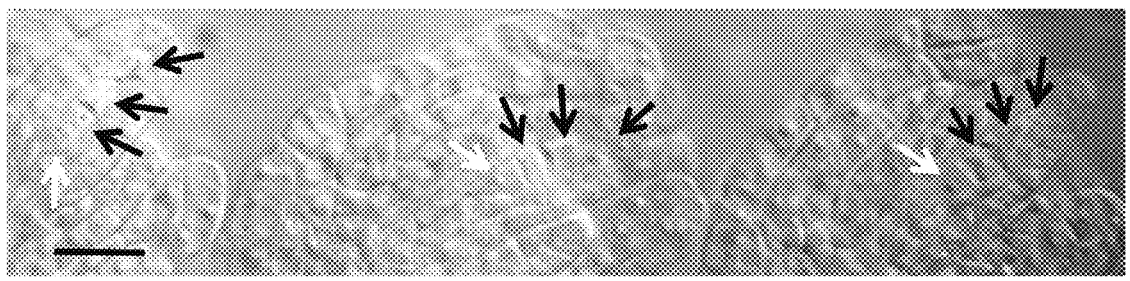
FIG. 7B          FIG. 7C          FIG. 7D
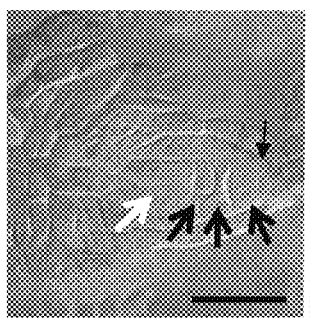 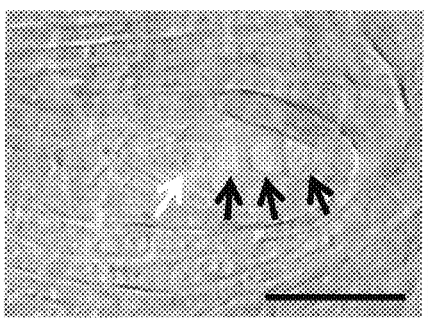 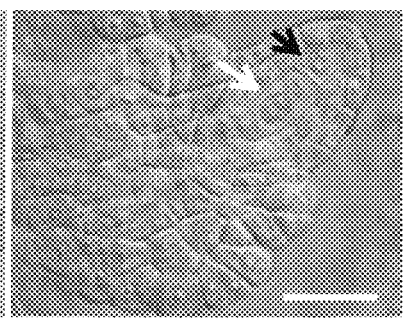
FIG. 7E          FIG. 7F          FIG. 7G
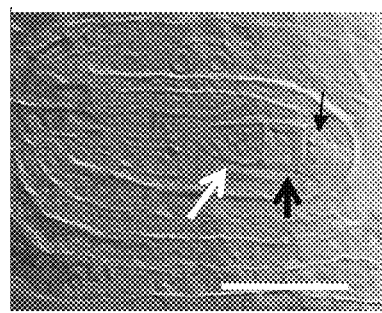 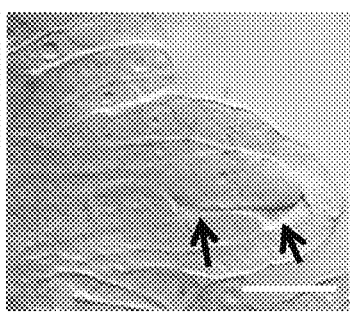 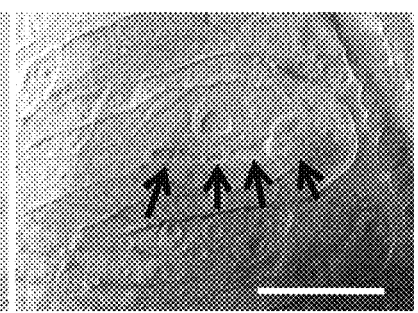
FIG. 7H          FIG. 7I          FIG. 7J
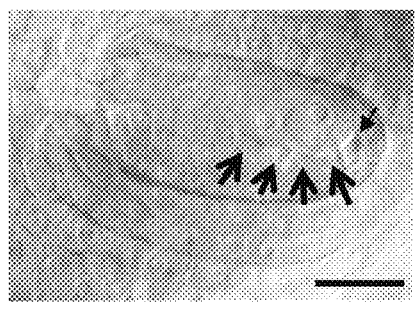 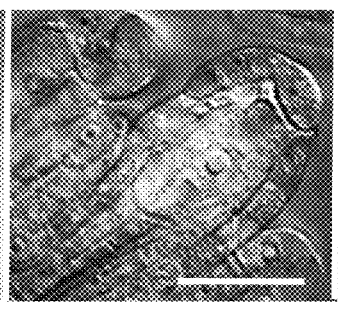 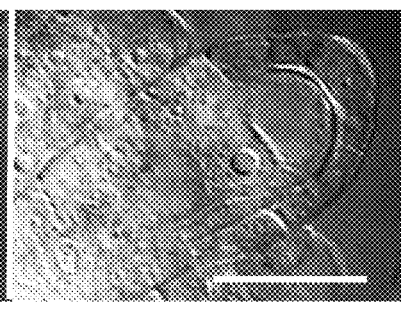

FIG. 11

|  |  | Sexual *B. formosa* vs. aposporous *B. microphylla* | |
| --- | --- | --- | --- |
| Gene | Name | Microarray | qPCR |
| AT1G32640 | MYC2 | 0.15 | 0.08 |
| AT5G20240 | PI | 0.04 | 0.29 |
| AT1G69120 | AP1 | 0.07 | 0.17 |
| AT5G53250 | AGP22 | 0.05 | 0.11 |
| AT4G09960 | STK | 11.1 | 2.5 |
| AT1G20930 | CDKB2 | 6.7 | 2.0 |
| AT5G51230 | EMF2 | 2.8 | 2.1 |
| AT3G52940 | FK | NS | 1.8 |
| AT3G13160 | PPR | NS | 2.0 |
| AT5G61380 | TOC1 | 4.5 | 7.2 |
| AT4G30270 | MERI5B | 4.2 | 1.2 |
| AT4G25100 | FSD1 | 0.09 | 0.06 |
| AT3G13580 | RPL7D | 73.7 | 2.0 |
| AT2G35940 | BLH1 | 0.15 | 0.05 |

FIG. 15

| Gene name | Primer | Tm | Size |
|---|---|---|---|
| AT2G40140 | AT2G40140_Forward:CAGATGTGTCGTGGGTGAAC | 60 | 163 |
| | AT2G40140_Reverse:TATGCCACAATCTGCTGCTC | 59.98 | |
| AT4G02730 | AT4G02730_Forward:TCGCATTACACTTGCTCTGC | 60.17 | 167 |
| | AT4G02730_Reverse:ATCGTCTCATCGAACGATCC | 60.04 | |
| AT3G52940 | AT3G52940_Forward:TTCAGGCTATTGGGGAATTG | 59.89 | 163 |
| | AT3G52940_Reverse:TCGAACCTCGTCTCTTCGTT | 59.99 | |
| AT3G13580 | AT3G13580_Forward: TCATCTGCGTTGAGGATCTG | 59.94 | 170 |
| | AT3G13580_Reverse: GATGAAGTTCTCGCGGTTTC | 59.82 | |
| AT2G48020 | AT2G48020_Forward:AGTTGACAGAGCCGGAAGAA | 59.99 | 179 |
| | AT2G48020_Reverse:CCATTCCTGCTGAAAACGAT | 60.07 | |

FIG. 16

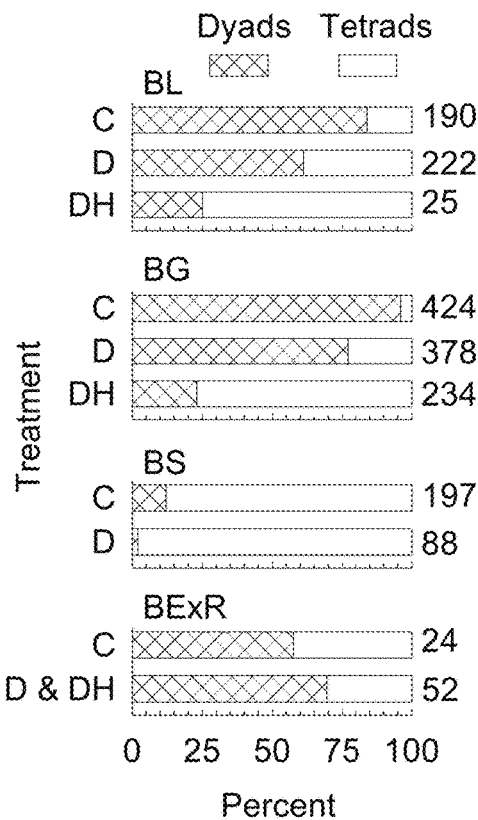

FIG. 34A  FIG. 34B  FIG. 34C  FIG. 34D
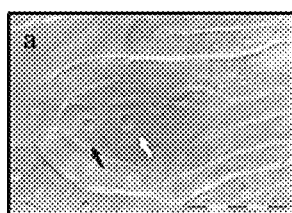  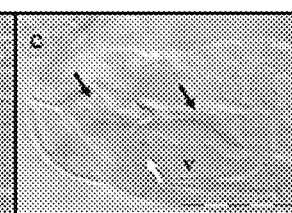 
FIG. 34E  FIG. 34F  FIG. 34G  FIG. 34H
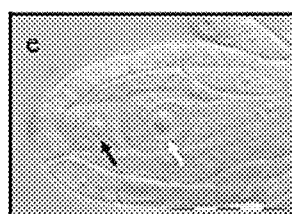  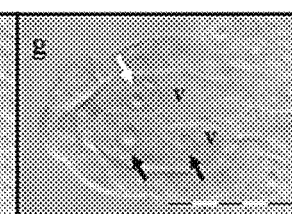 
FIG. 34I  FIG. 34J  FIG. 34K  FIG. 34L
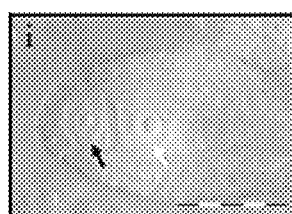 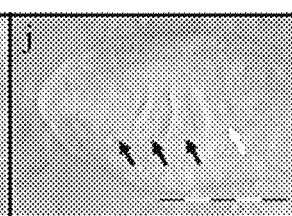 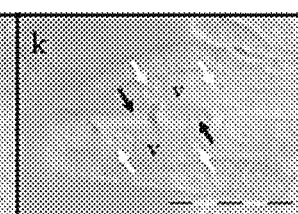 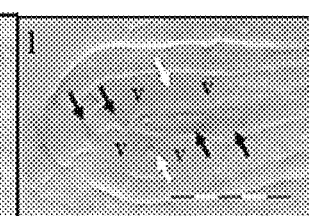

FIG. 36A
FIG. 36B
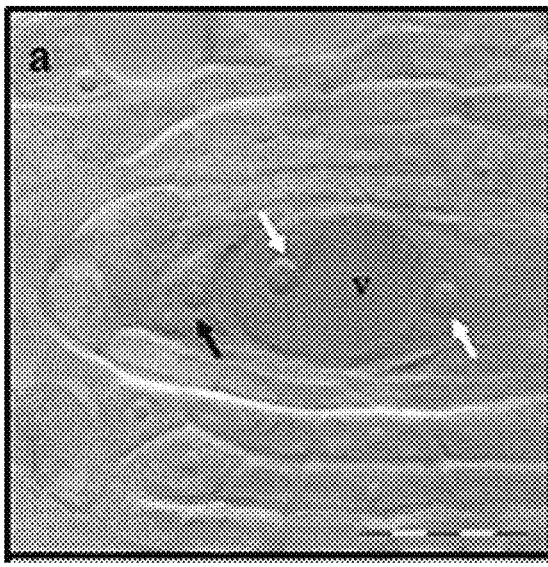
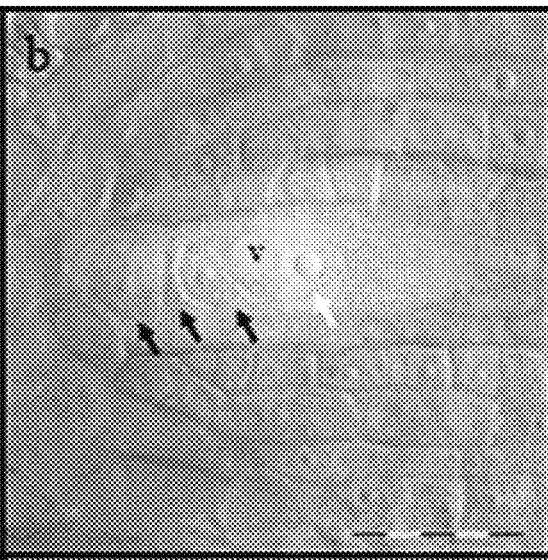
FIG. 36C
FIG. 36D
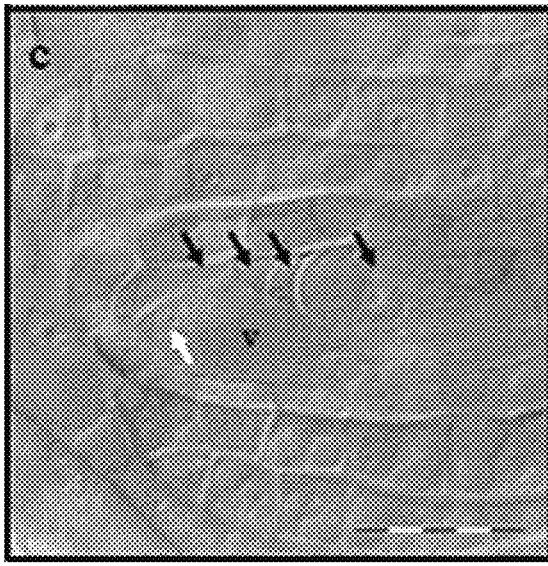
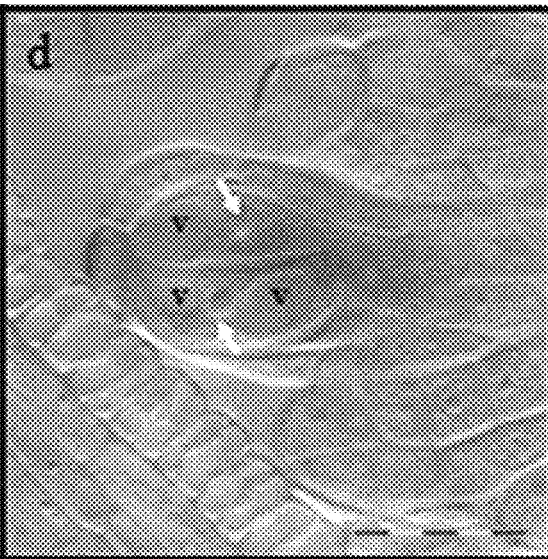

FIG. 43
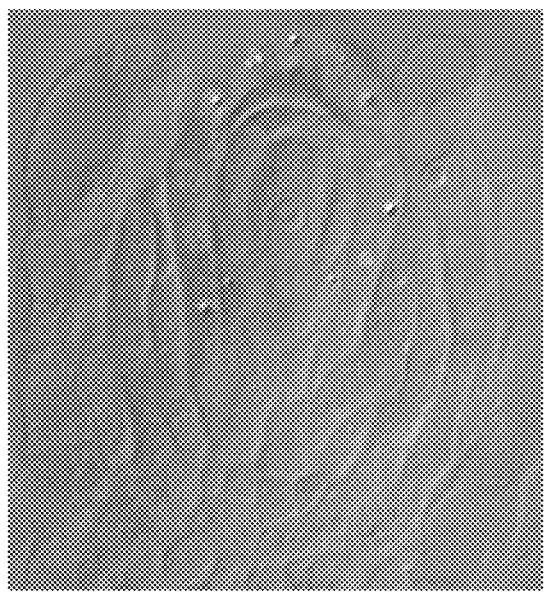 

FIG. 45A FIG. 45B
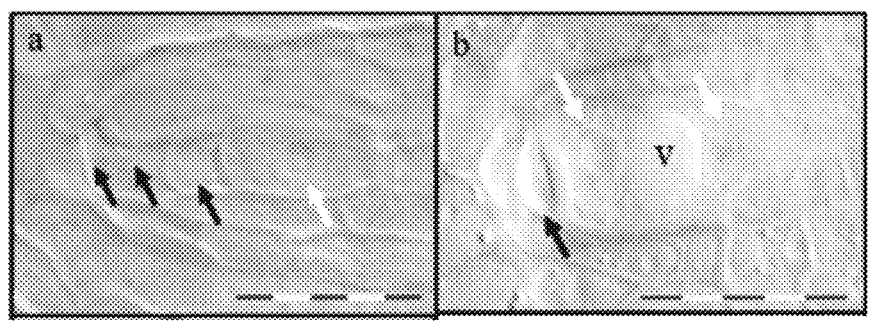
FIG. 45C FIG. 45D
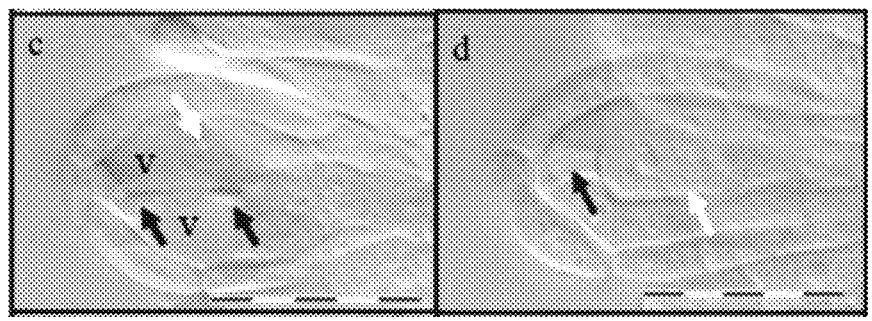
FIG. 45E FIG. 45F
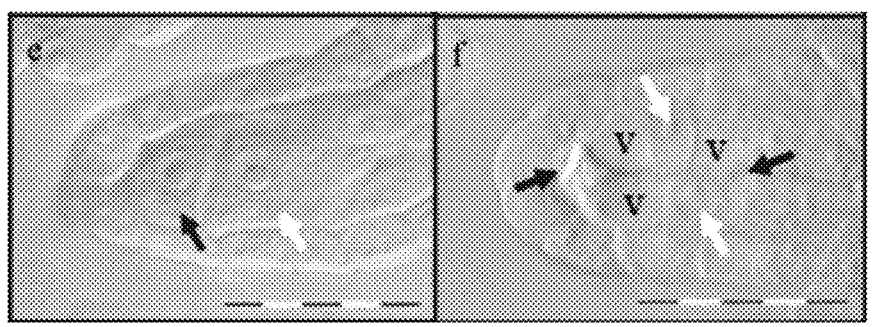
FIG. 45G
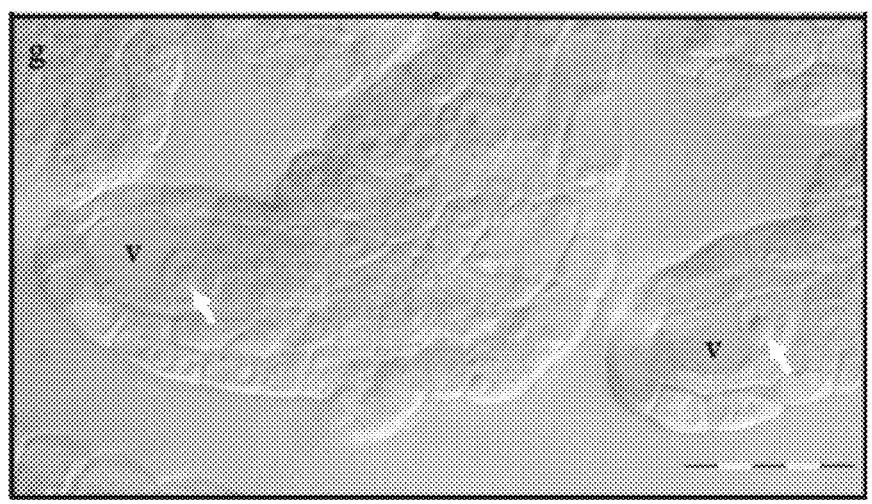

FIG. 49

| Treatment | Sexual | Antennaria type | Total |
|---|---|---|---|
| Sucrose control | 1 | 0 | 1 |
| Glucose control | 0 | 3 | 3 |
| epiBL | 3 | 4 | 7 |
| DTBA | 3 | 8 | 11 |
| epiBL + DTBA | 0 | 0 | 0 |
| 5-azaC | 3 | 9 | 12 |
| Total | 10 | 24 | 34 |

FIG. 51A
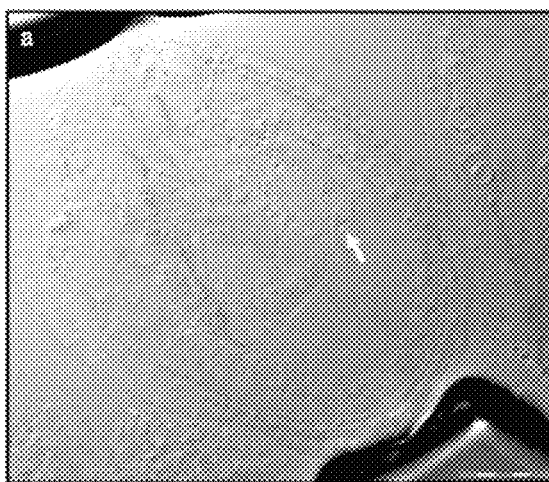
FIG. 51B
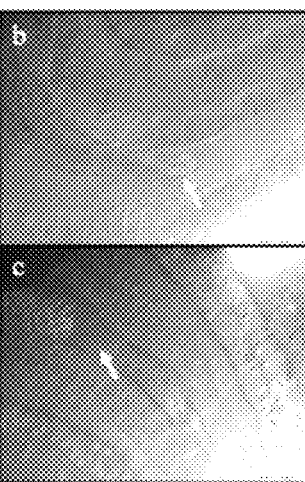
FIG. 51D
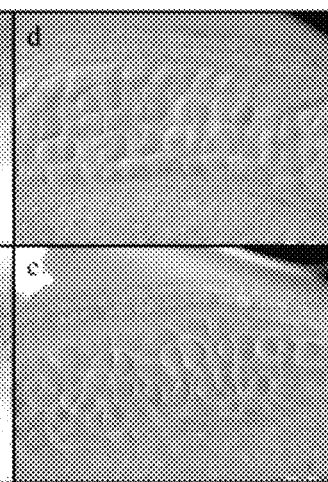
FIG. 51C          FIG. 51E

METHODS OF INDUCING APOMICTIC OR SEXUAL REPRODUCTION

CROSS-REFERENCE TO RELATED APPLICATIONS

This application claims the benefit of U.S. Provisional Patent Application No. 62/628,743, filed on Feb. 9, 2018. The contents of which are incorporated herein by reference in its entirety.

STATEMENT REGARDING FEDERALLY SPONSORED RESEARCH

This invention was made with government support under Cooperative Agreement No. 70NANB4H3039 awarded by the U.S. Department of Commerce, National Institute of Standards and Technology, Advanced Technology Program. The government has certain rights in the invention.

INCORPORATION BY REFERENCE IN ITS ENTIRETY

This application cites the Dissertations entitled "A Simple Metabolic Switch May Activate Apomixis in *Arabidopsis thaliana*," by David Alan Sherwood, and "Pharmacologically Induced Meiosis Apomeiosis Interconversions in *Boechera, Arabidopsis* and *Vigna*," by Lei Gao. The contents of each of which are incorporated herein by reference in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 9,187 byte ASCII (text) file named "Seq_List" created on Dec. 16, 2019.

TECHNICAL FIELD

The present disclosure relates to methods for inducing apomixis in sexual eukaryotes and inducing meiosis in apomictic eukaryotes. More specifically, this disclosure relates to using a chemical treatment to induce meiosis and/or syngamy or apomeiosis and/or parthenogenesis in plants.

BACKGROUND OF THE INVENTION

In eukaryotes, sexual reproduction is a two-step process involving the following: (i) meiosis, which produces genetically reduced (n) gametes or gametophyte-forming spores that eventually produce gametes, and (ii) fertilization (syngamy), where genetically reduced gametes fuse to form a viable 2n zygote. However, many eukaryotes exhibit an alternate mode of reproduction known as apomixis. Here, the two requirements of sexual reproduction are replaced, i.e., unreduced (2n) gametes, spores, or gamete-like cells form without meiosis (apomeiosis), and these unreduced cells develop into 2n zygotes/embryos without syngamy, by a process known as parthenogenesis.

Apomixis in plants (asexual seed formation) is i) sporophytic, where embryos form from 2n somatic (sporophytic) cells of the ovule wall, or ii) gametophytic, where one or more unreduced gametophytes (embryo sacs) form in the ovule, and the unreduced egg in the embryo sac develops into an embryo without fertilization (by parthenogenesis) (1). The form of apomixis reported herein is gametophytic. Gametophytic apomixis in plants is often verified by single seed flow cytometry, which measures embryo-to-endosperm genome ratios, e.g., 2c:3c seeds are sexual (the result of double fertilization) and 2c:5c or 2c:6c are apomictic (2-5). However, the type of gametophytic apomixis being expressed (FIG. 1) is determined cytologically (1, 6-8). In *Taraxacum*-type diplosporous apomixis, a first division meiotic restitution occurs followed by a normal second division, which produces two spores. This is a common form of apomeiosis in plants (8) and is the most common form of apomeiosis in animals (9). In plants, one of the 2n spores forms an unreduced apomictic embryo sac. The other spore degenerates in a manner similar to the three degenerating spores of a normal female sexual tetrad. *Hieracium*-type aposporous apomixis, where meiosis or early embryo sac formation abort and unreduced (2n) embryo sacs form adventitiously from adjacent somatic (usually nucellar) cells (FIG. 1) is also common in plants (8). Antennaria-type diplospory is a third type of apomixis that is common in plants (8). Here, the unreduced embryo sac forms directly from a megaspore mother cell that does not initiate meiosis (FIG. 1).

Apomixis is a natural but rare anomaly that occurs in less than 1% of angiospermous genera (10). It does not occur in most of the world's important food and fiber crops, including rice, wheat, maize, barley, millet, sorghum, soybeans, potatoes, most vegetable and oil crops, cotton and many others (1). It is among such crops that apomixis holds its greatest potential for providing commercial and humanitarian benefits. Conferring apomixis to world crops could benefit crop production in at least three ways.

First, inbred crops, such as wheat, rice and soybeans, could be converted to superior-yielding hybrid crops such that hybrid vigor is permanently inherited from seed to seed. Today, wheat hybrids yield up to 15% more grain than inbred varieties, but the vast majority of wheat grown internationally is varietal—not hybrid. The high cost of producing hybrid seed, compared to the low cost of producing varietal seed, currently limits the use of hybrid wheat seed to the very highest wheat production areas in the world.

It is the anatomy, physiology and genetics of most world crops that currently prevent the economic production of mass quantities of hybrid seed. These economics continue to prohibit a world-wide conversion from inferior varieties to superior hybrids. Apomixis could eliminate this economic bottleneck. For rice, the full exploitation of hybrid vigor could raise rice yields by 30% to 50% over yields of inbred varieties currently grown on the vast majority of rice acreage worldwide (11). By conferring apomixis to hybrids of rice and other major world crops, hybrid seed would be as cheap to produce as varietal seed. This is because apomictic hybrids clone themselves asexually from seed to seed, i.e. from one seed generation to the next. In essence, apomictic seed production systems do not require costly cross-pollination procedures for producing hybrid seed.

Second, apomixis could enhance crop production by reducing costs associated with producing hybrid seed of crops currently grown as hybrids. For example, hybrid seed of corn is produced by identifying genetically-divergent inbred parent lines that when crossed or double-crossed with each other produce superior-yielding hybrid progeny. Once appropriate parent lines are identified or bred, mass cross-pollinations are required to produce commercial quantities of hybrid seed. Apomixis could eliminate most of the cross-pollination costs, i.e. once an apomictic hybrid is produced, it clones itself through its own seed, generation after generation. Seed companies in the U.S. currently spend about $1 B per year to produce hybrid corn seed. Apomixis could eliminate the cross-pollination procedures and save U.S. corn seed producers more than $800 M annually.

Third, apomixis could be used to transfer biotechnological and productivity advances to marginal farmlands in the developed world and to resource poor farmers in developing nations (12). Currently, high costs associated with producing hybrid seed or conferring value-added agbiotech traits to crops prohibit the use of hybrids or value-added traits in resource poor areas of the world. Because apomixis perpetuates such value-added traits (hybridity or agbiotech modifications) from seed to seed, apomixis could become a cost-effective vehicle for delivering these traits to resource-poor farmers in poor nations.

To realize the major benefits of apomixis, there is a need to develop and perfect methods for inducing apomixis and enhancing its expression in major crops.

SUMMARY OF THE INVENTION

The present invention provides useful methods of switching between apomixis and sexual reproduction in a eukaryote, comprising increasing or decreasing glucose signaling, osmotic stress, oxidative stress, perceived oxidative stress, or a combination thereof in a female germline cell and/or a female germline-associated tissue in the eukaryote, wherein apomixis comprises apomeiosis and parthenogenesis and sexual reproduction comprises meiosis and syngamy.

In certain embodiments, the sexual eukaryote includes a plant selected from the group consisting of: alfalfa, amaranth, asparagus, barley, beans, beets, buckwheat, canary grass, cacao, carob, carrots, castor beans, chickpeas, chilis, clover, coffee, cotton, cowpea, cucumbers, cucurbits, durum, flax (linseed), fonio, Job's tears, kaniwa, lentils, lettuce, lupin beans, maize (corn), melons, mesquite, millet, oat, onions, peanuts, peas, peppers, pitseed goosefoot, *quinoa*, rapeseed, rice, rye, sorghum, soybeans, spelt, squashes, sunflowers, tamarind, teff, tomatoes, triticale, turnips, wheat, wheat, and wild rice. In certain implementations, the sexual eukaryote includes Brassicaceae and Fabaceae. In other implementations, the sexual eukaryote includes *Arabidopsis*, Drummond's rockcress, and cowpea.

In certain embodiments, the apomictic eukaryote includes forage and turf grasses such as bahiagrass (*Paspalum notatum*), signalgrass (*Brachiaria*, the most widely used forage grass in Central and South America), weeping lovegrass (*Eragrostis curvula*), Kentucky bluegrass (*Poa pratensis*), buffalograss (*Bouteloua dactyloides*), and Bermuda grass (*Cynodon dactylon*). The apomictic eukaryote is selected from the group consisting of: apomictic forage grass and turf grass. The apomictic eukaryote is selected from the group consisting bahiagrass (*Paspalum notatum*), signalgrass (*Brachiaria*), weeping lovegrass (*Eragrostis curvula*), Kentucky bluegrass (*Poa pratensis*), buffalograss (*Bouteloua dactyloides*), Bermuda grass (*Cynodon dactylon*), and combinations thereof. In certain implementations, the apomictic eukaryote also includes a sexual eukaryote that is switched to apomictic.

In one embodiment, the invention involves inducing apomeiosis, parthenogenesis, or both in the eukaryote by increasing glucose signaling, decreasing osmotic stress, decreasing oxidative stress, decreasing perceived oxidative stress, or a combination thereof, wherein the eukaryote is a sexual eukaryote.

The apomeiosis is of a diplosporous Antennaria-type, diplosporous *Taraxacum*-type, aposporous *Hieracium*-type, or a combination thereof.

In some implementations, at least 50% of the germline cells of the sexual eukaryote switch from meiosis to apomeiosis, syngamy to parthenogenesis, or both. In some implementations, the germline cell of the sexual eukaryote has at least a 50% probability of switching from meiosis to apomeiosis, syngamy to parthenogenesis, or both.

The female germline cell and/or female germline-associated tissue includes the megaspore mother cell, adjacent cells of the ovule nucellus, or integuments.

In some embodiments, increasing glucose signaling, decreasing osmotic stress, decreasing oxidative stress, decreasing perceived oxidative stress, or a combination thereof comprises increasing sugar level, increasing fatty acid catabolism by beta-oxidation, increasing brassinosteroid (BR) activity, increasing antioxidant activity, decreasing reactive oxygen species (ROS), decreasing abscisic acid (ABA) activity, decreasing sucrose non-fermenting 1 related kinase (SnRK) activity, increasing target of rapamycin complex 1 (TORC1) activity, decreasing meiosis-specific RNA directed DNA methylation (RdDM), or a combination thereof.

In some implementations, the increase in sugar level, fatty acid catabolism by beta-oxidation, BR activity, antioxidant activity, TORC1 activity, the decrease in ROS, ABA-biosynthesis, SnRK activity, RdDM, or a combination thereof is in an amount and time sufficient to induce apomeiosis, parthenogenesis, or both. In a non-limiting implementation, the time sufficient to induce apomeiosis, parthenogenesis, or both is between 0.05 and 48 hours.

In other implementations, increasing sugar level comprises applying a monosaccharide, a disaccharide, a short-chain polysaccharide, or a combination thereof; increasing BR activity comprises applying epibrassinolide (epiBL); increasing antioxidant comprises applying superoxide dismutase, glutathione, ABA, peroxidase, (S)-2-aminobutane-1,4-dithiol hydrochloride (DTBA), or a combination thereof; decreasing ABA activity comprises applying fluridone, increasing the activity of CYP707A, protein phosphatase 2C (PP2C), or a combination thereof; decreasing SnRK activity comprises decreasing an activity of SnRK1, SnRK2, or both; decreasing RdDM comprises applying DNA methyltransferase inhibitor 5-azacytidine (5-azaC), decreasing an activity of RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), or a combination thereof.

In limiting implementations, increasing sugar level comprises applying 30-90 mmol/L glucose to the female germline cell and/or female germline-associated tissue (e.g., a pistil) for 4-480 minutes, 72 to 6 hours before megasporogenesis onset, applying 30-70 mmol/L sucrose to the female germline cell and/or female germline-associated tissue (e.g., a pistil) for 0.1-480 minutes, 72 to 6 hours before megasporogenesis onset, or both; decreasing ABA activity comprises applying 2-20 µM fluridone to the female germline cell and/or female germline-associated tissue (e.g., a pistil) for 0.1-480 minutes, 72 to 6 hours before megasporogenesis onset; increasing antioxidant activity comprises applying 0.5-10 µM DTBA to the female germline cell and/or female germline-associated tissue (e.g., a pistil) for 0.1-480 minutes, 72 to 6 hours before megasporogenesis onset; decreasing RdDM comprises applying 50-1,000 µM 5-azaC to the female germline cell and/or female germline-associated tissue (e.g., a pistil) for 0.1-480 minutes, 96 to 6 hours before megasporogenesis onset; increasing BR activity comprises applying 0.05-15 µM epiBL to the female germline cell and/or female germline-associated tissue (e.g., a pistil) for 0.1-480 minutes, 72 to 6 hours before megasporogenesis onset; increasing sugar level and antioxidant activity comprises applying 30-140 mM glucose and 0.05-10 µM DTBA to the female germline cell and/or female germline-associated tissue (e.g., a pistil) for 0.1-480 minutes, 72 to 6 hours before anthesis or fertilization; increasing sugar level and BR activity comprises applying 30-140 mM glucose and 0.05-15 µM epiBL to the female germline cell and/or female germline-associated tissue (e.g., a pistil) for 0.1-480 minutes, 72 to 6 hours before anthesis or fertilization; and/or decreasing ABA activity comprises applying 2-20 µM fluridone to the female germline cell and/or female germline-associated tissue (e.g., a pistil) for 0.05-480 minutes, 72 to 6 hours before anthesis or fertilization.

In some implementations, decreasing SnRK activity comprises disrupting an endogenous SnRK gene in a eukaryote cell. In a non-limiting implementation, decreasing SnRK activity comprises introducing into the eukaryote cell a silencing element capable of decreasing or eliminating a polynucleotide or a polypeptide encoded by SnRK1, SnRK2, or both. In another non-limiting implementation, the silencing element is selected from the group consisting of: a double stranded RNA, a siRNA, a miRNA, and a hairpin suppression element. In yet another non-limiting implementation, the silencing element is operably linked to a cis-regulatory element active in germline cells, germline associated tissues, or both. In a further non-limiting implementation, the SnRK1 activity, SnRK2 activity, or both is decreased by 10-90% between 0.5 and 48 hours before megasporogenesis onset to 0.5 to 48 h after embryo formation. In some implementations, the method further comprises disrupting in the eukaryote, the eukaryote cell, or the eukaryote tissue, in addition to the SnRK gene, at least one other gene involved in meiosis wherein the at least one other gene is selected from the group consisting of: RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), an ortholog thereof, and combinations thereof.

In other embodiments, the invention involves inducing meiosis in an apomictic eukaryote by decreasing glucose signaling, increasing osmotic stress, increasing oxidative stress, increasing perceived oxidative stress, or a combination thereof. In some implementations, decreasing glucose signaling, increasing oxidative stress, increasing perceived oxidative stress, or a combination thereof comprises decreasing sugar level, decreasing fatty acid catabolism by beta-oxidation, decreasing brassinosteroid (BR) activity, increasing osmotic stress, decreasing antioxidant activity, increasing reactive oxygen species (ROS), increasing abscisic acid (ABA) activity, increasing sucrose non-fermenting 1 related kinase (SnRK) activity, decreasing target of rapamycin complex 1 (TORC1) activity, increasing meiosis-specific RNA directed DNA methylation (RdDM), or a combination thereof.

In some implementations, the decrease in sugar level, the decrease in fatty acid catabolism by beta-oxidation, the decrease in BR activity, the increase in osmotic stress, the decrease in antioxidant activity, the decrease in TORC1 activity, the increase in ROS, the increase in ABA activity, the increase in SnRK activity, the increase in RdDM, or a combination thereof is in an amount and time sufficient to induce meiosis. In a non-limiting implementation, the time sufficient to induce meiosis is between 0.05 and 72 hours.

In some implementations, decreasing sugar level comprises restricting a monosaccharide, a disaccharide, a short-chain polysaccharide, or a combination thereof; decreasing BR activity comprises applying brassinazole; increasing osmotic stress comprises applying PEG 6,000; increasing ROS comprises applying hydrogen peroxide; increasing ABA activity comprises applying ABA, decreasing the activity of CYP707A, protein phosphatase 2C (PP2C), or a combination thereof; increasing SnRK activity comprises increasing an activity of SnRK1, SnRK2, or both; increasing meiosis specific RdDM comprises increasing an activity of RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), or a combination thereof.

In some implementations, decreasing sugar level comprises restricting glucose to less than 6 mmol/L (e.g., 0.01 to 6 mmol/L, or 0.1 to 6 mmol/L) for 0.1-10 minutes, from 48 to 0.2 hours before megasporogenesis onset; increasing ROS comprises applying 20-500 mM hydrogen peroxide to the female germline cell and/or female germline-associated tissue (e.g., a pistil) for 5-60 minutes, 72 to 1 hours before megasporogenesis onset; increasing osmotic stress comprises applying 10-40 g/L PEG 6,000 to the female germline cell and/or female germline-associated tissue (e.g., a pistil) for 5-480 minutes, 72 to 1 hours before megasporogenesis onset; decreasing BR activity comprises applying 0.1-10 µM brassinazole to the female germline cell and/or female germline-associated tissue (e.g., a pistil) for 0.1-480 minutes, 72 to 1 hours before megasporogenesis onset; and/or increasing ABA activity comprises applying 0.5-10 µM abscisic acid to the female germline cell and/or female germline-associated tissue (e.g., a pistil) for 0.1-480 minutes, 72 to 1 hours before megasporogenesis onset.

The present invention further provides a sexual eukaryote that is induced to reproduce apomictically by inducing apomeiosis, parthenogenesis, or both in the sexual eukaryote by increasing glucose signaling, decreasing osmotic stress, decreasing oxidative stress, decreasing perceived oxidative stress, or a combination thereof.

The present invention also provides an apomictic eukaryote produced from a sexual eukaryote by decreasing SnRK activity by disrupting an endogenous SnRK gene in the sexual eukaryote.

BRIEF DESCRIPTION OF THE DRAWINGS

FIG. 4 Accession numbers, herbarium voucher numbers, collection location information, and *Boechera* Microsatellite Database (BMD) numbers for *Boechera* species and hybrids evaluated cytologically for mode of reproduction. Collection numbers are those of J. G. Carman (JC) and M. D. Windham (MW).

FIG. 5 qPCR primers (SEQ ID NOs. 1-28) used to test microarray accuracy.

FIGS. 7A-7J Representative images of megasporogenesis and ES formation in *Boechera*. (FIGS. 7A-7C) Reduced sexual tetrads forming in *B. stricta, B. yellowstonensis* and *B. exilis*, respectively. (FIGS. 7D-7E) Unreduced *Taraxacum* type dyads forming in *B. lignifera* and *B. crandallii×gracilipes*, respectively. (FIGS. 7F-7H) Unreduced *Hieracium* type aposporous ES forming in *B. retrofracta×stricta* (1-nucleate ES with degenerating dyad), *B.* sp. (SPE1, 1-nucleate ES with degenerating tetrad), and *B. cusickii×sparsiflora* (2-nucleate ES with degenerating tetrad). (FIGS. 7I-7J) Unreduced 1-nucleate Antennaria type diplosporous ES forming directly from MMC in *B. retrofracta×stricta*. Black arrows: degenerating megaspores; white arrows: surviving megaspores; p: parietal cell; v: vacuole; bars: 20 μm.

(FIG. 8A) Sexual seed of *B. stricta*. 2C: embryo peak; 3C: endosperm peak. (FIG. 8B) Apomictic seed of aposporous *B. microphylla*. 2C: embryo peak, 5C endosperm peak (fusion of two unreduced polar nuclei with a reduced pollen nucleus). (FIG. 8C) Apomictic seed of *B. lignifera*. 2C embryo peak, 6C endosperm peak (fusion of two unreduced polar nuclei with an unreduced pollen nucleus). (FIG. 8D) Apomictic seed of triploid *B.* cf. *gunnisoniana*. 3C: embryo peak; 9C: endosperm peak (fusion of two unreduced polar nuclei with an unreduced pollen nucleus).

(FIG. 9A) RLE-NUSE T2 values for the raw data of each chip. (FIG. 9B) log 2 values for perfect match probes of each chip. (FIG. 9C) Log intensity or log ratios for array data following RMA normalization. L, *B. lignifera*; M, *B. microphylla*; S, *B. stricta*; A, anthers; O, ovules; P, pistils; 1, MMC stage; 2, meiocyte stage; 3, early embryo sac stage; 4, late embryo sac stage.

FIG. 11 Fold-changes observed between ovules of apomictic and sexual *Boechera* for 14 genes based on microarray and qPCR analyses. Values >1 or <1 are up or down regulated in ovules of apomictic *B. microphylla*, respectively.

(FIG. 13A) Constitutively produced SnRK1 (plants), SNF1 (yeast), and AMPK (animals) are indirectly activated by stress. These activated kinases then convert TOR to its low-energy form by isolating RAPTOR from TOR. Isolated TOR and activated SnRK1 regulate transcription, translation and enzyme activation for energy conservation and survival under stress conditions (13-24). Our profiling results suggest that meiosis and fertilization dependent embryony are energy conservation and survival programs induced in maturing germline cells by stress-activated SnRK1, which then converts TOR to its low-energy form. This sex phenism selectively allows meiosis and syngamy specific enzymes to be produced and metabolically activated while otherwise accomplishing large-scale genetically and epigenetically-driven reductions in mRNA translation (protein synthesis). Our results also suggest that apomixis is induced when high energy conditions, e.g., high glucose levels and a high adenylate charge, occur in maturing germline cells. Here, SnRK1 is inactivated, and this allows RAPTOR to facilitate TOR phosphorylations of enzymes that induce gene expression for ribosome biosynthesis, gene transcription, mRNA translation and functional protein synthesis. We hypothesize that the apomixis phenism (apomeiosis plus fertilization independent embryony, i.e., parthenogenesis) is a high fecundity energy-activated program induced in maturing germline cells by energy-inactivated SnRK1 and energy activated RAPTOR TOR interactions. This side of the sex apomixis phenism upregulates epigenetic silencing mechanisms that suppress sex. (FIG. 13B) Model for TOR regulated brassinosteroid (BR) induced growth (25). Our findings also suggest that BR participates in the induction of apomixis downstream of energy in-activated SnRK1 and energy activated TOR RAPTOR interactions. The circled black and white numbers represent experiments we conducted to convert apomeiosis to meiosis and meiosis to apomeiosis, respectively (see text). ABA, abscisic acid; ABI1, ABA INSENSITIVE 1; AMP, adenosine monophosphate; BES1, BRI1-EMS-SUPPRESSOR 1; BZR1 P, inactive BRASSINAZOLE-RESISTANT 1; BZR1, active BRASSINAZOLE-RESISTANT 1; ER, endoplasmic reticulum; OST1, OPEN STOMATA 1; PP2C, REGULATORY COMPONENT OF ABA RECEPTOR 1; RBOH, NADPH OXIDASE; ROS, reactive oxygen species; SnRK1, SNF1-RELATED KINASE 1; TOR, TARGET OF RAPAMYCIN.

FIG. 15 qPCR primers (SEQ ID NOs. 29-38) used to test RNA-Seq accuracy.

FIG. 16 Mode of reproduction in *B. lignifera* (BL), *B.* cf. *gunnisoniana* (BG), *B. stricta* (BS) and *B. exilis×retrofracta* (BE×R) as affected by well-watered (C), drought (D) and drought plus heat (DH) conditions. Dyads are generally sexual and reduced if their frequencies are <0.15 and apomictic and unreduced if their frequencies are >0.25. Numbers to the right indicate informative ovules observed (correctly staged and oriented) (from Mateo de Arias (26)).

(FIGS. 27A, 27E, 27I) Unreduced dyads (typical of diplosporous apomeiosis in these apomicts). (FIGS. 27B, 27F, 27J) Meiotically-reduced tetrads (frequencies increased with drought stress). (FIGS. 27C, 27G, 27K) AES formation (frequencies increased with drought stress). White arrows: AES nuclei. (FIGS. 27D, 27H, 27L) Degenerating dyads and tetrad. V, vacuoles. Black arrows, degenerating megaspores; white arrows (FIGS. 27A-27B, 27E-27F, 27I-27J): surviving megaspores; scale bar: 20 μm.

(FIGS. 30A, 30E) Unreduced dyads. White arrows: surviving megaspores; black arrows: degenerating megaspores. (FIGS. 30B, 30F) Sexually-reduced tetrads in pistils exposed to sucrose starvation. White arrows: surviving megaspores; black arrows: degenerating megaspores. (FIGS. 30C, 30G) AES in pistils exposed to sucrose starvation. White arrows: AES nuclei; black arrows: degenerating megaspores. (FIGS. 30D, 30H) degenerating megaspores. v: vacuoles; scale bar: 20 μm.

FIGS. 34A-34L Ovules of *B.* cf. *gunnisoniana* (FIGS. 34A-34D), *B. lignifera* (FIGS. 34E-34H) and *B. retrofracta×stricta* (FIGS. 34I-34L) treated with $H_2O_2$. (FIGS. 34A, 34E, 34I) Unreduced dyads. White arrows: surviving megaspores; black arrows: degenerating megaspores. (FIGS. 34B, 34F, 34J) Meiotically-reduced tetrads. White arrows: surviving megaspores; black arrows: degenerating megaspores. (FIGS. 34C, 34D, 34G, 34H, 34K, 34L) AES. White arrows: AES nuclei; black arrows: degenerating megaspores; v, vacuoles; scale bar: 20 μm.

FIGS. 36A-36D Ovules of *B*. cf. *gunnisoniana* treated with BZR. (FIG. 36A) Unreduced dyad. White arrows: nuclei of surviving megaspore; black arrow: degenerating megaspore. (FIG. 36B) Meiotically-reduced tetrad. White arrows: surviving megaspore; black arrows: degenerating megaspore. (FIG. 36C) AES. White arrow: AES nucleus; black arrows: degenerating megaspores of a degenerating tetrad; (FIG. 36D) Two AES in one ovule. White arrows: the AES nuclei; v, vacuoles; scale bar: 20 μm.

(FIGS. 39A, 39B) Antennaria-type (A-type) MMC vacuolation. (FIG. 39C) 2-nucleate A-type embryo sac arising directly from an MMC. scale bar: 20 μm.

(FIGS. 41A, 41D) Reduced tetrads. White arrows: surviving megaspores; black arrows: degenerating megaspores. (FIGS. 41B, 41E) Unreduced dyads (typical of diplosporous apomeiosis in apomicts) in epiBL treated pistils, white arrows: surviving megaspores; black arrows: degenerating megaspores. (FIG. 41C) Triad (possible failure of 2nd meiotic division in the micropylar dyad member), alternatively, a diplosporous dyad with a parietal cell. White arrow: the putative surviving megaspore; black arrows: degenerating megaspores. (FIG. 41F) AES with degenerating tetrad. White arrow: the AES nuclei; black arrows: degenerating megaspores; v, vacuoles; scale bar: 20 μm.

FIG. 43 *Arabidopsis* ovules pre-meiotically treated with either 2 μM BR or 50 mM glucose developing by Antennaria-type diplospory with subepidermal layers of cells.

FIGS. 45A-45G Ovules of *Arabidopsis* treated with epiBL, DTBA, epiBL plus DTBA and 5-azaC in sucrose or glucose medium. (FIG. 45A) Meiotically-reduced tetrad in the sucrose control medium. White arrow: surviving megaspore; black arrows: degenerating megaspores. (FIG. 45B) 2-nucleate *Taraxacum*-type (T-type) diplosporous ES (ES2) from unreduced dyad in the epiBL-amended treatment. White arrows: ES2 nuclei; black arrow: degenerating megaspore. (FIG. 45C) AES in the DTBA-amended treatment. White arrows: AES nucleus; black arrows: degenerating megaspores of a degenerating tetrad. (FIG. 45D) Unreduced T-type diplosporous dyad in the DTBA-amended treatment. White arrow: surviving megaspore; black arrow: degenerating megaspore. (FIG. 45E) unreduced T-type diplosporous dyad in the 5-azaC-amended treatment. White arrow: surviving megaspore; black arrow: degenerating megaspore. (FIG. 45F) AES in the 5-azaC-amended treatment. White arrows: the AES nuclei, black arrows: degenerating megaspores of a degenerating tetrad. (FIG. 45G) AntES in the 5-azaC-amended treatment. White arrows: AntES nuclei, v, vacuoles; scale bar, 20 μm.

FIGS. 48A-48I Ovules of *B. stricta* treated with epiBL, DTBA, epiBL plus DTBA and 5-azaC in sucrose or glucose medium. (FIG. 48A) Meiotically-reduced tetrad in the sucrose control treatment. White arrow: surviving megaspore: black arrows: degenerating megaspores. (FIG. 48B) Meiotically-reduced tetrad in the epiBL-amended treatment. White arrow: surviving megaspore; black arrows: degenerating megaspores. (FIG. 48C) AES in the epiBL-amended treatment. White arrow: the AES nucleus; black arrows: degenerating megaspores of a degenerating tetrad. (FIG. 48D) Unreduced T-type diplosporous dyad in the DTBA-amended treatment. White arrow: surviving megaspore; black arrow: degenerating megaspore. (FIG. 48E) 1-nucleate ES (ES1) from unreduced T-type diplosporous dyad in DTBA treatment. White arrow, ES1 nucleus; black arrow: degenerating megaspore. (FIG. 48F) ES2 from unreduced T-type diplosporous dyad in the glucose control medium. White arrows: ES2 nuclei; black arrow: degenerating megaspore. (FIG. 48G) 2-nucleate AntES, forming directly from the MMC, in the DTBA-amended treatment. White arrows: AntES nuclei. (FIG. 48H) triad, possibly from a genetically imbalanced meiotic segregation, with an aposporous initial (AI) cell in the 5-azaC-amended treatment. White arrow: AI nucleus; black arrows: degenerating megaspores of a degenerating triad; p, parietal cells; v, vacuoles; scale bar, 20 µm.

FIG. 49 Numbers of cowpea (*Vigna unguiculata*) ovules developing either sexually (dyads, tetrads or embryo sacs from tetrads) or by Antennaria type diplospory as affected by epiBL; DTBA; BL plus DTBA, or 5-azaC in the tissue culture medium.

(FIG. 50A) Prophase MMC (white arrow) in a non-treated in vivo sample. (FIG. 50B) Meiotically-reduced tetrad in a non-treated in vivo sample. White arrow: surviving megaspore; black arrows: degenerating megaspores. (FIG. 50C) Reduced or T-type diplosporous unreduced dyad from the epiBL-amended treatment. White arrow: surviving megaspore; black arrow: degenerating megaspore. (FIG. 50D) AntES from the DTBA-amended treatment. White arrow: AntES nucleus. (FIG. 50E) Reduced or unreduced T-type diplosporous dyad from the 5-azaC-amended treatment. White arrow: surviving megaspore; black arrow: degenerating megaspore. (FIG. 50F) AntES from the 5-azaC-amended treatment. White arrow: AntES nucleus; v, vacuoles; scale bar, 20 µm.

FIGS. 51A-51E Parthenogenetic embryos and unreduced pollen microspores in *Arabidopsis* pistils and anthers cultured in vitro and treated with DTBA and epiBL, respectively. (FIGS. 51A, 51B, 51C) Parthenogenetic embryos (white arrows) induced by 0.1 µM DTBA on 2% glucose medium for 7 d. (FIGS. 51D, 51E) Unreduced pollen dyads of microspores among reduced pollen tetrads of microspores (two microspores in focal plane for dyads versus three microspores in focal plane for tetrads) induced by 0.1 µM epiBL on 2% sucrose medium for 24 h. Scale bars: 50 µm (FIG. 51A), 20 µm (FIGS. 51B-51E).

(FIGS. 53A-53C) Method of measuring ovule curvature (OC). Means were determined for the meiocyte, 1-nucleate embryo sac (ES1) and early 8-nucleate embryo sac (ES8) stages. (FIG. 53D) Aposporous initial (AI); these were defined as single nucleate nucellar cells as large or larger than the meiocyte but without a large vacuole. (FIG. 53E) Aposporous embryo sac (AES); these were defined as 1 to 2-nucleate nucellar cells as large as or larger than the meiocyte and containing a large vacuole. (FIG. 53F) Correlations between apospory associate traits for RIL grown in Texas and Utah combined. (FIG. 53G) Correlations for RIL grown in Texas vs. Utah (numbers above bars indicate frequencies). aes2, 2-nucleate AES; d, dyad; fm, functional megaspore; i, integument; LSC, large stack cell (AI like cell adjacent to the surviving megaspore at its chalazal end); n, nucellus; NS, not significant; OC1-2, OC at the meiocyte and ES1 stages; TT, twin tetrads (formation of two meiocytes in an ovule); bars, 50 µm.

(FIG. 56A) Left, pistil held by style for measurement; right, pistil prior to ovule excision; inset, ovule following excision. (FIG. 56B) Average pistil lengths (±SE) based on measurements from 240 A151 pistils and 264 S264 pistils, which spanned the MMC, meiocyte and ES2 stages. (FIG. 56C) Expression values for six genes obtained by microarray and by qPCR. (FIG. 56D) Numbers of differentially expressed genes (DEG), enriched gene ontology (GO) categories (E-GO), and overrepresented GO categories (0-GO) upregulated and downregulated in A151 compared to S264 at the MMC, meiocyte, and mid embryo sac stages and for all stages combined. (FIGS. 56E-56G) Numbers of DEG (by sib and stage) associated with top level biological process, molecular function and cellular component GO terms, respectively.

(FIG. 58B) Effects of $H_2O_2$ (P) and $H_2O_2$ plus 1.0 µmol $L^{-1}$ BR (PB) on apospory embryo sac formation. (FIG. 58C) Timing of topical glucose or BR applications to pistils; (FIG. 58D) 1 and 2-nucleate T-DES formation; (FIG. 58E) 1 and 2-nucleate AES formation; (FIG. 58F) 1 and 2-nucleate A-DES formation; (FIG. 58G) presence and absence of aniline blue detected callose (green florescence) in a sexual meiocyte (left) and a diplosporous dyad (right), respectively; (FIG. 58H) consistent callose florescence in a meiocyte staged pistil (left, florescence plus light microscopy; right, florescence only); (FIG. 58I) low frequency callose florescence in T-DES staged pistil (left, florescence plus light microscopy; right, florescence only). V, vacuole; photomicrograph bars, 20 µm; numbers of appropriately staged informative ovules analyzed appear next to treatment bars in A and B.

(FIG. 59A) Percentages of rockcress ovules that produced sexual tetrads, T-DES, A-DES and AES. AES ovules also produced a sexual tetrad, which was counted with tetrads. Pretreatment/treatment acronyms: C, control; S, sucrose; G, glucose; B, BR; D, DTBA; 5, 5-azaC. Data are sums of two replicates. BR and DTBA were at 1.0 µmol $L^{-1}$; 5-azaC was at 0.5 mmol $L^{-1}$. (FIG. 59B) Numbers of cowpea ovules that produced sexual tetrads or A-DES. Treatment acronyms are as in A. Data are sums from four single pistil per treatment replicates. BR and DTBA were at 1.0 µmol $L^{-1}$; 5-azaC was at 0.1 mmol $L^{-1}$. (FIGS. 59C-59G) rockcress: FIG. 59C, 1-nucleate T-DES; FIG. 59D, 2-nucleate T-DES; FIG. 59E, 1-nucleate A-DES; FIG. 59F, 2-nucleate A-DES; FIG. 59G, 1-nucleate AES. (FIGS. 59H-59K) cowpea: FIG. 59H, sexual dyad; FIG. 59I, sexual tetrad; FIG. 59J and FIG. 59K, 1-nucleate A-DES. v, vacuole; photomicrograph bars, 20 µm; numbers next to groups of treatment bars represent scored ovules.

DETAILED DESCRIPTION

Figure 1:
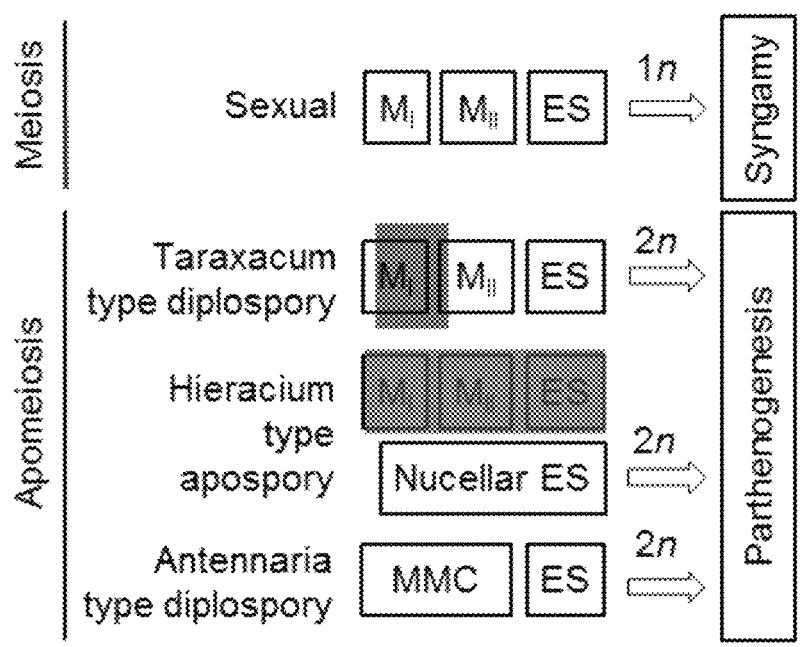
FIG. 1 Modes of reproduction observed in angiospermous plants. Shaded boxes indicate abortive phases of meiosis or early embryo sac (ES) formation. Restitution of the $1^{st}$ (reductional) division occurs in *Taraxacum* type diplospory. In *Hieracium* type apospory, meiosis or early ES formation fails, and an unreduced ES forms from a sporogenous nucellar cell. Meiosis does not initiate in Antennaria type diplospory, and the ES forms directly from the megaspore mother cell (MMC). Egg to embryo formation is syngamy dependent and independent (parthenogenetic) in sexual and apomictic seeds, respectively. ES8: 8-nucleate embryo sac; MI and MII, $1^{st}$ and $2^{nd}$ meiotic divisions.

The present disclosure covers composition and methods of inducing apomeiosis, parthenogenesis, or both in sexual eukaryotes and inducing sex in apomictic eukaryotes, most particularly in plants. In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

Definitions

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

The term "1n" refers to the number of chromosomes in spores or gametes and generally in most subsequent mitosis produced cells of spores, e.g., in gametophytes of organisms with alternating generations; this number often reflects different ploidy levels (multiples of the chromosome base number, x) plus or minus individual chromosomes (aneuploidy).

The term "2n" refers to the number of chromosomes in the zygote and generally in most subsequent asexual (somatic) cells produced by mitosis; this number often reflects different ploidy levels (multiples of the base number, x) plus or minus individual chromosomes (aneuploidy).

The term "antioxidant" refers to a substance that inhibits oxidation in living organisms by reducing or otherwise deactivating potentially damaging oxidizing agents such as reactive oxygen species (ROS).

The term "apomeiosis" refers to the formation of parthenogenesis-competent spores, gametes or gamete-like cells wherein the chromosome numbers are the same as those observed in zygotes.

The term "apomixis" refers to a process in eukaryotes consisting of two temporally-distinct processes, apomeiosis and parthenogenesis.

The term "autonomous apomixis" refers to seed formation in angiosperms wherein both the embryo and endosperm form without fertilization.

The term "cyclical apomixis" refers to alternations, generally seasonal, between periods of essentially exclusive sexual reproduction and periods of essentially exclusive apomictic reproduction.

The term "derepression" refers to a reversal of repression often by the chemical removal of a transcription repressor gene product from a regulatory DNA sequence.

The term "double fertilization" refers to a process unique to angiosperms wherein two 1n (haploid) sperm nuclei of a single male gametophyte are involved in fertilization, one fertilizes the 1n egg, to form the 2n embryo, and the other fertilizes the 2n central cell (fusion product of two 1n polar nuclei) to form the 3n endosperm.

The term "embryo sac" refers to the female megagametophyte in angiosperms.

The term "endosperm" refers to a triploid tissue in angiospermous seeds that is adjacent to the developing angiospermous embryo and is derived in sexual plants from the fusion product of two haploid female gametophyte cells (polar nuclei) and a haploid sperm cell. Endosperm is consumed by the embryo as it grows and germinates.

The term "enriched gene ontology (GO) category" refers to a statistically significant condition wherein genes of the GO category tend to be up or down-regulated in a particular treatment more so than would be expected by chance alone.

The term "epigenome" refers to a genome (DNA) plus all of the chemical compounds added to the genome that regulate gene expression. In living cells, epigenome modifications are generally in a state of flux and vary among different tissues and cells. We discovered, and report herein, that the apomixis epigenome differs substantially from the sexual epigenome.

The term "epigenomic state" refers to a static state of the genetic material wherein some genes tend to be silenced while others tend to be expressed. The epigenomic state of living organisms is in constant flux. For the purposes of this specification, we use the term epigenetic in a broad sense. Our use of the term includes covalent DNA and RNA modifications that affect gene expression such as chromatin modifications and mRNA splicing variants.

The term "eukaryogenesis" refers to an extended period of time, about 1.2 to 0.8 billion years ago, during which eukaryotes evolved from prokaryotes.

The term "eukaryote" refers to an organism whose cells contain a nucleus and other organelles enclosed by membranes.

The term "facultative apomixis" refers to sexual and apomictic reproduction occurring concurrently within an individual. It is often observed in plants that simultaneously produce seeds sexually and apomictically.

The term "gamete" refers to a mature haploid or diploid germ cell that is able to either i) unite with another gamete by syngamy (fertilization) to form a zygote, as in sexual reproduction, or ii) become a zygote-like cell by parthenogenesis, as in apomictic reproduction.

The term "gametophyte" refers to the 1n generation that produces gametes in organisms with an alternation-of-generations life cycle. In angiosperms, female megagametophytes (embryo sacs) form in ovules and in most cases consist of seven cells (including the egg, female gamete) and eight nuclei at maturity (central cell contains two polar nuclei). Microgametophytes (pollen grains) in angiosperms consist of three cells, two sperm (male gametes) and a pollen tube nucleus.

The term "genotype" refers to the full hereditary information of an organism. Inasmuch as progeny plants of an apomictic plant are clones of each other, they represent a single genotype.

The term "germline" refers to a series of cells destined to pass their genetic material to their progeny. In some multicellular organisms, including animals, the germline is continuous from one generation to the next. In other organisms, the germline is discontinuous. In flowering plants, the germline is initiated during flower formation and is terminated with the onset of embryogenesis.

The term "germline-associated tissues" refers to those tissues intimately associated with and thereby nutritionally and developmentally supportive of the germline. With regard to flowering plants, the term refers to the nucellus and other nutritive tissues of the ovule.

The term "*Hieracium*-type apospory" refers to a form of apomixis in angiosperms wherein sexual meiosis fails and the parthenogenetically-competent 2n gametophyte forms from a nucellar cell.

The term "meiosis" refers to spore or gamete formation wherein chromosome numbers are reduced to half of that observed in zygotes.

The term "nucellus" refers to a sporogenous-like nutritive tissue surrounding the meiocyte and later the developing embryo sac in angiospermous ovules.

The term "obligate apomixis" refers to reproduction by apomixis with an absence of sexual reproduction.

The term "parthenogenesis" refers to life cycle progression without syngamy from products of apomeiosis, e.g., embryo formation from unreduced eggs without fertilization. Parthenogenesis can also occur from products of meiosis. This is referred to as haploid parthenogenesis.

The term "phenism" refers to one of two or more phenotypes expressed polyphenically by a single genotype.

The term "phenotype" refers to observable characteristics of an individual genotype as a result of environment-genotype interactions.

The term "polyphenism" refers to a set of two or more phenotypes (phenisms) that occur in a single individual but at different times. Classic examples include metamorphism in insects, the transition from a tadpole to a frog, or the transition from a vegetative to a reproductive state in plants. Chromatin modifications that differentially silence genes, thus producing different epigenomic states, are responsible for polyphenisms.

The term "polyphyletic trait" refers to a trait that occurs in multiple taxa but evolved in each taxon independently of the other taxa The term "preapomeiotic" refers to the stage of apomictic reproduction wherein meiocyte mother cells are not yet mature or are still forming.

The term "premeiotic" refers to the stage of sexual reproduction wherein meiocyte mother cells are not yet mature or are still forming.

The term "prokaryote" refers to single-celled archaea and bacteria. They do not possess a distinct membrane-bound nucleus, mitochondria or other specialized organelles.

The term "pseudogamous apomixis" refers to seed formation in angiosperms wherein the embryo forms apomictically but the central cell must be fertilized for endosperm to form. Without fertilization, seeds of pseudogamous apomicts abort.

The term "reactive oxygen species (ROS)" refers to reactive chemicals that contain oxygen, such as peroxides, superoxide, hydroxyl radical and singlet oxygen.

The term "repression" refers to suppression of gene expression, which often occurs as a result of a repressor gene product that blocks transcription.

The term "sex" refers to a process in eukaryotes consisting of two temporally-distinct processes, meiosis and syngamy (fertilization).

The term "signaling molecule" refers to a molecule that interacts with cell surface receptors or otherwise participates as a component of a signal transduction pathway.

The term "simple sugar" refers to monosaccharides and disaccharides that provide energy to living cells and may also serve as signaling molecules.

The term "sporophyte" refers to the 2n generation in organisms with an alternation-of-generations life cycle. In sexual angiosperms, sporophytes produce 1n spores through meiosis.

The term "steroid" refers to a class of organic molecules that contain a characteristic four-ring configuration. Many steroids function as signaling molecules by activating steroid receptors.

The term "syngamy" refers to fusion of haploid gametes to produce zygotes.

The term "*Taraxacum*-type diplospory" refers to a form of apomixis in angiosperms wherein the unreduced spore forms as a result of 1st division restitution; 2n gametophyte formation and parthenogenesis then ensue.

The term "x" refers to the "base number" of chromosomes; it constitutes the lowest number of chromosomes that represent one complete set of chromosomes for a species.

The term "zygote" refers to a diploid cell resulting from the fusion of two haploid gametes.

Apomixis occurs infrequently in 20% of flowering plant families. If apomixis could be induced in inbred as well as hybrid crops, then superior-yielding hybrid seeds for all crops maybe cost-effectively produced. It has been assumed that the components of apomixis, apomeiosis and parthenogenesis are derived mutation dependent processes. The inventors have surprisingly found that apomeiosis does not require apomixis-specific mutations but is instead inducible at high frequencies by metabolically modifying wild type gene expression by decreasing SnRK activity, decreasing RdDM activity, increasing TORC1 activity, and/or inducing steroid signaling.

Inducing Apomixis in Sexual Eukaryotes.

The methods of inducing Apomixis in sexual eukaryotes disclosed herein enables clonal reproduction of desired genotypes. For example, inducing apomixis in hybrid plants of important world crops will decrease hybrid seed production costs for crops currently grown as hybrids, e.g., maize and sorghum. It will also enable hybrid seed production of crops currently grown as inbred varieties. Such crops, e.g., essentially all wheat and most rice, are currently grown as inbred crops, which are inferior in yield when compared to high-yielding experimental hybrids, the $F_1$ hybrid seeds of which cannot currently be produced economically in commercial quantities. An object of this invention is to induce apomixis in typically-sexual eukaryotes for the purpose of cloning through the germline (e.g., seeds, etc.) high-yielding (agronomically-important) heterozygous genotypes, e.g., superior-yielding hybrids of world crops.

Inducing Sex in Apomictic Eukaryotes. In contrast, the methods of inducing sexual reproduction in apomictic eukaryotes disclosed herein enable genetic improvement by conventional breeding, a technique of plant and animal improvement that requires sexual recombination, i.e., it cannot be accomplished in obligately apomictic plants or animals. Another object of this invention is to induce sexual reproduction in typically apomictic eukaryotes for the purpose of genetic improvement by conventional breeding. Thereafter, the methods of the present patent may be used to return the improved hybrid plants to apomixis for the efficient clonal production of hybrid seed.

Value of the methods of the invention. The present invention provides methods of inducing apomixis in sexual eukaryotes and sexual reproduction in apomictic eukaryotes. One of the many uses of the present invention is to stably clone high-yielding heterozygous hybrids or other superior but unique genotypes of world crops through their own seed. The invention provides a way to enhance global food security by:

i. simplifying hybrid seed production for crops currently grown as hybrids, e.g., a cost savings is expected of ca. $1 billion annually in the U.S. alone in the production of hybrid corn seed;

ii. converting inbred (or varietal) crops to hybrids a. essentially all world wheat production and more than half of world rice production is obtained from inbred varieties, the yields of which are inferior to experimental hybrids; currently, wheat and rice provide ca. 65% of all calories consumed by humans;

b. hybrid seeds of wheat, rice and many other inbred crops cannot currently be produced economically in sufficient quantities for commercial plantings;

c. experimental hybrids of wheat and rice yield 15% and 30% more grain than the best inbred wheat and rice varieties grown today, respectively; the value of the increased yield afforded by apomictically produced hybrids of wheat and rice in the U.S. alone could exceed $34 billion annually (based on 2010-2015 USDA statistics).

The current disclosure is not limited to agricultural crops. It may also be used, for example, in aquaculture, for the farming of high yielding apomictic hybrids of crustaceans and fish, and for the production of high yielding apomicts of forest and fiber (cotton, hemp) species. This technology, once fully implemented, has the potential of revolutionizing food, feed, fiber and timber production globally and producing economic and humanitarian benefits that dwarf those associated with the green revolution of the 1960s and the development of sexually-produced hybrid crops in the 1930s (28).

Why apomixis technology was not previously developed. While benefits of an apomixis technology have been recognized for over 80 years, progress toward achieving the necessary breakthroughs has been painfully slow (7, 10, 29-33). Our present discovery reveals that this sluggishness was a consequence of misconceptions concerning how apomixis evolved and how it is regulated. For 118 years, it has been taught and considered obvious that apomixis evolves from sex by mutation in each eukaryote kingdom (1, 9, 34-36). The putative mutations are thought to either cause apomixis directly (mutation-derived modifications of meiosis and syngamy that convert these processes into apomeiosis and parthenogenesis, respectively) (37-39) or to distort the two sexual processes epigenetically so as to bypass specific steps of meiosis and syngamy (7, 10, 33, 35, 36). An estimated $75 M worldwide has been spent during the past 40 years to identify the putative apomixis-causing mutant genes from naturally-occurring apomicts. The goal of these programs has been to identify the apomixis causing mutant genes, and more recently to design mutant genes, and to then transfer the mutations to important world crops by wide hybridization or genetic engineering (7, 35).

In contrast to the mutation based apomixis gene hypotheses, the present disclosure is based on the discovery based on the results herein, that sexual reproduction and apomixis have been polyphenisms of each other from the beginnings of eukaryote evolution. Polyphenic traits (two or more) are encoded by a single genome. Environmental signaling at the cell metabolism and signaling levels regulates which trait is expressed, and switching from one to another involves metabolism driven modifications of enzyme function and epigenetic modification of gene expression (40-42). Examples include caterpillars changing into butterflies, tadpoles changing into frogs, and vegetative plants changing into flowering plants. Altered metabolic and epigenomic states induce the formation of altered phenotypes, which are better suited for the environmental parameters that induced their onset.

One of the most ancient prokaryotic polyphenisms is the division spore polyphenism. The division phenism involves rapid cell division during metabolically favorable conditions, and the spore phenism involves cell division termination followed by stress resistant spore formation at the onset of metabolic stress (43-49). Based on the results herein sexual reproduction (meiosis/syngamy) and apomixis (apomeiosis/parthenogenesis) evolved during eukaryogenesis (1.2 to 0.8 billion years ago) as extensions of the prokaryotic division spore polyphenism (8, 50). That sex evolved during this period is well supported (43-46), but our result now support that apomixis evolved as a polyphenism of sexual reproduction during this timeframe, first taught and disclosed by the present inventors. Tenets of our apomixis antiquity teachings include:

i. eukaryotic apomixis evolved during eukaryogenesis as an add on to the division phenism of prokaryotes, the latter had been evolving for ca. 2.7 billion years prior to the evolution of sex (1.2 billion years ago) (51), which makes the defining elements of apomixis more ancient, and perhaps more conserved among extant eukaryotes, than those of sex;

ii. cellular metabolome and epigenome factors that induce and maintain apomixis occur in response to metabolically favorable conditions;

iii. sex evolved as an add-on to the spore phenism of prokaryotes (43); and iv. cellular metabolome and epigenome factors that induce and maintain sex occur in response to metabolically stressful conditions.

Four novel implications of the invention and embodiments set forth herein differentiate it from the conventional wisdom and practices which are based upon mutation-based theories:

i. the last common ancestor of extant eukaryotes, a primitive unicellular eukaryote, was cyclically apomictic, i.e., sex and apomixis in this ancestor were polyphenisms of each other and the expressions of each were environmentally regulated, conventional wisdom: apomixis is evolutionarily derived among eukaryotes, i.e., it arises polyphyletically (de novo in each eukaryotic taxon where it occurs) by mutations of the sexual pathway (7, 35, 36, 52);

ii. extant eukaryotes that exhibit a cyclical apomixis life cycle (9, 53-55) are primitive, i.e., their life cycle (apomixis and sex expressed as polyphenisms of each other in response to seasonal changes) is most similar to that of the last common ancestor of extant eukaryotes, conventional wisdom: sex is primitive, and apomixis is derived polyphyletically by mutation;

iii. extant eukaryotes that exhibit obligate sex or obligate or facultative apomixis are derived, i.e., their apomixis-sex switching mechanisms are ineffective due to genetic mutations, global changes in atmospheric or other environmental parameters that have occurred since eukaryogenesis, or metabolomic or epigenomic modifications caused by hybridization, polyploidization or other genome perturbations, conventional wisdom: obligate sex is ancestral in eukaryotes, and apomixis is derived;

iv. competencies for sex and apomixis are more-or-less imbedded (conserved) in the genomes of all eukaryotes, and in the best-case scenarios we need only tap into and control these competencies to develop an apomixis technology, conventional wisdom: competencies for sex are more-or-less imbedded in the genomes of all eukaryotes (56-58), and apomixis is derived.

Evidence for the latter (iv) is seen in the occasional triggering of apomixis in sexual organisms (from all eukaryote kingdoms) when metabolomes and epigenomes are disturbed, with little or no evidence of mutation, by wide hybridization, polyploidization or other perturbations (8, 10, 50).

Summary of experiments. We reasoned that if apomixis and sex evolved during eukaryogenesis, as a polyphenic pair, with reproduction occurring by apomixis under favorable conditions and by sex under stressful conditions, then extant obligate or near-obligate apomictic eukaryotes likely possess a genome that detoxifies metabolic stress in germline cells or associated tissues. In contrast, extant sexual eukaryotes likely possess a genome that is less efficient in detoxifying metabolic stress in germline or germline associated tissues during germline development. We conducted six sets of experiments that were designed to i) explore the validity of the unique premise described above, ii) elucidate the molecular biology and biochemistry of the putatively ancient apomixis-sex switch, and iii) develop methods for switching apomictic development to sexual development and sexual development to apomictic development. The six sets of experiments are briefly outlined as follows:

i. apospory associated QTL (Example 12)

ii. gene expression profiling in the cereal crop *Sorghum bicolor* (Poaceae, sorghum) to identify sorghum genes that promote aposporous embryo sac formation (Examples 1 and 13);

a. compared genes expression profiles from immature ovules of a weakly aposporous genotype to those from a non-aposporous genotype (selected from an $F_2$ mapping population);

iii. gene expression profiling comparisons between naturally apomictic and naturally sexual taxa of *Boechera* (Brassicaceae) (Example 2);

iv. whole plant environmental stress experiments (Examples 3);

a. switched apomictic development to sexual development in apomictic *Boechera*, b. compared gene expression profiling between naturally apomictic *Boechera* versus the same apomictic *Boechera* that were induced by stress to undergo sexual development;

v. whole plant and in vitro experiments using *Boechera* and involving pharmacological applications selected to switch apomixis to sex and to elucidate the molecular and biochemical pathways involved in apomixis-to-sex switching (Examples 4-7);

vi. whole plant and in vitro experiments using sexual *Boechera*, sexual *Arabidopsis thaliana* (Brassicaceae, arabidopsis), and the sexual legume crop *Vigna unguiculata* (Fabaceae, cowpea); these experiments involved pharmacological applications selected to switch sex to apomixis and to elucidate the molecular biology and biochemical pathways involved in sex-to-apomixis switching; cowpea is an important world food crop mandated for further improvement by the International Institute of Tropical Agriculture, Ibadan, Nigeria (Examples 9-11 and 14).

Summary of the Findings.

Our findings identified signal transduction pathways that regulate apomixis/sex switching. These were verified pharmacologically using signaling molecules that specifically altered biochemical and molecular pathways to induce sexual reproduction in apomictic plants and to induce apomictic reproduction in sexual plants. We found that interrupting peroxide signaling induces apomeiosis. Exposing MMC staged female germline cells and associated tissues to the antioxidant (S)-2-aminobutane-1,4-dithiol hydrochloride (DTBA) increases the frequency of apomeiosis in ovules (diplosporous *Taraxacum*-type) (Examples 10 and 14). We identified multiple ways of decreasing SnRK activity, and each of these induced apomeiosis. First, we observed that an inhibitor/down regulator of SnRK1 and SnRK2, AlP1, is upregulated in A151 by 3.0-fold (Example 13), and is linked to ovule volume QTL (Example 12). Second, we documented that interrupting peroxide signaling, which normally prevents PP2Cs from silencing SnRK, induces apomeiosis (Examples 10 and 14). Third, we documented that inhibiting the RNA directed DNA methylation (RdDM) specific to meiosis, which constitutes a signaling pathway between SnRK and meiosis, converts *Taraxacum* type to Antennaria type in apomictic plants and meiosis to Antennaria type in all three sexual species (Examples 10 and 14). We found that decreasing meiosis-specific RdDM activity induces apomeiosis. First, an upstream activator of RdDM, FUS3-COMPLEMENTING GENE 2 (AFC2), is upregulated in A151 by 7.0-fold (Example 13), and is linked to ovule curvature and volume QTL (Example 12). Second, a RdDM inhibitor, the DNA methyltransferase inhibitor 5-azacytidine (5-azaC), reduces the frequency of meiosis (Examples 10 and 14). We also found that increasing BR activity induces apomeiosis. First, a gene that suppresses BR signaling downstream of TORC1, SHAGGY-LIKE PROTEIN KINASE GROUP 2 3 (SK22, ATGSK1), was upregulated in A151 by 8.9-fold (Example 13), and is linked to ovule curvature QTL (Example 12). Second, a gene that suppresses BR signaling downstream of TORC1, BAK1-INTERACTING RECEPTOR-LIKE KINASE 1 (BIR1), is (i) upregulated in A151 by 2.3-fold (Example 13), and is linked to TT QTL (Example 12). Third, exposing immature *arabidopsis* pistils to BR induces apomeiosis (Examples 10 and 14).

Figure 57:
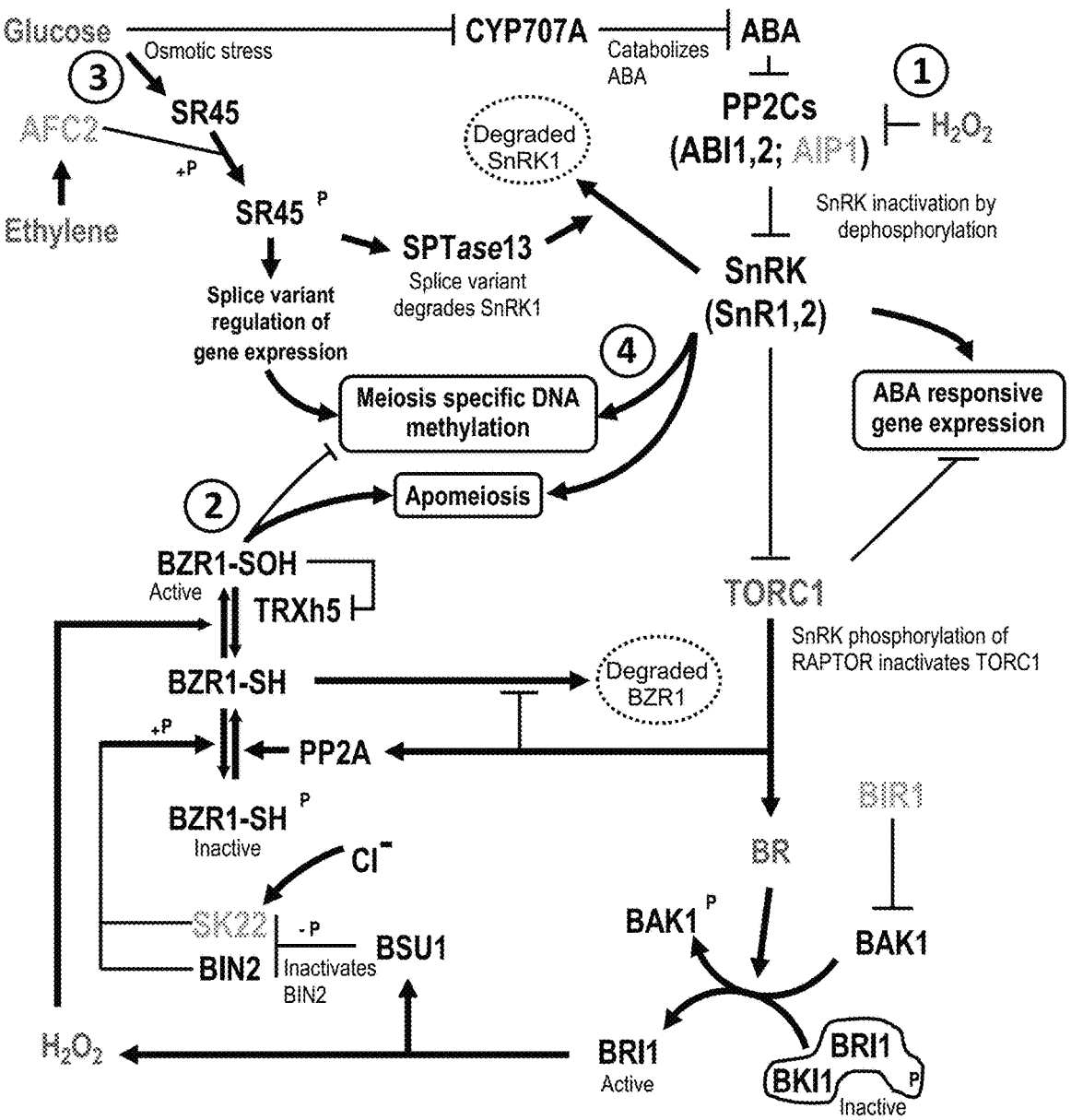
FIG. 57 Abbreviated molecular pathways of growth no-growth regulation in plants and their putative involvement in apomixis sex switching. Solid and dashed lines are well established or strongly suspected, respectively. AFC2; AIP1; BIR1; and SK22 genes were upregulated in A151. Glucose; Ethylene; $H_2O_2$; TORC1; and BR signaling pathways were differentially regulated between A151 and S264. Circled numbers indicate signaling pathways targeted for manipulation: (1) antioxidant homeostasis, (2) brassinosteroid signaling, (3) glucose signaling, and (4) meiosis specific RNA directed DNA methylation.

Without wishing to be bound by theory, it is believed that growth cessation and decreased metabolic activity occur when TORC1 is inactivated. In plants, this happens in two ways, by glucose starvation or by accumulation of abscisic acid (ABA). Both processes involve multistep molecular pathways (FIG. 57). Under low energy conditions, glucose signaling is terminated, and this terminates downstream degradation of SnRK1. SnRK1 then accumulates and phosphorylates RAPTOR causing TORC1 to dissociate. Downstream growth promoting processes then cease (13, 17). Under stress conditions, ABA accumulates, and multiple protein phosphatase 2C proteins (PP2C), including ABA INSENSITIVE 1 and 2 (ABI1, 2) and HIGHLY ABA-INDUCED PP2C GENE 2 (AIP1), are inactivated. SnRK1 and SnRK2 are then activated by autophosphorylation, and they proceed to inactivate TORC1, again possibly by phosphorylating RAPTOR (59, 60). Active SnRK kinases, which form under low-energy and/or high-stress conditions, activate other enzymes that cause downstream catabolism, autophagy and metabolite recovery through transmembrane transport (16).

Of the five currently recognized eukaryote kingdoms, plants and animals are the most evolutionarily divergent. Our research results compared with finding in the literature provide strong evidence that the same signaling pathways that control apomixis/sex switching in animals also control apomixis/sex switching in plants. The switching processes described here have worked on all five angiospermous species tested to date.

An object of this invention is to induce apomixis in typically-sexual eukaryotes for the purpose of cloning through the germline (e.g., seeds, etc.) high-yielding (agronomically-important) heterozygous genotypes, e.g., superior-yielding hybrids of world crops. Another object of this invention is to induce sexual reproduction in typically apomictic eukaryotes for the purpose of genetic improvement by conventional breeding. Thereafter, the methods of the present patent may be used to return the improved hybrid plants to apomixis for the efficient clonal production of hybrid seed.

In accordance with the invention, methods are provided for switching mode of reproduction from sex to apomixis and from apomixis to sex in three genera representing two families of angiospermous plants (kingdom Plantae, Eukaryota). The methods were developed based on results of tests performed to evaluate the initial hypothesis that apomixis and sex in eukaryotes are a polyphenic pair that co-evolved during eukaryogenesis. Further features of the methods of the invention and various other steps, procedures, and examples associated with practicing the invention are described below, including the elucidation of the biochemical and molecular signal transduction pathways of apomixis/sex switching and the development of pharmacological treatments that intentionally modify signal transduction pathway components so as to redirect reproductive development from apomixis to sex or from sex to apomixis.

In a first aspect of the present invention, there is provided a method of switching between apomixis and sexual reproduction in a eukaryote, comprising increasing or decreasing glucose signaling, osmotic stress, oxidative stress, perceived oxidative stress, or a combination thereof in a female germline cell and/or a female germline-associated tissue in the eukaryote, wherein apomixis comprises apomeiosis and parthenogenesis and sexual reproduction comprises meiosis and syngamy. Said methods are referred to hereinafter as the "methods of the invention."

In one embodiment of the present invention, there is provided a method of inducing apomeiosis, parthenogenesis, or both in a sexual eukaryote, which comprises increasing glucose signaling, decreasing osmotic stress, decreasing oxidative stress, decreasing perceived oxidative stress, or a combination thereof in a female germline cell and/or a female germline-associated tissue in the sexual eukaryote.

The methods set forth herein may be applied to sexual eukaryotes broadly. As used herein, the term "sexual eukaryote" refers to a eukaryote capable of sexually reproducing through meiosis and gamete fusion. As used herein, the term "sex" refers to a process in eukaryotes consisting of two temporally-distinct processes, meiosis and syngamy (fertilization). As used herein, the term "eukaryote" refers to an organism whose cells contain a nucleus and other organelles enclosed by membranes.

In particular, commercially important eukaryotic species that play a role in the food industry, plant products industry, and animal products industry may be used. Species reproduced commercially via sexual reproductive methods are desirable candidates for inducing apomictic reproduction therein. Non-limiting exemplary sexual eukaryotes that may be induced from sex to apomixis include economically important eukaryotes, e.g., agronomic crops, forest and fiber (e.g., cotton, hemp) species, or aquacultural crustaceans or fish. Non-limiting exemplary fish include salmon, trout, tilapia, tuna, etc. Non-limiting exemplary crustaceans include crabs, lobsters, crayfish, shrimp, etc.

In preferred embodiments, the sexual eukaryote is a plant. As used herein, the term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen, and microspores. Plant parts include differentiated and undifferentiated tissues including, but not limited to the following: roots, stems, shoots, leaves, pollen, seeds, tumor tissue and various forms of cells and culture (e.g., single cells, protoplasts, embryos, and callus tissue). The plant tissue may be in plant or a plant organ, tissue or cell culture. Non-limiting exemplary plants include grains, legumes, fruit, vegetable, grasses, tubers, and cash crop plant varieties. Non-limiting exemplary grains include rice, wheat, durum wheat, maize (corn), Job's tears, barley, millet, sorghum, oat, rye, triticale, teff, fonio, wild rice, spelt, canary grass, *quinoa*, amaranth, buckwheat, kaniwa, pitseed goosefoot, etc. Non-limiting exemplary cash crops include oilseeds generally, sunflowers, rapeseed, cotton, peanuts, flax (linseed), castor beans, coffee, cacao, etc. Non-limiting exemplary legumes include soybeans, cowpea, alfalfa, clover, peas, beans, chickpeas, lentils, lupin beans, mesquite, carob, peanuts, tamarind, etc. Non-limiting exemplary vegetables include tuber-included tomatoes, cucurbits, squashes, melons, cucumbers, onions, chilis, peppers, lettuce, beets, potatoes, asparagus, carrots, turnips, etc. In a preferred embodiment, the sexual eukaryote is a sexual Brassicaceae (e.g., *Arabidopsis* or Drummond's rockcress) or a sexual legume (e.g., cowpea).

As used herein, the term "germline" refers to a series of cells destined to pass their genetic material to their progeny.

In flowering plants, the germline is initiated during flower formation and is terminated with the onset of embryogenesis. As used herein, the term "germline cell" refers to a biological cell that gives rise to the gametes of an organism that reproduces sexually. As used herein, "germline cell" of a flowering plant refers to a meiotic spore mother cell (megasporocyte or MMC). As used herein, "germline-associated tissues" refers to those tissues intimately associated with and thereby nutritionally and developmentally supportive of the germline. With regard to flowering plants, the term refers to the nucellus and other nutritive tissues of the ovule. As used herein, the term "nucellus" refers to a sporogenous-like nutritive tissue surrounding the meiocyte and later the developing embryo sac in angiospermous ovules.

As used herein, "inducing apomeiosis" refers to producing viable non-reduced, or viable non-reduced and non-recombined, gametes. The apomeiosis maybe of a diplosporous Antennaria-type, a diplosporous *Taraxacum*-type, an aposporous *Hieracium*-type, or a combination thereof. As used herein, the term "aposporous apomict" refers to a form of apomixis wherein the reduced megaspore degenerates and is replaced by a somatic cell. As used herein, the term "*Hieracium*-type apospory" refers to a form of apomixis in angiosperms wherein sexual meiosis fails and the parthenogenetically-competent 2n gametophyte forms from a nucellar cell. As used herein, the term "diplosporous apomict" refers to a form of apomixis wherein the reductional meiosis is replaced by a restitutional meiosis or by mitosis. As used herein, the term "Antennaria-type diplospory" refers to a form of apomixis wherein the unreduced embryo sac forms directly from a megaspore mother cell that does not initiate meiosis. As used herein, the term "*Taraxacum*-type diplospory" refers to a form of apomixis in angiosperms wherein the unreduced spore forms as a result of 1st division restitution; 2n gametophyte formation and parthenogenesis then ensue. As used herein, the term "parthenogenesis" refers to life cycle progression without syngamy from products of apomeiosis, e.g., embryo formation from unreduced eggs without fertilization. Parthenogenesis can also occur from products of meiosis. This is referred to as haploid parthenogenesis.

In one implementation, the frequency or probability of switching from meiosis to apomeiosis, syngamy to parthenogenesis, or both, is between 1% and 100%, or any percent range in between, e.g., 1-75%, 1-50%, 1-25%, 5-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-100%, 10-90%, 10-80%, 10-70%, 10-60%, 10-50%, 10-40%, 10-30%, 10-20%, 20-80%, 25-100%, 25-75%, 25-50%, 30-100%, 30-95%, 30-90%, 30-85%, 30-80%, 30-75%, 30-70%, 30-65%, 30-60%, 30-55%, 30-50%, 40-100%, 40-90%, 40-80%, 40-70%, 40-60%, 40-50%, 50-100%, 50-95%, 50-90%, 50-80%, 50-75%, 50-70%, or 75-100%, etc. in the sexual eukaryote. In other embodiments, the frequency or probability of switching from meiosis to apomeiosis, syngamy to parthenogenesis, or both is at least 10%, for example, at least 20%, at least 30%, at least 40%, at least 50%, at least 60%, at least 70%, at least 80%, or at least 90%, etc. in the sexual eukaryote.

Glucose is an ancient and conserved eukaryotic signaling molecule. As used herein, the term "glucose signaling" refers to gene expression and enzyme function including cell-cycle progression, general metabolism and various aspects of development regulated by glucose. As used herein, the term "oxidative stress" refers to a cellular disturbance in the prooxidant-antioxidant balance in favor of prooxidants.

In some implementations, increasing glucose signaling, decreasing osmotic stress, decreasing oxidative stress, decreasing perceived oxidative stress, or a combination thereof comprises increasing sugar level, increasing fatty acid catabolism by beta-oxidation, increasing brassinosteroid (BR) activity, increasing antioxidant activity, decreasing reactive oxygen species (ROS), decreasing abscisic acid (ABA) activity, decreasing sucrose non-fermenting 1 related kinase (SnRK) activity, increasing target of rapamycin complex 1 (TORC1) activity, decreasing meiosis-specific RNA directed DNA methylation (RdDM), or a combination thereof. In some implementations, the increase in sugar level, fatty acid catabolism by beta-oxidation, BR activity, antioxidant activity, TORC1 activity, the decrease in ROS, ABA activity, SnRK activity, RdDM, or a combination thereof is in an amount and time sufficient to induce apomeiosis, parthenogenesis, or both. In some implementation, the time sufficient to induce apomeiosis, parthenogenesis, or both is between 0.05 and 48 hours.

In some implementations, increasing sugar level comprises applying a monosaccharide, a disaccharide, a short-chain polysaccharide, or a combination thereof; increasing BR activity comprises applying epibrassinolide (epiBL); increasing antioxidant comprises applying superoxide dismutase, glutathione, ABA, peroxidase, (S)-2-aminobutane-1,4-dithiol hydrochloride (DTBA), or a combination thereof; decreasing ABA activity comprises applying fluridone, increasing the activity of CYP707A, protein phosphatase 2C (PP2C), or a combination thereof; decreasing SnRK activity comprises decreasing an activity of SnRK1, SnRK2, or both; decreasing RdDM comprises applying DNA methyltransferase inhibitor 5-azacytidine (5-azaC), decreasing an activity of RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), or a combination thereof.

The term "reactive oxygen species (ROS)" refers to reactive chemicals that contain oxygen, such as peroxides, superoxide, hydroxyl radical and singlet oxygen. In one implementation, the reactive oxygen species comprises hydrogen peroxide. Non-limiting examples of the sugar include monosaccharide (e.g., glucose or fructose), disaccharide (e.g., sucrose), or short-chain polysaccharide. Non-limiting examples of a naturally occurring antioxidant include superoxide dismutase, glutathione, ABA, or peroxidase. A non-limiting example of synthetic antioxidant is (S)-2-aminobutane-1,4-dithiol hydrochloride (DTBA). In one implementation, the steroid comprises epibrassinolide. A non-limiting example of meiosis-specific DNA methylation is meiosis-specific RNA directed DNA methylation (RdDM). In some implementations, increasing BR activity comprises applying epibrassinolide (epiBL); increasing ABA activity comprises applying fluridone, increasing the activity of CYP707A, protein phosphatase 2C (PP2C), or a combination thereof; decreasing SnRK activity comprises decreasing an activity of SnRK1, SnRK2, or both; decreasing RdDM comprises applying DNA methyltransferase inhibitor 5-azacytidine (5-azaC), decreasing an activity of RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), or a combination thereof Chemical Application Chemical treatments for inducing apomixis in sexual eukaryotes include applying steroids (e.g., BR), antioxidants, sugars, and combinations thereof that are formulated and administered in an effective dose to repress the epigenome and/or metabalome responsible for sex and/or derepress the epigenome and/or metabalome responsible for apomixis. Exemplary steroids include epibrassinolide. Exemplary sugars include monosaccharides, disaccharides, and short-chain polysaccharides such as glucose, sucrose, and fructose. Exemplary antioxidants include naturally occurring antioxidants, superoxide dismutase, glutathione, ABA, peroxidases, synthetic antioxidants, (S)-2-aminobutane-1,4-dithiol hydrochloride (DTBA).

The chemical treatment may be administered exogenously or endogenously. Exogenous administration must be administered in an effective amount. The specific concentration and duration of administration and target tissue/cells is affected by the specific chemical treatment to be administered. For example, in administering hydrogen peroxide to induce sex in apomictic plants, a 2-500 mM concentration of hydrogen peroxide may be administered to premeiotic inflorescences. In another example, to induce apomixis in sexual plants, 0.1-5 µM of epibrassinolide may be administered to premeiotic inflorescences. In another example, to induce apomixis in sexual plants, 10-60 mM of glucose may be administered to premeiotic inflorescences. In other examples, glucose and a steroid, such as epibrassinolide, may be together administered in the above concentrations to induce apomixis in sexual plants. In some embodiments, the eukaryote is transgenically modified to produce the chemical treatment endogenously. In either case, the chemical treatment is administered to the premeiotic germline or germline-associated tissues. In some embodiments, multiple treatments of the chemical treatments may be administered to the subject organism beginning at the premeiotic stage and continuing through the preembryonic stage. In certain plant applications, this period of administering could last from about 3 to about 10 days.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

In one non-limiting implementation, increasing sugar level comprises applying glucose to the female germline cell and/or the female germline-associated tissue in the sexual eukaryote (e.g., a pistil). In a non-limiting implementation, glucose is applied to the female germline cell and/or the female germline-associated tissue in an amount and time sufficient to induce apomeiosis, parthenogenesis, or both in the sexual eukaryote. In a non-limiting implementation, glucose is applied in an amount between 20 and 120 mmol/liter (mM), or any number range in between, e.g., 20-110 mM, 25-110 mM, 25-100 mM, 30-100 mM, 30-90 mM, 35-90 mM, 45-90 mM, 45-85 mM, 50-85 mM, 50-80 mM, or 65-75 mM, etc. In another non-limiting implementation, the duration of glucose application (e.g., pre-treatment emersion) is between 2 and 600 minutes, or any number range in between, e.g., 2-480 minutes, 2-420 minutes, 2.5-420 minutes, 2-18 minutes, 2.5-360 minutes, 3-360 minutes, 3-17 minutes, 3.5-240 minutes, 3.5-120 minutes, 4-480 minutes, 4-120 minutes, 4-100 minutes, 4-16 minutes, 5-100 minutes, 5-80 minutes, 5-15 minutes, 6-80 minutes, 6-60 minutes, 6-14 minutes, 7-60 minutes, 7-40 minutes, 7-13 minutes, 8-40 minutes, 8-20 minutes, 8-12 minutes, 9-20 minutes, 9-11 minutes, 40-600 minutes, 60-600 minutes, 60-580 minutes, 80-580 minutes, 80-560 minutes, 100-560 minutes, 100-540 minutes, 120-540 minutes, 120-520 minutes, 140-520 minutes, 140-500 minutes, 160-500 minutes, 160-480 minutes, 180-480 minutes, 210-480 minutes, 210-460 minutes, 240-460 minutes, 240-440 minutes, 270-440 minutes, 270-420 minutes, 300-420 minutes, 300-400 minutes, 320-400 minutes, 320-380 minutes, or 340-380 minutes, etc. In a further non-limiting implementation, to induce apomeiosis, the time to begin glucose application is between 1 and 96 hours before megasporogenesis onset, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In one non-limiting implementation, increasing sugar level comprises applying sucrose to the female germline cell and/or the female germline-associated tissue in the sexual eukaryote (e.g., a pistil). In a non-limiting implementation, sucrose is applied to the female germline cell and/or the female germline-associated tissue in an amount and time sufficient to induce apomeiosis, parthenogenesis, or both in the sexual eukaryote. In a non-limiting implementation, sucrose is applied in an amount between 20 and 100 mmol/liter (mM), or any number range in between, e.g., 20-90 mM, 25-90 mM, 25-80 mM, 30-80 mM, 30-70 mM, 35-70 mM, 45-70 mM, 45-65 mM, 50-65 mM, 50-60 mM, or 45-55 mM, etc. In another non-limiting implementation, the duration of sucrose application (e.g., pre-treatment emersion) is less than 480 minutes, e.g., less than 360 minutes, less than 240 minutes, less than 120 minutes, less than 80 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of sucrose application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In a further non-limiting implementation, to induce apomeiosis, the time to begin sucrose application is between 1 and 96 hours before megasporogenesis onset, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In one non-limiting implementation, increasing ABA activity comprises applying fluridone is applied to the female germline cell and/or the female germline-associated tissue (e.g., a pistil). In a non-limiting implementation, fluridone is applied in an amount and time sufficient to induce apomeiosis, parthenogenesis, or both in the sexual eukaryote. In a non-limiting implementation, fluridone is applied in an amount between 1 and 30 micromol/liter (µM), or any number range in between, e.g., 1-25 µM, 2-25 µM, 2-20 µM, 3-20 µM, 3-18 µM, 4-18 µM, 4-16 µM, 5-16 µM, 5-15 µM, 7-13 µM, 8-12 µM, or 9-11 µM etc. In another non-limiting implementation, the duration of fluridone application (e.g., pre-treatment emersion) is less than 480 minutes, e.g., less than 360 minutes, less than 240 minutes, less than 120 minutes, less than 80 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of fluridone application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In a further non-limiting implementation, to induce apomeiosis, the time to begin fluridone application is between 1 and 96 hours before megasporogenesis onset, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset. In a yet further non-limiting implementation, to induce parthenogenesis, the time to begin fluridone application is between 1 and 96 hours before anthesis or fertilization, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc.

In one non-limiting implementation, increasing antioxidant activity comprises applying DTBA to the female germline cell and/or the female germline-associated tissue (e.g., a pistil). In a non-limiting implementation, DTBA is applied in an amount and time sufficient to induce apomeiosis, parthenogenesis, or both in the sexual eukaryote. In a non-limiting implementation, DTBA is applied in an amount between 0.05 and 10.0 micromol/liter (µM), or any number range in between, e.g., 0.1-10 µM, 0.1-9 µM, 0.1-8 µM, 0.1-7 µM, 0.1-6 µM, 0.1-5 µM, 0.1-4.5 µM, 0.2-4.5 µM, 0.3-4.5 µM, 0.3-4.0 µM, 0.4-4.0 µM, 0.4-3.0 µM, 0.5-10.0 µM, 0.5-3.0 µM, 0.5-2.0 µM, 0.5-1.5 µM, 0.7-1.3 µM, 0.8-1.2 µM, or 0.9-1.1 µM, etc. In another non-limiting implementation, the duration of DTBA application (e.g., pre-treatment emersion) is less than 480 minutes, e.g., less than 360 minutes, less than 240 minutes, less than 120 minutes, less than 80 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of DTBA application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In a further non-limiting implementation, to induce apomeiosis, the time to begin DTBA application is between 1 and 96 hours before megasporogenesis onset, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc.

In one embodiment, increasing sugar level and antioxidant activity comprises applying glucose and DTBA to the female germline cell and/or the female germline-associated tissue (e.g., a pistil). In a non-limiting implementation, glucose and DTBA are applied in an amount and time sufficient to induce apomeiosis, parthenogenesis, or both in the sexual eukaryote. In a non-limiting implementation, DTBA is applied in an amount between 0.01 and 10.0 micromol/liter (04), or any number range in between, e.g., 0.01-4 µM, 0.02-4 µM, 0.02-3 µM, 0.03-3 µM, 0.03-2 µM, 0.04-2 µM, 0.04-1 µM, 0.05-1 µM, 0.05-0.5 µM, 0.06-0.5 µM, 0.06-0.4 µM, 0.07-0.4 µM, 0.07-0.3 µM, 0.08-0.3 µM, 0.08-0.2 µM, 0.08-0.12 µM, 0.09-0.2 µM, or 0.09-0.11 µM, 0.05-10 µM, 0.1-10 µM, 0.1-9 µM, 0.1-8 µM, 0.1-7 µM, 0.1-6 µM, 0.1-5 µM, 0.1-4.5 µM, 0.2-4.5 µM, 0.3-4.5 µM, 0.3-4.0 µM, 0.4-4.0 µM, 0.4-3.0 µM, 0.5-10.0 µM, 0.5-3.0 µM, 0.5-2.0 µM, 0.5-1.5 µM, 0.7-1.3 µM, 0.8-1.2 µM, or 0.9-1.1 µM, etc. In another non-limiting implementation, glucose is applied in an amount between 10 and 200 mmol/liter (mM), or any number range in between, e.g., 10-180 mM, 20-180 mM, 20-160 mM, 30-160 mM, 30-150 mM, 30-140 mM, 40-150 mM, 40-140 mM, 50-140 mM, 50-135 mM, 60-135 mM, 60-130 mM, 70-130 mM, 70-125 mM, 80-140 mM, 80-125 mM, 80-120 mM, 90-130 mM, 90-120 mM, or 90-115 mM, etc. In another non-limiting implementation, the duration of DTBA and glucose application (e.g., pre-treatment emersion) is less than 480 minutes, e.g., less than 360 minutes, less than 240 minutes, less than 120 minutes, less than 80 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of DTBA and glucose application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In yet another non-limiting implementation, to induce parthenogenesis, the time to begin DTBA and glucose application is between 1 and 96 hours before anthesis or fertilization, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, 12-72 hours, 12-66 hours, 15-66 hours, 15-60 hours, 18-60 hours, 18-54 hours, 21-54 hours, 21-48 hours, 24-48 hours, 24-45 hours, 27-45 hours, 27-42 hours, 30-42 hours, 30-39 hours, or 33-39 hours, etc. before anthesis or fertilization.

In one non-limiting implementation, increasing ABA activity comprises applying 5-azacytidine (5-azaC) to the female germline cell and/or the female germline-associated tissue (e.g., a pistil). In a non-limiting implementation, 5-azaC is applied in an amount and time sufficient to induce apomeiosis, parthenogenesis, or both in the sexual eukaryote. In a non-limiting implementation, 5-azaC is applied in an amount between 5 and 5,000 micromol/liter (µM), or any number range in between, e.g., 5-4,000 µM, 15-4,000 µM, 15-3,000 µM, 25-3,000 µM, 25-2,000 µM, 35-2,000 µM, 35-1,500 µM, 45-1,500 µM, 45-1,000 µM, 50-1,000 µM, 50-900 µM, 150-900 µM, 150-800 µM, 250-800 µM, 250-700 µM, 350-700 µM, 350-600 µM, 450-600 µM, or 450-550 µM, etc. In another non-limiting implementation, the duration of 5-azaC application (e.g., pre-treatment emersion) is less than 480 minutes, e.g., less than 360 minutes, less than 240 minutes, less than 120 minutes, less than 80 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of 5-azaC application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In a further non-limiting implementation, to induce apomeiosis, the time to begin 5-azaC application is between 1 and 96 hours before megasporogenesis onset, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-96 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc.

In one non-limiting implementation, increasing BR activity comprises applying epibrassinolide (epiBL) to the female germline cell and/or the female germline-associated tissue (e.g., a pistil). In a non-limiting implementation, epiBL is applied in an amount and time sufficient to induce apomeiosis, parthenogenesis, or both in the sexual eukaryote. In a non-limiting implementation, epiBL is applied in an amount between 0.02 and 20 micromol/liter (µM), or any number range in between, e.g., 0.02-19 µM, 0.03-19 µM, 0.03-18 µM, 0.04-18 µM, 0.04-17 µM, 0.05-17 µM, 0.05-18 µM, 0.05-15 µM, 0.06-15 µM, 0.06-14 µM, 0.07-14 µM, 0.07-13 µM, 0.08-13 µM, 0.08-12 µM, 0.09-12 µM, 0.10-11 µM, or 0.10-10 µM, etc. In another non-limiting implementation, the duration of epiBL application (e.g., pre-treatment emersion) is less than 480 minutes, e.g., less than 360 minutes, less than 240 minutes, less than 120 minutes, less than 80 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of epiBL application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In a further non-limiting implementation, to induce apomeiosis, the time to begin epiBL application is between 1 and 96 hours before megasporogenesis onset, or any length of time in between, e.g. 1-84 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In one non-limiting implementation, increasing sugar level and BR activity comprises applying glucose and epibrassinolide (epiBL) to the female germline cell and/or the female germline-associated tissue (e.g., a pistil). In a non-limiting implementation, glucose and epiBL are applied in an amount and time sufficient to induce apomeiosis, parthenogenesis, or both in the sexual eukaryote. In a non-limiting implementation, epiBL is applied in an amount between 0.05 and 15 micromol/liter (µM), or any number range in between, e.g., 0.05-10 µM, 0.1-15 µM, 0.1-10 µM, 0.1-8.5 µM, 0.2-8.5 µM, 0.2-7.0 µM, 0.3-7.0 µM, 0.3-5.5 µM, 0.4-5.5 µM, 0.4-5.0 µM, 0.5-5.0 µM, 0.5-4.5 µM, 0.5-4 µM, 1.0-4 µM, 1.0-3.5 µM, 1.5-3.5 µM, 1.5-3.0 µM, or 1.5-2.0 µM, etc. In another non-limiting implementation, glucose is applied in an amount between 3 and 200 mmol/liter (mM), or any number range in between, e.g., 3-180 mM, 3-140 mM, 10-180 mM, 20-180 mM, 20-160 mM, 30-160 mM, 30-150 mM, 40-150 mM, 40-140 mM, 50-140 mM, 50-135 mM, 60-135 mM, 60-130 mM, 70-130 mM, 70-125 mM, 80-140 mM, 80-125 mM, 80-120 mM, 90-130 mM, 90-120 mM, or 90-115 mM, etc. In yet another non-limiting implementation, the duration of epiBL and glucose application (e.g., pre-treatment emersion) is between 0.01 and 600 minutes, or any number range in between, e.g., 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 3-250 minutes, 3-200 minutes, 4-200 minutes, 4-150 minutes, 5-150 minutes, 5-100 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, 9-11 minutes, 40-600 minutes, 60-600 minutes, 60-580 minutes, 80-580 minutes, 80-560 minutes, 100-560 minutes, 100-540 minutes, 120-540 minutes, 120-520 minutes, 140-520 minutes, 140-500 minutes, 160-500 minutes, 160-480 minutes, 180-480 minutes, 210-480 minutes, 210-460 minutes, 240-460 minutes, 240-440 minutes, 270-440 minutes, 270-420 minutes, 300-420 minutes, 300-400 minutes, 320-400 minutes, 320-380 minutes, or 340-380 minutes etc. In a further non-limiting implementation, to induce parthenogenesis, the time to begin epiBL and glucose application is between 6 and 72 hours before anthesis or fertilization, or any length of time in between, e.g., 12-66 hours, 15-66 hours, 15-60 hours, 18-60 hours, 18-54 hours, 21-54 hours, 21-48 hours, 24-48 hours, 24-45 hours, 27-45 hours, 27-42 hours, 30-42 hours, 30-39 hours, or 33-39 hours, etc. before anthesis or fertilization.

Transgenic Upregulation or Downregulation

In some embodiments, increasing glucose signaling, decreasing osmotic stress, decreasing oxidative stress, decreasing perceived oxidative stress, or a combination thereof comprises decreasing sucrose non-fermenting 1 related kinase (SnRK) activity, decreasing meiosis-specific RNA directed DNA methylation (RdDM), increasing target of rapamycin complex 1 (TORC1) activity, increasing brassinosteroids (BR) activity, increasing ABA activity (e.g., increasing PP2C, CYP707A, or both), or a combination thereof in a female germline cell, a female germline-associated tissue, or both of the sexual eukaryote.

As used herein, "target gene" refers to any gene that one desires to increase or decrease the activity in a eukaryote, the eukaryote cell, or the eukaryote tissue (e.g., the female germline cell, the female germline-associated tissue, or both) of the sexual eukaryote. In some embodiments, decreasing the activity of the target gene in the female germline cell, the female germline-associated tissue, or both decreases reduction and/or recombination in meiosis. In some embodiments, decreasing the activity of the target gene in the female germline cell, the female germline-associated tissue, or both prevents reduction and/or recombination in meiosis. In some implementations, the target gene encodes SnRK1. In other implementations, the target gene encodes SnRK2. In further implementations, the target gene encodes RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, or HISTONE H2A 11 (HTA11).

As used herein, "decreasing activity" of a target gene refers to causing, directly or indirectly, reduction in the transcription of the target gene, reduction in the amount, stability or translatability of transcription products (e.g., RNA) of said target gene, reduction in translation of the polypeptide(s) encoded by the target gene and/or reduction in the amount, stability, or alteration of biochemical function of the polypeptides encoded by the target gene, so as to reduce the amount or function of the target gene products. As used herein, "increasing activity" of a target gene refers to causing, directly or indirectly, increase in the transcription of the target gene, increase in the amount, stability or translatability of transcription products (e.g., RNA) of said target gene, reduction in translation of the polypeptide(s) encoded by the target gene and/or increase in the amount, stability, or alteration of biochemical function of the polypeptides encoded by the target gene, so as to increase the amount or function of the target gene products.

A decrease or increase in the target gene activity can be monitored, e.g., by direct detection of gene transcripts (e.g., by PCR), by detection of polypeptide(s) encoded by the gene (e.g., by Western blot or immunoprecipitation), by detection of biological activity of polypeptides encode by the gene (e.g., catalytic activity, ligand binding, etc), or by monitoring changes in a cell or organism resulting from reduction in expression of the gene.

In one implementation, the target gene activity is decreased (e.g., SnRK and/or RdDM) or increased (e.g., TORC1, BR, PP2C, and/or CYP707A) by 1%-100%, or any percent number in between, e.g., 1-75%, 1-50%, 1-25%, 5-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-100%, 10-90%, 10-80%, 10-70%, 10-60%, 10-50%, 10-40%, 10-30%, 10-20%, 25-100%, 25-75%, 25-50%, 30-100%, 30-95%, 30-90%, 30-85%, 30-80%, 30-75%, 30-70%, 30-65%, 30-60%, 30-55%, 30-50%, 40-100%, 40-90%, 40-80%, 40-70%, 40-60%, 40-50%, 50-100%, 50-95%, 50-90%, 50-80%, 50-75%, 50-70%, or 75-100% in one or more plant cells as compared to the target gene of that would exist in the same plant tissue(s) without the decrease or increase. In another implementations, the target gene activity is decreased (e.g., SnRK or RdDM) or increased (e.g., TORC1, BR, PP2C, and/or CYP707A) by at least 10%, for example, at least 20%, at least 30%, at least 40%, at least 50%, at least 60%, at least 70%, at least 80%, or at least 90% in one or more plant cells as compared to the target gene of that would exist in the same plant tissue(s) without the decrease.

In one implementation, the decrease or increase of the target gene activity is detectable pre-meiosis, e.g., is detectable at least one-, two-, four-, eight-, twelve-, or eighteen-hours pre-meiosis, or is detectable at least one-, two-, three-, or four-days pre-meiosis. As used herein, the term "pre-meiosis" or "premeiotic" refers to the stage of sexual reproduction prior to when meiosis typically occurs, wherein meiocyte mother cells are not yet mature or are still forming.

In one implementation, the decrease or increase of the target gene activity is permanent, i.e., resulting in reduction or increase of gene expression for the lifetime of the organism and/or its future generations. In an alternative implementation, the decrease or increase of the target gene activity is transient, e.g., for the duration of the presence of a silencing element or downregulating agent. In a specific implementation, the decrease or increase of the target gene activity lasts at least 24 hours, at least 48 hours, at least 72 hours, at least 96 hours, at least 120 hours, at least 144 hours, at least 168 hours, at least 192 hours, at least 216 hours, or at least 240 hours. In another implementation, the decrease of the target gene activity lasts for about 24-240 hours, about 24-144 hours, about 24-96 hours, about 24-48 hours, about 48-240 hours, about 48-192 hours, about 48-144 hours, about 48-72 hours, about 72-249 hours, about 72-192 hours, about 72-144 hours, about 96-144 hours, or about 120-240 hours. In some embodiments, the decrease of the target gene activity begins pre-meiosis, at least one-hour before megasporogenesis onset, e.g., at least two-hours, at least four-hours, at least eight-hours, at least 12-hours, at least 18-hours, at least 24-hours pre-meiosis, at least 48-hours, or at least 72-hours pre-meiosis, etc. before megasporogenesis onset. In some implementations, the SnRK1 activity, SnRK2 activity, or both is decreased by 10-90% between 0.5 and 48 hours before megasporogenesis onset to 0.5 to 48 h after embryo formation.

Gene Disruption

In some embodiments of the present disclosure, the activity of the target gene is decreased or eliminated by disrupting the gene encoding the polypeptide. In one embodiment, SnRK activity is decreased by disrupting an endogenous SnRK gene in the female germline cell, the female germline-associated tissue, or both. In a particular implementation, the endogenous SnRK gene is selected from the group consisting of: SnRK1, SnRK2, an ortholog thereof, and combinations thereof.

In another embodiment, RdDM activity is decreased by disrupting an endogenous RdDM gene in the female germline cell, the female germline-associated tissue, or both. In a particular implementation, the endogenous RdDM gene is selected from the group consisting of: RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), an ortholog thereof, and combinations thereof.

In a further embodiment, in addition to disrupting the SnRK gene, at least one other endogenous gene involved in meiosis is disrupted. In one implementation, the at least one other endogenous gene is selected from the group consisting of: RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), an ortholog thereof, and combinations thereof.

The gene encoding the polypeptide may be disrupted by any method known in the art, for example, by genome editing, transposon tagging or mutagenizing plants using random or targeted mutagenesis and selecting for plants that have decreased activity. A plant cell other than the female germline cell and/or female germline-associated tissue may be used for the gene disruption technology.

A. Genome Editing and Induced Mutagenesis

In some embodiments, the target gene (e.g., SnRK1 and/or SnRK2) is modified using gene editing technology, including without limitation double-strand-break-inducing agent, such as but not limited to a CRISPR-Cas guideRNA or other polynucleotide-guided double strand break reagent, a Zinc Finger endonuclease, a meganuclease, or a TALEN endonuclease.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times, also referred to as CRISPR-repeats) which are partially palindromic. The repeated sequences (usually specific to a species) are interspaced by variable sequences of constant length (typically 20 to 58 bp depending on the CRISPR locus (WO2007/025097 published Mar. 1, 2007).

CRISPR loci were first recognized in *Escherichia coli* (Ishino et al., (1987) *J. Bacteriol.* 169:5429-33; Nakata et al., (1989) *J. Bacteriol.* 171:3553-56). Similar interspersed short sequence repeats have been identified in *Haloferax mediterranei, Streptococcus pyogenes, Anabaena*, and *Mycobacterium tuberculosis* (Groenen et al., (1993) *Mol. Microbiol.* 10:1057-65; Hoe et al., (1999) *Emerg. Infect. Dis.* 5:254-263; Masepohl et al., (1996) *Biochim. Biophys. Acta* 1307:26-30; Mojica et al., (1995) *Mol. Microbiol.* 17:85-93). The CRISPR loci differ from other simple sequence repeats (SSRs) by the structure of the repeats, which have been termed short regularly spaced repeats (SRSRs) (Janssen et al., (2002) *J. Integ. Biol.* 6:23-33; Mojica et al., (2000) *Mol. Microbiol.* 36:244-46). The repeats are short elements that occur in clusters, which are always regularly spaced by variable sequences of constant length (Mojica et al., (2000) *Mol. Microbiol.* 36:244-46).

Cas gene relates to a gene that is generally coupled, associated or close to, or in the vicinity of flanking CRISPR loci. The terms "Cas gene", "CRISPR-associated (Cas) gene" are used interchangeably herein. A comprehensive review of the Cas protein family is presented in Haft et al., (2005) *PLoS Comput Biol* 1: e60. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. application Ser. No. 15/571,510, filed May 6, 2016). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

The Cas endonuclease gene can encode Cas9 endonuclease, or a functional fragment thereof, such as but not limited to the Cas9 genes listed in WO2007/025097, published Mar. 1, 2007. The Cas endonuclease gene can be a plant, maize or soybean optimized Cas9 endonuclease, such as but not limited to a plant codon optimized *Streptococcus pyogenes* Cas9 gene. The Cas endonuclease can be introduced directly into a cell by any method known in the art, for example, but not limited to, transient introduction methods, transfection, and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide" relates to a polynucleotide sequence that can form a complex with a Cas endonuclease and enables the Cas endonuclease to recognize and optionally cleave a DNA target site (U.S. application Ser. No. 15/571,510, filed May 6, 2016). The guide polynucleotide can be a single molecule or a double molecule. The guide polynucleotide sequence can be an RNA sequence, a DNA sequence, or a combination thereof (an RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide), comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments, the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments, the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, an RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide) that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide polynucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide, a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

B. Transposon Tagging

In one embodiment, transposon tagging is used to decrease or eliminate the activity of one or more polypeptides. Transposon tagging comprises inserting a transposon within an endogenous gene in the pathway to decrease or eliminate expression of the polypeptide.

In this embodiment, the expression of one or more polypeptides is decreased or eliminated by inserting a transposon within a regulatory region or coding region of the gene encoding the polypeptide. A transposon that is within an exon, intron, 5' or 3' untranslated sequence, a promoter or any other regulatory sequence of a gene may be used to decrease or eliminate the expression and/or activity of the encoded polypeptide.

Methods for the transposon tagging of specific genes in plants are well known in the art. See, e.g., Maes et al., (1999)

Trends Plant Sci. 4:90-96; Dharmapuri & Sonti, (1999) FEMS Microbiol. Lett. 179:53-59; Meissner et al., (2000) Plant J. 22:265-74; Phogat et al., (2000) J. Biosci. 25:57-63; Walbot, (2000) Curr. Opin. Plant Biol. 2:103-07; Gai et al., (2000) Nucleic Acids Res. 28:94-96; Fitzmaurice et al., (1999) Genetics 153:1919-28. In addition, the TUSC process for selecting Mu insertions in selected genes has been described in Bensen et al., (1995) Plant Cell 7:75-84; Mena et al., (1996) Science 274:1537-40; and U.S. Pat. No. 5,962,764, each of which is herein incorporated by reference.

C. Mutant Plants with Decreased Activity

Additional methods for decreasing or eliminating the expression of endogenous genes in plants are also known in the art and may be similarly applied to the instant disclosure. These methods include other forms of mutagenesis, such as ethyl methanesulfonate-induced mutagenesis, deletion mutagenesis, and fast neutron deletion mutagenesis used in a reverse genetics sense (with PCR) to identify plant lines, in which the endogenous gene has been mutated or deleted. For examples of these methods see Ohshima et al., (1998) Virology 243:472-81; Okubara et al., (1994) Genetics 137: 867-74; and Quesada et al., (2000) Genetics 154:421-36, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant disclosure. See McCallum et al., (2000) Nat. Biotechnol. 18:455-57, herein incorporated by reference.

Mutations may impact gene expression or interfere with the activity of an encoded target gene (e.g., SnRK1 and/or SnRK2) protein. Insertional mutations in gene exons usually result in null-mutants. Mutations in conserved residues are particularly effective in inhibiting the activity of the encoded protein. Conserved residues of plant polypeptides suitable for mutagenesis with the goal to eliminate activity have been described. Such mutants may be isolated according to well-known procedures and mutations in different target gene (e.g., SnRK1 and/or SnRK2) loci may be stacked by genetic crossing. See, e.g., Gruis et al., (2002) Plant Cell 14:2863-82.

In another embodiment, dominant mutants is used to trigger RNA silencing due to gene inversion and recombination of a duplicated gene locus. See, e.g., Kusaba et al., (2003) Plant Cell 15:1455-67.

The disclosure encompasses additional methods for decreasing or eliminating the activity of one or more target polypeptides. Examples of other methods for altering or mutating a genomic nucleotide sequence in a plant are known in the art and include, but are not limited to, the use of RNA:DNA vectors, RNA:DNA mutational vectors, RNA: DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984, each of which are herein incorporated by reference. See also WO 1998/49350, WO 1999/07865, WO 1999/25821, and Beetham et al., (1999) Proc. Natl. Acad. Sci. USA 96:8774-78, each of which is herein incorporated by reference.

Silencing Elements

As used herein, "silencing element" refers to a polynucleotide that is capable of reducing or eliminating the level or expression of a target polynucleotide or the polypeptide encoded thereby. The silencing element employed can decrease or eliminate the expression level of the target sequence by influencing the level of the target RNA transcript or, alternatively, by influencing translation and thereby affecting the level of the encoded polypeptide. A single polynucleotide employed in the methods can comprise one or more silencing elements to the same or different target polynucleotides. The silencing element can be produced in vivo (i.e., in a host cell such as a plant) or in vitro.

In some embodiments, decreasing the target gene (e.g., SnRK1 and/or SnRK2) activity comprises introducing into the female germline cell and/or the female germline-associated tissue a silencing element thereby reducing or eliminating the level or expression of a polynucleotide or a polypeptide encoded by the target gene. In a specific implementation, decreasing SnRK activity comprises introducing into the female germline cell and/or the female germline-associated tissue a silencing element capable of decreasing or eliminating a polynucleotide or a polypeptide encoded by SnRK1, SnRK2, or both. In another specific implementation, decreasing RdDM activity comprises introducing into the female germline cell and/or the female germline-associated tissue a silencing element capable of decreasing or eliminating a polynucleotide or a polypeptide encoded by RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, and/or HISTONE H2A 11 (HTA11).

In specific embodiments, the target sequence is endogenous to the plant. In other embodiments, while the silencing element regulates non-reduction and non-recombination of meiosis, preferably the silencing element has no effect on the parts of the plant that do not constitute the female germline, the female germline-associated tissue, or both.

Non-limiting examples of silencing elements include, a sense suppression element, an antisense suppression element, a double stranded RNA, a siRNA, an amiRNA, a miRNA, or a hairpin suppression element. Non-limiting examples of silencing elements that can be employed to decrease expression of these target sequences or additionally sequences targeting genes involved in recombination comprise fragments and variants of the sense or antisense sequence or consists of the sense or antisense sequence of wild type polynucleotide or polypeptide sequences, variant polynucleotides, variant polypeptides, cognate promoter sequences, ortholog sequences, variants or fragments thereof. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. Enhancer suppressor elements can also be employed in conjunction with the silencing elements.

In some implementations, introducing the silencing element decreases the polynucleotide level and/or the polypeptide level of the target sequence to less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control.

A. Sense Suppression/Cosuppression

In some embodiments, decreasing expression of the target gene (e.g., SnRK1 and/or SnRK2) is obtained by sense suppression or cosuppression. For cosuppression, an expression cassette is designed to express an RNA molecule corresponding to all or part of a messenger RNA encoding a polypeptide in the "sense" orientation. Over expression of the RNA molecule may result in decreased expression of the native gene. Accordingly, multiple plant lines transformed with the cosuppression expression cassette are screened to identify those that show the desired degree of inhibition of polypeptide expression.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. In other implementations, the sense suppression element is, for example, 15, 16, 17, 18 19, 20, 22, 25, 30, 50, 100, 150, 200, 250, 300, 350, 400, 450, 500, 600, 700, 900, 1000, 1100, 1200, 1300 nucleotides or longer of the target polynucleotides. In other implementations, the sense suppression element is, for example, about 15-25, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides.

The polynucleotide used for cosuppression may correspond to all or part of the sequence encoding the polypeptide, all or part of the 5' and/or 3' untranslated region of a polypeptide transcript or all or part of both the coding sequence and the untranslated regions of a transcript encoding a polypeptide. In some embodiments where the polynucleotide comprises all or part of the coding region for the polypeptide, the expression cassette is designed to eliminate the start codon of the polynucleotide so that no protein product will be translated.

Cosuppression has been used to inhibit the expression of plant genes to produce plants having undetectable protein levels for the proteins encoded by these genes (see, e.g., Broin et al., (2002) *Plant Cell* 14:1417-32), and to inhibit the expression of multiple proteins in the same plant (see, e.g., U.S. Pat. No. 5,942,657). Methods for using cosuppression to inhibit the expression of endogenous genes in plants are described in Flavell et al., (1994) *Proc. Natl. Acad. Sci. USA* 91:3490-96; Jorgensen et al., (1996) *Plant Mol. Biol.* 31:957-73; Johansen & Carrington, (2001) *Plant Physiol.* 126:930-38; Broin et al., (2002) *Plant Cell* 14:1417-32; Stoutjesdijk et al., (2002) *Plant Physiol.* 129:1723-31; Yu et al., (2003) *Phytochemistry* 63:753-63; and U.S. Pat. Nos. 5,034,323, 5,283,184, and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication No. 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323, herein incorporated by reference.

B. Antisense Suppression

In some implementations, decreasing expression of the target gene (e.g., SnRK1 and/or SnRK2) is obtained by antisense suppression. For antisense suppression, the expression cassette is designed to express an RNA molecule complementary to all or part of a messenger RNA encoding the polypeptide. Over expression of the antisense RNA molecule may result in decreased expression of the target gene. Accordingly, multiple plant lines transformed with the antisense suppression expression cassette are screened to identify those that show the desired degree of inhibition of polypeptide expression.

The polynucleotide for use in antisense suppression may correspond to all or part of the complement of the sequence encoding the polypeptide, all or part of the complement of the 5' and/or 3' untranslated region of the target transcript or all or part of the complement of both the coding sequence and the untranslated regions of a transcript encoding the polypeptide. In addition, the antisense polynucleotide may be fully complementary (i.e., 100% identical to the complement of the target sequence) or partially complementary (i.e., less than 100% identical to the complement of the target sequence) to the target sequence. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 20, 22, 25, 50, 100, 200, 300, 400, 450 nucleotides or greater of the target gene sequence may be used. Methods for using antisense suppression to inhibit the expression of endogenous genes in plants are described, e.g., in Liu et al. (2002) *Plant Physiol.* 129:1732-43 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication No. 2002/0048814, herein incorporated by reference.

C. Double-Stranded RNA Interference

In some embodiments, decreasing the expression of the target gene (e.g., SnRK1 and/or SnRK2) is obtained by double-stranded RNA (dsRNA) interference. A "double stranded RNA silencing element" or "dsRNA" comprises at least one transcript that is capable of forming a dsRNA. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions mediate the decrease of expression of a target sequence, for example, by mediating RNA interference "RNAi" or gene silencing in a sequence-specific manner. The dsRNA is capable of decreasing or eliminating the level or expression of a target polynucleotide or the polypeptide, for example, SnRK1 and/or SnRK2.

The dsRNA can decrease or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, e.g., Verdel et al., (2004) *Science* 303:672-76; Pal-Bhadra et al., (2004) *Science* 303: 669-72; Allshire (2002) *Science* 297:1818-19; Volpe et al., (2002) *Science* 297:1833-37; Jenuwein (2002) *Science* 297: 2215-18; and Hall et al., (2002) *Science* 297:2232-37. As used herein, the term "dsRNA" is meant to encompass other terms used to describe nucleic acid molecules that are capable of mediating RNA interference or gene silencing, including, e.g., short-interfering RNA (siRNA), double-stranded RNA (dsRNA), micro-RNA (miRNA), hairpin RNA, short hairpin RNA (shRNA), post-transcriptional gene silencing RNA (ptgsRNA), etc.

For dsRNA interference, a sense RNA molecule like that described above for cosuppression and an anti sense RNA molecule that is fully or partially complementary to the sense RNA molecule are expressed in the same cell, resulting in inhibition of the expression of the corresponding endogenous messenger RNA.

Expression of the sense and antisense molecules may be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the desired degree of inhibition of polypeptide expression. Methods for using dsRNA interference to inhibit the expression of endogenous plant genes are described in Waterhouse et al., (1998) *Proc. Natl. Acad. Sci. USA* 95:13959-64, Liu et al., (2002) *Plant Physiol.* 129: 1732-43 and WO 1999/49029, WO 1999/53050, WO 1999/61631 and WO 2000/49035, each of which is herein incorporated by reference.

D. Hairpin RNA Interference and Intron-Containing Hairpin RNA Interference

In some embodiments, decreasing the expression of the target gene (e.g., SnRK1 and/or SnRK2) is obtained by hairpin RNA (hpRNA) interference or intron-containing hairpin RNA (ihpRNA) interference. These methods are highly efficient at inhibiting the expression of endogenous genes. See, Waterhouse & Helliwell, (2003) *Nat. Rev. Genet.* 4:29-38, and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene whose expression is to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, e.g., Chuang & Meyerowitz, (2000) *Proc. Natl. Acad. Sci. USA* 97:4985-90; Stoutjesdijk et al., (2002) *Plant Physiol.* 129:1723-31; and Waterhouse & Helliwell, (2003) *Nat. Rev. Genet.* 4:29-38. Methods for using hpRNA interference to inhibit or silence the expression of genes are described, e.g., in Chuang & Meyerowitz, (2000) *Proc. Natl. Acad. Sci. USA* 97:4985-90; Stoutjesdijk et al., (2002) *Plant Physiol.* 129:1723-31; Waterhouse &d Helliwell, (2003) *Nat. Rev. Genet.* 4:29-38; Pandolfini et al., *BMC Biotechnology* 3:7; and US Patent Application Publication No. 2003/0175965, each of which is herein incorporated by reference. A transient assay for the efficiency of hpRNA constructs to silence gene expression in vivo has been described by Panstruga et al., (2003) *Mol. Biol. Rep.* 30:135-40, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, e.g., Smith et al., (2000) *Nature* 407:319-20. In fact, Smith et al., show 100% suppression of endogenous gene expression using ihpRNA-mediated interference. Methods for using ihpRNA interference to inhibit the expression of endogenous plant genes are described, for example, in Smith et al., (2000) *Nature* 407:319-20; Wesley et al., (2001) *Plant J.* 27:581-90; Wang & Waterhouse, (2001) *Curr. Opin. Plant Biol.* 5:146-50; Waterhouse & Helliwell, (2003) *Nat. Rev. Genet.* 4:29-38; Helliwell & Waterhouse, (2003) *Methods* 30:289-95; and US Patent Application Publication No. 2003/0180945, each of which is herein incorporated by reference.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances, to optimize the siRNA sequences employed in the hairpin, the synthetic oligodeoxyribonucleotide/RNAse H method can be used to determine sites on the target mRNA that are in a conformation that is susceptible to RNA silencing. See, e.g., Vickers et al., (2003) *J. Biol. Chem.* 278:7108-18 and Yang et al., (2002) *Proc. Natl. Acad. Sci. USA* 99:9442-47, herein incorporated by reference. These studies indicate that there is a significant correlation between the RNase-H-sensitive sites and sites that promote efficient siRNA-directed mRNA degradation.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, e.g., WO 2002/00904; Mette et al., (2000) *EMBO J* 19:5194-201; Matzke et al., (2001) *Curr. Opin. Genet. Devel.* 11:221-27; Scheid et al., (2002) *Proc. Natl. Acad. Sci. USA* 99:13659-62; Aufsaftz et al., (2002) *Proc. Natl. Acad. Sci.* 99:16499-506; Sijen et al., *Curr. Biol.* (2001) 11:436-40, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al., (2002) *Proc. Natl. Acad. Sci.* 99:16499-506 and Mette et al., (2000) *EMBO J.* 19:5194-201.

E. Amplicon Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the polypeptide). Methods of using amplicons to inhibit the expression of endogenous plant genes are described, for example, in Angell and Baulcombe, (1997) *EMBO J.* 16:3675-3684; Angell and Baulcombe, (1999) *Plant* 20:357-362; and U.S. Pat. No. 6,646,805, each of which is herein incorporated by reference.

F. Ribozymes

In some embodiments, the polynucleotide expressed by the expression cassette is a catalytic RNA or has ribozyme activity specific for the messenger RNA of the polypeptide. Thus, the polynucleotide causes the degradation of the endogenous messenger RNA, resulting in decreased expression of the polypeptide. This method is described, e.g., in U.S. Pat. No. 4,987,071, herein incorporated by reference.

G. Small Interfering RNA or Micro RNA

In some embodiments of the disclosure, decreasing the expression of the target gene (e.g., SnRK1 and/or SnRK2) is obtained by RNA interference by expression of a gene encoding a micro RNA (miRNA) or short-interfering RNA (siRNA) (Meister & Tuschl (2004) *Nature* 431:343-49 and Bonetta et al., (2004) *Nature Methods* 1:79-86). miRNAs are regulatory agents consisting of about 22 ribonucleotides. miRNAs are highly efficient at inhibiting the expression of endogenous genes. See, e.g., Palatnik et al., (2003) *Nature* 425:257-63, herein incorporated by reference. The miRNA can be an "artificial miRNA" or "amiRNA" which comprises a miRNA sequence that is synthetically designed to silence a target sequence.

For miRNA interference, the expression cassette is designed to express an RNA molecule that is modeled on an endogenous miRNA gene. For example, the miRNA gene encodes an RNA that forms a hairpin structure containing a 22-nucleotide sequence that is complementary to another endogenous gene (target sequence). In some embodiments, the 22-nucleotide sequence is selected from a transcript sequence from the target gene (e.g., SnRK1 and/or SnRK2) and contains 22 nucleotides of the target gene in sense orientation and 21 nucleotides of a corresponding antisense sequence that is complementary to the sense sequence. In some embodiments, in addition to targeting the target gene directly, genes involved in recombination may also be targeted. Accordingly, in some embodiments, the 22-nucleotide sequence is selected from a transcript sequence from a gene involved in recombination and contains 22 nucleotides of the gene involved in recombination in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

The heterologous polynucleotide being expressed need not form the dsRNA by itself, but can interact with other sequences in the plant cell to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then decrease the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or, alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

While the various target sequences disclosed herein can be used to design any silencing element that encodes a miRNA; or active variants or fragments thereof.

H. Polypeptide-Based Inhibition of Gene Expression

In one embodiment, the polynucleotide encodes a zinc finger protein that binds to a gene encoding a polypeptide, resulting in decreased expression of the gene. In other embodiments, the zinc finger protein binds to a messenger RNA encoding a polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication No. 2003/0037355, each of which is herein incorporated by reference.

I. Polypeptide-Based Inhibition of Protein Activity

In some embodiments of the disclosure, the polynucleotide encodes an antibody that binds to at least one polypeptide and decreases the activity of the polypeptide. In another embodiment, the binding of the antibody results in increased turnover of the antibody complex by cellular quality control mechanisms. The expression of antibodies in plant cells and the inhibition of molecular pathways by expression and binding of antibodies to proteins in plant cells are well known in the art. See, for example, Conrad & Sonnewald, (2003) *Nature Biotech.* 21:35-36, incorporated herein by reference.

Expression Constructs

In some non-limiting implementations, the silencing element is operably linked to a cis-regulatory element active in germline cells, germline associated tissues, or both. In other non-limiting implementations, the silencing element is operably linked to a cis-regulatory element active in megaspore mother cells (megasporocytes), nucellar cells, or both.

Methods and compositions are provided to modify the level of expression or activity of a target gene (e.g., endogenous SnRK1 and/or SnRK2) polypeptide in the eukaryote (e.g., a plant cell), for example, in a female germline cell. In some embodiments, a plant cell is transformed with a DNA construct or expression cassette for expression of at least one silencing element. In specific embodiments, modulation of target gene expression level and/or activity of the target gene polypeptide promotes non-reduction, or non-reduction and non-recombination, during meiosis resulting in the production of non-reduced, or non-reduced and non-recombined, female gametes. Such methods and compositions can employ an expression construct comprising an element that when expressed decreases target gene polynucleotide and/or target gene polypeptide expression level or activity and is operably linked to a promoter functional in a plant cell. In certain embodiments, the promoter is a female sporogenesis-related promoter, in particular a promoter expressing in ovule primordia or ovule tissue, including but not limited to a target gene promoter.

The expression cassette can include 5' and 3' regulatory sequences operably linked to a polynucleotide of interest, e.g., a silencing element, or an active variant or fragment thereof "Operably linked" is intended to mean a functional linkage between two or more elements. For example, an operable linkage between a polynucleotide of interest and a regulatory sequence (i.e., a promoter) is a functional link that allows for expression of the polynucleotide of interest, for example, a silencing element. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional polynucleotides can be provided on multiple expression cassettes. Such an expression cassette is provided with a plurality of restriction sites and/or recombination sites for insertion of the element to be under the transcriptional regulation of the promoter. The expression cassette may additionally contain selectable marker genes.

In some embodiments, the expression cassette will include in the 5'-3' direction of transcription an ovule-specific promoters, ovule-preferred promoters, female-gametophyte specific promoters, female-gametophyte preferred promoters, female-gamete-specific promoters, female-gamete-preferred promoters, a female sporogenesis-related promoter or an active variant or fragment thereof, a silencing element and a transcriptional and translational termination region (i.e., termination region) functional in the host cell (i.e., the plant). The regulatory regions and/or the silencing elements may be heterologous to the host cell, e.g. plant cell, or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence. In an aspect, the promoter is a heterologous promoter.

The termination region may be native with the transcriptional initiation region, may be native with the operably linked silencing element or with the ovule tissue-preferred promoter sequences, may be native with the plant host, or may be derived from another source (i.e., foreign or heterologous) to the promoter, the silencing element, the plant host, or any combination thereof. Convenient termination regions are available from the Ti-plasmid of *Agrobacterium tumefaciens*, such as the octopine synthase and nopaline synthase gene termination regions. See also Guerineau et al., (1991) *Mol. Gen. Genet.* 262:141-44; Proudfoot, (1991) *Cell* 64:671-74; Sanfacon et al., (1991) *Genes Dev.* 5:141-49; Mogen et al., (1990) *Plant Cell* 2:1261-72; Munroe et al., (1990) *Gene* 91:151-58; Ballas et al., (1989) *Nucleic Acids Res.* 17:7891-903; and Joshi et al., (1987) *Nucleic Acids Res.* 15:9627-39.

Where appropriate, the polynucleotides may be optimized for increased expression in the transformed plant. That is, the polynucleotides can be synthesized using plant-preferred codons for improved expression. See, for example, Campbell & Gown, (1990) *Plant Physiol.* 92:1-11 for a discussion of host-preferred codon usage. Methods are available in the art for synthesizing plant-preferred genes. See, for example, U.S. Pat. Nos. 5,380,831 and 5,436,391, and Murray et al., (1989) *Nucleic Acids Res.* 17:477-98, herein incorporated by reference.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The constructs or expression cassettes may additionally contain 5' leader sequences. Such leader sequences can act to enhance translation. Translation leaders are known in the art and include: picornavirus leaders, for example, EMCV leader (Encephalomyocarditis Virus 5' noncoding region) (Elroy-Stein et al., (1989) *Proc. Natl. Acad. Sci. USA* 86:6126-30); potyvirus leaders, for example, TEV leader (Tobacco Etch Virus) (Gallie et al., (1995) *Gene* 165:233-38), MDMV leader (Maize Dwarf Mosaic Virus) (Johnson et al., (1986) *Virology* 154:9-20), and human immunoglobulin heavy-chain binding protein (BiP) (Macejak et al., (1991) *Nature* 353:90-94); untranslated leader from the coat protein mRNA of Alfalfa Mosaic Virus (AMV RNA 4) (Jobling et al., (1987) *Nature* 325:622-25); tobacco mosaic virus (TMV) leader (Gallie et al., (1989) in *Molecular Biology of RNA*, ed. Cech (Liss, N.Y.), pp. 237-56), and Maize Chlorotic Mottle Virus (MCMV) leader (Lommel et al., (1991) *Virology* 81:382-85). See also Della-Cioppa et al., (1987) *Plant Physiol.* 84:965-68. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, substitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers, such as β-galactosidase and fluorescent proteins, for example green fluorescent protein (GFP) (Su et al., (2004) *Biotechnol Bioeng* 85:610-19 and Fetter et al., (2004) *Plant Cell* 16:215-28), cyan florescent protein (CYP) (Bolte et al., (2004) *J. Cell Science* 117:943-54 and Kato et al., (2002) *Plant Physiol* 129:913-42), yellow florescent protein (PhiYFP™ from Evrogen, see Bolte et al., (2004) *J. Cell Science* 117:943-54), and red fluorescent protein (DsRED, see Baird et al., (2000) *Proc. Natl. Acad. Sci. USA.* 97:11984-89). For additional selectable markers, see, generally, Yarranton, (1992) *Curr. Opin. Biotech* 3:506-11; Christopherson et al., (1992) *Proc. Natl. Acad. Sci. USA* 89:6314-18; Yao et al., (1992) *Cell* 71:63-72; Reznikoff, (1992) *Mol. Microbiol.* 6:2419-22; Barkley et al., (1980) in *The Operon*, pp. 177-220; Hu et al., (1987) *Cell* 48:555-66; Brown et al., (1987) *Cell* 49:603-612; Figge et al., (1988) *Cell* 52:713-22; Deuschle et al., (1989) *Proc. Natl. Acad. Aci. USA* 86:5400-04; Fuerst et al., (1989) *Proc. Natl. Acad. Sci. USA* 86:2549-53; Deuschle et al., (1990) *Science* 248:480-483; Gossen, (1993) Ph.D. Thesis, University of Heidelberg; Reines et al., (1993) *Proc. Natl. Acad. Sci. USA* 90:1917-21; Labow et al., (1990) *Mol. Cell. Biol.* 10:3343-56; Zambretti et al., (1992) *Proc. Natl. Acad. Sci. USA* 89:3952-56; Baim et al., (1991) *Proc. Natl. Acad. Sci. USA* 88:5072-76; Wyborski et al., (1991) *Nucleic Acids Res.* 19:4647-53; Hillenand-Wissman, (1989) *Topics Mol. Struc. Biol.* 10:143-62; Degenkolb et al., (1991) *Antimicrob Agents Chemother* 35:1591-95; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-19; Hlavka et al., (1985) *Handbook of Experimental Pharmacology*, Vol. 78 (Springer-Verlag, Berlin); Gill et al., (1988) *Nature* 334:721-24. Such disclosures are herein incorporated by reference. The above list of selectable marker genes is not meant to be limiting. Any selectable marker gene can be used.

It is further recognized that various expression constructs other than the target gene silencing expression construct are described herein. For example, expression constructs having silencing elements for genes involved in recombination and/or sequences encoding marker sequences are also described herein. One of skill will understand how to apply the language discussed above, to any expression construct.

SnRK1 or SnRK2 sequence can be derived from members of the SnRK family members known to date and their EMBL, PLRJ, or Genbank accession numbers. Non-limiting examples of SnRK family can be found (e.g., Halford & Hardie, Plant Mol. Biol. (37) 735-48 (1998)).

Apomixis to Meiosis and/or Parthenogenesis to Syngamy

In accordance with another of its embodiments, the invention involves treating the preapomeiotic germline and/or associated tissues of apomictic eukaryotes with chemicals that induce sexual reproduction and suppress apomictic reproduction. In accordance with this aspect of the invention, we show that compounds belonging to the class of compounds consisting of reactive oxygen species (ROS) when applied to female germline cells or germline-associated tissues of apomictic plants prior to when apomeiosis typically occurs prevent apomeiosis from occurring and instead induce the occurrence of sexual meiosis. This aspect of the invention accomplishes a metabolic shift from lower to higher oxidative stress or stress perception in germline cells or associated tissues, and it anticipates the use of other chemicals that might also accomplish the same shift, i.e., from lower to higher oxidative stress or stress perception. This invention also anticipates either exogenously applied chemicals or chemicals that are synthesized by the organism endogenously because of genetic transformation or other manmade genetic manipulation, either with or without an external induction signal. The invention therefore enables induction of sexual reproduction in apomictic eukaryotes thereby enabling improvement by conventional breeding.

In a non-limiting embodiment of the present invention, there is provided a method of inducing meiosis, syngamy, or both in an apomictic eukaryote, which method comprises decreasing glucose signaling, increasing osmotic stress, increasing oxidative stress, increasing perceived oxidative stress, or a combination thereof in a female germline cell and/or a female germline-associated tissue in the apomictic eukaryote.

In some implementations, the frequency or probability of switching from apomixis to meiosis, parthenogenesis to syngamy, or both is between 1% and 100%, or any percent range in between, e.g., 1-75%, 1-50%, 1-25%, 5-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-100%, 10-90%, 10-80%, 10-70%, 10-60%, 10-50%, 10-40%, 10-30%, 10-20%, 20-80%, 25-100%, 25-75%, 25-50%, 30-100%, 30-95%, 30-90%, 30-85%, 30-80%, 30-75%, 30-70%, 30-65%, 30-60%, 30-55%, 30-50%, 40-100%, 40-90%, 40-80%, 40-70%, 40-60%, 40-50%, 50-100%, 50-95%, 50-90%, 50-80%, 50-75%, 50-70%, or 75-100%, etc. in the sexual eukaryote. In other embodiments, the frequency or probability of switching from apomixis to meiosis, parthenogenesis to syngamy, or both is at least 10%, for example, at least 20%, at least 30%, at least 40%, at least 50%, at least 60%, at least 70%, at least 80%, or at least 90%, etc. in the apomictic eukaryote.

In some embodiments, the apomictic eukaryote is a plant induced to be apomictic. Non-limiting examples of such plants include grains (e.g., rice, wheat, durum wheat, maize (corn), Job's tears, barley, millet, sorghum, oat, rye, triticale, teff, fonio, wild rice, spelt, canary grass, *quinoa*, amaranth, buckwheat, kaniwa, pitseed goosefoot, etc.), cash crops (e.g., oilseeds such as sunflowers, rapeseed, cotton, peanuts, flax (linseed), castor beans, coffee, cacao, etc.), legumes (e.g., soybeans, cowpea, alfalfa, clover, peas, beans, chickpeas, lentils, lupin beans, mesquite, carob, peanuts, tamarind, etc.), vegetables (e.g., tuber-included tomatoes, cucurbits, squashes, melons, cucumbers, onions, chilis, peppers, lettuce, beets, potatoes, asparagus, carrots, turnips, etc.) In a non-limiting embodiment, the apomictic eukaryote is a Brassicaceae (e.g., *Arabidopsis* or Drummond's rockcress) or a legume (e.g., cowpea). Chemical treatments that induce sexual reproduction in apomictic plants could be used by plant breeders to introduce additional genetic variation into important apomictic forage and turf grasses including bahiagrass (*Paspalum notatum*), signalgrass (*Brachiaria*, the most widely used forage grass in Central and South America), weeping lovegrass (*Eragrostis curvula*), Kentucky bluegrass (*Poa pratensis*), buffalograss (*Bouteloua dactyloides*), and Bermuda grass (*Cynodon dactylon*). In some implementations, the apomictic eukaryote is selected from the group consisting of: apomictic forage grass and turf grass. In other implementations, the apomictic eukaryote is selected from the group consisting of: bahiagrass (*Paspalum notatum*), signalgrass (*Brachiaria*), weeping lovegrass (*Eragrostis curvula*), Kentucky bluegrass (*Poa pratensis*), buffalograss (*Bouteloua dactyloides*), Bermuda grass (*Cynodon dactylon*), and combinations thereof.

Chemical treatments for inducing sex in apomictic eukaryotes include reactive oxygen species such as hydrogen peroxide administered in an effective dose to derepress the epigenome and/or metabalome responsible for sex or repress the epigenome and/or metabalome responsible for apomixis.

In one implementation, decreasing glucose signaling, increasing osmotic stress, increasing oxidative stress, increasing perceived oxidative stress, or a combination thereof comprises decreasing sugar, increasing reactive oxygen species, increasing BR activity, inhibiting brassinosteroid biosynthesis, or a combination thereof.

In a non-limiting implementation, decreasing glucose signaling, increasing oxidative stress, increasing perceived oxidative stress, or a combination thereof comprises decreasing sugar level, decreasing fatty acid catabolism by beta-oxidation, decreasing brassinosteroid (BR) activity, increasing osmotic stress, decreasing antioxidant activity, increasing reactive oxygen species (ROS), increasing abscisic acid (ABA) activity, increasing sucrose non-fermenting 1 related kinase (SnRK) activity, decreasing target of rapamycin complex 1 (TORC1) activity, increasing meiosis-specific RNA directed DNA methylation (RdDM), or a combination thereof.

In another non-limiting implementation, the decrease in sugar level, the decrease in fatty acid catabolism by beta-oxidation, the decrease in BR activity, the increase in osmotic stress, the decrease in antioxidant activity, the decrease in TORC1 activity, the increase in ROS, the increase in ABA activity, the increase in SnRK activity, the increase in RdDM, or a combination thereof is in an amount and time sufficient to induce meiosis. In a further non-limiting implementation, the time sufficient to induce meiosis is between 0.05 and 72 hours.

In another embodiment, decreasing glucose signaling, increasing oxidative stress, increasing perceived oxidative stress, or a combination thereof comprises contracting the female germline cell and/or the female germline-associated tissue with at least one compound selected from the group consisting of: hydrogen peroxide, PEG 6,000, brassinazole, abscisic acid, and a combination thereof.

In one non-limiting implementation, decreasing sugar level comprises restricting a monosaccharide, a disaccharide, a short-chain polysaccharide, or a combination thereof; decreasing BR activity comprises applying brassinazole; increasing osmotic stress comprises applying PEG 6,000; increasing ROS comprises applying hydrogen peroxide; increasing ABA activity comprises applying ABA, decreasing the activity of CYP707A, protein phosphatase 2C (PP2C), or a combination thereof; increasing SnRK activity comprises increasing an activity of SnRK1, SnRK2, or both; increasing meiosis specific RdDM comprises increasing an activity of RING/FYVE/PHD zinc finger superfamily protein, SUVH1, MED17, HEAT INTOLERANT 4 (HIT4), HISTONE 1.2 (H1.2), ANTHESIS PROMOTING FACTOR 1 (APRF1), SUO, THO1, HISTONE H2A 11 (HTA11), or a combination thereof.

In one non-limiting implementation, decreasing glucose signaling comprises restricting glucose applied to the female germline cell and/or the female germline-associated tissue (e.g., a pistil). In a non-limiting implementation, glucose is applied in a restricted amount and time to induce meiosis, syngamy, or both in the apomictic eukaryote. In a non-limiting implementation, glucose is applied in an amount between 0 and 30 mmol/liter (mM), or any number range in between, e.g., 0-25 mM, 0-20 mM, 0-15 mM, 0-10 mM, 0-6 mM, 0-5 mM, 0-4 mM, 0-3 mM, 0-2 mM, 0-1 mM, 0-0.05 mM, etc. In another non-limiting implementation, the duration of glucose restriction is less than 60 minutes, e.g., less than 55 minutes, less than 50 minutes, less than 45 minutes, less than 40 minutes, less than 35 minutes, less than 30 minutes, less than 25 minutes, less than 20 minutes, less than 15 minutes, or about 10 minutes, etc. In yet another non-limiting implementation, the duration of glucose restriction is between 0.1 and 60 minutes, or any length of time in between, e.g., 0.1-50 minutes, 0.1-10 minutes, 2-50 minutes, 2-45 minutes, 3-45 minutes, 3-40 minutes, 4-40 minutes, 4-35 minutes, 5-35 minutes, 5-30 minutes, 6-30 minutes, 6-25 minutes, 7-25 minutes, 7-20 minutes, 7-13 minutes, 8-12 minutes, or 9-11 minutes, etc. In a further non-limiting implementation, to induce meiosis, the time to begin glucose restriction is between 0.2 and 72 hours before megasporogenesis onset, or any length of time in between, e.g. 0.2-60 hours, 0.2-48 hours, 0.2-36 hours, 0.2-24 hours, 0.2-12 hours, 12-68 hours, 13-68 hours, 13-64 hours, 14-64 hours, 14-60 hours, 15-60 hours, 15-56 hours, 16-56 hours, 16-52 hours, 17-52 hours, 17-48 hours, 18-48 hours, 21-48 hours, 21-46 hours, 24-46 hours, 24-44 hours, 27-44 hours, 27-42 hours, 30-42 hours, 30-40 hours, 33-40 hours, 33-38 hours, or 34-38 hours, etc.

In one non-limiting implementation, increasing oxidative stress comprises applying hydrogen peroxide to the female germline cell and/or the female germline-associated tissue (e.g., a pistil). In a non-limiting implementation, hydrogen peroxide is applied in an amount and time sufficient to induce meiosis, syngamy, or both in the apomictic eukaryote. In a non-limiting implementation, hydrogen peroxide is applied in an amount between 20 and 500 mmol/liter (mM), or any number range in between, e.g., 20-400 mM, 20-350 mM, 35-350 mM, 35-300 mM, 50-300 mM, 50-250 mM, 65-250 mM, 65-200 mM, 80-200 mM, 80-150 mM, 85-150 mM, 85-130 mM, 90-130 mM, 90-110 mM, or 95-105 mM, etc. In another non-limiting implementation, the duration of hydrogen peroxide application (e.g., pre-treatment emersion) is between 2 and 90 minutes, or any length of time in between, e.g., 2-75 minutes, 3-75 minutes, 3-50 minutes, 4-50 minutes, 4-25 minutes, 5-60 minutes, 5-25 minutes, 5-23 minutes, 7-23 minutes, 7-21 minutes, 9-21 minutes, 9-19 minutes, 11-19 minutes, 11-17 minutes, 13-17 minutes, or 14-16 minutes, etc. In a further non-limiting implementation, to induce meiosis, the time to begin hydrogen peroxide application is between 1 and 96 hours before megasporogenesis onset, or any length of time in between, e.g. 1-84 hours, 2-84 hours, 1-72 hours, 2-72 hours, 3-72 hours, 3-60 hours, 3-48 hours, 4-48 hours, 4-36 hours, 5-36 hours, 5-24 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In one non-limiting implementation, increasing osmotic stress comprises applying PEG 6,000 to the female germline cell and/or the female germline-associated tissue (e.g., a pistil). In a non-limiting implementation, PEG 6,000 is applied in an amount and time sufficient to induce meiosis, syngamy, or both in the apomictic eukaryote. In a non-limiting implementation, PEG 6,000 is applied in an amount between 10 and 60 g/liter, or any number range in between, 10-54 g/liter, 10-40 g/liter, 12-54 g/liter, 12-48 g/liter, 14-48 g/liter, 14-42 g/liter, 16-42 g/liter, 16-36 g/liter, 18-36 g/liter, 18-30 g/liter, 20-30 g/liter, 21-29 g/liter, 22-28 g/liter, 23-27 g/liter, or 24-26 g/liter, etc. In another non-limiting implementation, the duration of PEG 6,000 application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 2-300 minutes, 2-250 minutes, 2-90 minutes, 2-75 minutes, 2-50 minutes, 2-45 minutes, 3-250 minutes, 3-200 minutes, 3-75 minutes, 3-50 minutes, 3-45 minutes, 3-40 minutes, 4-200 minutes, 4-150 minutes, 4-50 minutes, 4-25 minutes, 5-480 minutes, 5-150 minutes, 5-100 minutes, 5-25 minutes, 5-23 minutes, 4-40 minutes, 4-35 minutes, 5-35 minutes, 5-30 minutes, 6-30 minutes, 6-25 minutes, 7-25 minutes, 7-23 minutes, 7-21 minutes, 7-20 minutes, 7-13 minutes, 8-12 minutes, 9-21 minutes, 9-19 minutes, 9-11 minutes, 11-19 minutes, 11-17 minutes, 13-17 minutes, or 14-16 minutes, etc. In a further non-limiting implementation, to induce meiosis, the time to begin PEG 6,000 application is between 1 and 96 hours before megasporogenesis onset, or any length of time in between, e.g. 1-84 hours, 1-72 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In one non-limiting implementation, decreasing BR activity comprises applying brassinazole to the female germline cell and/or the female germline-associated tissue (e.g., a pistil). In a non-limiting implementation, brassinazole is applied in an amount and time sufficient to induce meiosis, syngamy, or both in the apomictic eukaryote. In a non-limiting implementation, brassinazole is applied in an amount between 0.1 and 10 micromol/liter (µM), or any number range in between, e.g., 0.2-10 µM, 0.2-9 µM, 0.3-9 µM, 0.3-7 µM, 0.4-7 µM, 0.4-5 µM, 0.5-10 µM, 0.5-4 µM, 0.6-4 µM, 0.6-3 µM, 0.7-3 µM, 0.7-2 µM, 0.7-1.3 µM, 0.8-2 µM, 0.8-1.2 µM, or 0.9-1.1 µM, etc. In another non-limiting implementation, the duration of brassinazole application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 1-60 minutes, 1-50 minutes, 2-300 minutes, 2-250 minutes, 2-90 minutes, 2-75 minutes, 2-50 minutes, 2-45 minutes, 3-250 minutes, 3-200 minutes, 3-75 minutes, 3-50 minutes, 3-45 minutes, 3-40 minutes, 4-200 minutes, 4-150 minutes, 4-50 minutes, 4-40 minutes, 4-35 minutes, 4-25 minutes, 5-480 minutes, 5-150 minutes, 5-100 minutes, 5-35 minutes, 5-30 minutes, 5-25 minutes, 5-23 minutes, 6-30 minutes, 6-25 minutes, 7-25 minutes, 7-23 minutes, 7-21 minutes, 7-20 minutes, 7-13 minutes, 8-12 minutes, 9-21 minutes, 9-19 minutes, 9-11 minutes, 11-19 minutes, 11-17 minutes, 13-17 minutes, or 14-16 minutes, less than 60 minutes, e.g., less than 55 minutes, less than 50 minutes, less than 45 minutes, less than 40 minutes, less than 35 minutes, less than 30 minutes, less than 25 minutes, less than 20 minutes, or less than 15 minutes, etc. In a further non-limiting implementation, to induce meiosis, the time to begin brassinazole application is between 1 and 96 hours before megasporogenesis onset, or any length of time in between, e.g. 1-84 hours, 1-72 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In one non-limiting implementation, increasing ABA activity comprises applying abscisic acid to the female germline cell and/or the female germline-associated tissue (e.g., a pistil). In a non-limiting implementation, abscisic acid is applied in an amount and time sufficient to induce meiosis, syngamy, or both in the apomictic eukaryote. In a non-limiting implementation, abscisic acid is applied in an amount between 0.1 and 10 micromol/liter (µM), or any number range in between, e.g., 0.2-10 µM, 0.2-9 µM, 0.3-9 µM, 0.3-7 µM, 0.4-7 µM, 0.4-5 µM, 0.5-10 µM, 0.5-5 µM, 0.5-4 µM, 0.6-4 µM, 0.6-3 µM, 0.7-3 µM, 0.7-2 µM, 0.7-1.3 µM, 0.8-2 µM, 0.8-1.2 µM, or 0.9-1.1 µM, etc. In another non-limiting implementation, the duration of abscisic acid application (e.g., pre-treatment emersion) is between 0.05 and 480 minutes, or any length of time in between, e.g., 0.1-480 minutes, 0.1-450 minutes, 0.5-450 minutes, 0.5-400 minutes, 1-400 minutes, 1-350 minutes, 1-300 minutes, 1-60 minutes, 1-50 minutes, 2-300 minutes, 2-250 minutes, 2-90 minutes, 2-75 minutes, 2-50 minutes, 2-45 minutes, 3-250 minutes, 3-200 minutes, 3-75 minutes, 3-50 minutes, 3-45 minutes, 3-40 minutes, 4-200 minutes, 4-150 minutes, 4-50 minutes, 4-40 minutes, 4-35 minutes, 4-25 minutes, 5-480 minutes, 5-150 minutes, 5-100 minutes, 5-35 minutes, 5-30 minutes, 5-25 minutes, 5-23 minutes, 6-30 minutes, 6-25 minutes, 7-25 minutes, 7-23 minutes, 7-21 minutes, 7-20 minutes, 7-13 minutes, 8-12 minutes, 9-21 minutes, 9-19 minutes, 9-11 minutes, 11-19 minutes, 11-17 minutes, 13-17 minutes, or 14-16 minutes, less than 60 minutes, e.g., less than 55 minutes, less than 50 minutes, less than 45 minutes, less than 40 minutes, less than 35 minutes, less than 30 minutes, less than 25 minutes, less than 20 minutes, or less than 15 minutes, etc. In a further non-limiting implementation, to induce meiosis, the time to begin abscisic acid application is between 1 and 96 hours before megasporogenesis onset, or any length of time in between, e.g. 1-84 hours, 1-72 hours, 2-84 hours, 2-72 hours, 3-72 hours, 3-60 hours, 3-48 hours, 4-48 hours, 4-36 hours, 5-36 hours, 5-24 hours, 6-72 hours, 6-24 hours, 6-22 hours, 7-22 hours, 7-20 hours, 8-20 hours, 8-18 hours, 9-18 hours, 9-16 hours, 10-16 hours, 10-14 hours, 11-14 hours, or 11-13 hours, etc. before megasporogenesis onset.

In a further aspect of the invention, there is provided sexual eukaryotes that reproduce apomictically, an apomictic eukaryote produced from a sexual eukaryote, an apomictic eukaryote that reproduces sexually according to the methods of the invention.

The following examples are illustrative only and are not intended to limit the disclosure in any way.

EXAMPLES

The following non-limiting examples illustrate further aspects of the invention.

Example 1. Genes Associated with Aposporous Embryo Sac Formation in Sorghum as Identified by Expression Profiling Background. In sorghum, complete apomixis has not been observed, but aposporous embryo sacs occasionally form in some genotypes (50). The studies in sorghum described here involved expression profiling to identify genes associated with apospory.

Materials and methods. These methods are sufficiently detailed to provide one skilled in the art with information needed to repeat the experiments.

We used an $F_2$ sorghum mapping population as previously described (50). For expression profiling, we used two sibs from the $F_2$ population, plant 151, with 14% aposporous embryo sac (ES) formation, and plant 264, with no aposporous ES formation (50). These were cloned by excising and growing tillers. For expression profiling, ovules were excised in nuclease free water, measured, and retained if their length matched a designated length corresponding to the MMC, meiocyte or ES stages (50). Excised ovules were placed in RNAlater® (Ambion), and five samples were collected for each of the six sib/stage combinations for a total of 601, 699 and 499 ovules for the MMC, meiocyte and ES stages of the non-AES forming sib, respectively and 508, 604 and 499 for the AES-forming sib, respectively. RNA was extracted, quality checked, amplified and labeled with Cy3 or Cy5. Quality of antisense RNA (aRNA) was checked, and 10 μg from each sample was labeled and purified on the day of microarray hybridization. Labeled aRNA (3 μg) was fragmented, and final aRNA concentrations and labeling efficiencies were measured. A saturated loop microarray design was used, which compared all two-way transcriptome comparisons among the six sib/stage combinations (15 microarrays total). Microarray probe sequences were designed and synthesized by CombiMatrix, Inc., on their CustomArray™ 12K format (Mukilteo, WA). Twelve thousand unique 35 nt sequences were designed from the sorghum Unigene EST database. Most ESTs represented on the microarray originated from reproductive tissues (ovules, embryos, panicles, pollen). Between 25-32% of sorghum open reading frames were represented (61). Microarray hybridizations were scanned, and all images were saved. Image analysis and data extraction were completed using Imagene (Biodiscovery, Inc., El Segundo, CA) microarray analysis software. Median pixel intensity values for each probe were used for data input. Data normalization and statistical analysis were performed using R/maanova and the Java interface J/maanova (62, 63). p values were false discovery rate (FDR) corrected, and significance was set at p=0.05.

Several genes identified as differentially expressed (DE) in this study were selected for quantitative RT-PCR (qPCR) validation. Primers were designed, checked for secondary structures, and subjected to BLAST searches to identify short, nearly exact sequences (word size, 7; expect value, 1000). Only sequences unique to sorghum were retained. Primer pairs, designed from S. bicolor sequence data, were tested for amplification of the expected cDNA region. Total RNA was isolated, digested, and cDNA synthesis was carried out. qPCR reactions were carried out using the following reaction conditions: 50° C., 2 min, 95° C., 10 min, 40 cycles of 95° C. for 30 sec, 54° C. for 30 sec and 72° C. for 30 sec. All reactions were set up in triplicate. Melting curves were used to determine specificity, and relative quantification values and standard deviations were calculated using the comparative CT method. Values were normalized to the expression of the reference. Differences in expression were identified using the Student's t-test.

For each gene found to be significantly up or down-regulated, the set of homologous EST sequences in the UniGene set was downloaded and aligned into a single "consensus" sequence. Each consensus sequence was BLASTx searched to determine its amino acid sequence homology to other plant sequences in the NCBI database. Where possible, putative gene names were assigned based on homologies to other annotated sequences. The significant genes were then located on the ten chromosomes of Sorghum bicolor by BLAST (64) searching the probe sequences against the genome assembly available through Phytozome.

Using TAIR accession identifiers, sorghum DE genes statistically up-regulated in experimental comparisons (up regulated in the treatments used as numerators in the gene expression ratios) were used to identify gene ontology (GO) categories (biological process, molecular function, cellular component) that were overrepresented by the respective up regulated genes. Panther Overrepresentation Tests (Apr. 17, 2013 release, Nov. 27, 2017 GO Ontology database release, Panther™ Classification System(65), Ver. 13.0) were used for these analyses. DE genes down regulated in the respective experimental comparisons (up regulated in the treatments used as denominators in the gene expression ratios) were likewise analyzed. Bonferroni corrections are conservative in overrepresentation and enrichment analyses. In this respect, our overrepresentation and enrichment objectives did not include identifying GO categories with extremely high levels of confidence. Instead, we i) identify molecular pathways that putatively cause sex apomixis switching (based on less conservative GO analyses), and ii) conducted thereafter specific experiments (Section III and Examples) to test the postulated pathways. While GO analyses were conducted at the P≤0.05 level of confidence, Bonferroni corrections were not performed.

Results and discussion. For DE gene detection, samples of stage 1 and 2 ovules from the sexual line were combined and compared to samples of stage 1 and 2 from the weakly aposporous line. This analysis identified 96 genes and 20 genes that were upregulated in the sexual and weakly aposporous samples, respectively. When stage 3 samples were compared, only two genes were upregulated in the sexual line, but 229 genes were upregulated in the weakly aposporous line. When Panther GO analyses were conducted, genes upregulated in stage 1 and 2 ovules from the sexual line identified 405 overrepresented GO categories. Genes upregulated in stage 1 and 2 ovules from the weakly aposporous line identified 258 overrepresented GO categories. The two genes upregulated in stage 3 ovules from the sexual line did not produce overrepresented GO categories. The 229 genes upregulated in stage 3 ovules from the weakly aposporous line identified 486 overrepresented GO categories.

Figure 2:
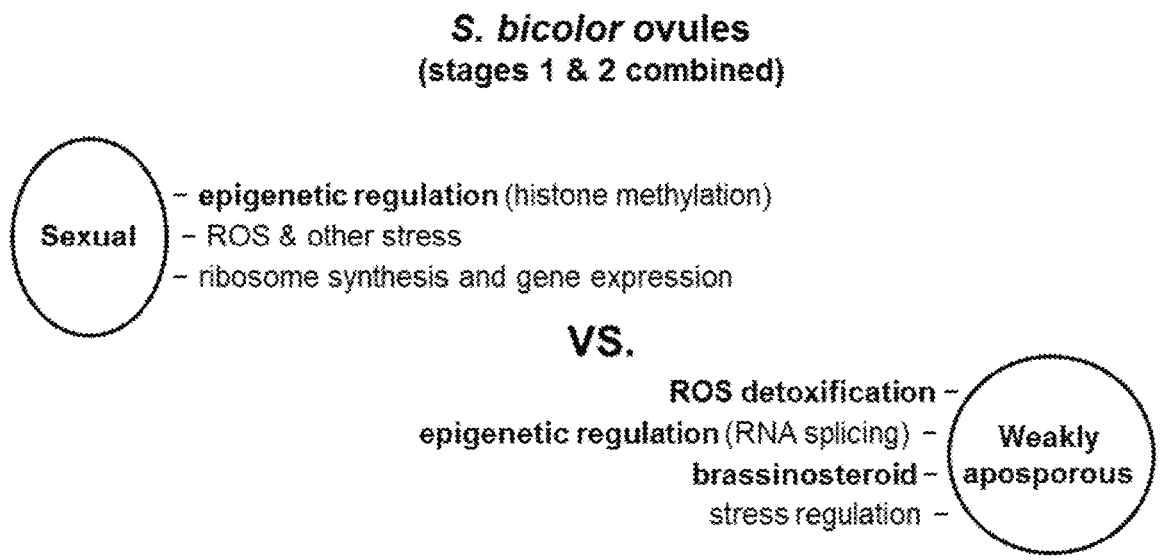
FIG. 2 Gene ontology (GO) categories of potential importance in determining reproductive mode during ovule development in *S. bicolor*. Stages 1 and 2 span early MMC formation through early ES formation.

Of all overrepresented GO categories identified, several loosely associated groups of categories are intriguing in terms of their possible involvement in shifting reproduction between apomixis and sex. In the stage 1 and 2 analyses (FIG. 2), ROS stresses, other stresses and epigenetic regulation, mostly involving histone modifications, were associated with sexual reproduction and the absence of apospory. In contrast, ROS detoxification, active regulation of cellular stresses, and brassinosteroid production and responses were associated with apospory. The two lines compared were sibs of an F2 mapping population, which showed variation for low frequency apospory[50]. Such observations are consistent with apomixis and sex being polyphenisms of each other, with the ability to switch between phenisms (in response to environmental parameters) being regulated by the genotype's ability to detoxify ROS and other metabolic stresses.

Example 2. Gene Expression Profiles Associated with Sexual Reproduction and Aposporous and Diplosporous Reproduction in *Boechera*

Background *Boechera* Á. Löve & D. Löve (Brassicaceae), a close relative of *Arabidopsis* (66), evolved ca. 2.5 myr ago (67) and contains ca. 83 inbreeding sexual species, many of which are localized endemics with restricted geographic ranges. It also contains many thousands of diploid to tetraploid interspecific hybrids, which sexually are semisterile. While producing some seeds sexually, in general the majority of these hybrids produce their seeds apomictically. This dual capability of producing seeds sexually or apomictically (facultative apomixis) is characteristic of most if not all angiospermous apomicts (1). Additionally, most angiospermous apomicts also exhibit geographic parthenogenesis, meaning their niche preferences extend from in to well beyond the habitats of their sexual relatives (8). In these respects, *Boechera* is no exception (68-74). Among the many thousands of naturally occurring apomictic hybrids of *Boechera*, 40 are recognized as having obtained broad distributions and being taxonomically distinct, and these have been elevated to species status (69-71, 75).

Apomixis in *Boechera* is gametophytic, i.e., ovules produce genetically unreduced embryo sacs (gametophytes), and the unreduced eggs in the embryo sacs develop into embryos parthenogenetically. *Taraxacum*-type diplospory (1st division restitution, FIG. 1) is common in *Boechera* (3, 4, 71, 76-79), and until recently, it was thought to be the only type of apomixis expressed in *Boechera*. *Hieracium*-type apospory (FIG. 1) has also been observed in *B. microphylla* (Nuttall) Dorn (77). Herein we report low frequency Antennaria-type diplospory (FIG. 1) for some *Boechera* hybrids. To identify genes associated with apomixis in *Boechera*, we conducted gene expression profiling experiments using mRNA obtained from immature ovules and pistils of apomictic and sexual *Boechera*.

Materials and methods. These methods provide one skilled in the art with sufficient information to repeat the experiments.

Cytological analyses of reproductive mode were performed using fixed floral buds of plants growing in native habitats, plants transplanted from native habitats to greenhouses or growth chambers, or plants grown from seeds (FIG. 4). For the latter, seeds were placed on moist filter paper, stratified for 21 d, and planted. Potted seedlings or transplants were grown in pots that contained Sunshine Mix #1 potting soil (Sun Gro Horticulture Canada Ltd, Vancouver, BC). Plants were vernalized for 10-12 weeks with minimal lighting and then transferred to controlled-environment greenhouses or growth chambers that maintained a 16/8 h day/night photoperiod using supplemental light provided by a combination of cool white florescent bulbs, incandescent bulbs, and high-pressure sodium-vapor lamps. These provided a minimum photosynthetic photon flux of 400 µmol m$^{-2}$ sec$^{-1}$ at the tops of the canopies. Day/night temperatures were maintained at 22/16° C., and plants were watered regularly with a dilute solution (250 mg L$^{-1}$) of Peters Professional 20:20:20 fertilizer (Scotts, Maryville, OH, USA).

Clusters of floral buds at the pre-anthesis stage were fixed in formalin acetic acid alcohol (FAA) for 48 h. The buds were then cleared in 2:1 benzyl benzoate to dibutyl phthalate (BBDP) (80) as follows: 70% EtOH, 30 min; 95% EtOH, 4 h (2×); 2:1 95% EtOH to BBDP, 2 h; 1:2 95% EtOH to BBDP, 4 h; 100% BBDP, 4 h; and 100% BBDP overnight. Pistils were then dissected from the floral buds. Pistil lengths, measured from the base of the pedicel to the top of the stigma (±0.05 mm), were then obtained using a dissection microscope, and the pistils were mounted on slides with a minimal amount of 2:1 BBDP clearing solution. The developmental stages of each ovule in each pistil were studied using a BX53 microscope (Olympus, Center Valley, Pa., USA) equipped with differential interference contrast (DIC) optics. Photographs of ovule development were taken using a MicroFire 599809 camera (Olympus).

Ovules were scored based on germline development. The following conditions were quantified: i) pre-meiotic megaspore mother cell (MMC), ii) meiotic or diplosporous dyad, iii) sexual tetrad of megaspores, iv) enlarged functional megaspore (FM) with three degenerating megaspores (sexually derived), v) early-stage 1 or 2-nucleate embryo sac with three degenerating megaspore remnants visible, vi) enlarged functional megaspore (FM) with only one degenerating megaspore (derived by *Taraxacum*-type diplospory), vii) early-stage 1 or 2-nucleate embryo sac with only one degenerating megaspore remnant (derived by *Taraxacum*-type diplospory), viii) early-stage 1 or 2-nucleate embryo sac with no degenerating megaspores present (derived by Antennaria-type diplospory), ix) presence of one or more enlarged non-vacuolate nucellar cells (aposporous initial, AI) that equal or surpass the size of the meiocyte (meiotically active MMC, dyad or early-stage tetrad), x) enlarged nucellar cell with one or more distinct vacuoles and 1-2 nuclei (early-stage aposporous embryo sac, AES). Because of increased uncertainties, the origins of embryo sacs (sexual, diplosporous or aposporous) were not reported beyond the 2-nucleate stage. Pistil length and the developmental stage of the majority of scorable ovules in the pistil were recorded for each pistil.

Relative levels of nuclear DNA in embryo and endosperm cells of single seeds and small groups of seeds were determined. Nuclei of mature seeds were isolated using a mortar, pestle and a few drops of DAPI (4,6-diamidino-2-phenylindole) containing Partec (Partec North America, Inc., Swedesboro, N.J., USA) buffer. Pestles were used to crack the seeds, and seed fragments were lightly crushed. Fragments were exposed to buffer for several minutes, and the nuclei-containing solutions were then filtered through 30 µm nylon filters into 1.2 mL tubes. Nuclear fluorescence was determined using a Partec I flow cytometer according to the manufacturer's instructions. Seeds with a 2:3 C embryo to endosperm ratio were considered to have formed sexually, while seeds with 2:5, 2:6, 2:7 or 3:9 C ratios were considered to have formed apomictically (2).

For expression profiling of sexual *B. stricta*, diplosporously apomictic *B. lignifera* and aposporously apomictic *B. microphylla*, average pistil lengths (n=20) for two embryological stages of ovule development were obtained: i) premeiotic megaspore mother cell (MMC) stage to the meiotic tetrad stage, and ii) early embryo sac stage to the pre-fertilized mature embryo sac (MES) stage. These averages were used to select pistils for expression profiling. Pistils from each species were excised in nuclease-Free water. Total RNA was extracted from pistils (100 per replication), excised ovules (1500 per replication), or excised anthers (80 per replication) as above and purified. mRNA samples from four stages (two replications per stage) were prepared for *B. lignifera* and *B. microphylla* ovules: pre-MMC, active meiocyte, early embryo sac, and late embryo sac to early embryony. mRNA samples from two stages (two replications per stage) were prepared for *B. stricta* and *B. lignifera* pistils: pre-MMC to active meiocyte and early to late embryo sac formation. Affymetrix (Santa Clara, Calif.)

two-cycle cDNA synthesis kits were used for cDNA synthesis and RNA amplification. cRNA were fragmented and loaded on Affymetrix *A. thaliana* GeneChip® microarrays (ATH1), one ATH1 microarray per biological replicate. Raw CEL files were assessed for quality using RMAExpress (chips with RLE-NUSE T2 values above the cautionary line were excluded from analyses), and lists of expressed genes were generated in BRB-ArrayTools, Version 4.6 using RMA normalization of only those CEL files involved in each differential expression test.

For downstream analyses, genes were excluded when <20% of their expression data (spots on arrays) had a ≥1.2 fold change in either direction from the gene's median (invariant or non-expressed genes) or when percent missing values exceeded 50%. After removal of the excluded genes, the BRB Class Comparison program was used to identify DE genes as determined by the significance threshold of univariate tests ($P<0.001$). Using TAIR accession identifiers, DE genes statistically up-regulated in experimental comparisons (up regulated in the treatments used as numerators in the gene expression ratios) were used to identify gene ontology (GO) categories (biological process, molecular function, cellular component) that were overrepresented by the respective up regulated genes. Panther Overrepresentation Tests (Apr. 13, 2017 release, Oct. 23, 2017 GO Ontology database release, Panther™ Classification System (65), Ver. 13.0) were used for these analyses. DE genes down regulated in the respective experimental comparisons (up regulated in the treatments used as denominators in the gene expression ratios) were likewise analyzed. Log base 2 values of expression ratios of genes that passed the BRB filter (significant or not) for each comparison were used to identify significantly enriched GO categories using Panther Enrichment Tests. EntrezID numbers were used for these enrichment analyses. When EntrezID numbers were represented by multiple *A. thaliana* Affymetrix probe set IDs, fold change values across the probe set IDs were averaged. Bonferroni corrections are conservative in overrepresentation and enrichment analyses. In this respect, our overrepresentation and enrichment objectives did not include identifying GO categories with extremely high levels of confidence. Instead, we i) identify molecular pathways that putatively cause sex apomixis switching (based on less conservative GO analyses), and ii) conducted thereafter specific experiments (Section III and Examples) to test the postulated pathways. While GO analyses were conducted at the $P \leq 0.05$ level of confidence, Bonferroni corrections were not performed.

qPCR verification for ZCW32 (At1g59640), MYC2 (At1g32640), PI (At5g20240), AP1 (AT1G69120), AGP22 (At5g53250), SHP1 (At3g58780), AGL6 (At2g45650), SEP3 (At1g24260), STK (At4g09960) and CDKB2 (At1g20930) were performed as above except that primers were designed from *A. thaliana* cDNA sequence data so as to amplify 150-250 bp from each *Boechera* gene and an 18S rRNA control gene (FIG. 5). Reaction conditions were: 50° C. for 2 min, 95° C. for 10 min, followed by 40 cycles of 95° C. for 30 sec, 54° C. for 30 sec and 72° C. for 30 sec. All reactions were performed in triplicate.

Figure 20:
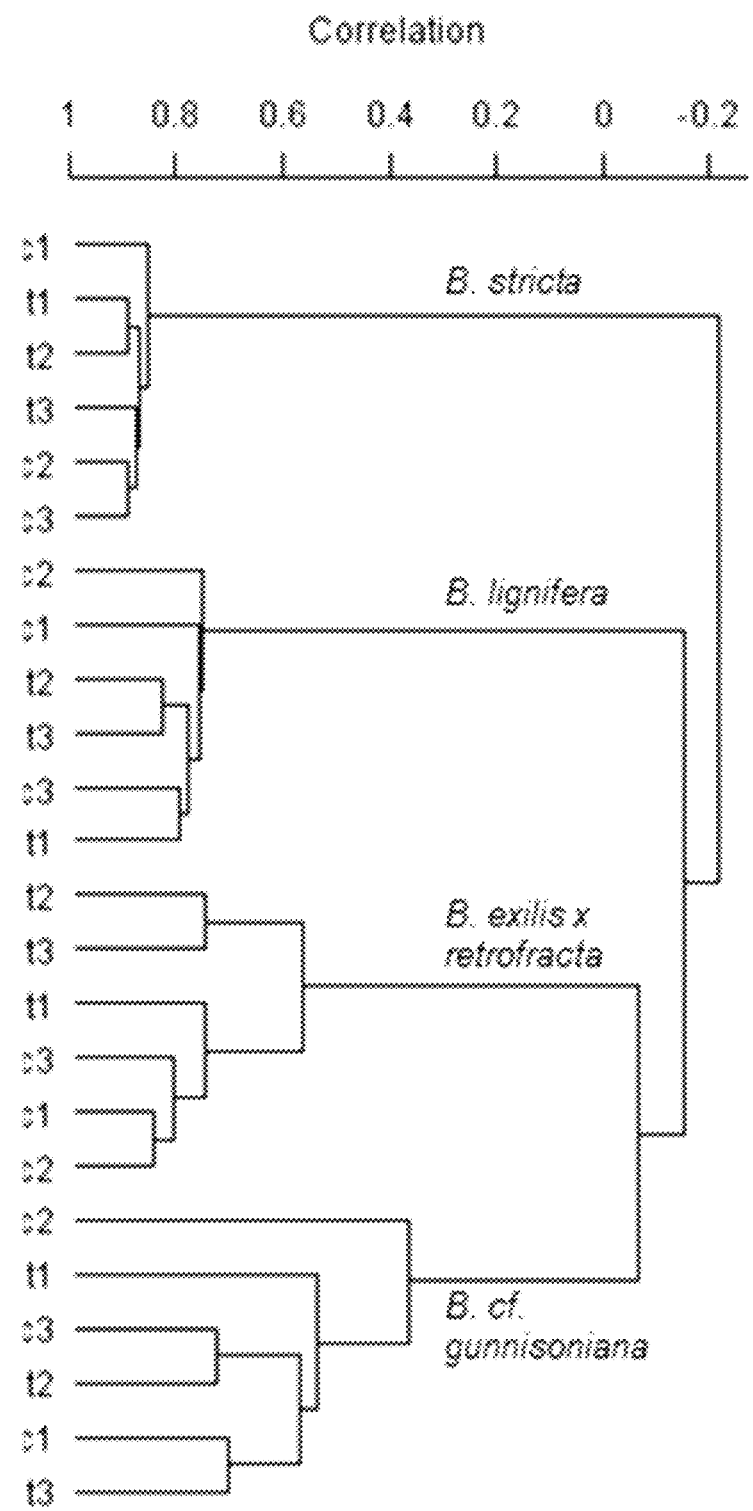
FIG. 20 Pairwise correlations among the 24 RNASeq taxa by treatment by replicate libraries after DESeq normalization and removal of low-count genes.

Results and discussion. We cytoembryologically analyzed 67 *Boechera* taxa (species and species hybrids, FIG. 4) to obtain a better understanding of the types of apomixis that occur in *Boechera* and the extensiveness of each type. All three of the major types of apomixis (FIG. 1) were observed. Diplospory of the *Taraxacum* type and apospory of the *Hieracium* type were about equal in occurrence. *Taraxacum* type diplospory tended to be weak or strong (<25 or >75% of ovules involved). In contrast, apospory was generally observed at frequencies >60% (FIG. 20). However, frequency values for apospory are likely underestimates because scoring for apospory was limited to the meiocyte to early 2-nucleate embryo sac stage (best for detecting diplospory), and aposporous embryo sacs can form after these stages. We also observed low frequency Antennaria type diplospory in two taxa (FIG. 6, taxa 48, 49; FIGS. 7A-7J).

Figure 6:
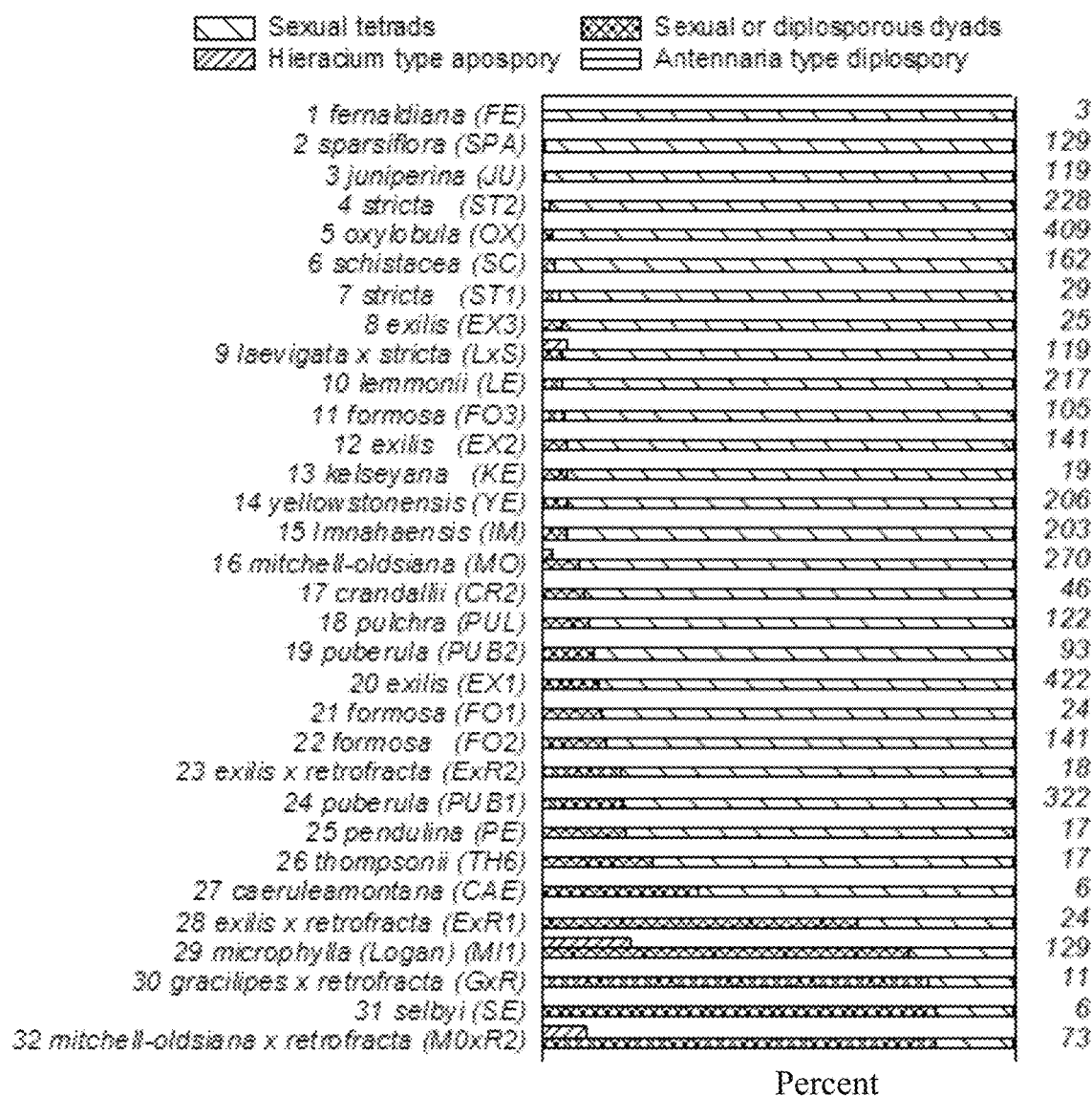
FIG. 6 Frequencies of sexual tetrads, sexual or *Taraxacum*-type diplosporous dyads, aposporous embryo sacs (enlarged single or multi-nucleate nucellar cells with one or more enlarge vacuoles), and Antennaria-type diplosporous MMC (where MMC skip meiosis and directly undergo gametophyte formation) for 67 *Boechera* taxa (see FIG. 4 for phylogenetic and collection location details). Frequencies of sexual tetrads, sexual or diplosporous dyads, and Antennaria-type diplosporous MMC per taxon sum to 100%. Aposporous ESs develop adventitiously, and their formation was usually accompanied by tetrad formation. Hence, frequencies of aposporous ES formation are shown separately. Generally, when a tetrad plus one or more aposporous embryo sacs formed, all megaspores of the tetrad degenerated. Numbers of informative ovules (dyad to tetrad stage through the early 2-nucleate ES stage) observed per taxon are shown to the right.
Figure 6:
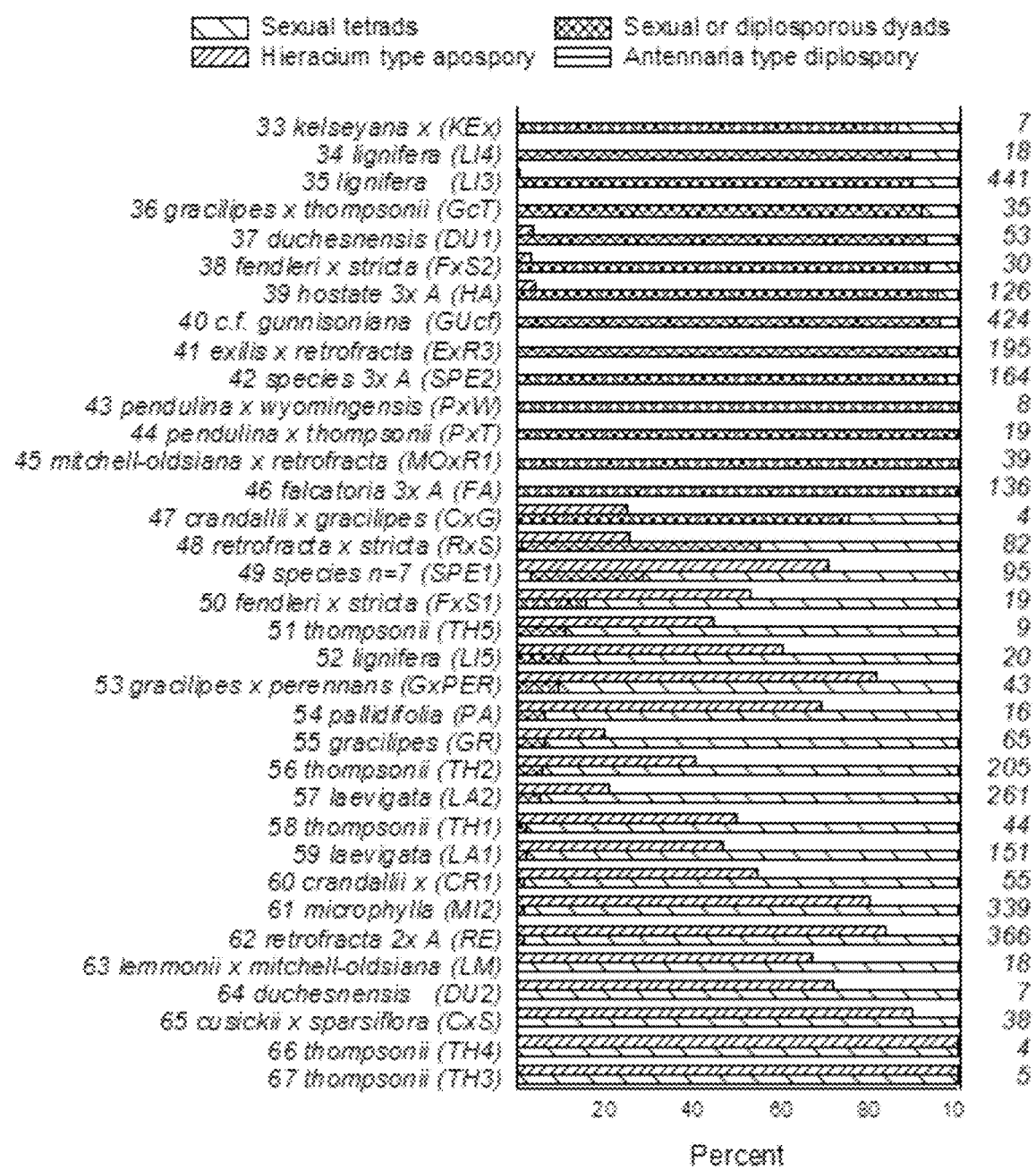
Figure 8A:
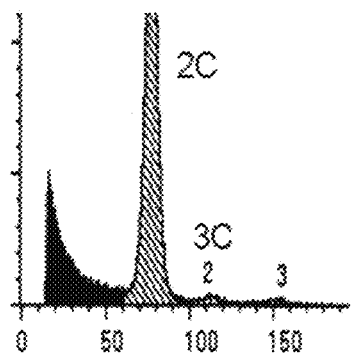
FIGS. 8A-8D Single-seed flow cytometry.
Figure 8C:
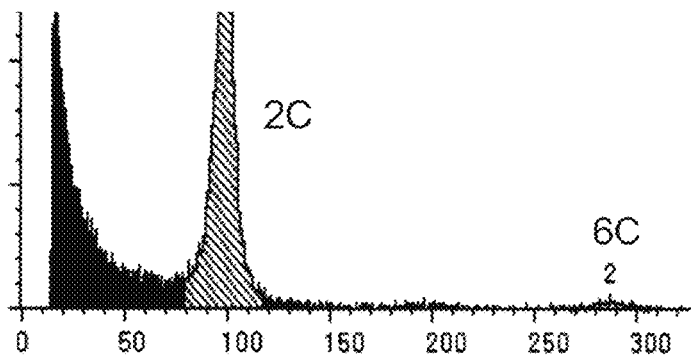
Figure 8B:
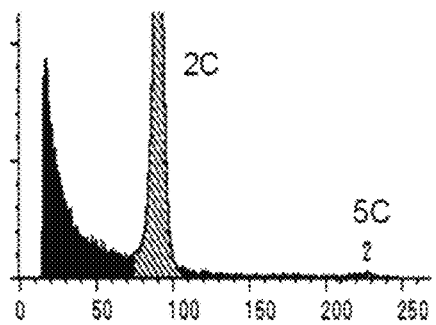
Figure 8D:
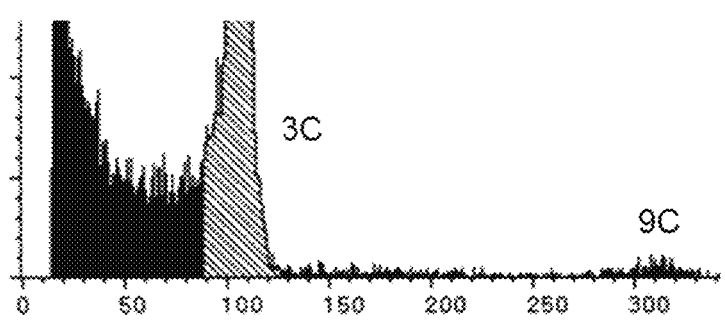

Some accessions of *B. microphylla* were more strongly aposporous than others (FIG. 6). While embryology suggested high frequency sexual seed set, single seed flow cytometry of *B. microphylla* seeds indicated that apomictic seed set is common and sexual seed set is rare in this collection (26). Central cells of aposporous embryo sacs (4n) of *B. microphylla* had been fertilized by genetically reduced sperm (1n) to produce 5n endosperm (FIGS. 8A-8D). Thus, for *B. microphylla* both sexual megasporogenesis and sexual microsporogenesis occurred to produce genetically reduced megaspores and microspores, but the reduced megaspores generally degenerated. It remains to be seen if other aposporous *Boechera*, which produce nonfunctional megaspores by meiosis, also produce genetically reduced pollen. In contrast with aposporous *B. microphylla*, both megaspores and microspores of diplosporous *Boechera* are generally unreduced (74, 75).

Figure 9A:
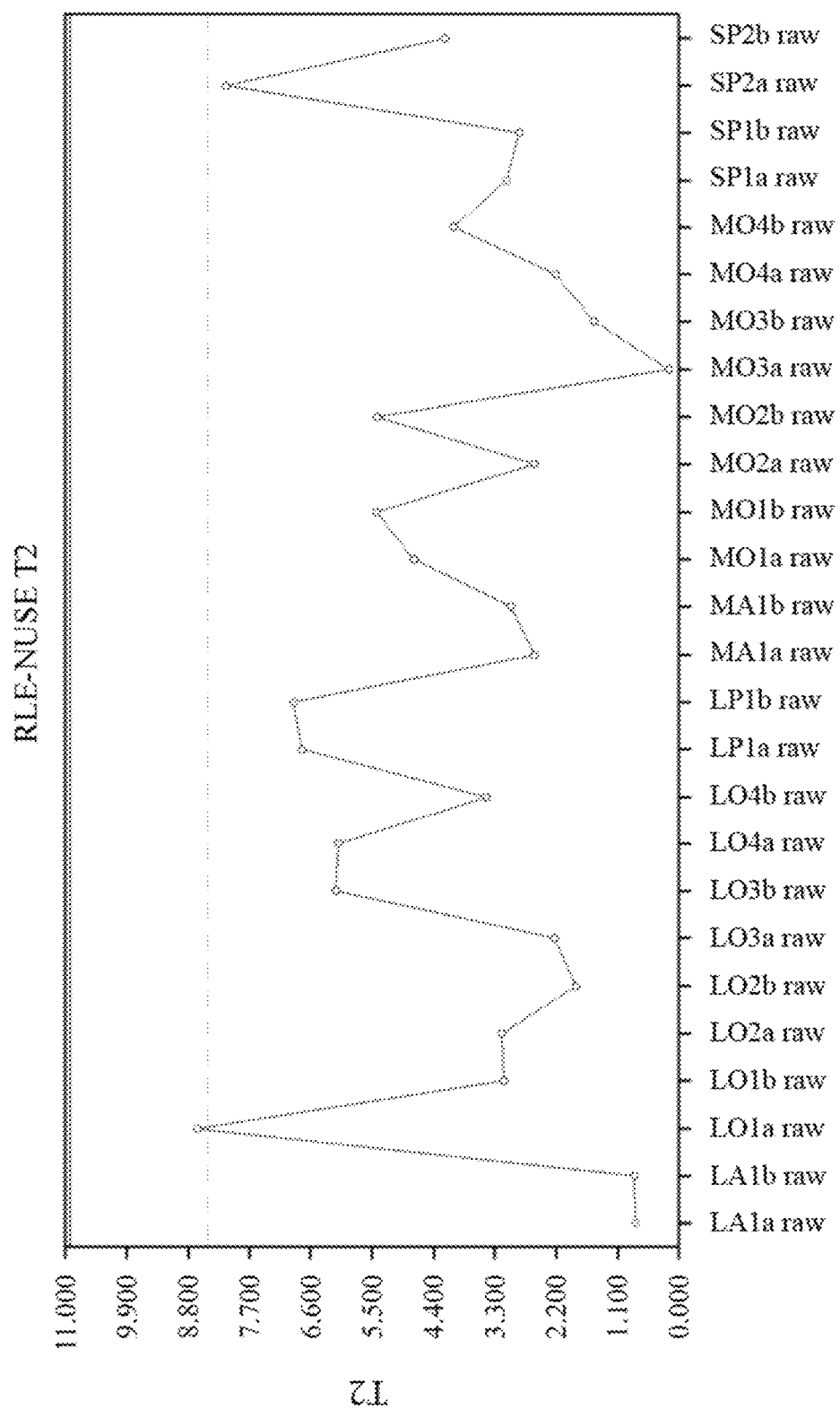
FIGS. 9A-9C Quality control analyses for Affymetrix microarray chips (ATH1-121501) used in the 10 experimental comparisons reported herein.
Figure 9B:
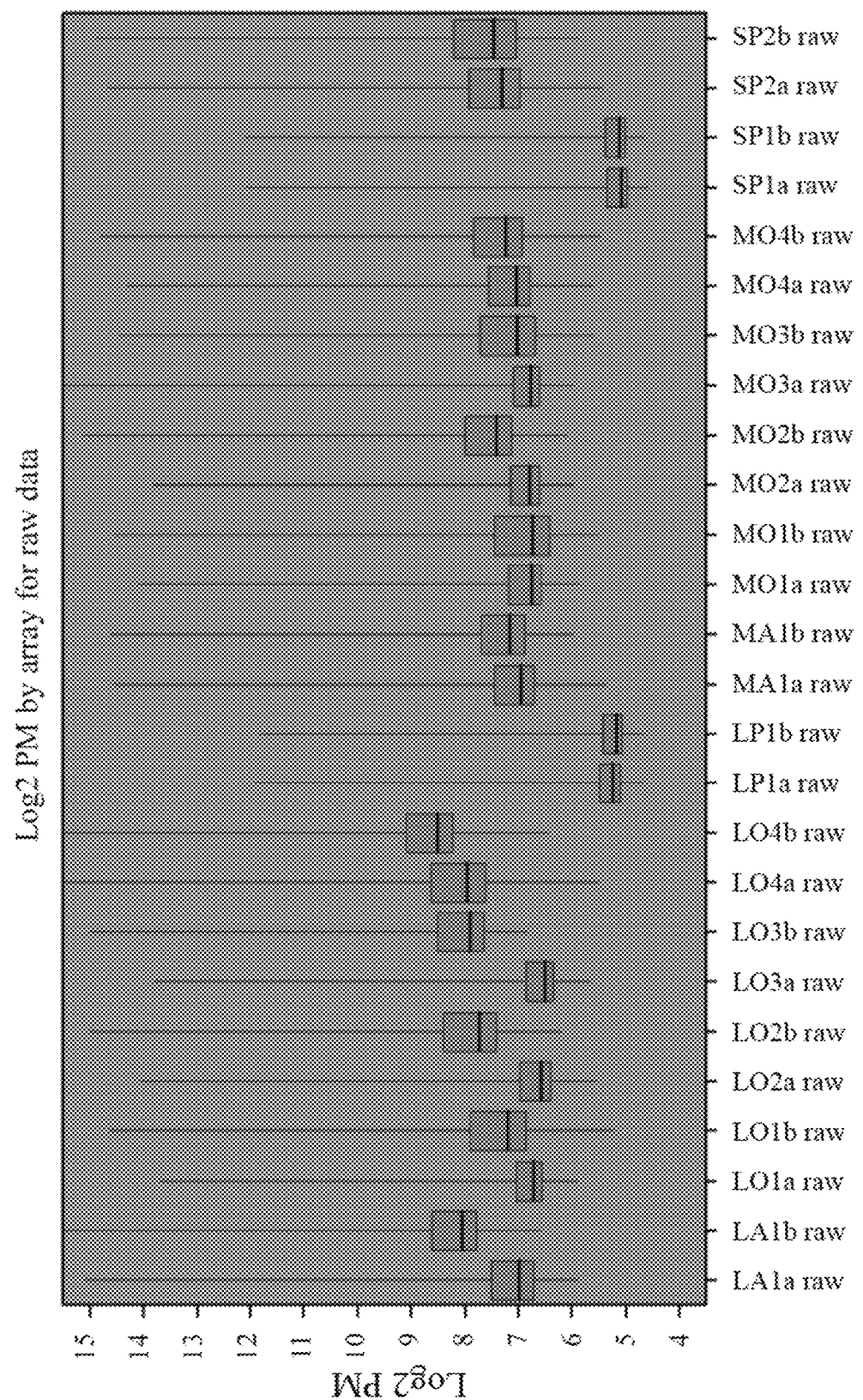
Figure 9C:
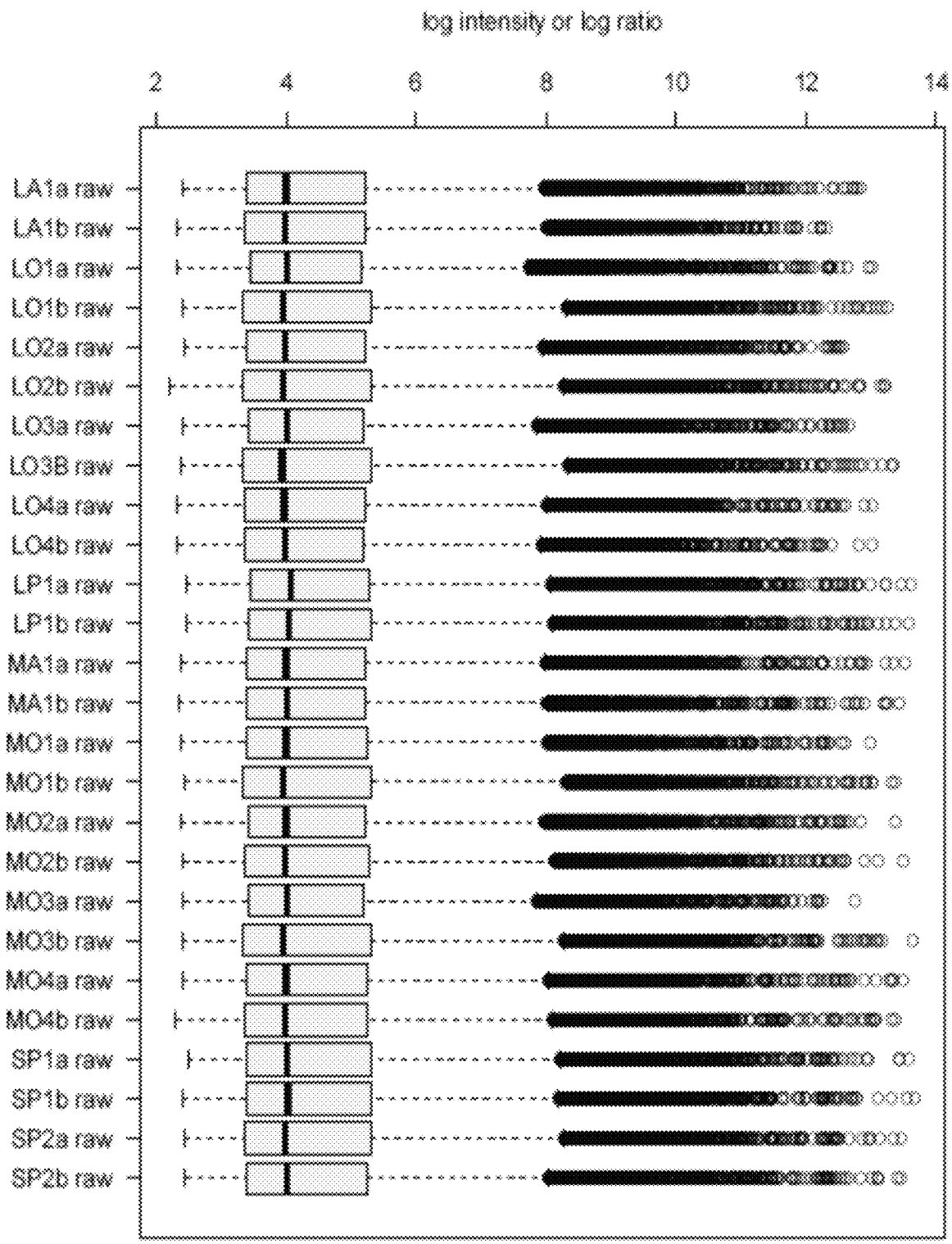
Figure 10:
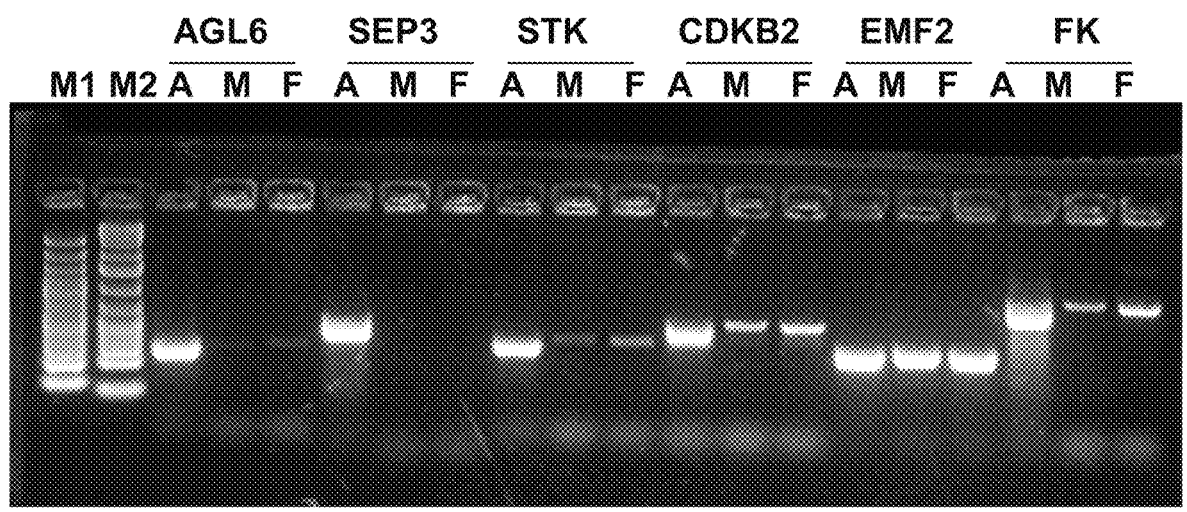
FIG. 10 Representative DNA amplifications for six of 16 genes selected for qPCR verification of the microarray analyses. Sequences for the first two genes did not amplify from *Boechera* DNA and were not used for qPCR. A: *Arabidopsis*; M: aposporous *B. microphylla*; F: sexual *B. formosa*.

From our cytological analyses of *Boechera* (FIG. 6 and FIGS. 7A-7J), we selected one sexual *Boechera*, *B. stricta*, and two apomictic *Boechera*, diplosporous *B. lignifera* (*Taraxacum* type diplosporous 2n egg formation and asexual 2n sperm formation by diplosporous like meiotic 1st division restitution) and aposporous *B. microphylla* (normal meiosis, surviving megaspore abortion, aposporous embryo sac formation and sexual 1n sperm formation) for gene expression profiling. Stages tested (with corresponding pistil lengths in mm) were: i) *B. lignifera*, MMC to 4-nucleate embryo sac (1.2-2.2) and 4-nucleate to mature embryo sac (2.4-4.0), ii) *B. microphylla*, MMC to 4-nucleate embryo sac (1.2-1.8) and 4-nucleate to mature embryo sac (2.0-4.0), and iii) *B. stricta*, MMC to 4-nucleate embryo sac (1.8-2.6) and 4-nucleate to mature embryo sac (3.2-4.0). Microarray chips that met quality control standards were used (FIGS. 9A-9C). To evaluate microarray accuracy, quantitative real time PCR (qPCR) primers were designed based on *Arabidopsis* sequences for 16 genes found to be DE in the microarray data. Primers for 14 of 16 selected genes (FIG. 4) efficiently amplified *Boechera* gene sequences (FIG. 10), and the direction of gene expression differences for these 14 genes was consistent across quantification methods (FIG. 11).

In the following list of comparisons, numbers of DE genes identified per comparison are shown in parentheses:
1. ovules, diplosporous *B. lignifera*, MMC to 4-nucleate vs. 4-nucleate to mature embryo sac stages (0),
2. ovules, aposporous *B. microphylla*, MMC to 4-nucleate vs. 4-nucleate to mature embryo sac stages (14),
3. ovules, *B. lignifera* vs. *B. microphylla*, MMC to 4-nucleate embryo sac stages (211),
4. ovules, *B. lignifera* vs. *B. microphylla*, 4-nucleate to mature embryo sac stages (64),
5. ovules, *B. lignifera* vs. *B. microphylla*, MMC to mature embryo sac stages (359),
6. anthers vs. ovules, *B. microphylla*, sporocyte to early gametophyte development (1345),
7. anthers vs. ovules, *B. lignifera*, sporocyte to early gametophyte development (802),
8. anthers, *B. lignifera* vs. *B. microphylla*, sporocyte to early gametophyte development (1378).

Comparisons 1-5 involved gene expression in ovules of diplosporous *B. lignifera* (1$^{st}$ division restitution) and/or ovules of aposporous *B. microphylla* (normal meiosis, surviving megaspore abortion, aposporous embryo sac formation). No DE genes were identified when early vs. late staged *B. lignifera* ovules were compared, and only 14 DE genes were identified between these stages for *B. microphylla*. Hence, stages within species were combined, and overrepresentation and enrichment GO analyses were conducted only for Comparison 5. This analysis identified more DE genes than Comparisons 3 and 4 (early vs. early and late vs. late).

Overrepresented and enriched GO categories in *B. microphylla* ovules (meiotically successful but sexually aborted and aposporous) compared to *B. lignifera* ovules (diplosporous) included those suggestive of energy deficient conditions, e.g., cellular stresses, meiosis and autophagy, as well as opposite categories suggestive of energy rich conditions, e.g., ribosome biosynthesis, gene expression and embryo sac formation. Those suggestive of energy deprived conditions and meiosis included:
    hypoxia
    alternative respiration
    glycolysis
    ROS
    superoxide
    senescence
    programmed cell death
    catabolism
    other stresses
    meiosis.

Those suggestive of energy rich conditions and the onset of aposporous embryo sac formation include:
    antioxidant activity
    histone methylation
    ribosome biosynthesis and function, a strong indicator of active TOR (17)
    transcription factor activity
    cell signaling
    embryo sac formation.

Hypoxia, as observe in *B. microphylla* ovules, can suppress ROS detoxification processes and increase ROS and superoxide levels, alternative respiration, catabolism and glycolysis (81-83). These data suggest that severe hypoxia and related stresses may have not only induced meiosis but also functional megaspore abortion. This stress may have also caused nucellar cells to abort their normal route of programmed cell death and to instead undergo apospory. Alternatively, apospory might have been induced by a temporally delayed expression of the apomixis phenism, which would have then silenced sex post-meiotically, at the functional megaspore stage (causing all megaspores to abort), and induced aposporous embryo sac formation. Interestingly, the up-regulated genes associated with ribosome synthesis and transcription factor activity suggest an energy rich environment, which contrasts sharply with the observed stress associated GO categories. Cells undergoing stress-induced autophagy may have supplied aposporous nucellar cells with sufficient nutrients to support embryo sac development.

Ovules with their nucellar cells are evolutionary innovations of sporangia (84), which in lower plants, e.g., ferns, contain multiple spore mother cells (evolutionary progenitors of nucellar cells) that in many species are meiosis, apomeiosis and apogamy competent (adventitious embryo formation from gametophytes) (38). Hence, from an evolutionary perspective, nucellar cells could reasonably possess latent capacities to form meiotic or apomeiotic mother cells, sexual or asexual spores, sexual or asexual gametophytes, or complete embryos adventitiously.

Evidence that post-meiotic abortion and autophagy coupled with apospory in *B. microphylla* was caused by either oxidative stress or a delayed onset of apomixis was also obtained from comparisons of *B. microphylla* ovules vs. *B. microphylla* anthers. In ovules, sex advanced through meiosis and then aborted, but in anthers sex continued through to functional pollen formation. The following GO categories were associated with meiosis followed by sexual failure and apospory in *B. microphylla* ovules (compared to anthers). Those putatively associated with inducing meiosis and causing its collapse include:
    low energy levels
    ROS and superoxide formation
    unfolded protein response
    meiosis.

Those putatively associated with late onset of the apomixis (apospory) program: steroid production; epigenetic silencing; ribosome biogenesis, transcription and translation.

Figure 12:
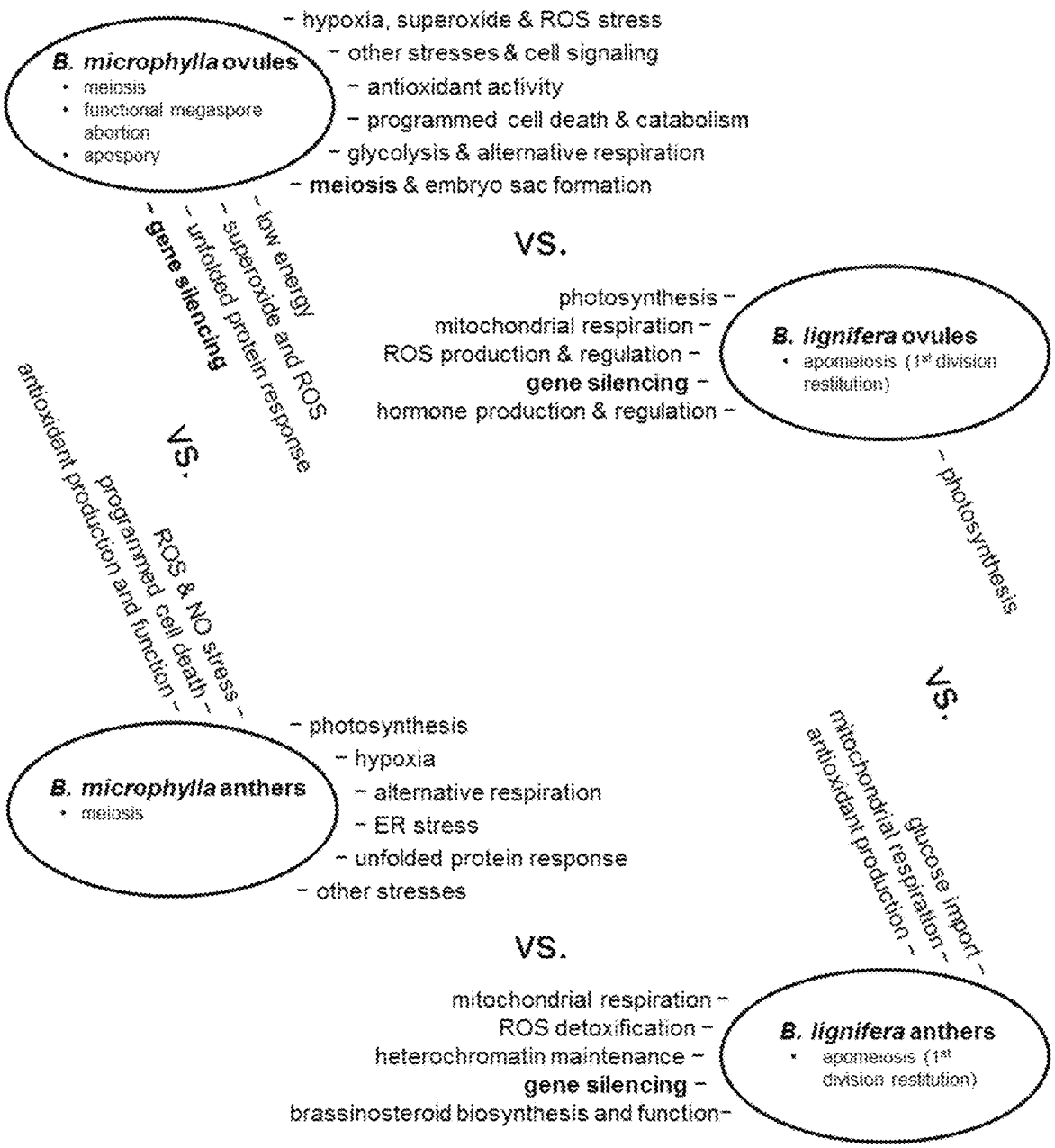
FIG. 12 Summary of overrepresented and enriched GO categories symptomatic of the metabolically enriched and metabolically challenged conditions that are putatively responsible for the polyphenic apomixis/sex switch in *Boechera* as detailed in the text.

It remained unclear from these data as to what induced the apomixis phenism in *B. microphylla* ovules, the tissues of which experienced high levels of oxidative stress. However, when apomixis was induced, genes required to complete the sex phenism were apparently silenced (FIG. 12).

Silenced genes in apomictic ovules of *B. lignifera* and *B. microphylla* included those that would have encoded (had they not been silenced) the progression of the sexual phenism, i.e., meiosis, reduced embryo sac formation, parthenogenesis suppression, and establishment of a requirement that syngamy precede embryony (fertilization requirement or dependence). Notable among the upregulated epigenetic silencing machinery in apomictic ovules were:
    heterochromatin maintenance genes
    RNA polymerase IV genes, which produce siRNAs that silence genes by RNA directed DNA methylation
    hi stone H3-K9 genes that silence genes by methylation
    deacetylation genes
    chromatin silencing genes in general
    genes responsible for negative epigenetic regulation of gene expression.

That gene silencing coincided temporally with the cytologically detectable silencing of sex is evidence that gene silencing machinery, putatively part of the apomixis phenism machinery, was responsible for silencing sex.

From an evolutionary perspective, it seems reasonable that apomixis would keep sex silenced during favorable growth conditions (maintain a heterochromatic state upon genes required for sex). Apomixis in the life cycles of many protists and extant cyclical animal apomicts, e.g., many species of water fleas, aphids and other insects (9), is responsible for rapid population expansion in favorable environments. In contrast, stress suppresses apomixis and induces sex in many organisms, which thereafter produce dormant spores or overwintering eggs. Our profiling results are consistent with these life cycle observations. For example, GO categories associated with epigenetic silencing were overrepresented and enriched to a greater extent in diplosporously apomictic *B. lignifera* ovules compared to aposporously apomictic *B. microphylla* ovules. The latter suppress sex much later in ovule development, i.e., after meiosis. This suggests that the difference between diplospory and apospory is one of timing, i.e., the timing in which the apomixis phenism is expressed, early for diplospory and later (after meiosis) for apospory.

Cells and tissues of diplosporous *B. lignifera* ovules were experiencing favorable metabolic conditions as evidenced by the following overrepresented and enriched categories (compared to ovules of aposporous *B. microphylla*):
  oxygen and energy production by photosynthesis
  ATP production by mitochondrial respiration
  ROS production (byproduct of active photosynthesis and respiration) but with mechanisms that effectively detoxify it
  gene silencing, i.e., production of epigenetic regulation enzymes, which regulate the expression and silencing of genes, presumably silencing genes required for the expression of the sexual phenism
  production of enzymes that produce and regulate hormones, which in turn regulate the active growth and development processes expected if apomixis is induced by favorable metabolic and growth and development conditions.

While ovules of diplosporous *B. lignifera* were experiencing favorable conditions, they were also epigenetically silencing genes that in *B. microphylla* ovules were encoding meiosis, i.e., genes that were upregulated in *B. microphylla* ovules (presumably because of stress) compared to *B. lignifera* ovules. These observations are consistent with our teachings and methods that i) favorable metabolic conditions induce the apomixis phenism, which includes epigenetic silencing of meiosis (sex), and ii) stressful conditions induce the sexual phenism, which includes the silencing of the apomixis phenism possibly through H3-K9 methylation.

Ovules and anthers differ morphologically. During development individual ovules produce and nourish a single gametophyte. In contrast, a single anther produces and nourishes thousands of gametophytes. The latter is accomplished by episodes of programmed cell death (autophagy) where dying anther cells relinquish nutrients that are absorbed by developing gametophytes(85). The following overrepresented GO categories in *B. microphylla* anthers (compared to *B. microphylla* ovules) may be indicative of these autophagic episodes:
  ROS stress nitric oxide stress and programmed cell death
  antioxidant production and function.

As noted above, apomeiotic *B. lignifera* and meiotic *B. microphylla* ovules developed in metabolically stable and unstable conditions, respectively. *Boechera lignifera* anthers, which produce unreduced pollen, also developed in metabolically stable conditions. Cellular energy resources between apomeiotic *B. lignifera* ovules and anthers differed. In ovules, photosynthesis appeared to provide glucose for respiration, while in anthers sugars were imported. Levels of oxidative stress did not differ between ovules and anthers of *B. lignifera*, but were, as noted above, lower compared to those in *B. microphylla* ovules. GO categories associated with antioxidants were overrepresented in anthers, which might reflect the ROS induced programmed cell death experienced by autophagic anther tissues during pollen development.

Gene silencing as observed in apomeiotic *B. lignifera* ovules vs. meiotic *B. microphylla* ovules was also seen in apomeiotic *B. lignifera* anthers compared to meiotic *B. microphylla* anthers (Comparison 8). GO categories that were overrepresented or enriched in *B. lignifera* anthers and relevant to energy production and use, ROS detoxification, and gene silencing included:
  active mitochondrial respiration
  ribosome biogenesis and function (indicative of a high energy status)
  brassinosteroid (BR) biosynthesis and function
  ROS detoxification
  gene silencing and heterochromatin maintenance.

GO categories overrepresented or enriched in *B. microphylla* anthers and relevant to metabolic stress and photosynthesis included:
  hypoxia
  alternative respiration
  endoplasmic reticulum stress, including responses to unfolded proteins
  other stresses
  photosynthesis and glucose transport.

Apparently, the observed photosynthesis in *B. microphylla* anthers was not producing sufficient oxygen and energy to avoid the observed stresses. As discussed below, photosynthesis, autophagy, and the tricarboxylic acid cycle can be activated by stress (13, 17).

Cellular stress and photosynthesis, as observed in meiotic *B. microphylla* ovules and anthers, is consistent with energy reserves being regulated by stress-activated SNF1-Related Kinase 1 (SnRK1). During stress, this enzyme regulates energy production and use by i) activating photosynthesis enzymes and other enzymes by phosphorylation, ii) inducing transcription of autophagy enzymes, and iii) suppressing growth and development by silencing TARGET OF RAPAMYCIN (TOR) (13, 16, 17). Compared with stressed and meiotically active ovules and anthers of *B. microphylla*, ovules and anthers of apomeiotic *B. lignifera* were developing in high-energy environments where they actively respired, detoxified ROS, silenced genes and regulated energy and growth (FIG. 12). This high-energy scenario is consistent with i) inactivation of SnRK1 by sugar phosphates and protein phosphatases, ii) TOR activation, and iii) growth being balanced with energy availability by BR signaling (13, 16, 17, 25).

Figure 13A:
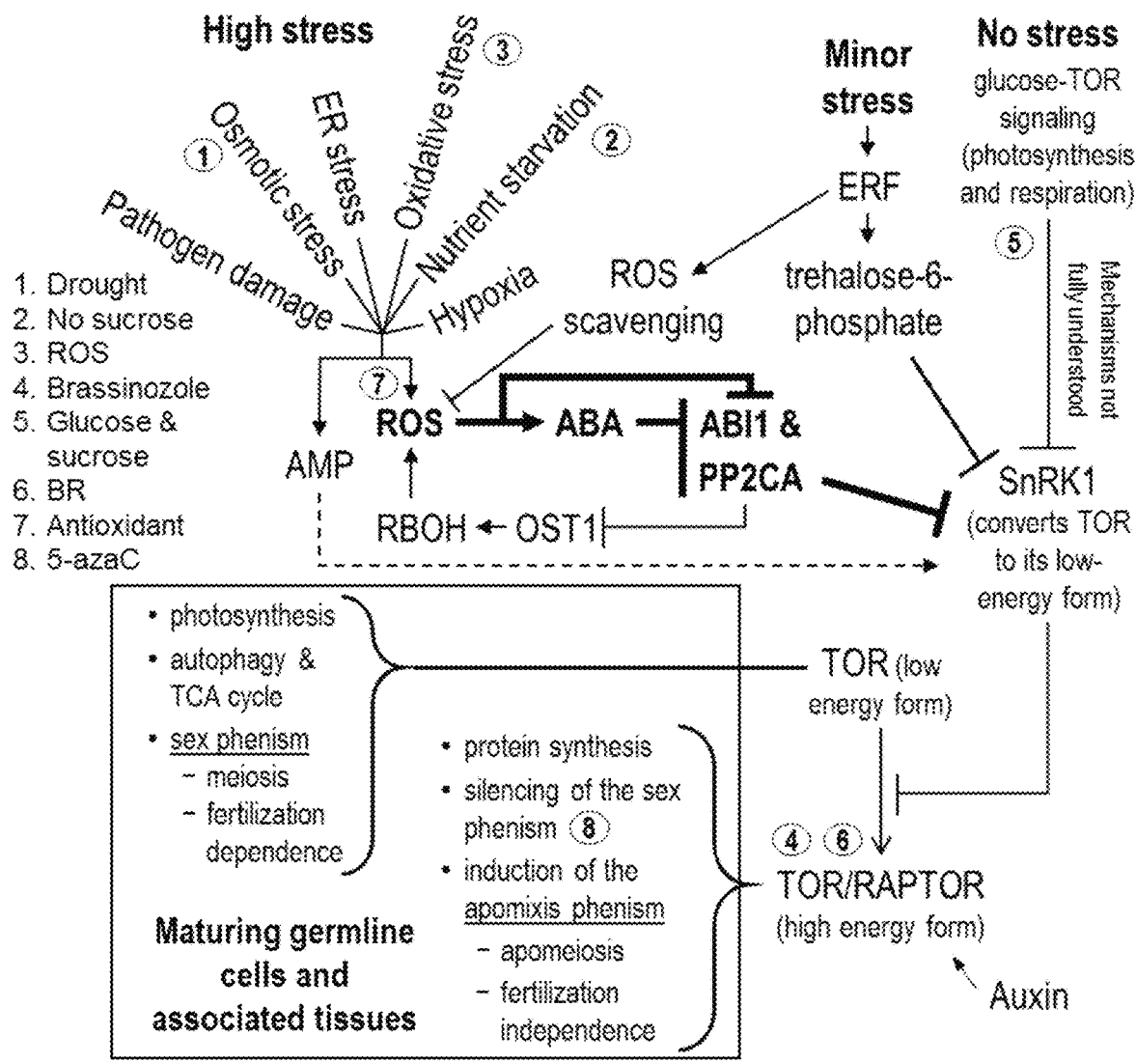
FIGS. 13A-13B Abbreviated model of energy regulated apomixis sex switching.
Figure 13B:
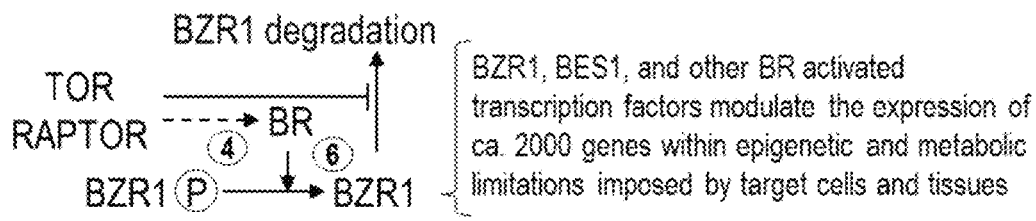

Putative components of a stress-regulated apomixis-sex switch are presented in FIGS. 13A-13B. This figure displays the antagonistic relationship between two enzyme complexes, TOR and SnRK1. This antagonistic relationship occurs between orthologs of these enzyme systems in all kingdoms of eukaryotes[13], which makes this switch mechanism attractive as the potentially ancient switching mechanism that has controlled sex apomixis switching in eukaryotes since the evolution of eukaryotes, i.e., eukaryogenesis. In eukaryotes, this switch balances energy availability against growth and development. The most ancient of the enzyme complexes is the central cellular energy sensor, which has sequence and function homologies extending deep into prokaryotic lineages. The orthologs of this sensor in Kingdoms Fungi, Animalia and Plantae are Sucrose Non-Fermenting 1 (SNF), AMP-Activated Kinase (AMPK), and SnRK1, respectively (13). Energy poor or other stress conditions activate these sensors, and the active forms induce downstream responses that promote survival. Central to these responses is a selective but severe curtailment of translation and protein processing, which represent the highest energy sinks in eukaryotic cells. In favorable metabolic conditions, TOR phosphorylates ribosomal protein S6, which enables translation. During stress, SNF, AMPK or SnRK1 silence TOR thereby greatly reducing rates of ribosome biosynthesis and protein translation (the highest ATP user processes in cells). Active forms (post-translational modifications (13)) of SNF, AMPK and SnRK1 perform many additional functions by allosterically regulating transcription factors, metabolism enzymes and other regulatory proteins (13, 16, 17, 25). The energy conserving effects include i) remobilization of nutrients by senescence, autophagy and catabolism, ii) induction of photosynthesis, and iii) activation of alternative ATP synthesis processes. To the extent that SNF, AMPK and SnRK1 signaling causes a hunkering down of growth and development, active TOR signaling does the opposite. It antagonistically counters SnRK1 signaling (16, 86) and induces DNA synthesis, mitosis, translation and respiration, and epigenetic modifications required for active and energy-dependent developmental programs from flowering through seed formation, germination, and plant growth and maturation (18, 19).

In responding to metabolically favorable or stressful cellular conditions, the antagonistic interactions between SnRK1 (or its orthologs in other Kingdoms) and TOR constitute the central molecular switch system that pits energy use or conservation against growth and development in diverse cells and tissues across all eukaryotes. Based on our gene expression results, we discovered that i) rather massive changes in gene expression occur in germline cells when active forms of SNF, AMPK and SnRK1 are present, and ii) these gene expression changes, when they occur in epigenetically determined germline cells, will induce meiosis. We also discovered that gene expression changes induced by TOR activation in germline cells will silence meiosis and induce apomeiosis (FIGS. 13A-13B). Our data are remarkably consistent with this explanation, i.e., that sex or apomixis expression in *Boechera* is regulated by crosstalk between SnRK1 and TOR. Important to our teachings is that the causal crosstalk occurs within the epigenetic and metabolomic limits imposed by germline cells and associated tissues, i.e., developmental processes associated with sex or apomixis would not be expected in other cells or tissues (FIGS. 13A-13B).

Our teachings, as represented in FIGS. 13A-13B, are based on observations from ovules and anthers of two apomictic *Boechera*, one that undergoes meiosis (*B. microphylla*) in ovules and anthers and one that undergoes apomeiosis (*B. lignifera*) in ovules and anthers. To further test our teachings, we determined gene expression levels in young pre-fertilization pistils (not ovules) of a fully sexual species, *B. stricta*, and in like-staged pistils of the diplosporous *B. lignifera*. Limited financial resources precluded the microdissection of ovules for these analyses. We then made the following comparisons:

1. diplosporous *B. lignifera* pistils vs. sexual *B. stricta* pistils, MMC to 4-nucleate embryo sac stages (836)
2. diplosporous *B. lignifera* ovules vs. diplosporous *B. lignifera* pistils, MMC to 4-nucleate embryo sac stages (159)
3. diplosporous *B. lignifera* ovules vs. sexual *B. stricta* pistils, MMC to 4-nucleate embryo sac stages (309)
4. aposporous *B. microphylla* ovules vs. sexual *B. stricta* pistils, MMC to 4-nucleate embryo sac stages (1006)

Using pistils for gene analyses, not ovules, introduced to our analyses additional tissue types, e.g., immature ovary walls, styles, stigmas, and additional vascular tissues. Such tissues were avoided when microexcised ovules were analyzed. Also, different *Boechera* species contain different numbers of ovules per pistil. Sexual *B. stricta* pistils contain 110-216 ovules, while *B. lignifera* pistils contain 48-74 (75). However, silique lengths at maturity differ, which compensates for differences in ovule numbers per pistil such that ovule to ovary tissue ratios are likely similar across species. In an attempt to parse confounding influences of pistil tissues from ovule tissues, we made pistil vs. pistil and ovule vs. pistil comparisons within and across species.

Consistent with meiotic ovules (and anthers) of *B. microphylla*, gene expression in pistil tissues of meiotic *B. stricta* (compared to diplosporous *B. lignifera*, analysis 9) was characterized during megasporogenesis by overrepresented or enriched GO categories related to ROS and ER stress, cell detoxification, and meiosis.

ROS stress
ER stress, apoptosis, catabolism, and abscisic acid
ROS induced $Ca^+$ transport and glycolysis
meiosis.

However, the *B. stricta* pistils also showed signs of energetic development.

respiration
ribosome biosynthesis and function
gene expression.

A possible interpretation of these findings, which is consistent with our teachings (FIGS. 13A-13B), is that the outer pistil tissues of sexual *B. stricta* were bioenergetic while the ovules within these tissues were energy deficient, i.e., they experienced ROS and ER stress and in turn underwent meiosis. In contrast, gene expression in pistil tissues of diplosporous *B. lignifera* (compared to those of sexual *B. stricta*) were actively photosynthesizing, respiring, detoxifying ROS, and silencing genes, presumably including genes associated with the sexual phenism.

photosynthesis
respiration
ROS detoxification
gene silencing

However, pistils of both species experienced various levels of stress and active hormone activity.

stress
hormone activity

Stress-related gene expression in *B. lignifera* pistils is not initially consistent with our teaching. To better locate the source of this stress, whether from internal ovules, external pistil tissues, or both, we conducted two additional analyses (10-11). Analysis 10, *B. lignifera* ovules vs. *B. lignifera* pistils, failed to locate the source, i.e., stress response GO categories were not overrepresented or enriched in pistil samples. This would have suggested that the stress was coming from exterior pistil tissues. However, pistils contain ovules, and together, these were compared to samples of just ovules. The presence of ovules in both samples may have diluted the comparison. Even with ovule dilution, GO categories associated with epigenetic silencing were overrepresented in the ovule-only samples. This supports our teachings that silencing mechanisms are active in ovules of apomicts where they silence, or keep silent, the sex phenism. In like manner, photosynthesis GO categories were overrepresented or enriched in ovules. Thus, the photosynthetically active ovules of *B. lignifera* apparently caused the photosynthesis differences noted above between *B. lignifera* pistils and *B. stricta* pistils. Photoperiodism related GO categories were also overrepresented or enriched in ovules. In contrast, external *B. lignifera* pistil tissues were energetically active as suggested by the following GO categories that were overrepresented or enriched in pistils:

respiration and gluconeogenesis
ribosome biosynthesis and function
transcription.

Multiple but mostly different stress related GO categories were overrepresented or enriched in pistils of both diplosporous *B. lignifera* and sexual *B. stricta* (when compared, analysis 9). Also, the *B. lignifera* ovule vs. pistil analyses (analysis 10) failed to exonerate *B. lignifera* ovules from exhibiting stress responses. However, when *B. lignifera* ovules were compared to sexual *B. stricta* pistils (analysis 11), stress response GO categories, and those associated with meiosis, were only overrepresented or enriched in the B. stricta pistils.

various stresses
ROS and ER stress
meiosis

Thus, stress responses observed in B. lignifera pistils (vs. B. stricta pistils) likely originated from the external pistil tissues. As expected, photosynthesis and gene silencing activities were largely restricted to B. lignifera ovules (analysis 11). Evidence of BR signaling in the apomictic ovules was also observed.

photosynthesis
gene silencing
BR signaling

The following GO categories were overrepresented or enriched in B. stricta pistils compared to B. lignifera ovules, and this indicates that B. stricta pistils contain energetic tissues, which are probably located among the external tissues of the pistil.

respiration
ribosome biosynthesis and function
gene expression

Our analyses of diplosporous B. lignifera ovules and anthers compared to like tissues of meiotically successful but aposporous B. microphylla and to pistils of sexual B. stricta reveal large swings in gene expression (1000s of genes), which resemble those regulated by SnRK1 and RAPTOR TOR in response to energy abundance or scarcity. Apomeiotic (diplosporous) embryo sac formation in ovules and unreduced pollen formation in anthers of B. lignifera (onset of the apomixis phenism) occurred when germline cells and associated ovule or anther tissues were bioenergetically active. In contrast, meiosis occurred (onset of the sex phenism) in aposporous B. microphylla and sexual B. stricta (male and female) when these tissues were (or appeared to be) bioenergetically starved. From these observations, we recognized that the highly conserved stress vs. growth regulation functions of SnRK1 and RAPTOR TOR (and their orthologs throughout Eukaryota) likely regulate apomixis sex switching among eukaryotes (FIGS. 13A-13B).

The situation in aposporous B. microphylla does not conform to that observed in diplosporous B. lignifera. In B. lignifera, apomeiosis involves a modification of meiosis that causes the $1^{st}$ meiotic division to fail. Thereafter, the apomixis phenism takes over, and a dyad of unreduced spores forms. Within only a few days, one of these develops into the unreduced embryo sac, the egg of which is parthenogenetically competent. In B. microphylla, meiosis is induced by stress, as detailed above, and it generally produces four reduced spores. Sex is then terminated, i.e., all four spores degenerate. Occurring simultaneously with this failed onset of sex is the adventitious formation of one or more unreduced embryo sacs from sporogenous nucellar cells of the ovule wall. These unreduced embryo sacs also produce parthenogenetically competent eggs. As discussed above, the distinction between apospory and diplospory may simply be one of timing. In diplospory, the apomixis phenism is induced earlier than in apospory resulting in conversion of meiosis to apomeiosis by a $1^{st}$ division restitution. In apospory, the apomixis phenism is induce as meiosis is being completed. The sexual phenism, which includes gene expression required to form syngamy dependent eggs, is then epigenetically silenced. The apomixis phenism rarely converts a sexually formed spore to an embryo sac that contains a genetically reduced and parthenogenetically competent egg. Instead, all four spores abort. Simultaneously, the process of adventitious embryo sac formation (apomixis phenism, which produces syngamy independent eggs) begins.

In the B. microphylla vs. B. lignifera ovule comparison (detailed above), strong indicators of stress were observed in the meiotically active B. microphylla ovules. In general, these indicators of stress were also observed in B. microphylla ovules in the B. microphylla ovule vs. B. stricta pistil comparison (analysis 12), but additional differences were also observed. GO categories overrepresented or enriched in B. microphylla ovules that support the notion of stress-induced meiosis include:

hypoxia and ER stress
autophagy and catabolism
other stresses
meiosis

GO categories overrepresented or enriched in B. microphylla ovules that might reflect a post-meiosis derailment of the sexual phenism followed by an energy requiring apomixis phenism (apospory) include:

positive regulation of TOR, in the midst of indicators of strong stress
imprinting
photoperiodism
photosynthesis
epigenetic silencing, which presumably includes post-meiotic termination of the sexual phenism Analysis 12, like previous analyses involving sexual B. stricta pistils, revealed a mixture of GO categories representing both bioenergetically stressed and non-stressed conditions. This likely reflects differences between ovule tissues and exterior pistil tissues. Overrepresented or enriched GO categories in B. stricta pistils that suggest a stress-induced meiosis include:

ROS and ER stress
other stresses
meiosis

Overrepresented or enriched GO categories in B. stricta pistils that suggest the presence of bioenergetically active tissues include:

aerobic respiration
ribosome biosynthesis and activity
gene expression

Figure 14:
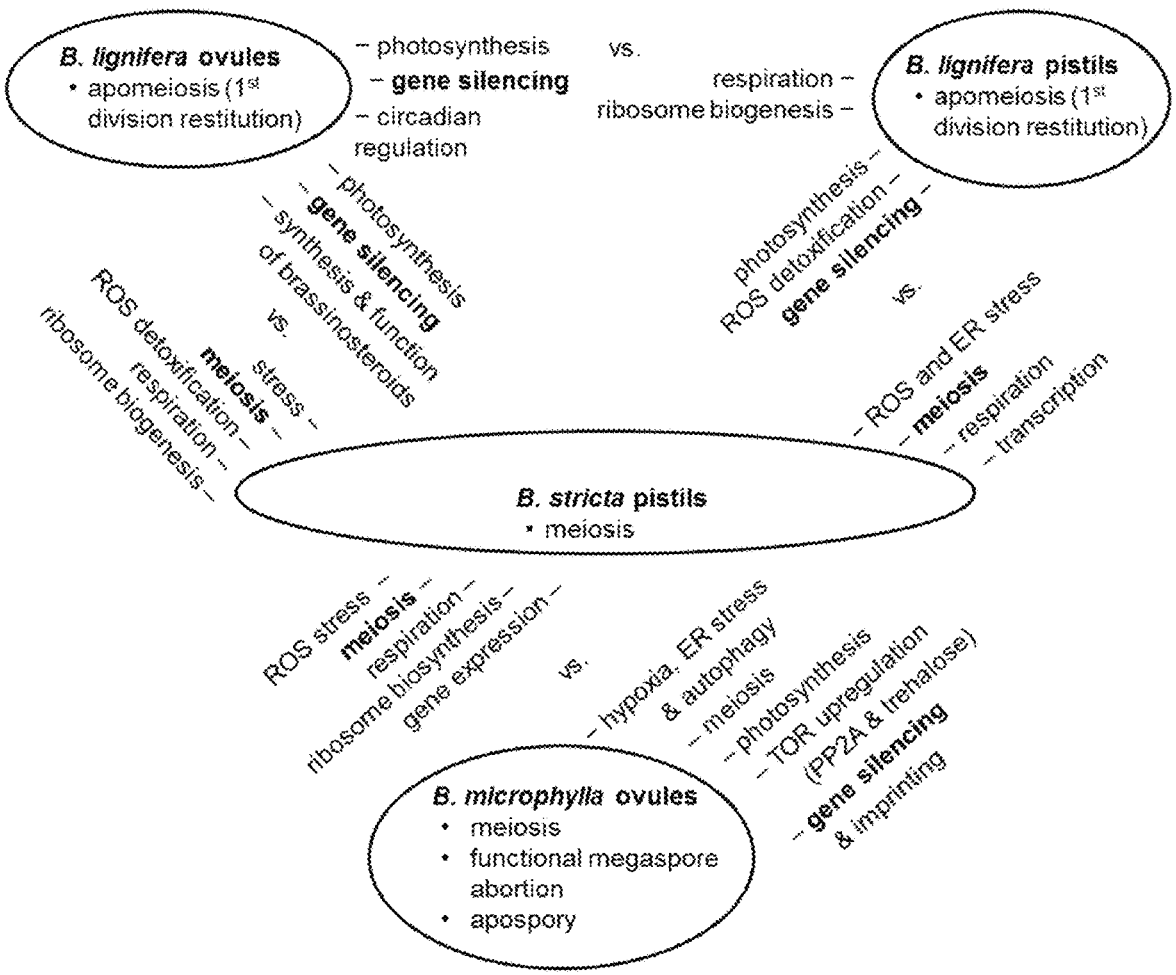
FIG. 14 Summary of overrepresented and enriched GO categories symptomatic of the metabolically enriched (apomixis inducing) and metabolically challenged (sex inducing) conditions that are putatively responsible for the polyphenic apomixis/sex switch in *Boechera*.

A visual summarization of GO category divergences between pistils of sexual B. stricta, pistils and ovules of diplosporous B. lignifera, and ovules of aposporous B. microphylla is presented in FIG. 14.

Comparisons of aposporous B. microphylla ovules and anthers against those of diplosporous B. lignifera and against pistils of sexual B. stricta revealed large differences in gene expression. Overrepresentation and enrichment of meiosis related GO categories consistently occurred in conjunction with those associated with metabolic stress, as seen in sexual ovules and anthers of B. microphylla and sexual pistils of B. stricta. In contrast, diplosporous ovules and anthers of B. lignifera consistently revealed metabolically favorable cellular environments when compared to sexual ovules, anthers or pistils (FIG. 12 and FIGS. 53A-53G). A unique feature of both diplospory (FIG. 12) and apospory (FIG. 14), when compared to sex, was an abundance of overrepresented and enriched GO categories associated with epigenetic regulation and gene silencing. That this gene silencing activity in aposporous B. microphylla ovules is part of the apomixis phenism and is induced by active TOR is suggested by i) overrepresentation or enrichment of GO categories associated with ribosome biosynthesis, a strong indicator of active TOR(17), and histone methylation in the

*B. microphylla* vs. diplosporous *B. lignifera* ovule comparison, and ii) overrepresentation or enrichment of GO categories associated with positive regulation of TOR and epigenetic silencing in the *B. microphylla* ovule vs. *B. stricta* pistil comparison.

Our data indicate that the total numbers of genes and their expression levels required for sex differ substantially from those required for apomixis. We hypothesized that such differences control whether sex or apomixis occurs. This is an important and novel hypothesis because, if it is correct, genes specific to apomixis (but not sex) or genes specific to sex (but not apomixis) do not exist, i.e., sex and apomixis are polyphenic. Accordingly, the same eukaryote genome can express sex or apomixis depending on its epigenetic status. Our data further indicate that the epigenetic status, which putatively controls the mode of reproduction expressed, depends on the bioenergetic status of germline cells and associated tissues. This observation suggests that female germline cells or associated tissues of eukaryotes that have evolved obligate apomixis or sex will experience during meiosis bioenergetic stability or stress (real or perceived), respectively.

Genes controlled by BR signaling promote growth (25) and ROS detoxification (87). Interestingly, the molecular pathways appear to be bioenergetically revved up in the apomicts and functioning cyclically, i.e., active TOR enhances BR synthesis and photosynthesis, BR promotes ROS detoxification, absence of ROS and presence of sugars inactivate SnRK1, and inactivated SnRK1 permits TOR activation (FIGS. 13A-13B). Normally, this molecular bioenergetics cycle is regulated by feedback mechanisms that maintain a balance between energy consumption and growth, under favorable conditions, and energy conservation, when stressed (13, 19, 21). Our research suggests that this energy balance is disturbed toward TOR activity and growth in the apomicts, and the resulting imbalance is responsible for the apomixis phenism.

The profiling experiments reported herein involved mRNA extraction from ca. 20,000 microexcised ovules (each ca. 40-80 μm in diameter) and additional extractions from hundreds of whole pistils and anthers. To our knowledge, this is the most extensive expression profiling comparison made to date of closely related apomictic and sexual organisms. The results are consistent with ovules and anthers of sexual *Boechera* either being unable to molecularly dissipate levels of metabolic stress, a condition that induces sexual reproduction (meiosis followed by an epigenetics based syngamy requirement), or to perceive low levels of stress or no stress incorrectly as sex inducing high levels of stress. Alternatively, as suggested above, ovules and anthers of apomictic *Boechera* may possess a capacity to either i) eliminate the metabolic stress that normally would induce sexual reproduction or ii) incorrectly perceive normal levels of stress as an absence of stress. The experiments described in the following section were designed to test these alternative scenarios.

Example 3. Heat and Drought Stress Induce Sexual Reproduction in Apomictic *Boechera* and Cause their Pistil Expression Profiles to Mimic Those of Sexual *Boechera*

Background. In 1951, Bocher (76) reported stress-induced shifts from apomeiosis to meiosis in pollen mother cells (PMC) of *Boechera*. Four reduced (1n) spores tended to form by meiosis (tetrads) instead of two unreduced (2n) spores by apomeiosis (dyads). He speculated that these stress-induced shifts might also occur in ovules of apomictic *Boechera*, a stress-induced phenomenon that was later documented in several other angiospermous apomicts (88-91). To investigate Bocher's suspicion, we grew sexual and apomictic *Boechera* in well-watered, droughted, and droughted plus high heat conditions. We also collected sufficient numbers of pistils to produce qPCR and RNASeq expression profiles of pistils (MMC to early embryo sac stages) of well-watered and droughted plants. Effects of stress on reproductive mode were then determined cytologically (percentage apomictic or sexual) and on gene expression profiles for apomictic and sexual *Boechera*.

Assuming stress would shift reproduction from apomixis to sex, as seen in *Boechera* anthers and in pistils of other angiospermous apomicts, we were particularly interested in determining if the effects of stress on gene expression would be greater in pistils of apomictic plants compared to those of sexual plants. Larger shifts in apomictic plants, especially if they produced profiles typical of pistils from sexual *Boechera*, would suggest that apomictic plants possess mechanisms for dissipating low levels of metabolic stress, i.e., levels that in sexual plants would otherwise induce sexual reproduction. When stress becomes excessive in apomictic plants, surpassing a threshold, then sex would be induced. Such results would also suggest that apomixis, as the fair-weather reproductive phenism (in *Boechera* and possibly other eukaryotes), actively suppresses (silences or keeps silent) gene expression required for sexual reproduction. If this is correct, it should be possible to induce apomixis in sexual *Boechera* and other eukaryotes by strengthening each organisms' capacity to dissipate metabolic stress in its germline or germline associated cells.

Materials and methods. These methods are sufficiently detailed to provide one skilled in the art with information needed to repeat the experiments.

Seeds of sexual *B. stricta* (ST2) and apomictic *B. lignifera* (LI3), *B.* cf. *gunnisoniana* (GU cf), *B. exilis×retrofracta* (ExR1), and *B. microphylla* (MI2) (FIG. 4) were imbibed, stratified, planted, and grown as above. Plants were then randomly assigned to three groups, well-watered, drought-stressed, and heat plus drought-stressed, with 8-12 plants of each taxon in each group. After vernalization, plants designated for well-watered and drought-stressed treatments were grown in a greenhouse and plants targeted for heat plus drought-stress were grown in a controlled-environment growth chamber (32° C., 500 μmol m−2 sec−1 PPF, 16/8 d/n photoperiod). Treatments were imposed by adding a layer of perlite to the surface of each pot, to inhibit evaporation, obtaining a field capacity weight for each pot (weighed 2 h after drenching), adding enough water each day to the well-watered plants (measured by pot weight) to bring them back to field capacity, and adding enough water to the drought-stressed plants each day to equal 50% of the transpiration rate of the well-watered plants. Upon flowering, pistils were collected for cytology, qPCR analyses and RNA-Seq analyses.

Pistil samples for RNA-Seq were collected from well-watered and droughted plants of all taxa except *B. microphylla*, which performed too poorly under stress conditions to obtain sufficient numbers of pistils for RNA-Seq. Pistil length intervals corresponding to ovules in the MMC to early 8-nucleate embryo sac stage were identified cytologically. To avoid sampling bias, pistil length intervals for each species were divided into four sub-intervals, and 15 pistils per sub-interval were collected (60 total). To reduce circadian rhythm bias, pistils were excised between 9:30 A.M. and 12:30 P.M., immediately placed in RNALater and stored at −80° C. Total RNA was isolated using RNeasy kits (Qiagen), and 24 sequencing libraries (4 taxa×2 treatments×3 rep) were prepared using TruSeq mRNA-Seq kits (Illumina, San Diego, Calif.). The purified libraries were checked for quality and quantity before normalization and sample pooling. Sample pools were clustered and sequenced on an Illumina HiSeq 2500 system with TruSeq SBS Rapid v1 chemistry. Samples were single end sequenced (50 cycles) to a target depth of 10 M reads per sample. A python script was used to truncate reads at the first base with a quality score <16. Remaining reads<24 bp were stripped. Libraries were aligned to the *B. stricta* genome (JGI-phytozome, v1.2) using bowtie2 2.1.0(92) and tophat 2.0.9(93) with two as the maximum read mismatch, gap length and edit distance. Maximum insertion and deletion lengths were set to three. Reads were also aligned using a value of four for the maximum read mismatch, gap length and edit distance, and the two criteria were compared by principle component analyses (PCA) following normalization by library size. Samtools 0.1.19(94) was used to sort gene alignments. Expressed genes were counted using htseq-count 0.6.1p1 using *B. stricta* annotations (JGI-phytozome, v1.2). Splice variants were not counted.

For differential gene expression and gene ontology analyses, *Boechera* genes that mapped to a single TAIR10 locus were summed. Genes were retained if their replicate mean transcript count was ≥5 for each taxa by treatment category and if at least one replicate mean transcript count among the categories was ≥10. The retained genes were then used to produce pairwise correlation and multidimensional scaling (principal component) plots of TAIR10-mapped genes plus *Boechera* unique genes. Sixteen gene expression comparisons were then conducted, four that compared control versus treatment samples within taxa, six that compared control samples across taxa, and six that compared treatment samples across taxa. For each of these sixteen analyses, genes were retained if their replicate mean transcript count was ≥5 for each treatment being compared and if at least one replicate mean transcript count for the treatments being compared was ≥10. Retained genes for each of the 16 analyses were then DESeq normalized (95) and BRB-ArrayTools 4.6.0 (developed by Dr. Richard Simon and the BRB-ArrayTools Development Team) was used to identify DE genes (FDR, P≤0.05).

*Boechera* loci that mapped to TAIR10 genes were used for GO analyses. DE genes up-regulated in experimental comparisons (up regulated in treatments used as numerators in the gene expression ratios) were used to identify GO categories (biological process, molecular function, cellular component) that were overrepresented by the respective up regulated genes. Panther Overrepresentation Tests (Apr. 13, 2017 release, Dec. 27, 2017 GO Ontology database release, Panther™ Classification System 76, Ver. 13.0) were used for these analyses. DE genes down regulated in the respective experimental comparisons (up regulated in the treatments used as denominators in the gene expression ratios) were likewise analyzed. Log base 2 values of expression ratios of all retained genes of each comparison were used to identify enriched GO categories by Panther Enrichment Tests. GO analyses were conducted at the P≤0.05 level of confidence, but, for reasons stated in Section II, Bonferroni corrections were not performed.

qPCR analyses of five genes, AT2G40140, AT4G02730, AT3G52940, AT3G13580 and AT2G48020, were performed, and results were compared to those obtained by RNA-Seq. Pistils for qPCR (ovules in the MMC to early embryo sac formation stages) were excised from control and drought-stressed sexual *B. stricta* and diplosporously-apomictic *B. lignifera* and *B. retrofracta*×*exilis*. Three samples of 80-150 pistils each were collected for each set of control plants and for each set of drought-stressed plants. The pistils were immediately placed in RNALater (Qiagen), and stored at −80° C. RNA was extracted and treated with DNaseI, cDNA was synthesized, and qPCR reactions were performed using a DNA Engine, Opticon 2, Continuous Fluorescence Detection System (Bio-Rad), and primers as shown in FIG. 15. For each gene, two technical replicates of each sample were analyzed (three samples per treatment by taxa combination). This provided six qPCR expression values per treatment by taxa combination for each gene. Each gene by taxa by treatment combination also included six technical replicates of the BoechACT2/Actin 2 housekeeping gene (96), which were used to normalize the results. qPCR expression values were calculated for each gene as the difference between PCR cycle values and the average of the technical replicates of the housekeeping gene (delta Ct method). Delta Ct values were then normalized against the mean value for the sexual *B. stricta* control (delta delta Ct method). The data were subjected to analyses of variance with samples nested within treatments and taxa using SYSTAT(97). The P≤0.05 level was chosen to represent significance. Relative expression values were determined by raising 2 to the power of the negative delta-delta Ct mean values for each treatment-by-taxon combination.

Figure 17:
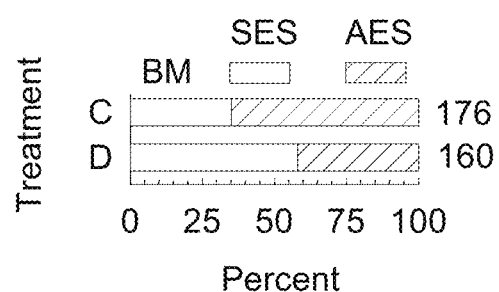
FIG. 17 Frequencies of sexual (SES) and aposporous (AES) ES formation in ovules of *B. microphylla* (BM) as affected by well-watered (C) and drought (D) conditions. Numbers to the right indicate informative ovules observed (correctly staged and oriented) (from Mateo de Arias (26)).

Results and discussion. Pistil lengths used to quantify mode of reproduction and to obtain samples for RNASeq (meiocyte to early embryo sac formation stages) were as follows: *B. stricta* (1.6-2.7 mm), *B. lignifera* (1.1-2.6 mm), *B.* c.f. *gunnisoniana* (1.4-2.5 mm) and *B. exilis*×*retrofracta* (1.3-2.0 mm). As Bocher (76) suspected, stress (drought or drought plus heat) shifted apomeiosis to meiosis in diplosporous *B. lignifera* and *B.* cf. *gunnisoniana* (FIG. 16) and in aposporous *B. microphylla* (FIG. 17). But this was not observed in the facultatively-apomictic *B. exilis*×*retrofracta*, which was already mostly sexual (FIG. 16). The stress-induced shift from aposporous to sexual embryo sac formation observed in *B. microphylla* (FIG. 17) is consistent with apospory representing a late (post-meiotic) onset of the apomixis phenism as discussed in Section II. These data indicate that stress can prevent apomixis-induced silencing of the sexual phenism even in post-meiotic apomixis (apospory).

Figure 18:
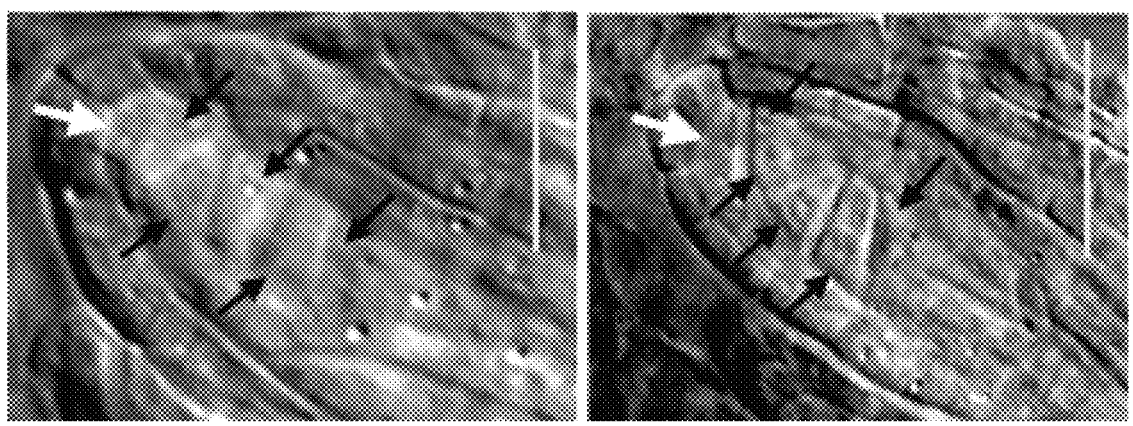
FIG. 18 Abnormally-reduced pentads of genetically-unbalanced megaspores in sexual ovules of drought-stressed and typically-apomictic triploid *B.* cf *gunnisoniana*. Black arrows: megaspores; white arrows: parietal cells that occur infrequently at the micropylar ends of dyads and tetrad; bars: 20 μm (from Mateo de Arias (26)).

Heat prevented flowering from occurring in the mesic-favoring *B. stricta* and *B. microphylla*. Thus, a heat effect could not be measured for these lines. In addition to drought induced meiosis in ovules of the diplosporous triploid *B.* cf. *gunnisoniana*, extra meiotic divisions occurred in some ovules. These produced genetically-unbalanced pentads and hexads (FIG. 18). Bocher (76) also observed extra meiotic divisions occurring infrequently in PMC of triploid *Boechera* that were growing under stressful late-season conditions. Under favorable conditions, such PMC produced apomeiotic dyads (76).

For RNASeq, three replicate samples of immature pistils of sexual *B. stricta*, diplosporous *B. lignifera*, diplosporous *B.* cf. *gunnisoniana* and diplosporous and aposporous *B. exilis*×*retrofracta* were obtained from well-watered and droughted plants. These produced 306 M reads (12.76±1.94 M SD per library), which represented 26,072 *B. stricta* genes (a mapping efficiency of 0.90±0.03 SD), of which 18,911 corresponded to separate *Arabidopsis* TAIR10 genes. An additional 6324 *B. stricta* genes corresponded to 2413 TAIR10 genes (21,324 TAIR10 matches total). Of these 6324 genes, two *Boechera* genes corresponded to each of 1765 TAIR10 genes, three corresponded to 594, four to 226, and 5-56 to 577. Blastn to TAIR10 failed for 837 *Boechera* genes (27).

Figure 19A:
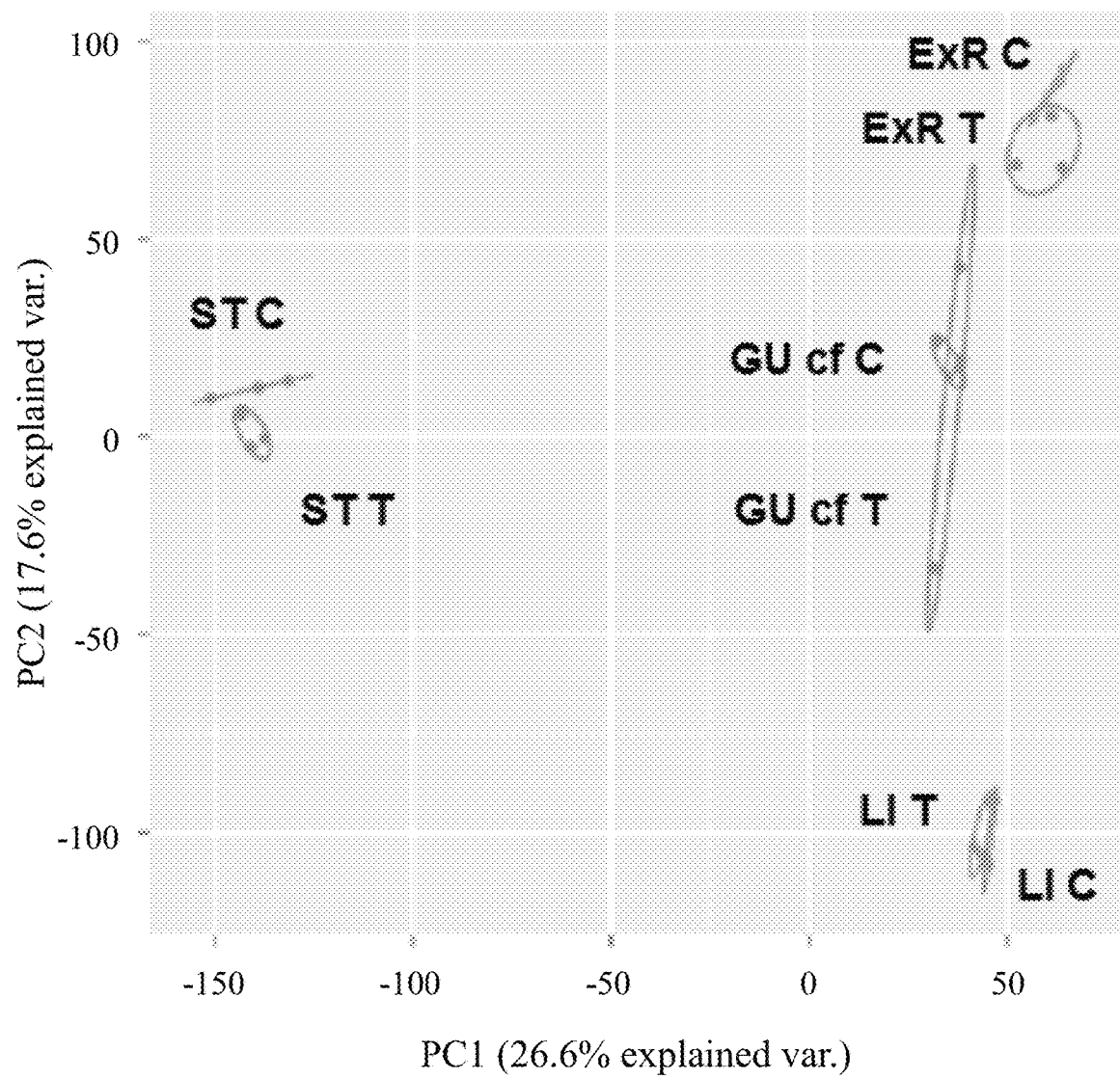
FIGS. 19A-19B Biplots of PCA performed on (FIG. 19A) gene expression values normalized by library size (n=26, 072) and (FIG. 19B) presence and absence of gene expression over genes that varied in expression (n=7,192). E×R C and T, *B. exilis×retrofracta* control and treatment; GU cf C and T, *B.* cf. *gunnisoniana* control and treatment; LI C and T, *B. lignifera* control and treatment; ST C and T, *B. stricta* control and treatment (from Shilling (27)).
Figure 19B:
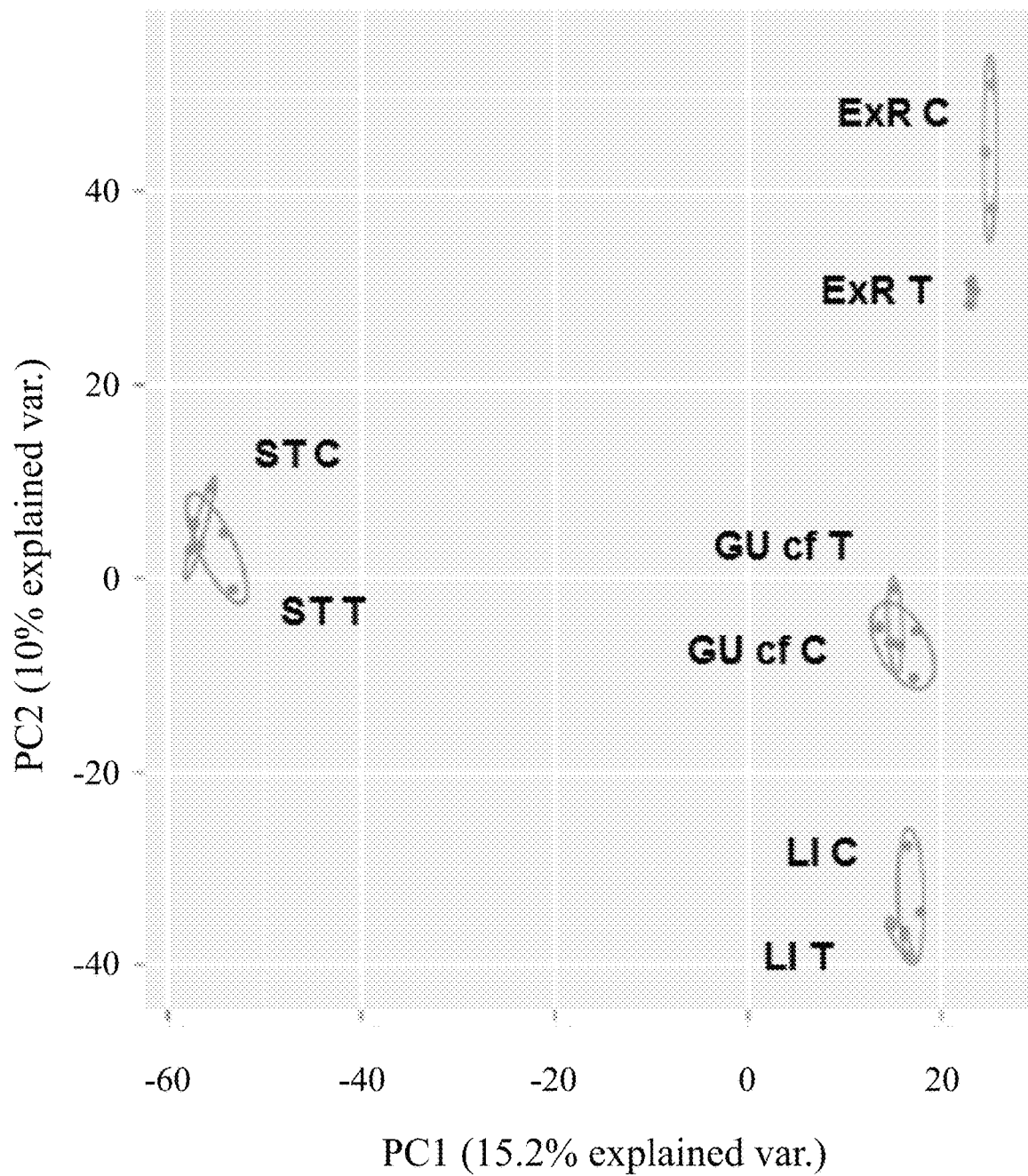
Figure 21:
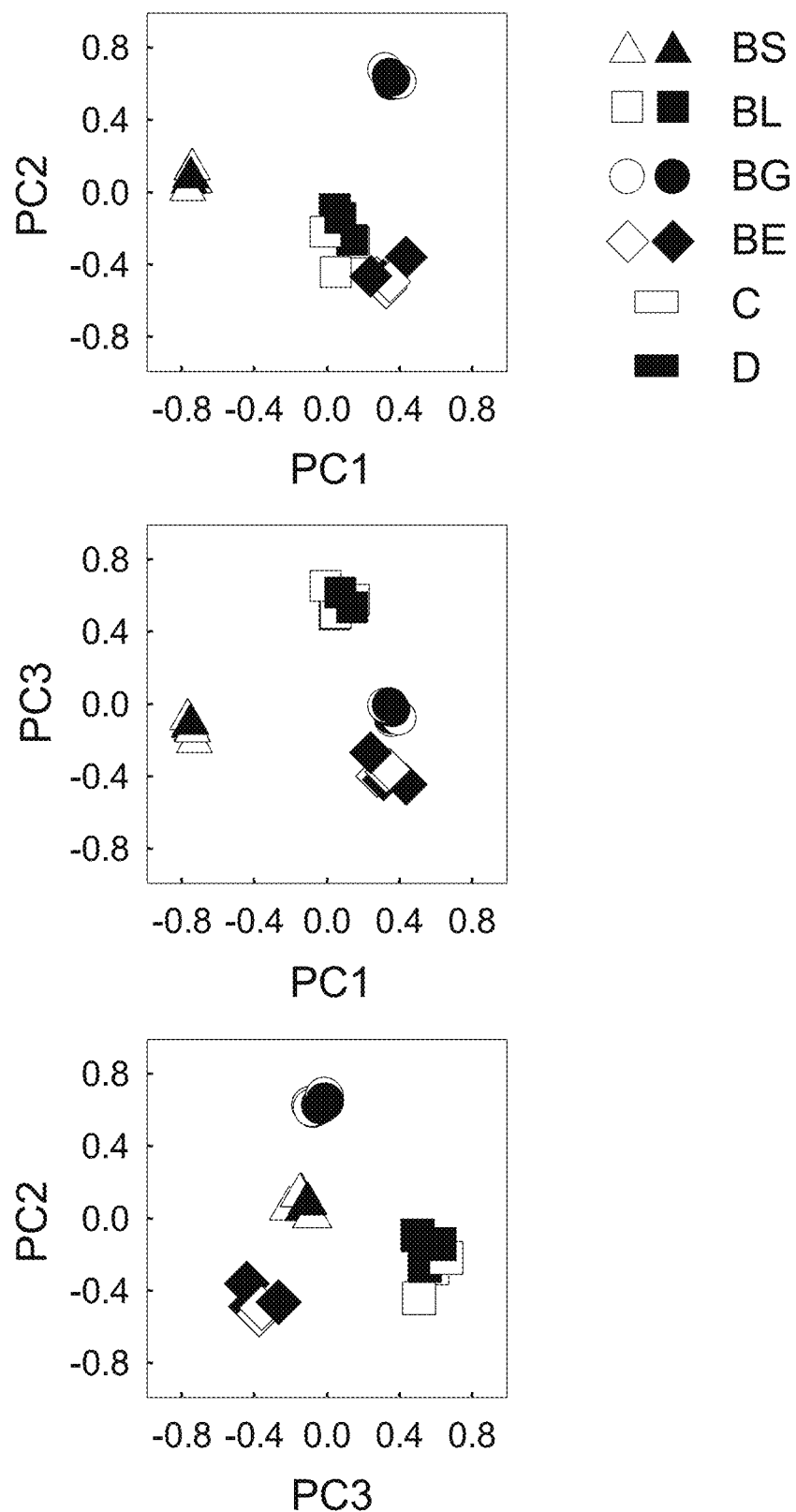
FIG. 21 Biplots of PCA performed on DESeq normalized gene expression values after removing low-count genes. BE, *B. exilis×retrofracta*; BG, *B.* cf. *gunnisoniana*; BL, *B. lignifera*; B S, *B. stricta*.

PCA were performed on expression counts normalized by library size and by expression counts based on 7,192 genes that showed considerable expression variation among taxa (FIGS. 19A-19B) (27). PC1 separated sexual *B. stricta* from the apomicts, and PC1 and 2 separated the apomicts from each other. After removing low-count genes, 16,449 TAIR10-matched and 213 *Boechera*-unique genes remained (16,662 total). Using these genes, pairwise correlation analyses were performed, which successfully partition the 24 libraries (four taxa, two treatments, three reps) into four groups of six libraries each, each corresponding to one of the four taxa (FIG. 20). The putatively-youthful *B. exilis*× *retrofracta* and triploid *B.* cf. *gunnisoniana* exhibited high read-count variation among treatments and reps. In contrast, the more established *B. stricta* and *B. lignifera* exhibited low read-count variation among treatments and reps (FIG. 20). PCA performed using the 16,662 genes also separated sexual *B. stricta* from the three apomicts (PC1). PC2 separated triploid *B.* cf. *gunnisoniana* from the three diploids, and PC3 separated apomictic *B. lignifera* from the other three taxa (FIG. 21). All three PCA indicated that gene expression in these taxa was far more influenced by species differences than by treatment effects. This indicates that species differences must be considered when making gene expression comparisons among taxa that differ in reproductive mode. Accordingly, we first analyzed gene expression differences between treatments but within species. We then made within-treatment but between-species comparisons to clarify differences observed in the within-species, between-treatment analyses.

As expected from PCA, numbers of DE genes were low between treatment but within species, the average being 153 DE genes per species, but high between species but within treatments, the average being 3973 DE genes between species pairs but within treatments. Even though numbers of DE genes were relatively low for within-species between-treatment comparisons, numbers of overrepresented GO categories (based on DE genes) and enriched GO categories (based on all genes meeting minimum expression criteria, see Materials and Methods), were informative and averaged 387, 493, 423 and 790 GO categories for *B. stricta, B. lignifera, B* cf. *gunnisoniana* and *B. exilis*×*stricta*, respectively. Numbers of DE genes were much higher for comparisons among the control treatments of each species and among the droughted treatments of each species.

Figure 22:
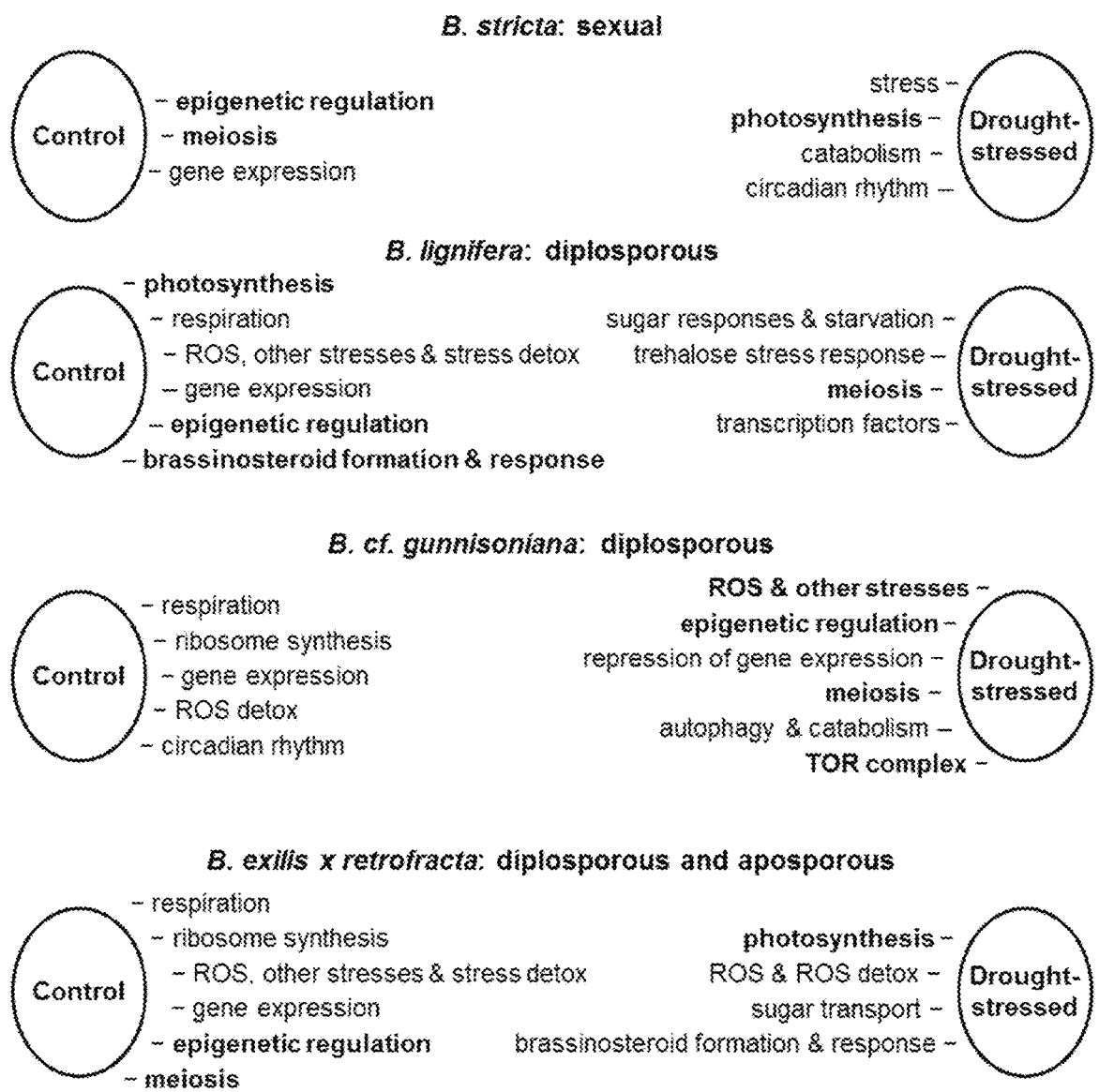
FIG. 22 Summary of overrepresented and enriched GO categories symptomatic of the metabolically enriched and metabolically challenged conditions that are putatively responsible for apomixis or sex in *Boechera* as detailed in the text.

The expression of meiosis specific genes in the four taxa followed closely the observation of meiosis in these taxa as affected by stress. While overrepresented or enriched GO categories associated with epigenetic regulation often accompanied those related to meiosis, this was not consistently observed. For example, GO categories associated with epigenetic regulation tended to be overrepresented or enriched in the controls of diplosporous *B. lignifera* though meiosis was induced by stress in this taxon (FIG. 22). Careful analyses of the GO categories reveals that both apomeiosis and meiosis are associated with epigenetic regulation, but elucidating the details of these relationships requires further study.

Figure 23:
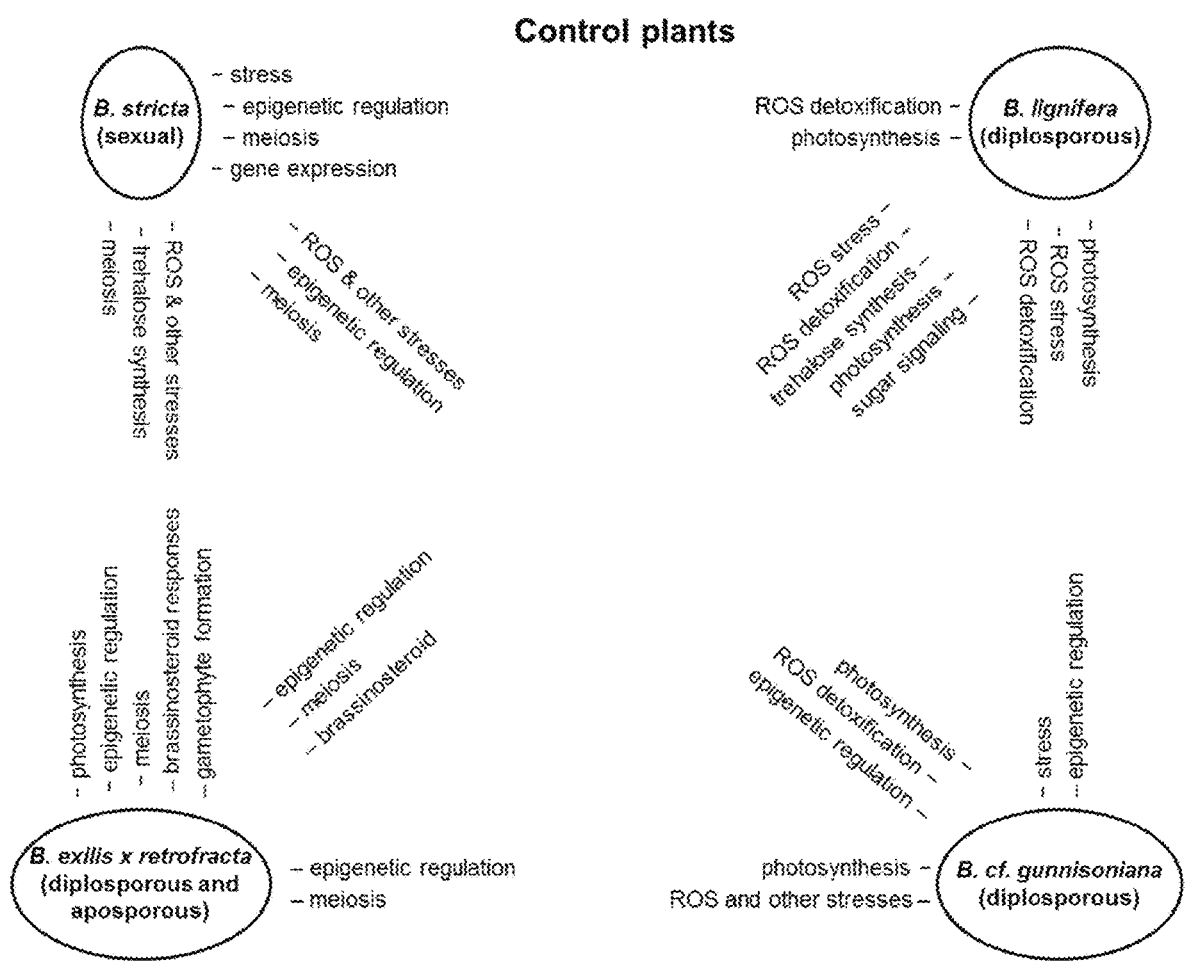
FIG. 23 Summary of overrepresented and enriched GO categories symptomatic of the metabolically enriched and metabolically challenged conditions that are putatively responsible for apomixis or sex in the control plants of *Boechera* as detailed in the text.
Figure 24:
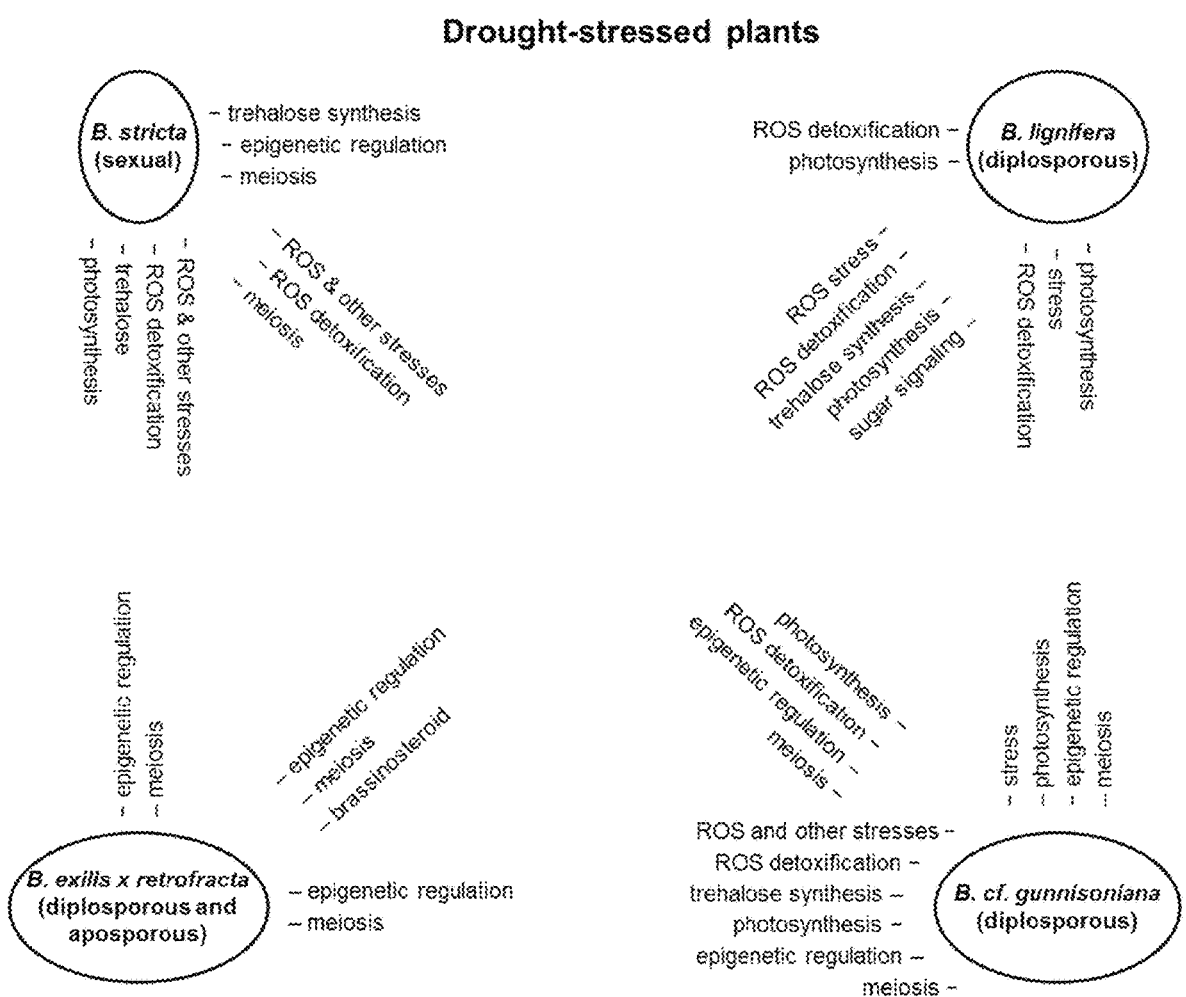
FIG. 24 Summary of overrepresented and enriched GO categories symptomatic of the metabolically enriched and metabolically challenged conditions that are putatively responsible for apomixis or sex in the drought-stressed plants of *Boechera* as detailed in the text.

As expected from the PCA, many genes and overrepresented and enriched GO categories were identified when comparisons across taxa were made. As shown in FIG. 23-24, these analyses reveal relationships between stress, mode of reproduction and epigenetic regulation. In general, well-watered apomicts were producing and metabolizing sugars (highly energetic), producing antioxidants, which detoxify ROS, growing rapidly, and reproducing apomictically. When these plants were drought-stressed, photosynthesis and ROS detoxification generally declined, growth tended to cease, gene expression patterns specific to epigenome reprogramming and sex were up-regulated, and sex ensued. From these and other GO category differences, we identified biochemical and molecular pathway components of the sex/apomixis switch and linked these components together (FIGS. 13A-13B). We then tested the pathway components using chemical treatments of pistils attached to plants as well as in-vitro cultured pistils. Without mutation, we induced sex to occur in apomictic plants by stressing immature pistils in vitro and in situ (osmotic stress, sugar starvation, and/or hydrogen peroxide), and we induced apomixis (unreduced egg-cell formation) to occur in sexual plants by treating immature floral buds in vitro and in situ with brassinolide, antioxidants, and/or carbohydrates. Chemical induction of apomixis in sexual plants or animals without genetic modification has not heretofore been reported.

The following examples are illustrative only and are not intended to limit the disclosure in any way.

Example 4. Converting Apomeiosis to Meiosis in MMC and Death of Nucellar Cells to Apospory by Osmotic Stress Imposed within 48 Hours of Apomeiosis Based on our gene expression profiling studies, we questioned whether the stress-induced genomic, epigenomic and/or biochemical reprogramming required for shifts from apomictic to sexual reproductive development occur gradually during flower development, i.e., requiring long exposures to stress, or can such shifts be induced by short exposures to stress, e.g., as late as immediately prior to the onset of apomeiosis in MMC just hours before they undergo apomeiosis? Herein multiple stress treatments were used to determine how temporally close to the onset of apomeiosis in MMC a stress could be applied and still achieve a pronounced effect. In previous studies (26), the effects of drought and heat were synergistic. Here, drought or related stresses were applied individually and at specific stages of ovule development.

To study the effects of short-term drought on converting apomictic development to sexual development, pistils of apomictic *B. retrofracta*×*stricta, B.* cf. *gunnisoniana* and *B. lignifera* were excised and cultured at pre-apomeiotic stages of ovule development. Pistils exposed to treatments in vitro were harvested when they had grown to a length that corresponded with those of greenhouse grown plants that contained ovules that had concluded meiosis or apomeiosis. For pistils grown on basal medium (MS with sucrose), growth averaged 0.2 mm d$^{-1}$.

Figure 25:
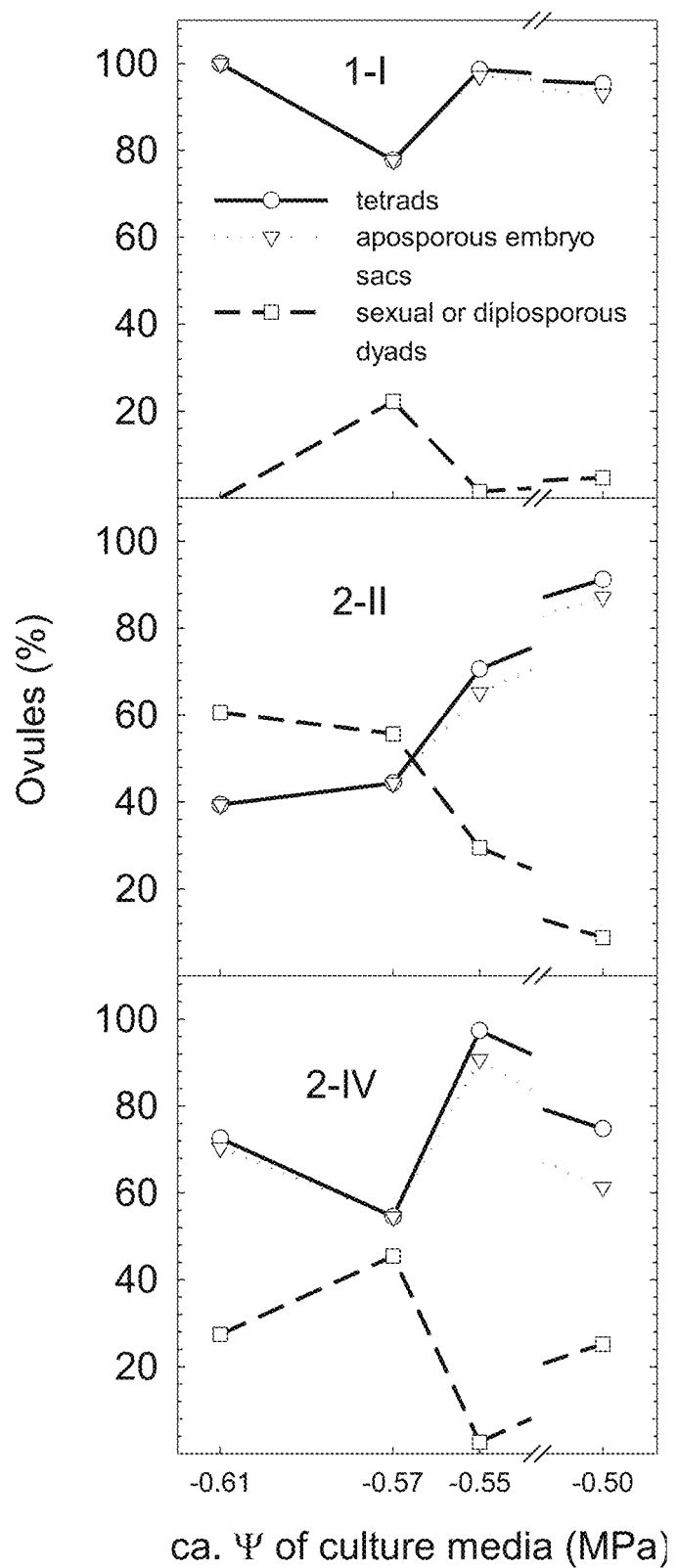
FIG. 25 Frequencies of *B. retrofracta×stricta* ovules that were undergoing sexual tetrad, sexual or diplosporous dyad, or AES formation at the end of pistil culture as affected by i) decreasing culture media Ψ (from right to left) and ii) ovule stage at pistil culture initiation (1-I, 2-II, 2-IV). Numbers of correctly staged ovules (containing a 1-2 nucleate AES and/or a dyad or tetrad) at each of the 12 Ψ by pistil stage treatments averaged 89 and ranged from 8-151.

From 40-100% of ovules in *B. retrofracta*×*stricta* pistils were producing aposporous embryo sacs (includes a degenerating sexual tetrad) at the end of culture, and this high frequency of apospory coupled with sexual megaspore degeneration was most pronounced (80-100% of ovules) in pistils that had been cultured at the earliest stage of ovule development regardless of Ψ treatment. A sharp increase in apospory and sexual tetrad formation was observed in response to the least severe drop in Ψ (−0.55 MPa treatment), but only in the most mature pistils (FIG. 25, ovule stage 2-IV). Pearson Chi-square tests for independence were highly significant (P<0.001) for i) the main effect that compared pistil age at culture initiation versus reproductive mode at the end of pistil culture and ii) the main effect of Ψ treatment versus reproductive mode at the end of pistil culture. *Boechera lignifera* pistils were much smaller at the culture initiation stages used for this experiment than those of the two other taxa, and most of their ovules aborted. Thus, sufficient data from *B. lignifera* pistils could not be obtained for statistical analyses.

Figure 26:
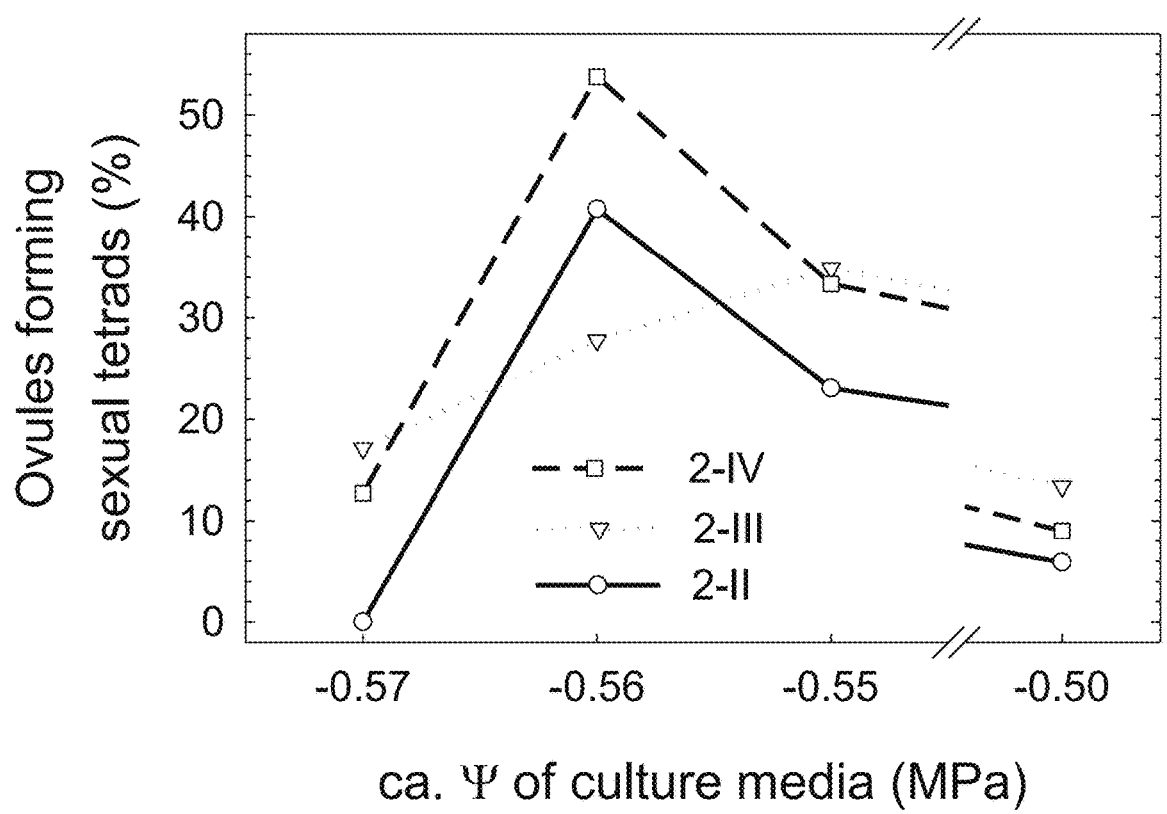
FIG. 26 Frequencies of *B.* cf. *gunnisoniana* ovules that were undergoing sexual tetrad formation at the end of pistil culture as affected by i) ovule stage at culture initiation (2-II, 2-III, 2-IV) and ii) decreasing culture media Ψ (from right to left). Numbers of correctly staged ovules (containing a dyad or tetrad) at each of the 12 Ψ by pistil stage treatments averaged 81 and ranged from 22-164.
Figure 27A:
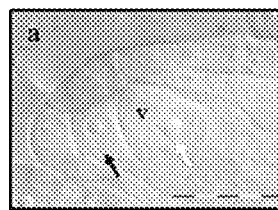
FIGS. 27A-27L Ovules of *B. gunnisoniana* (FIGS. 27A-27D), *B. lignifera* (FIGS. 27E-27H) and *B. retrofracta×stricta* (FIGS. 27I-27L) from the drought stress experiments.
Figure 27B:
Figure 27C:
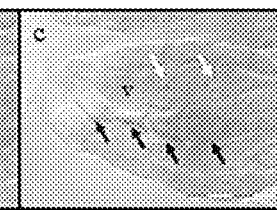
Figure 27D:
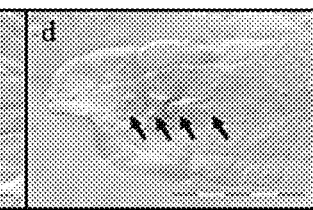
Figure 27E:
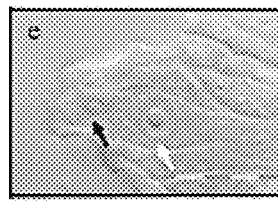
Figure 27F:
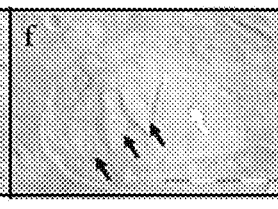
Figure 27G:
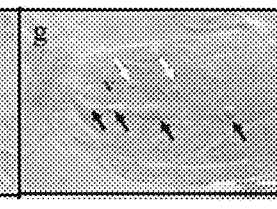
Figure 27H:
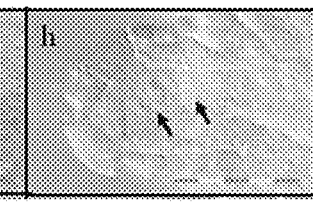
Figure 27I:
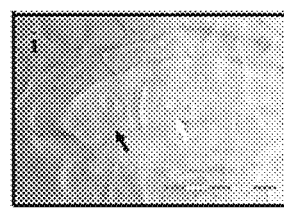
Figure 27J:
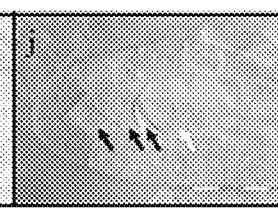
Figure 27K:
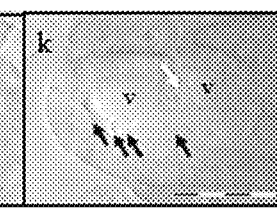
Figure 27L:
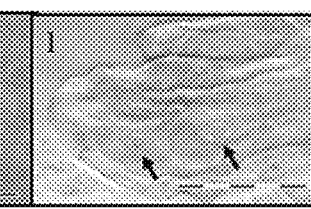

Triploid *B.* cf. *gunnisoniana* is highly diplosporous, but when pistils were exposed to low Ψ, the frequency of sexual meiosis increased to 55% (FIG. 26). Note that this was not accompanied by a corresponding increase in apospory, as occurred with *B. retrofractaxstricta*. As a triploid, it is expected that meiosis-produced megaspores will be inviable due to genetic imbalances that negatively affect gametophyte formation and gamete viability. Hence, megaspore inviability by itself (due to segregational genetic imbalance) does not explain the positive correlation between sexual tetrad formation and apospory in *B. retrofractaxstricta* and the lack of such a correlation in triploid *B. gunnisoniana*. Pearson Chi-square tests for independence were significant (P<0.003) for pistil age at culture initiation versus reproductive mode and highly significant (P<0.001) for Ψ versus reproductive mode. Aposporous, diplosporous and sexual embryo sac formation occurred in all three species, though apospory was rare in *B.* cf. *gunnisoniana* (FIGS. 27A-27L).

Significance of discovery: As reviewed above, the fact that stress can shift reproduction from apomixis to sex is well understood, especially for cyclical apomicts such as aphids and water fleas. However, how this shift occurs and the duration of stress required to induce the shift has not previously been reported. Of the many molecular pathways influenced by stress, we show that drought stress imposed within 48 hours of apomeiosis (in the germ cell) is sufficient to reprogram the biology (metabolome and genome) of the germ cell to pursue a different mode of reproductive development.

Figure 28:
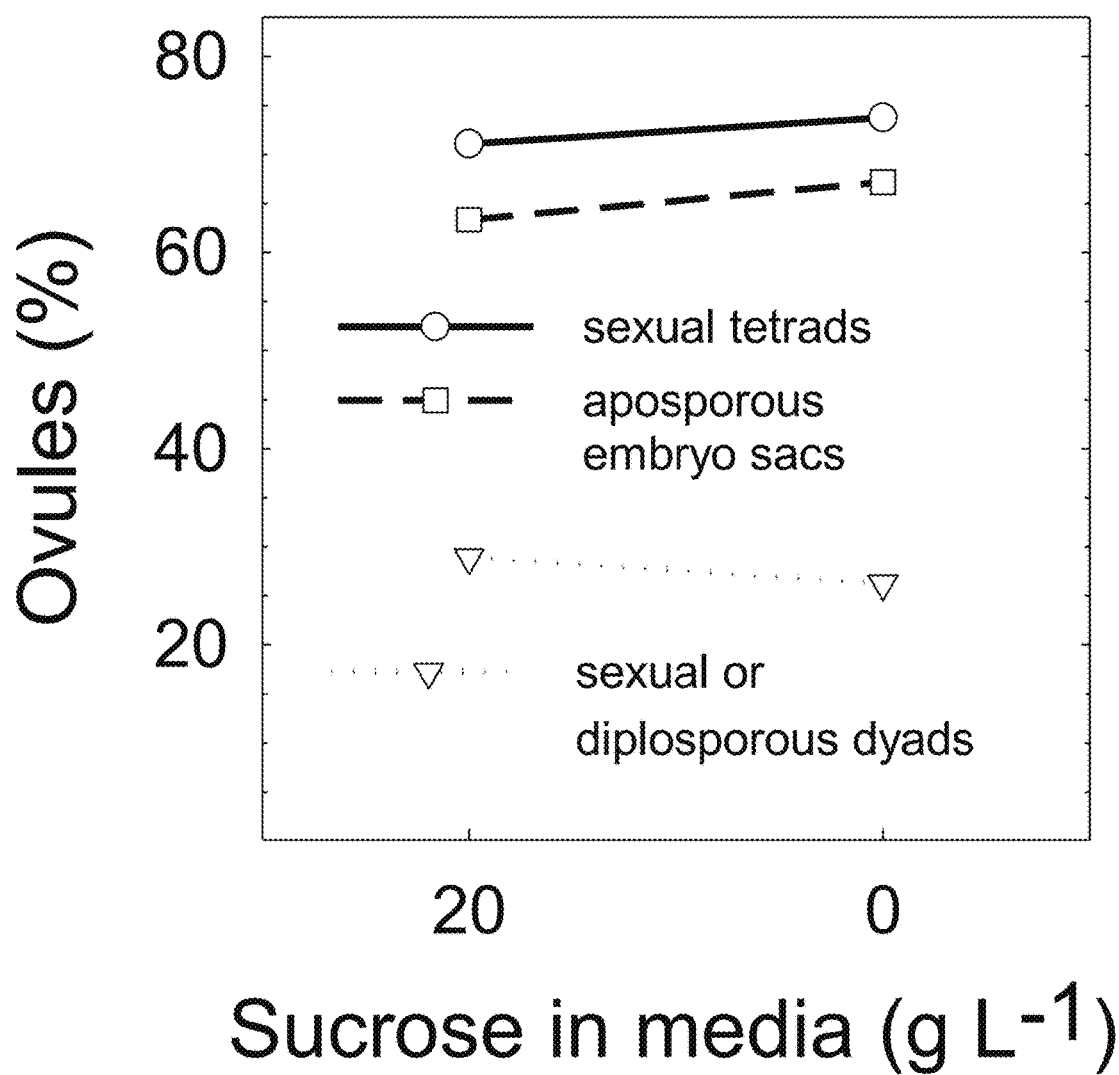
FIG. 28 Frequencies of *B. retrofracta×stricta* ovules that were undergoing sexual tetrad, sexual or diplosporous dyad, or AES formation at the end of the pistil culture treatment as affected by removal of sucrose from the culture medium. Pistils were cultured at the 2-IV stage. Numbers of correctly staged ovules (containing a 1-2 nucleate AES and/or a dyad or tetrad) for the 20.0 and 0.0 g L1 sucrose treatments were 61 and 90, respectively.
Figure 29:
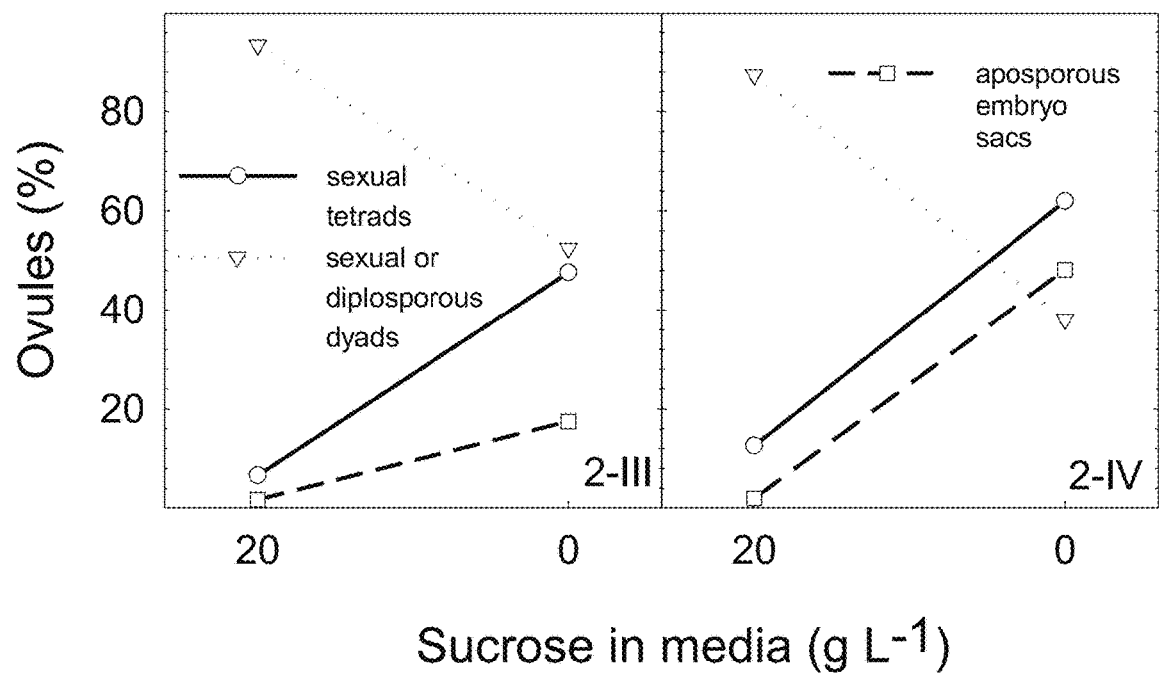
FIG. 29 Frequencies of *B.* cf. *gunnisoniana* ovules that were undergoing sexual tetrad, sexual or diplosporous dyad, or AES formation at the end of pistil culture as affected by i) removal of sucrose from culture media and ii) ovule stage at pistil culture initiation (2-III or 2-IV). Numbers of correctly staged ovules (containing a 1-2 nucleate AES and/or a dyad or tetrad) at each of the four sucrose concentration by pistil stage treatments averaged 222 and ranged from 103-289.
Figure 30A:
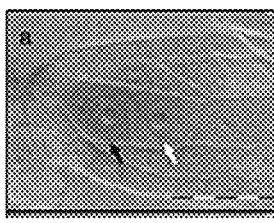
FIGS. 30A-30H Ovules of *B.* cf. *gunnisoniana* (FIGS. 30A-30D) and *B. retrofracta×stricta* (FIGS. 30E-30H) from the sucrose starvation experiments.
Figure 30B:
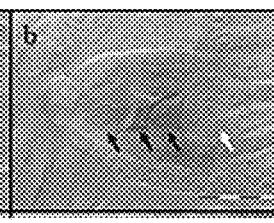
Figure 30C:
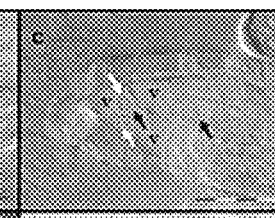
Figure 30D:
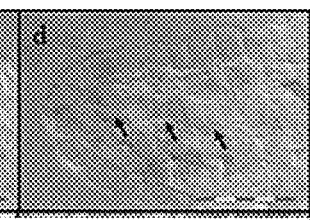
Figure 30E:
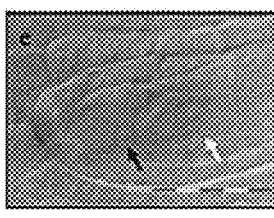
Figure 30F:
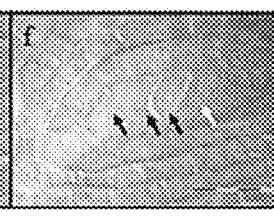
Figure 30G:
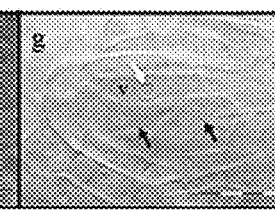
Figure 30H:
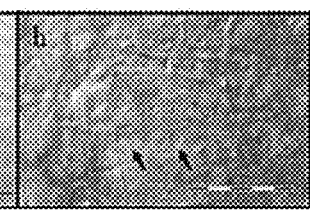

Example 5. Converting Apomeiosis to Meiosis in MMC and Death of Nucellar Cells to Apospory by Bioenergetic Starvation Imposed within 48 Hours of Apomeiosis Since drought drains carbohydrates from tissues, we tested whether changes in sugar signaling, induced by sucrose starvation, constitutes part of the signal transduction pathway responsible for stress-induced shifts from apomeiosis to meiosis. Pistils were cultured on basal medium with and without sucrose. Preliminary experiments indicated that sucrose starvation killed ovules when pistils were cultured too young. Hence, 2-III and 2-IV staged pistils (*Arabidopsis* scale) were used. The small *B. lignifera* pistils were too sensitive to sucrose starvation, so data for this species was not obtained. When the experiment was conducted using stage 2-IV pistils (late MMC stage) of aposporous *B. retrofractaxstricta*, no differences were induced by sucrose starvation in frequencies of aposporous, diplosporous or sexual development (FIG. 28; the Pearson Chi-square test for independence based on presence or absence of sucrose versus mode of development was not significant, P<0.05). However, when the experiment was conducted with the highly diplosporous *B.* cf. *gunnisoniana*, sucrose starvation significantly increased frequencies of sexual tetrad formation at both stages of pistil development (FIG. 29). In this case of severe carbohydrate starvation (pistil detached from its photoassimilate supply and not provided with a substitute sugar source), positive correlations were observed between a decreasing apomeiosis to meiosis ratio and the occurrence of apospory. At both culture initiation stages, diplosporous dyad frequencies decreased sharply (FIG. 29). Pearson Chi-square tests of independence were highly significant (P<0.001) for pistil age versus reproductive mode and for presence or absence of sucrose versus reproductive mode. Photomicrographs of sexual, diplosporous and aposporous development from these sugar starvation experiments are shown in FIGS. 30A-30H.

Significance of discovery: As with osmotic stress, sugar starvation, in the absence of osmotic stress, imposed within 48 hours of apomeiosis (in the germ cell) was sufficient to reprogram the biology (metabolome and genome) of the apomictic germ cell to pursue sexual development. This discovery indicates that bioenergetics stress is sufficient in the absence of osmotic stress to shift reproduction from apomixis to sex.

Example 6. Converting Apomeiosis to Meiosis in MMC and Death of Nucellar Cells to Apospory by 11202 Treatments Imposed within 48 Hours of Apomeiosis TARGET OF RAPAMYCIN (TOR) is a major regulator of cell energetics that is highly-conserved among eukaryotes. This serine/threonine protein kinase activates or inactivates enzymes by its serine-threonine phosphorylation function(18). As a regulator of bioenergetics, TOR is inactivated by ROS, and its inactivation suppresses growth. Furthermore, high levels of ROS accumulate in plant cells in response to low glucose levels (98). However, glucose/TOR signaling in high ROS low glucose environments is selective, with cell cycle regulation being specifically targeted (21). Interestingly, this is consistent with the somewhat surprising results that stress-induced switching from apomeiosis to meiosis can occur very late in MMC development, possibly after apomeiotic prophase has initiated. Since major cell cycle alterations are central to apomixis/sex switching, we asked whether ROS/TOR signaling functions downstream from stress (drought or sugar starvation) perception. To address this question, we pretreated for 5 min appropriately staged pistils in solutions containing $H_2O_2$, cultured the pistils under otherwise favorable Ψ and sucrose conditions, and observed, one to a few days later, whether apomeiosis to meiosis shifts had been induced. $H_2O_2$ is a relatively long-lived ROS that permeates whole cells and cell organelles (48). A ROS-induced reduction in apomeiosis to meiosis ratios would be consistent with TOR being part of the causal signal transduction (switch mechanism) pathway.

Figure 31:
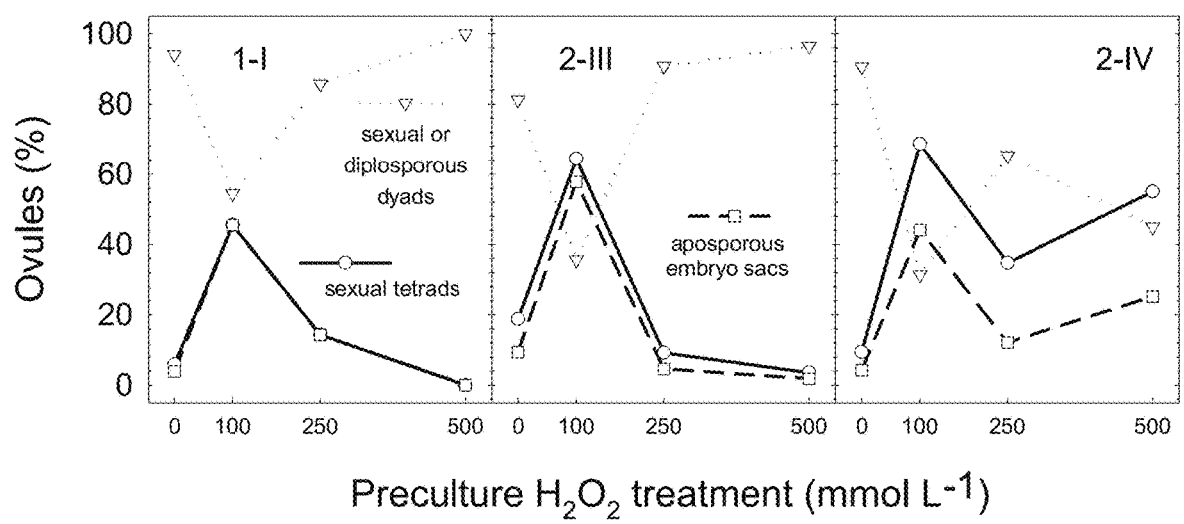
FIG. 31 Frequencies of *B. retrofracta×stricta* ovules that were undergoing sexual tetrad, sexual or diplosporous dyad, or AES formation at the end of the pistil culture treatment as affected by i) increasing concentrations of $H_2O_2$ in the pistil preculture treatment and ii) ovule stage at pistil culture initiation (1-I, 2-III and 2-IV). Numbers of correctly staged ovules (containing a 1-2 nucleate AES and/or a dyad or tetrad) at the $12H_2O_2$ concentration by pistil stage treatments averaged 77 and ranged from 6-138.
Figure 32:
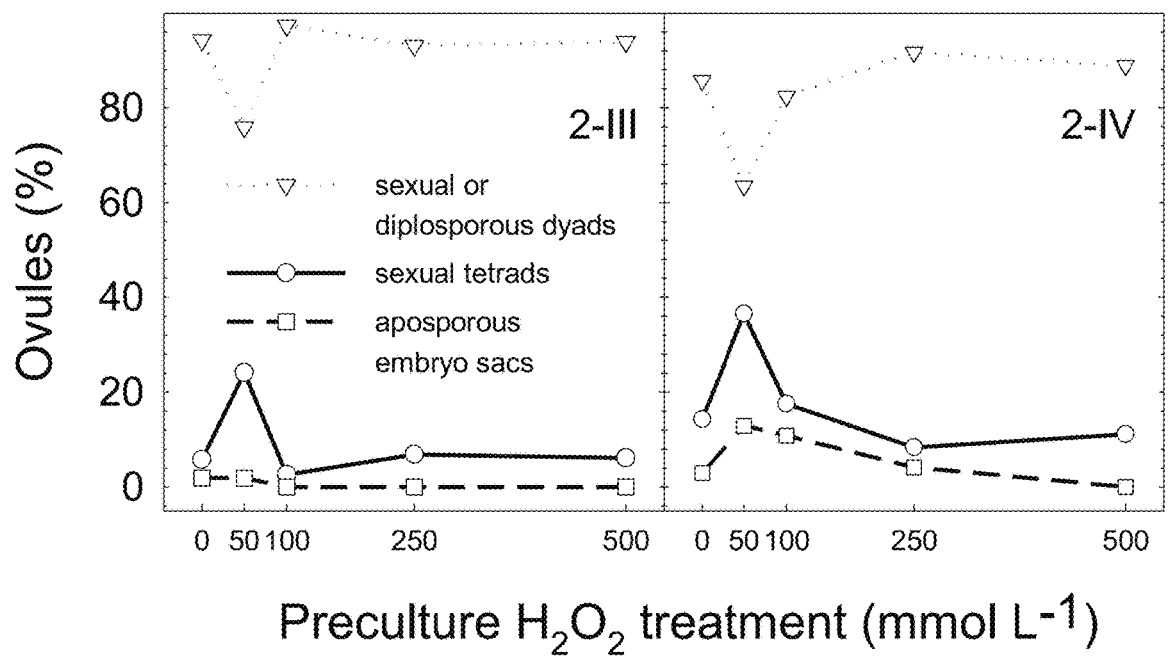
FIG. 32 Frequencies of *B.* cf. *lignifera* ovules that were undergoing sexual tetrad, sexual or diplosporous dyad, or AES formation at the end of the pistil culture treatment as affected by i) increasing concentrations of $H_2O_2$ in the pistil preculture treatment and ii) ovule stage at pistil culture initiation (2-III and 2-IV). Numbers of correctly staged ovules (containing a 1-2 nucleate AES and/or a dyad or tetrad) at the $10H_2O_2$ concentration by pistil stage treatments averaged 70 and ranged from 29-168.
Figure 33:
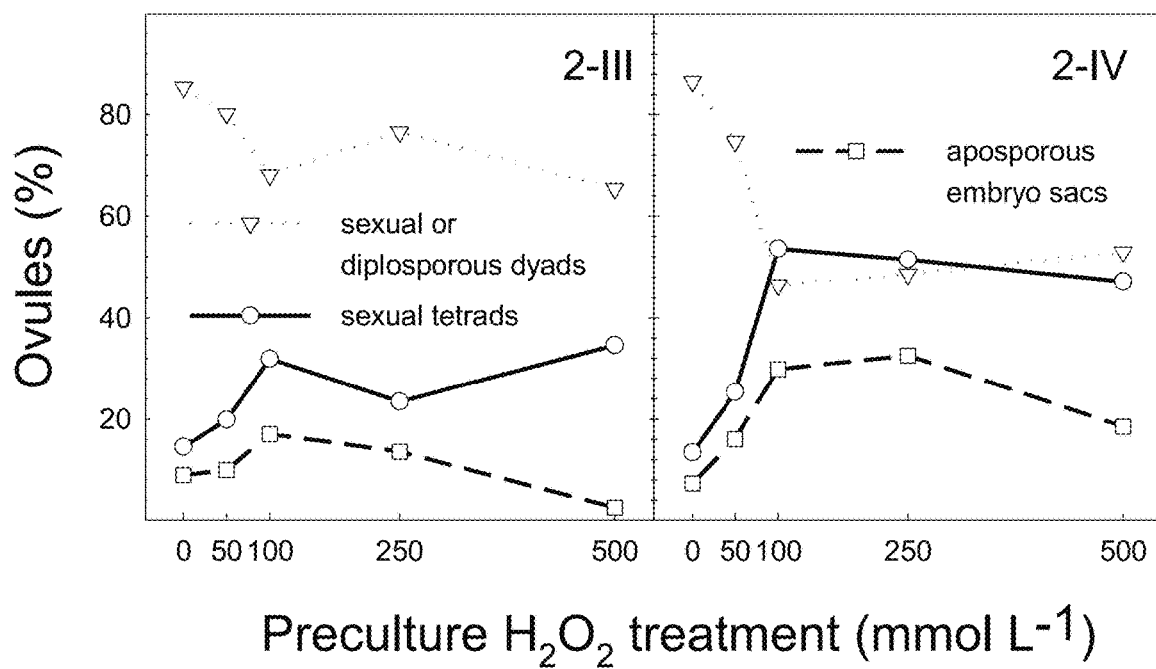
FIG. 33 Frequencies of *B.* cf. *gunnisoniana* ovules that were undergoing sexual tetrad, sexual or diplosporous dyad or AES formation at the end of pistil culture as affected by i) increasing $H_2O_2$ concentrations in the pistil preculture treatment solution and ii) ovule stage at pistil culture initiation (2-II and 2-IV). Numbers of correctly staged ovules (containing a 1-2 nucleate AES and/or a dyad or tetrad) at the $10H_2O_2$ concentration by pistil stage treatments averaged 217 and ranged from 78-465.
Figure 35:
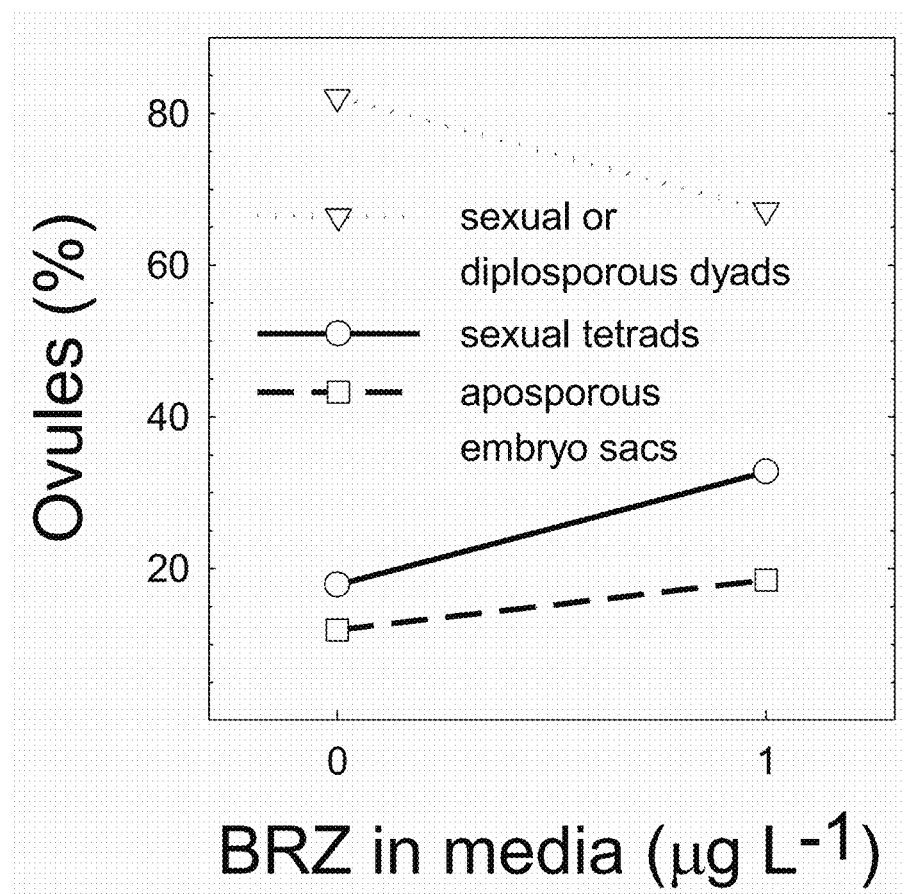
FIG. 35 Frequencies of *B*. cf. *gunnisoniana* ovules that were undergoing sexual tetrad, sexual or diplosporous dyad, or AES formation at the end of pistil culture as affected by BRZ concentration. Pistils were cultured at the 2-IV stage. Numbers of correctly staged ovules (containing a 1-2 nucleate AES and/or a dyad or tetrad) were 84 and 119 for the 0.0 and 1.0 BRZ levels, respectively.

The 50 and/or 100 mmol L−1 $H_2O_2$ treatments effectively switched apomeiosis to meiosis in apomictic *B. retrofractax stricta* (FIG. 31), *B. lignifera* (FIG. 32) and *B.* cf. *gunnisoniana* (FIG. 33). In these cases, the switch from diplospory (production of apomictic dyads of unreduced megaspores) to sex (production of tetrads of reduced megaspores) was mirrored by adventitious embryo sac formation from evolutionarily-sporogenous nucellar cells (apospory). In most cases of apospory, a sexual tetrad had also formed, but all four megaspores were degenerating. The replacement of surviving megaspores of tetrads by aposporous embryo sacs was most apparent in the aposporous-leaning *B. retrofractax stricta* (FIG. 31), but it also occurred to a fairly high degree (30% of ovules) in *B.* cf. *gunnisoniana* (FIG. 33), in which apospory is only rarely observed in nature. Apparently, the decision of nucellar cells to undergo apoptosis and yield their protoplast nutrients to the developing female gametophyte, is redox sensitive. In the three *Boechera* species tested, the nucellus, regardless of genetics, displayed four inherent developmental potentialities: i) apomeiosis (*Taraxacum*-type diplospory), ii) meiosis, iii) apoptosis, with nutrients becoming available to the growing gametophyte, and iv) aposporous female gametophyte (embryo sac) formation. Interestingly, the switch from apoptosis to apospory was redox activated. Photomicrographs of these four developmental fates are shown for the $H_2O_2$ treatment experiments in FIGS. 34A-34L.

The most effective timing in the 2-IV stage for inducing meiosis with $H_2O_2$ treatments differed depending on the species. For *B*. cf. *gunnisoniana*, the best timing occurred when pistils were 2.1 mm long, which is near the end of the 2-IV stage. For *B. lignifera*, the best timing was when pistils were 1.5 mm long, which was near the middle of 2-IV stage. For *B. retrofracta×stricta*, the best time was when the pistils were 2.0 mm long, which is at the beginning of the 2-IV stage.

Significance of discovery: As with osmotic stress and sugar starvation, $H_2O_2$ imposed within 48 hours of apomeiosis (in the germ cell), in the absence of either osmotic stress or sugar starvation, was sufficient to reprogram the biology (metabolome and genome) of the apomictic germ cell to pursue sexual development. This discovery indicates that $H_2O_2$ is sufficient in the absence of osmotic stress or bioenergetic starvation to shift reproduction from apomixis to sex. This is an important discovery. With this experiment, we narrowed in on the molecular pathway responsible for sex apomixis switching, from innumerable potential stress-induced pathways, down to a single chemical, $H_2O_2$, that functions within the switch pathway.

Example 7. Converting Apomeiosis to Meiosis in MMC and Death of Nucellar Cells to Apospory by Inhibiting Brassinosteroid Signaling within 48 Hours of Apomeiosis The observed rapid shift from apomeiosis to meiosis in late-stage MMC as affected by H2O2 treatments is consistent with the activity status of TOR being a key regulator of the apomixis/sex switch. By a mechanism not yet elucidated (25), TOR stimulates the production of brassinosteroids (BR), which are plant steroids that regulate growth, including many growth and development functions of ovules (25). By dephosphorylation, BR activates BRASSINAZOLE-RESISTANT 1 (BZR1), which is a major BR-regulated transcription factor that targets ca. 2000 genes. Thus, to determine if BR functions downstream of TOR in the apomeiosis meiosis switch, we treated sets of *B*. cf. *gunnisoniana* pistils with the BR biosynthesis inhibitor brassinozole (BRZ). Pistils were collected during the 2-III and 2-IV stages. Pistils in the 2-III stage did not grow sufficiently to collect data. However, for pistils cultured at the 2-IV stage, BR synthesis inhibition caused a significant shift (P<0.05) from apomeiosis to meiosis and from apoptosis to apospory (FIGS. 35, 36A-36D). Thus, the TOR/BR/BZR1 pathway is a component of the apomixis/sex switch in *Boechera*.

Figure 37:
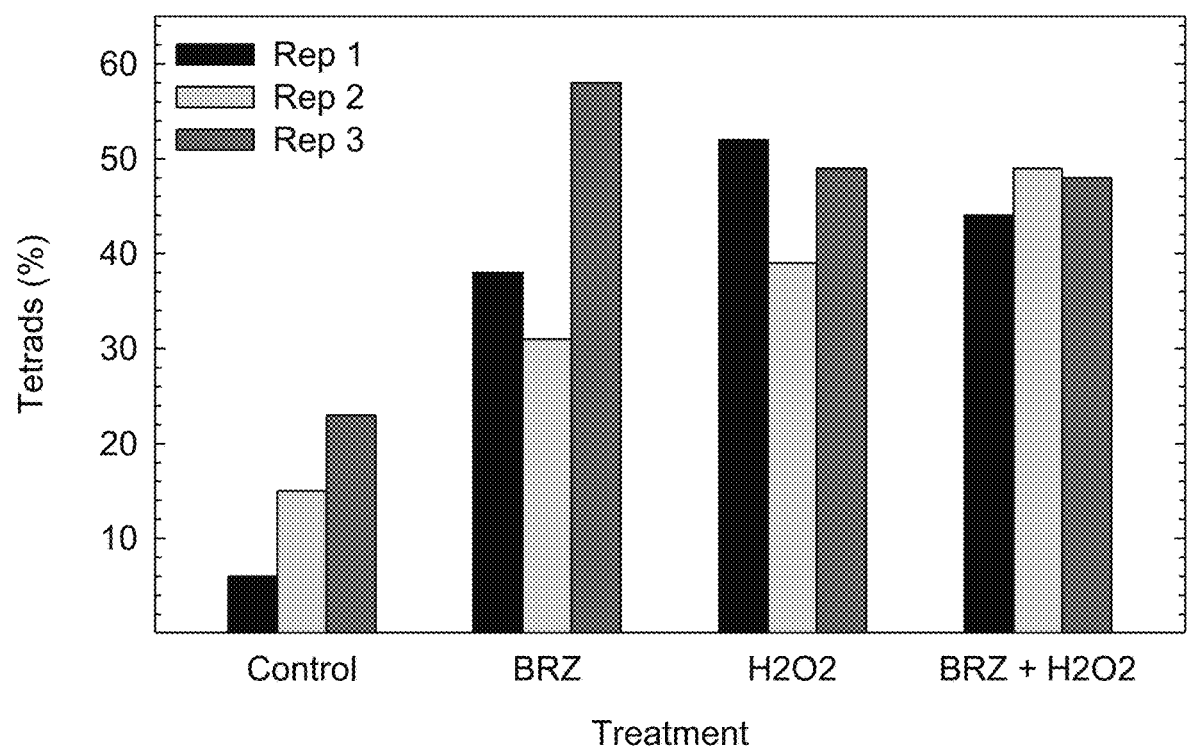
FIG. 37 Frequencies of *B*. cf. *gunnisoniana* ovules that were undergoing sexual tetrad formation at the end of pistil culture as affected by additions of BRZ, $H_2O_2$, and BRZ and $H_2O_2$ combined. Pistils were cultured at the 24V stage.
Figure 38:
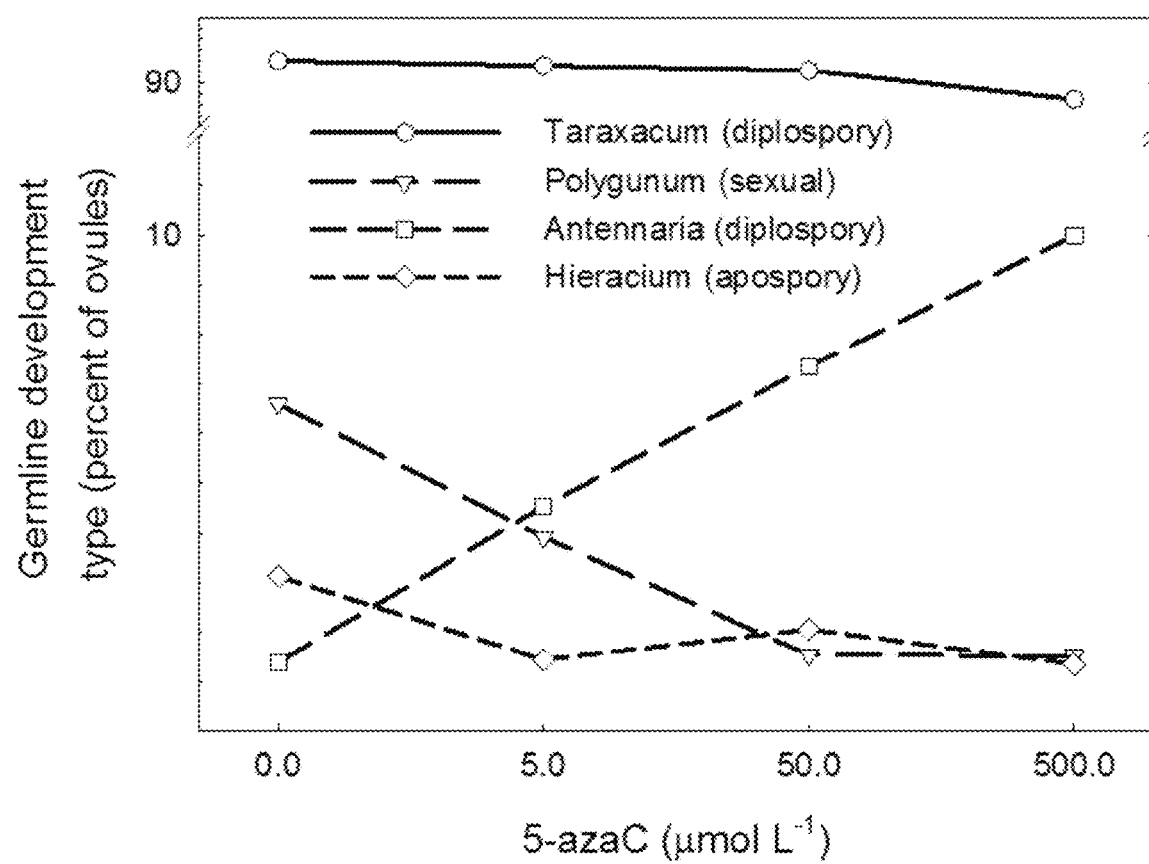
FIG. 38 Frequencies of triploid *B*. cf. *gunnisoniana* ovules that were initiating *Taraxacum*-type diplospory, *Polygonum*-type sexual development, *Antennaria*-type diplospory, or *Hieracium*-type apospory at the end of pistil culture treatment as affected by a 5 min pre-culture soak in solutions containing 5-azacytidine (5-azaC). Pistils were initiated in culture at the 1-I stage. Numbers of ovules per level of 5-azaC averaged 487 and ranged from 288-590.
Figures 39A, 39B, 39C:
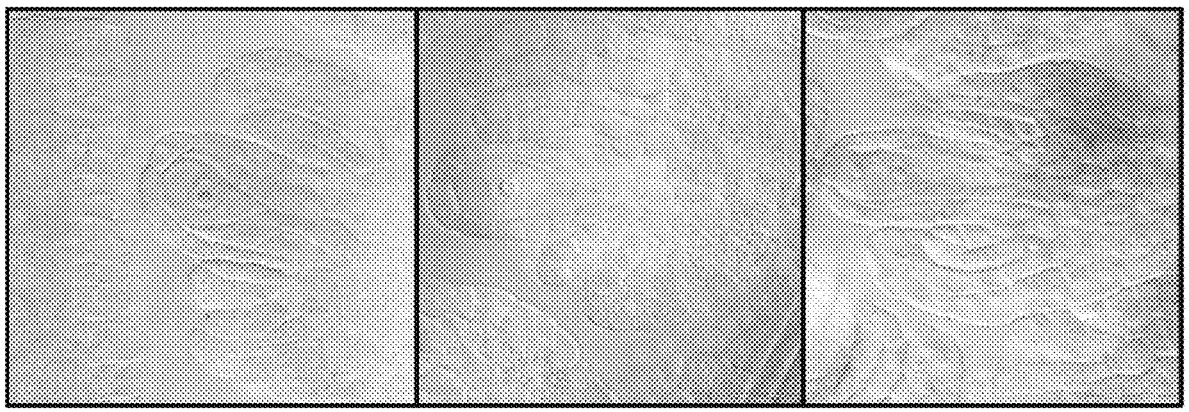
FIGS. 39A-39C Ovules from pistils of *B. gunnisoniana* treated at the pre-MMC stage with 5-azaC as a pretreatment solution and then cultured on 5-azaC-containing tissue culture media for 48 h.

To determine if apomixis to sex switching by $H_2O_2$ involves pathways independent of BR, we compared three treatments to controls, BRZ alone (1.0 μmol), $H_2O_2$ alone (500 μmol), and BRZ and $H_2O_2$ combined (FIG. 37). All three treatments produced a highly significant (p<0.001) shift from apomeiosis (dyad formation) to meiosis (tetrad formation), but there was no additive effect and no difference among the three chemical treatments (P<0.05). This result indicates that suppression of BR synthesis by $H_2O_2$, which forms during episodes of stress, is a downstream component of the apomixis/sex switch that does not require additional ROS signaling.

Figure 3:
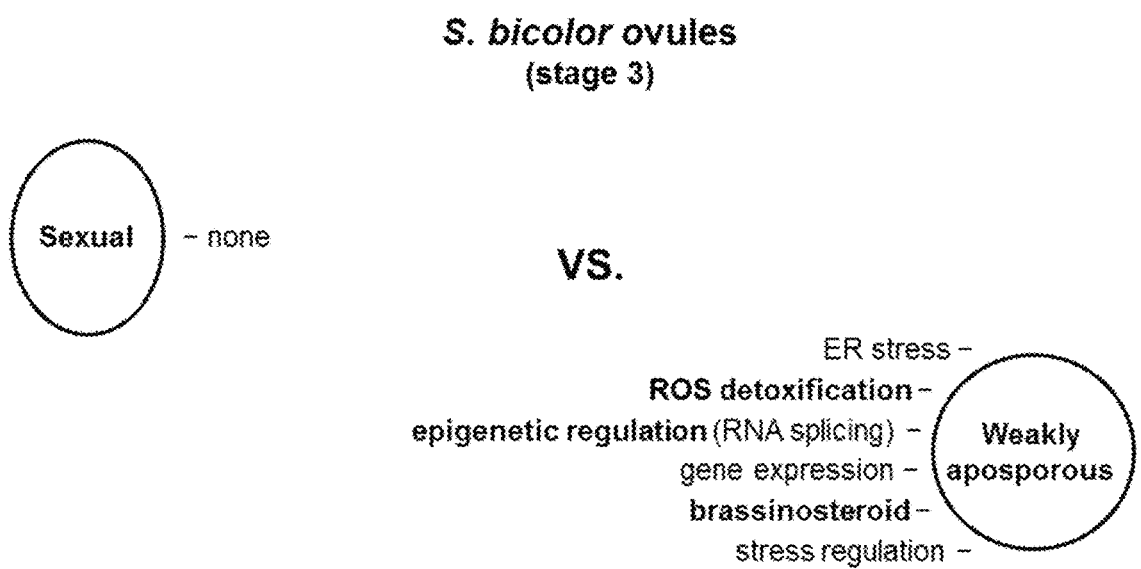
FIG. 3 GO categories of potential importance in determining reproductive mode during ovule development in *S. bicolor*. Stage 3 spans early to late ES formation.

Significance of discovery: These experiments indicate that BR synthesis suppression reverts apomeiosis to meiosis, and they point to a likely BR regulated transcription factor, BZR1 (FIGS. 13A-13B). The implication here is that BR is important to apomixis expression, and this is consistent with our gene expression profiling where brassinosteroid metabolism and signaling GO categories were associated with apomixis expression (FIG. 12, 111-3).

The experiments described in Examples I-IV elucidate major components of the molecular pathway responsible for apomixis to sex switching. This information does not appear in the literature. Our discovery of this pathway enabled us to reverse the process, i.e., to chemically induce apomixis in sexual plants without genetic modifications.

Example 8. Converting *Taraxacum*-Type Diplospory to Antennaria-Type Diplospory by Suppressing MMC DNA Methylation in *B*. cf. *Gunnisoniana*

Gametophytic apomixis in angiosperms involves the formation of a genetically unreduced gametophyte that produces an unreduced egg that develops into an embryo parthenogenetically, with endosperm forming either pseudogamously (with fertilization of the gametophyte central cell) or autonomously (without central cell fertilization). There are several developmental pathways through which the embryo sac (gametophyte) may form, and these constitute different types of gametophytic apomixis. The most common types are *Hieracium*-type apospory, where the embryo sac forms from a nucellar cell after meiotic failure, *Taraxacum*-type diplospory, where meiosis fails at the 1st division and the embryo sac forms from an unreduced product of a mitotic-like meiosis, and Antennaria-type diplospory, where meiosis fails prior to the 1st meiotic division and the embryo sac forms directly from the MMC (1, 7, 10). Multiple types of apomixis occurring in the same species has only rarely been observed (1), and this has led scientists to suspect that these three major types of apomixis are regulated by different genetic mechanisms. As described above, we have shown that *Taraxacum* type diplospory and *Hieracium*-type apospory are common in *Boechera* and that Antennaria-type diplospory also occurs, apparently rarely, in the genus. Here, we hypothesized that T-type diplospory represents a partial suppression of meiosis, while A-type diplospory represents complete meiotic suppression.

The observations that i) epigenome reprogramming is required for sexual reproduction (35) and ii) inactivation of DNA methylation can induce apomixis-like phenotypes (7) suggest that apomixis may be the default pathway with sex being the more derived add-on program. Thus, if methylation in sexual plants can be prevented, or if DNA can be demethylated, the apomictic pathway might surface as the default pathway. 5-azaC, an inhibitor of DNA-cytosine methyltransferases, produces upon DNA replication hypomethylated DNA. It is a chemical analogue of cytosine that is incorporated into DNA by competition with cytosine during DNA synthesis. In 5-azaC, the carbon-5 of the cytosine ring, which is essential to DNA methyltransferase function, is replaced by nitrogen, and this causes failure of methylation at each 5-azaC site(99). Here, we incorporated 5-azaC into archesporial nucellar cells of *Taraxacum*-type diplosporous *B*. cf. *gunnisoniana* prior to the mitoses that produce the MMC from the archesporial cell. The highest concentration of 5-azaC (500 μmol L−1) induced Antennaria-type diplospory in 10% of the ovules (FIGS. 38, 39A-39C).

Significance of discovery: In Examples I-IV, we repeatedly demonstrated that ovules of *Taraxacum*-type diplosporous apomicts can readily switch to *Hieracium*-type apospory when their metabolic states are altered. Here we show that *Taraxacum*-type diplospory switches to Antennaria-type diplospory when epigenetic modifications associated with *Taraxacum*-type diplospory are prevented from occurring. Collectively, these experiments indicate that the three major types of apomixis in angiosperms are interchangeable within a common genotype. We demonstrate below that sexual reproduction is also interchangeable with apomixis within common genotypes. These demonstrations are counterintuitive with regard to the present state of the art of apomixis research, which has (for over 100 years) provided evidence that apomixis is under genetic, not metabolic, control. We understand that different genotypes have different capacities for expressing sex or apomixis. But we suspect that the genetic differences in most cases reflect differences in how ovules interpret or detoxify their metabolic environments, and not in genetic mutations that somehow directly affect sexual or apomictic development.

Figure 40:
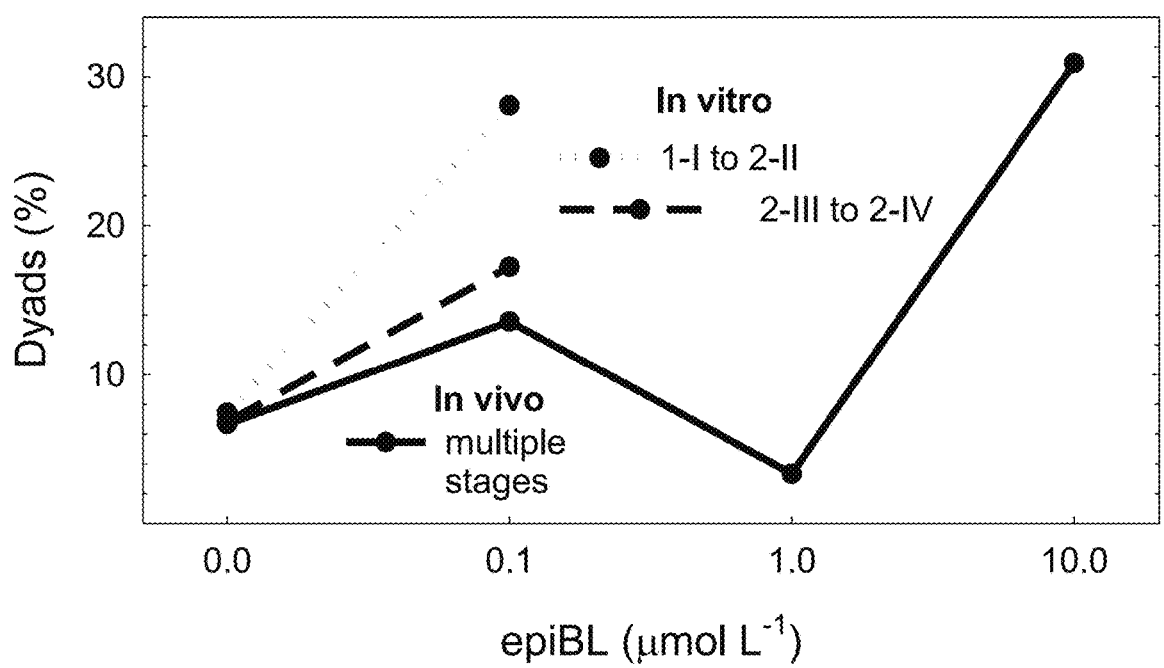
FIG. 40 Frequencies of *B. stricta* ovules (dyads and tetrads) that were undergoing dyad formation (sexual or diplosporous) at the end of pistil treatment as affected by i) a 3 h in vivo floral dip in solutions containing epibrassinolide (epiBL) or ii) culturing of pistils in epiBL-containing media with in vitro culture of pistils initiated when pistils were in the 1-I or the 2-III to 2-IV stages. Numbers of correctly-staged ovules (dyads plus tetrads) per data point averaged 53 and ranged from 27-82.
Figures 41A, 41B, 41C:
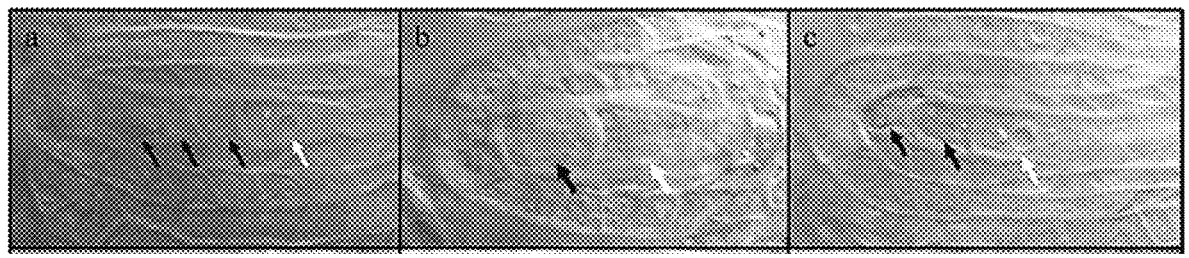
FIGS. 41A-41F Ovules of *B. stricta* treated with epiBL in vivo (FIGS. 41A-41C) and in vitro (FIGS. 41D-41F).
Figures 41D, 41E, 41F:
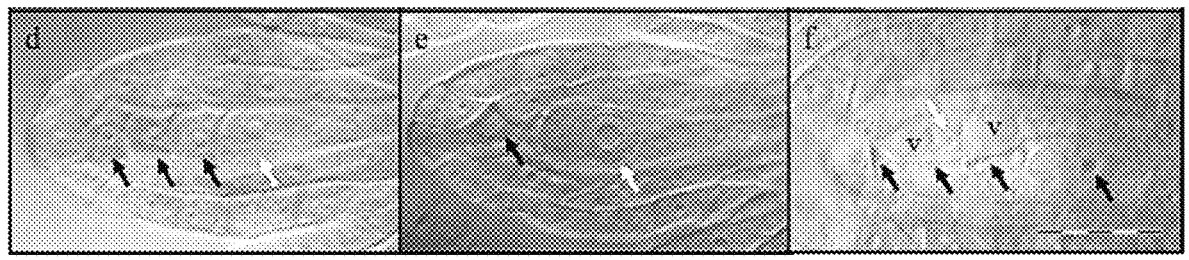

Example 9. Converting Meiosis to Apomeiosis with BR or Glucose epiBL is the naturally occurring and most biologically active form of BR. Applications of epiBL to pistils of sexual *B. stricta*, in vivo or in vitro, caused MMC to abort meiosis and instead produce dyads (FIG. 40). In vivo, the most effective treatment involved dipping flower buds of *B. stricta* for 3 h in a 10 μmol L−1 solution of epiBL. This induced 31% dyad formation, compared to 7% for the controls (a frequency often observed in sexual plants where they represent an intermediate stage of sexual meiosis). A similar dyad induction frequency (29%) was obtained by culturing 1-I to 2-II staged *B. stricta* pistils on a 0.1 μmol L−1 epiBL medium for 2 d (FIG. 40).

The *B. stricta* accession we used is an obligate sexual plant (26), and the sexual dyad stage, during meiosis, is very short. It is often difficult to catch the sexual dyad stage in pistil fixations because it is so brief (usually less than 10% of meiocyte-staged fixations). In contrast, the dyad stage of *Taraxacum*-type diplosporous apomixis (1st division restitution resulting in a dyad of unreduced megaspores) is a lengthy stage, like the tetrad stage of sexual plants. Hence, the dyad stage is readily observed in ovule fixations of diplosporous *Boechera*. Although ratios of observed dyads increased to 30% in the epiBL treatments (higher than expected for sexual meiosis), unreduced embryo sacs forming from epiBL-induced dyads (with prominent embryo sac vacuoles) were only rarely observed (FIGS. 41A-41F). Such embryo sacs should have been more frequently observed if the dyads were consistently developing diplosporously, i.e., the surviving megaspore (chalazal member) would have started to develop large vacuoles and would have begun consuming the degenerating dyad member and adjacent nucellar cells. Low frequencies of such observations (FIG. 41E) suggest that BR alone may be insufficient to effectively convert meiosis to apomeiosis.

Figure 42:
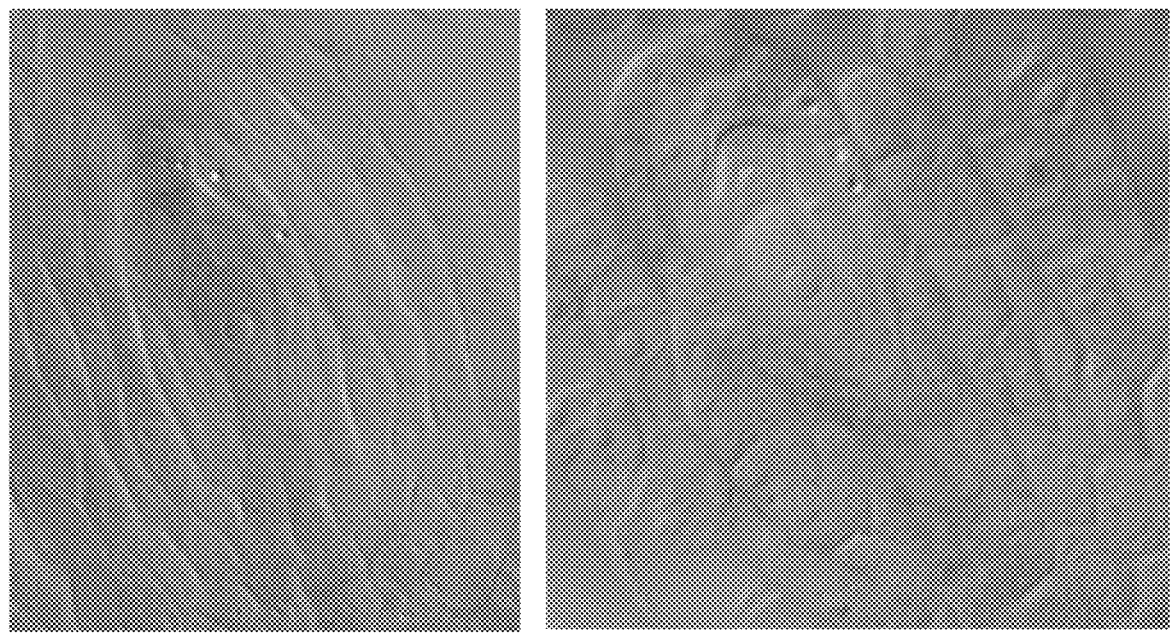
FIG. 42 *Arabidopsis* ovules pre-meiotically treated with either 2 μM BR or 50 mM glucose developing by *Taraxacum* type diplospory with subepidermal layers of cells.

Treatment of intact pistils of *Arabidopsis* with BR or glucose solutions induced high frequency apomeiotic dyad formation. Most of the functional megaspores from these treatments originated by *Taraxacum*-type diplospory (FIG. 42) with frequent subepidermal layer of cells with or without a parietal cell. A few cases of Antennaria-type diplospory were also observed (FIG. 43).

Significance of discovery: In *B. stricta*, the inability of BR alone to rapidly induce apomixis may reflect the overall metabolic state of the ovules in question. From our expression profiling studies, ovules of sexual plants consistently exhibited overrepresented or enriched GO categories associated with bioenergetic stress and redox instability (FIGS. 38, 22-24). Accordingly, we tested additional components.

Example 10. Converting Meiosis to Apomeiosis in Sexual *B. stricta, Arabidopsis* and Cowpea with 5-azaC, BR, Antioxidants and Sugars To address redox instability, pistils were exposed to the antioxidant DTBA, an antioxidant that protects thiol groups in proteins from oxidization. To address bioenergetic stress, pistils were exposed to sugars. Glucose signaling is one of the most ancient and central signaling pathways in animals and plants and is involved in gene expression, primary and secondary metabolism, and regulation of growth and development (98). In *Arabidopsis*, rates of glycolysis and mitochondrial bioenergetics are sensed by TOR, which then control root meristem activation (18). If sufficient sugar is supplied, TOR should be activated. Active TOR protects BZR1 and other important BR-regulated enzymes from degradation, and this leads to plant growth (25). Factorial experiments were designed to test the effects of sucrose, glucose, epiBL, DTBA and 5-azaC on apomixis induction. These were designed for each of three sexual species, *B. stricta, arabidopsis* and cowpea. The experiments were performed and ratios of apomeiosis to meiosis were documented.

Figure 44:
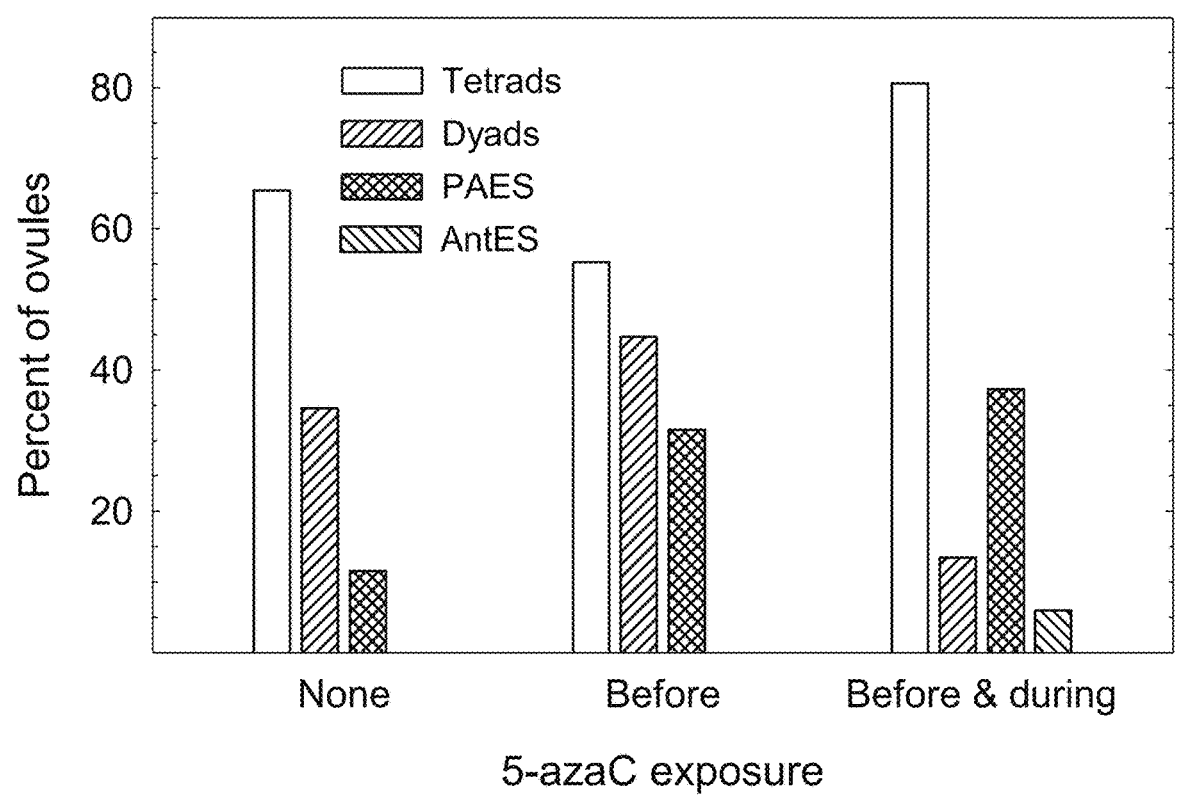
FIG. 44 Frequencies of *Arabidopsis* ovules undergoing tetrad, dyad, putative AES (PAES), and Antennaria type diplosporous ES (AntES) formation at the end of pistil culture as affected by i) absence of 5-azaC in the pretreatment solution and the tissue culture medium (none), ii) 5-azaC in the pretreatment only (before), or iii) 5-azaC in the pretreatment and culture medium (before and during). Numbers of correctly-staged ovules (dyads plus tetrads) per 5-azaC condition averaged 42 and ranged from 26-63.
Figure 46:
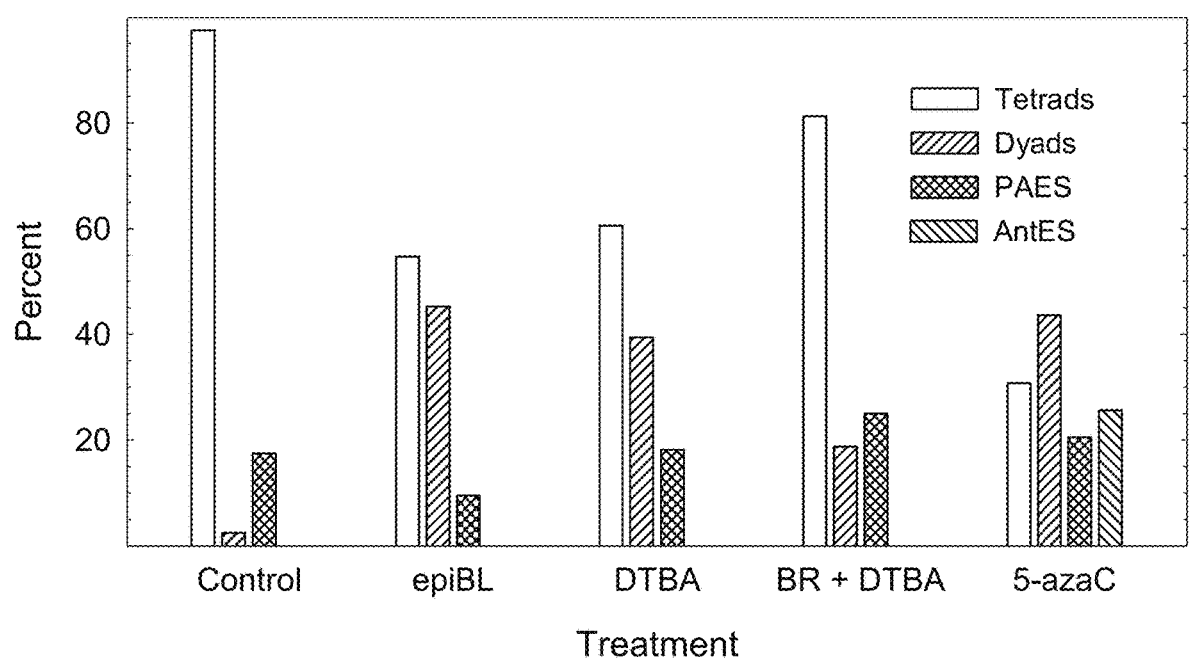
FIG. 46 Frequencies of *Arabidopsis* ovules undergoing tetrad, dyad, PAES, and AntES formation at the end of pistil culture as affected by epiBL; DTBA; BL plus DTBA; or 5-azaC. Numbers of correctly-staged ovules per treatment averaged 34 and ranged from 16-42.

Two factorial experiments were conducted using immature *arabidopsis* pistils. In the first experiment, no 5-azaC, 5-azaC in the pretreatment only, or 5-azaC in both the pretreatment and the tissue culture medium were tested. 5-azaC effectively induced onset of aposporous embryo sac formation from nucellar cells (FIG. 44). In 6% of ovules, 5-azaC in the pretreatment and tissue culture media caused sexual meiosis to abort and to be replaced with Antennaria-type diplosporous embryo sac formation (FIGS. 45A-45G). In the second factorial experiment, conducted with cultured *arabidopsis* pistils, all treatments greatly increased dyad frequencies (putative *Taraxacum*-type diplosporous embryo sacs), and 5-azaC as pretreatment and in the culture medium induced Antennaria-type diplospory in 26% of ovules. Between AES formation, *Taraxacum*-type diplospory and Antennaria-type diplospory, 90% of the 5-azaC-treated *arabidopsis* ovules initiated apomixis (FIGS. 45A-45G, 46).

Figure 47:
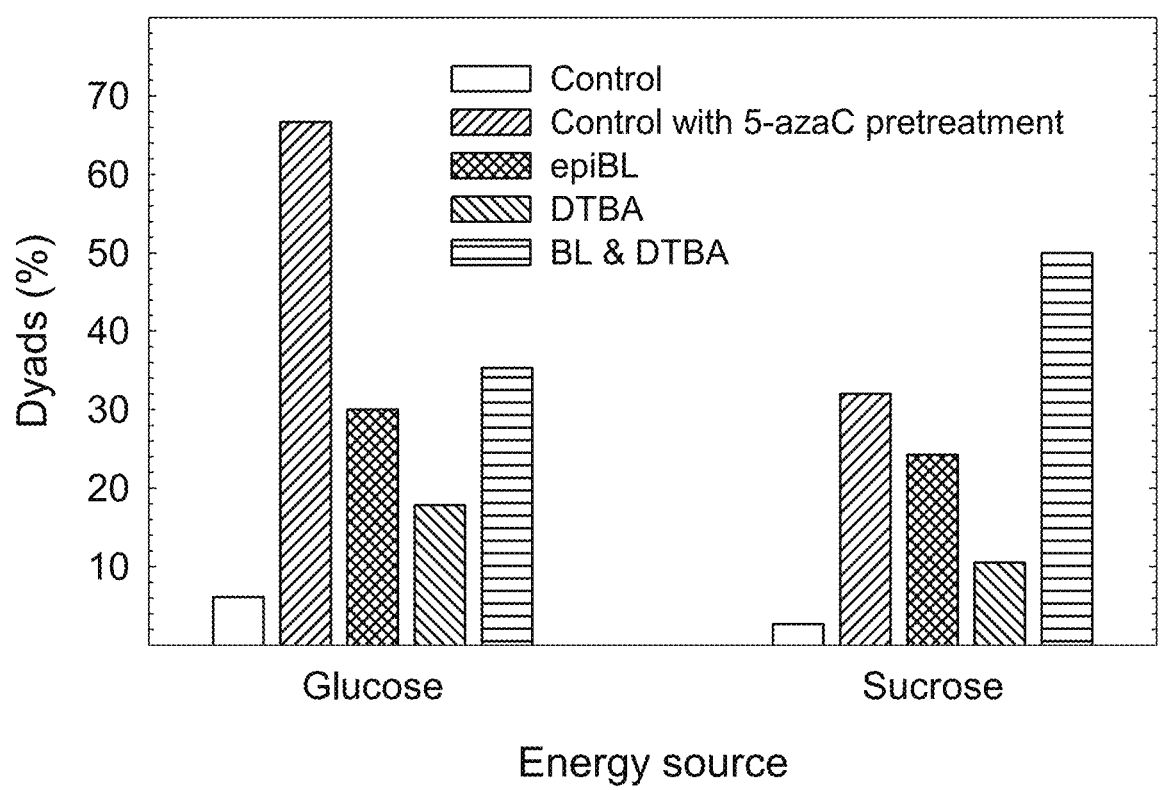
FIG. 47 Frequencies of *B. stricta* ovules that were undergoing dyad formation at the end of pistil culture as affected by i) energy source (glucose or sucrose) and ii) five treatments. 5-azaC; epiBL; DTBA. Numbers of correctly-staged ovules per data point averaged 32 and ranged from 12-75.
Figure 48A:
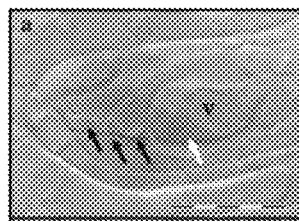
Figure 48B:
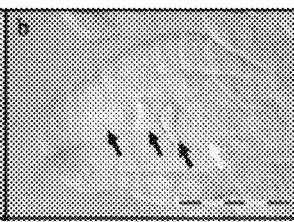
Figure 48C:
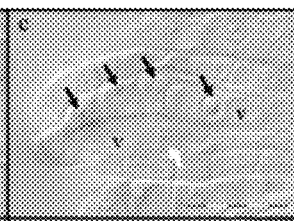
Figure 48D:
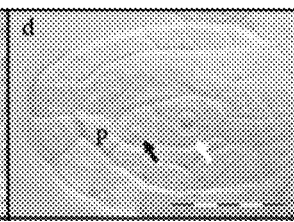
Figure 48E:
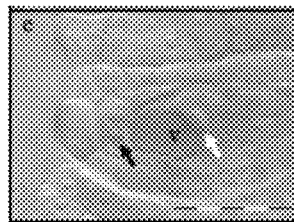
Figure 48F:
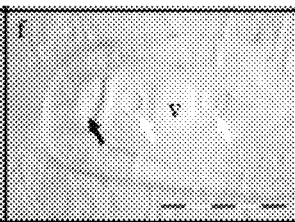
Figure 48G:
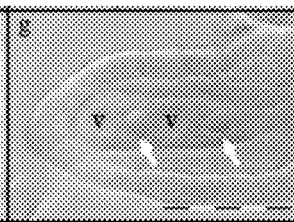
Figure 48H:
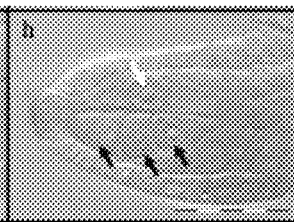
Figures 50A, 50B, 50C:
FIGS. 50A-50F Ovules of cowpea (*V. unguiculata*) treated with epiBL, DTBA, epiBL plus DTBA, and 5-azaC in either sucrose or glucose-containing media.
Figures 50D, 50E, 50F:
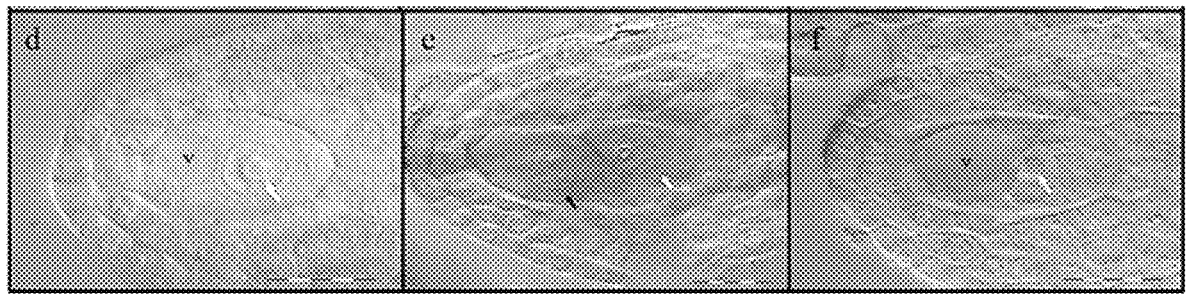

In the factorial experiment conducted using immature *B. stricta* pistils, all treatments, including glucose instead of sucrose, induced *Taraxacum*-type diplospory (FIG. 47). Both the carbohydrate variable and the other components variable were highly significant (P<0.001). Additionally, three ovules from the sucrose plus epiBL treatment (epiBL in the pretreatment and in the medium) had formed aposporous embryo sacs (AES). Also, two ovules, one from the sucrose-epiBL-epiBL treatment and one from the glucose-DTBA-DTBA treatment, had formed Antennaria-type diplosporous embryo sacs (FIGS. 48A-48H).

The cowpea experiment involved 34 ovules from among multiple treatments. Of the 34 ovules, 24 had initiated Antennaria-type diplospory (FIGS. 49, 50A-50F). Nine of these were from the 5-azaC treatment (pretreatment and in the culture medium), and 8 were from the DTBA treatment (in both the pretreatment and the culture medium).

Significance of discovery: By providing sexual ovules with favorable metabolic states as observed in apomictic ovules (as observed in the expression profiling results), apomixis was induced at high frequencies. This discovery will enable the development of plants, and probably many animals as well, e.g., aquaculture (crustacean and fish farming), that undergo apomeiosis instead of meiosis.

Figure 52:
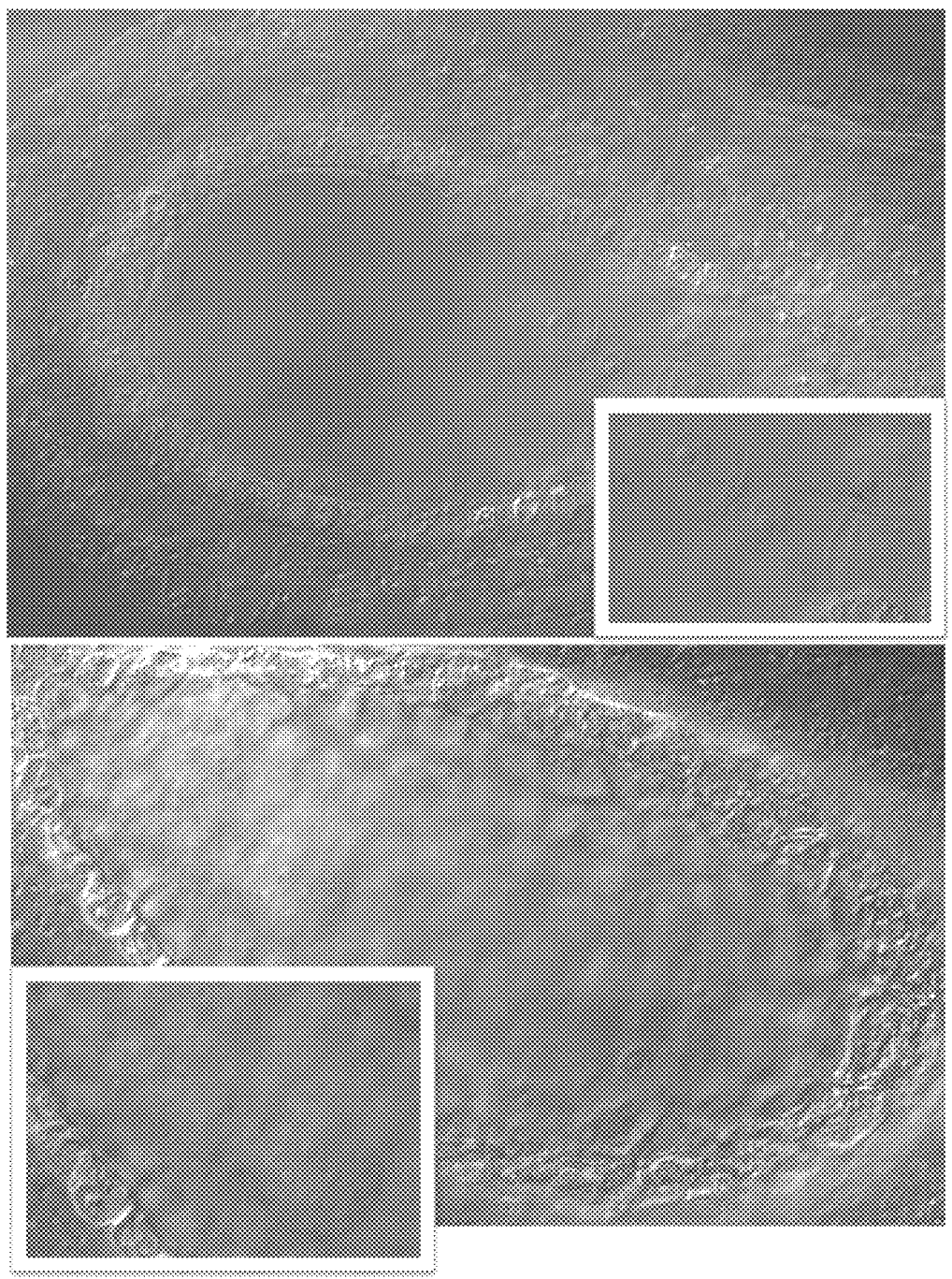
FIG. 52 Parthenogenesis in putatively diploid *Arabidopsis* embryo sacs induced by treatment of pistils in emasculated flowers with 2 µM BR or 50 mM glucose. To prevent fertilization, stigmas of pistils were clipped while anthers were immature. These pistils were also treated premeiotically with BR and glucose.

Example 11. Inducing Parthenogenesis and Autonomous Endosperm Formation in *Arabidopsis* with epiBL, Antioxidants and Sugars Functional apomixis requires not only apomeiosis but also parthenogenesis and, in plants, endosperm formation. By inducing apomeiosis, we hypothesized, based on strong correlations observed between epigenetic GO categories and modes of reproduction (FIG. 12, 111-113), that the resulting unreduced embryo sacs would possess eggs that are epigenetically programmed, as apomicts, for parthenogenesis and possibly even autonomous endosperm formation. In our studies, *Arabidopsis* pistils cultured on medium before pistils or anthers were mature exhibited low-frequency parthenogenetic embryo formation (FIGS. 51A-51E). Treatment of *Arabidopsis* pistils with 2 µM BR or 50 mM glucose prior to central cell callose deposition prevented stress-associated callose deposition and activated parthenogenesis and autonomous endosperm formation in apomeiotically unreduced embryo sacs (FIG. 52). These parthenogenetic embryos were developing precociously relative to wild type pollinated embryos.

Significance of discovery: Birth of the gametophyte generation in short-lived annuals such as *Arabidopsis* begins at the end of meiosis or apomeiosis and ends only a few days later when either the egg is fertilized or begins to develop parthenogenetically. Our results indicate that ovules and embryo sacs of sexual plants that are provided, during this time frame, with metabolic conditions consistent with those observed in ovules of apomictic plants will undergo all three phases of apomixis, i.e., apomeiosis, parthenogenesis and autonomous endosperm formation. These discoveries provide new and promising directions for achieving fully functional apomixis technologies.

Examples 12-14

Gametophytic apomixis in angiosperms terminates sexual reproduction and produces unreduced embryo sacs (apomeiosis) that generally contain an unreduced egg and two polar nuclei. These undergo parthenogenesis and autonomous or pseudogamous endosperm formation, respectively. Progeny of apomicts are maternal, a property viewed by seed producers as a potential tool for efficiently producing hybrid seed. Apomixis does not occur in major crops, but termination of meiosis coupled with apomeiosis occasionally occurs at low frequencies in sorghum. Using sorghum $F_2$ and recombinant inbred line populations, we identified apomeiosis associated quantitative trait loci. We then identified differentially expressed genes and gene ontology categories that differentiate immature ovules of an apomeiotic $F_2$ sib from those of a sexual sib. Ovules of the apomeiotic sib experienced high-energy low-stress cellular metabolism conditions, including glucose, ethylene and brassinosteroid signaling, ribosome and protein biosynthesis, and reactive oxygen species scavenger production. From these, we identified gene networks that putatively regulate apomixis sex switching, and we tested these networks using pharmacological treatments designed to shift energy and stress signaling from meiosis to apomeiosis. Different treatments induced different types of apomeiosis (Antennaria, *Taraxacum*, *Hieracium*) in sexual *Arabidopsis thaliana* and *Boechera stricta* (Brassicaceae). Antennaria type apomeiosis was also induced in the legume crop cowpea (*Vigna unguiculata*, Fabaceae). Herewith we add apomeiosis to parthenogenesis as an apomixis process that is readily inducible by modifying wild type gene expression. These findings encourage a rethinking of apomixis evolution and regulation theory and should accelerate the development of apomixis technologies for crop improvement.

Asexual seed formation (apomixis) in angiosperms involves four single cell processes. The first is termination of sexual reproduction. This occurs either before, during or after female meiosis. The second is apomeiosis, which is the formation of a genetically unreduced egg or egg-like cell. The third is parthenogenesis, which produces a clonal embryo from the unreduced egg or egg-like cell, and the fourth is fertilization dependent or independent central cell activation, which produces endosperm (7). Apomixis in other eukaryotes involves three processes, termination of sexual reproduction, apomeiosis and parthenogenesis. Across eukaryotes, a broad diversity of specialized life cycles, life cycle morphologies, and life cycle components have evolved around these three defining processes. Examples include apomictic parasites, which have sexual and apomictic life cycle phases that include multiple hosts, and apomictic insects, which employ genetic reduction followed by parthenogenesis to produce haploid males or females (9, 100). Apomixis occurs as an alternative to sex at multiple taxonomic levels in single or multi-celled organisms of all eukaryote kingdoms (1, 9, 34, 38). However, we do not know how expansive such occurrences are among extant eukaryotes. Of the 8.7 million eukaryote species (101), ecotype-intensive cytological verifications of reproductive mode are available for relatively few (9, 45, 102). Furthermore, the fossil record is completely silent concerning how frequent the expression of apomixis may have been among extinct progenitors of modern eukaryotes.

In cyclically apomictic protists and animals, favorable conditions induce apomixis, while stress induces sex (9, 34). Likewise, many facultatively apomictic angiosperms tend to switch from apomixis to sex when confronted with stress (26, 103-106). That apomixis occurs alternatively with sex in certain species from all eukaryote kingdoms suggests that sex and apomixis may be anciently polyphenic. Polyphenisms are alternative phenotypes (phenisms), which often are induced by changing seasons (107). In cyclically apomictic aphids and water fleas, fecundity is exponentially driven by apomictic females during the summer. In the fall, apomictic females produce sexual males and females. These produce fertilized eggs that remain dormant during the winter but hatch into apomictic females in the spring (108, 109).

Apomixis researchers in the $20^{th}$ century considered apomixis to be a derived trait where one to a few mutations changed meiosis to apomeiosis and mixis to parthenogenesis (39, 110). It was hypothesized late in the century that apomixis arises fortuitously due to confusions in gene expression following interspecific hybridization or polyploidization (10, 103). This hypothesis is consistent with apomixis arising, apparently without mutation, after hybridization in animals (110) and plants (74, 103, 111, 112). However, thousands of eukaryote genera contain apomictic species, and hypotheses that rely on fortuitous mutations or confusions in gene expression to produce functional alternatives to sex seem incomplete at best. Here we provide evidence for a third hypothesis, that the molecular processes of meiosis and mixis are anciently polyphenic with those of apomeiosis and parthenogenesis, and that switching between phenisms, as suggested by cyclical apomicts, is metabolically regulated (8, 50). Accordingly, apomixis genes might not be mutated meiosis or mixis genes, but genes that regulate metabolic homeostasis. This hypothesis represents a major shift in visualizing apomixis evolution and regulation, and we provide herein important supporting evidence for it.

In a previous study (50), we verified weakly penetrant apomeiosis in certain *Sorghum bicolor* (L.) Moench (sorghum; Poaceae) genotypes. Three groups of plants were studied, 150 genotypes from 65 accessions, 300 $F_2$ segregates, and 116 segregates of a recombinant inbred line (RIL) population. Plants with the highest frequencies of apomeiosis were identified by K-means separation. In these plants, sexual meiosis and ES formation occurred at less advanced physical stages of ovule development. We considered three explanations for what triggered this precocious meiosis and apomeiosis: i) a simple tendency for early germline development, ii) meiotic instability due to recent hybridity, iii) heterozygosity due to recent hybridity, and iv) weak expression of an apomixis program that induces precocious germline development. We dismissed explanations 1-3 because not all precociously meiotic plants were apomeiotic and because some apomeiotic plants were RIL that had not experienced recent hybridization. We concluded that weak expression of an apomeiosis-inducing process induced precocious reproduction, whether sexual or apomeiotic.

Herein we report quantitative trait loci (QTL) for apomeiosis associated traits in sorghum (50). We also report differentially expressed genes (DEG) between ovules excised from two sorghum sibs, one apomeiotic and one sexual. Molecular pathways regulating sex apomixis switching are postulated. Components of these pathways were tested by exposing pistils of two sexual Brassicaceae species, *Arabidopsis thaliana* (L.) Heynh. (*arabidopsis*) and *Boechera stricta* (A. Gray) A. Löve & D. Löve (Drummond's rockcress), and a sexual legume (Fabaceae) species, *Vigna unguiculata* (L.) Walp. (cowpea) to chemicals that enhance or suppress stress signaling or DNA methylation. Several treatments induced high frequency apomeiosis. To our knowledge, this is the first report of metabolism-induced apomeiosis in sexual plants.

Example 12. QTL Mapping

Materials and Methods Mapping populations were grown at Logan, Utah (41.7587° N –111.8126° W). Forty-six RIL were tiller propagated and also grown at Crosbyton, Texas) (33.6637°-101.2378°. Publically available chromosome linkage maps and genotype data (113) were used for RIL mapping (Table 8, Datafile S2). $F_2$ linkage maps were produced at Texas A&M University as in Menz et al. (114) using 175 of the 302 $F_2$ (Table 9, Datafile S3). Pearson correlation coefficients across environments (Texas and Utah) were obtained for all apospory associated traits. Means for the Utah grown $F_2$s and the Texas and Utah grown RIL (averaged across tiller-replicated plants) were used for mapping by MapQTL (115). Interval mapping (116) was performed initially for presence of a QTL for each position on the map (p≤0.05) (117, 118). Nearest flanking markers in putative QTL regions were chosen as co-factors for multiple QTL mapping using backward elimination (119). Thousand-permutation tests were used to decide logarithm of odds thresholds (p≤0.05) (120). Phenotypic variance explained by each QTL was calculated as the square of the partial correlation coefficient ($R^2$) of each variable adjusted for co-factors. Additive effects of each QTL were estimated as half the difference between the two homozygous classes. Numbers after dashes in QTL names represent chromosome numbers. usu denotes Utah State University. Sub-numbering indicates more than one QTL per trait per chromosome. Markers and QTL were drawn using MapChart (121).

Figure 53A:
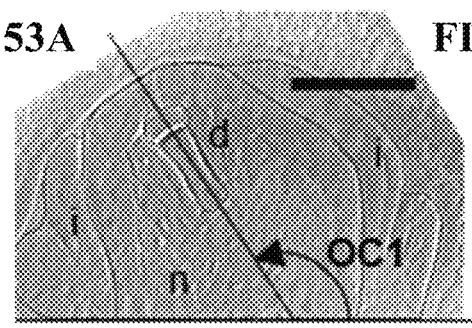
FIGS. 53A-53G Apospory associated traits in sorghum ovules.
Figure 53B:
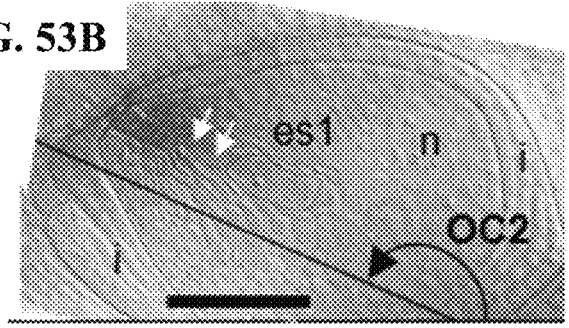
Figure 53C:
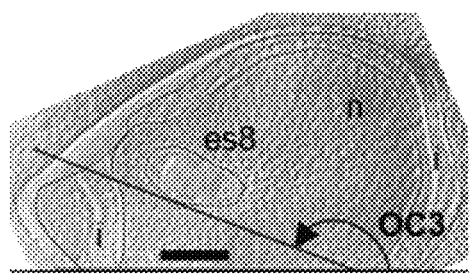
Figure 53D:
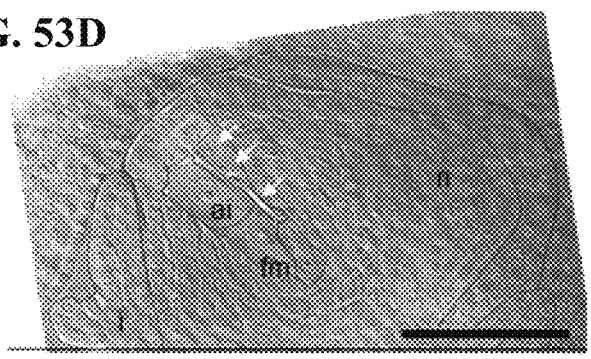
Figure 53E:
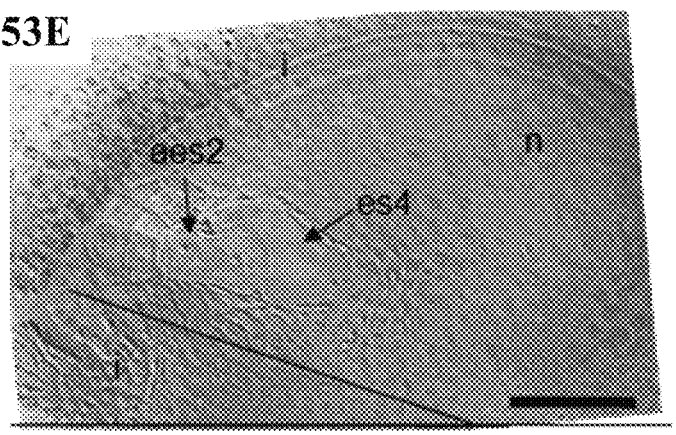
Figure 53F:
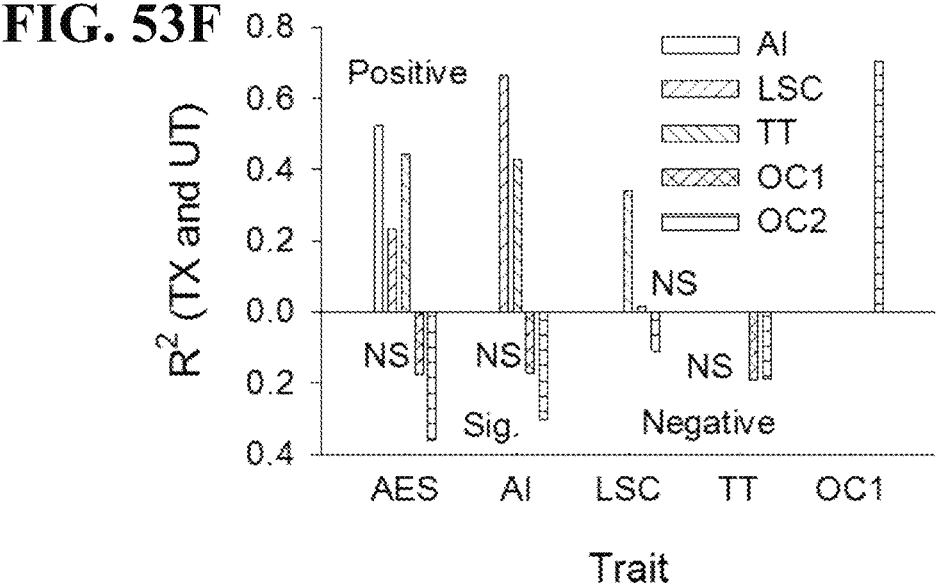
Figure 53G:
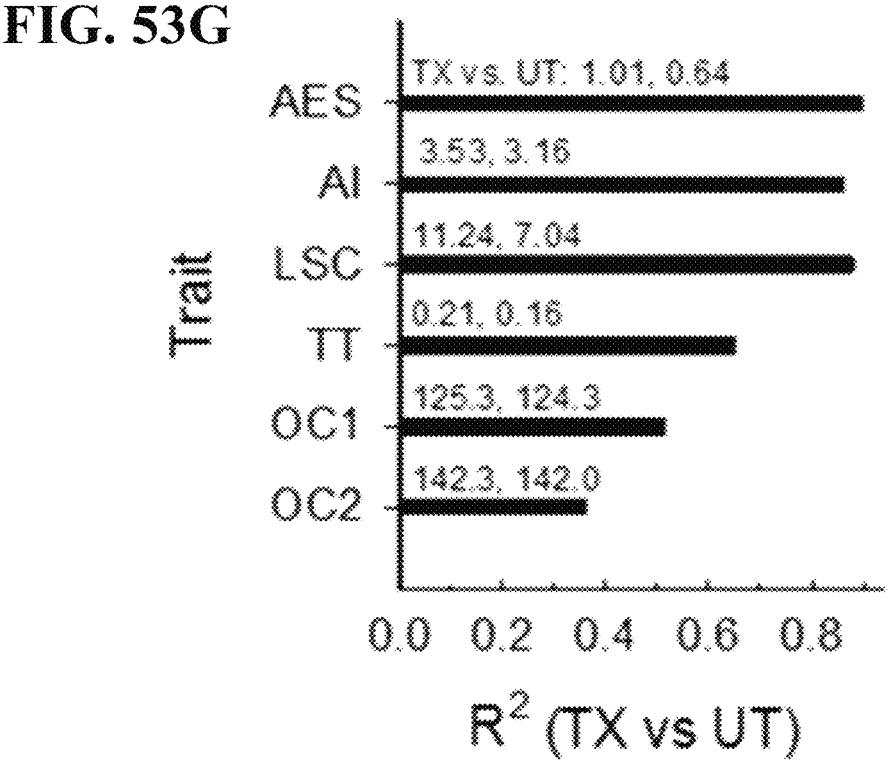

Results QTL mapping was performed using $F_2$ (50) and RIL (113) populations. Mapped traits (FIGS. 53A-53G) included aposporous embryo sacs (AES), aposporous initials (AI), large stack cells (LSC), twin tetrads (TT), and ovule curvature and/or volume values at the meiocyte (OC1, OV1), 1-nucleate ES (OC2, OV2), and 8-nucleate ES (OV3) stages. AI and AES frequencies were skewed toward 0% (50). This suggests that few QTL combinations favor AI or AES formation. AI, AES, LSC and TT frequencies were positively correlated with each other. In contrast, OC2 values were negatively correlated with AES and AI frequencies (FIGS. 53B, 53F), which indicates that AI and AES tend to form in genotypes where sexual or apomictic germline development occurs during early ovule development. Environment (TX vs UT) affected meiosis and ES onset timing as seen by low $R^2$ values for OC1 and 2 values correlated across states (FIG. 53G). Transgressive segregation among RIL was apparent for AI, OC1 and OC2 (Table 1).

Figure 54:
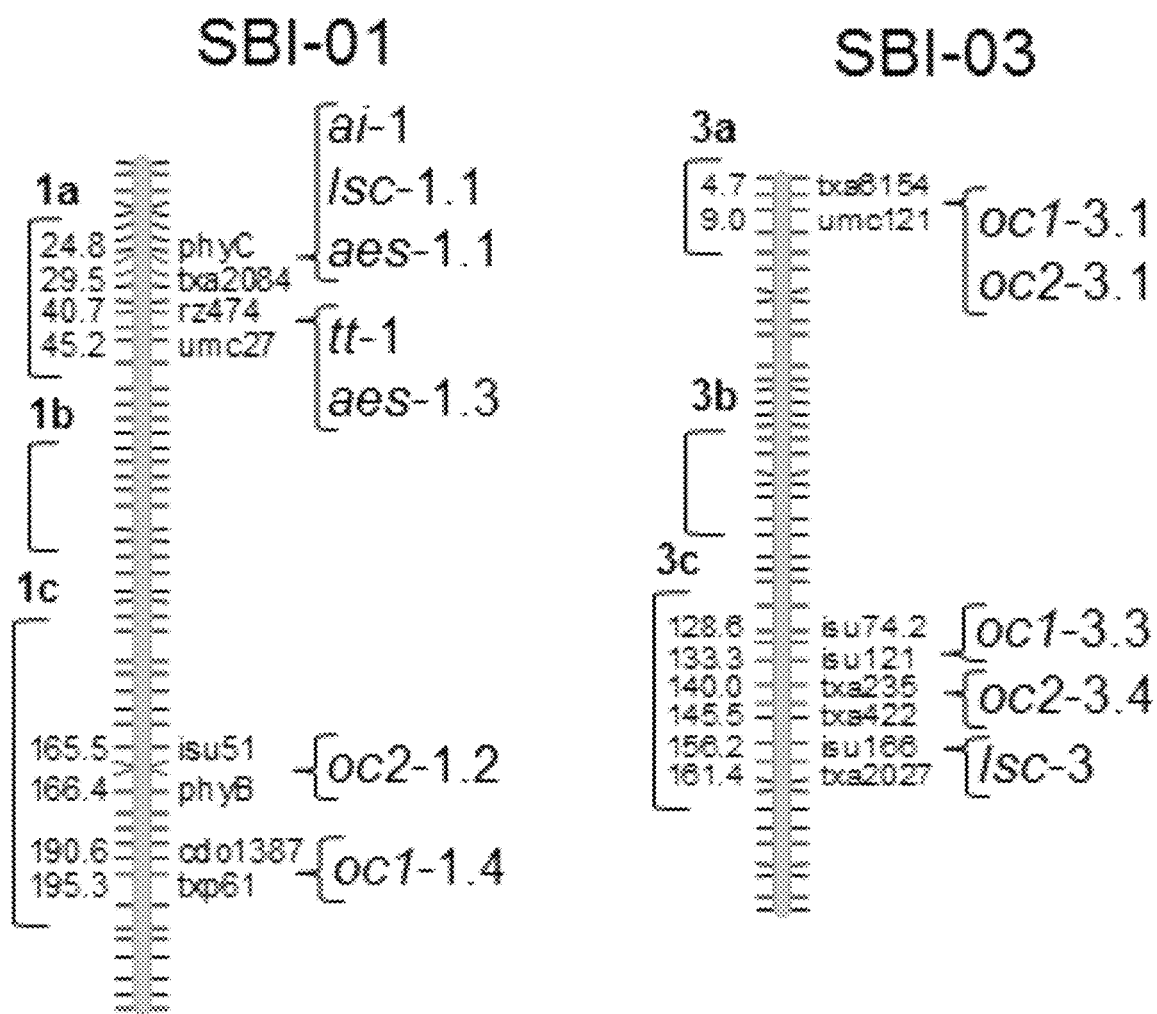
FIG. 54 Apospory associated QTL and nearest flanking markers identified in the RIL mapping population. See Table 2 for full QTL names and marker details. Broad chromosome regions containing QTL are identified alphanumerically. AES, apospory embryo sac; AI, apospory initial; LSC, large stack cell; OC1-2, ovule curvature at the meiocyte and ES1 stages; ovule volumes (estimated from ovule area measurements in sagittal ovule sections) at the meiocyte, ES1 and early ES8 stages (OV1-3); PT, persistent tetrad (delayed degeneration of non-surviving megaspores); TT, twin tetrads.
Figure 54:
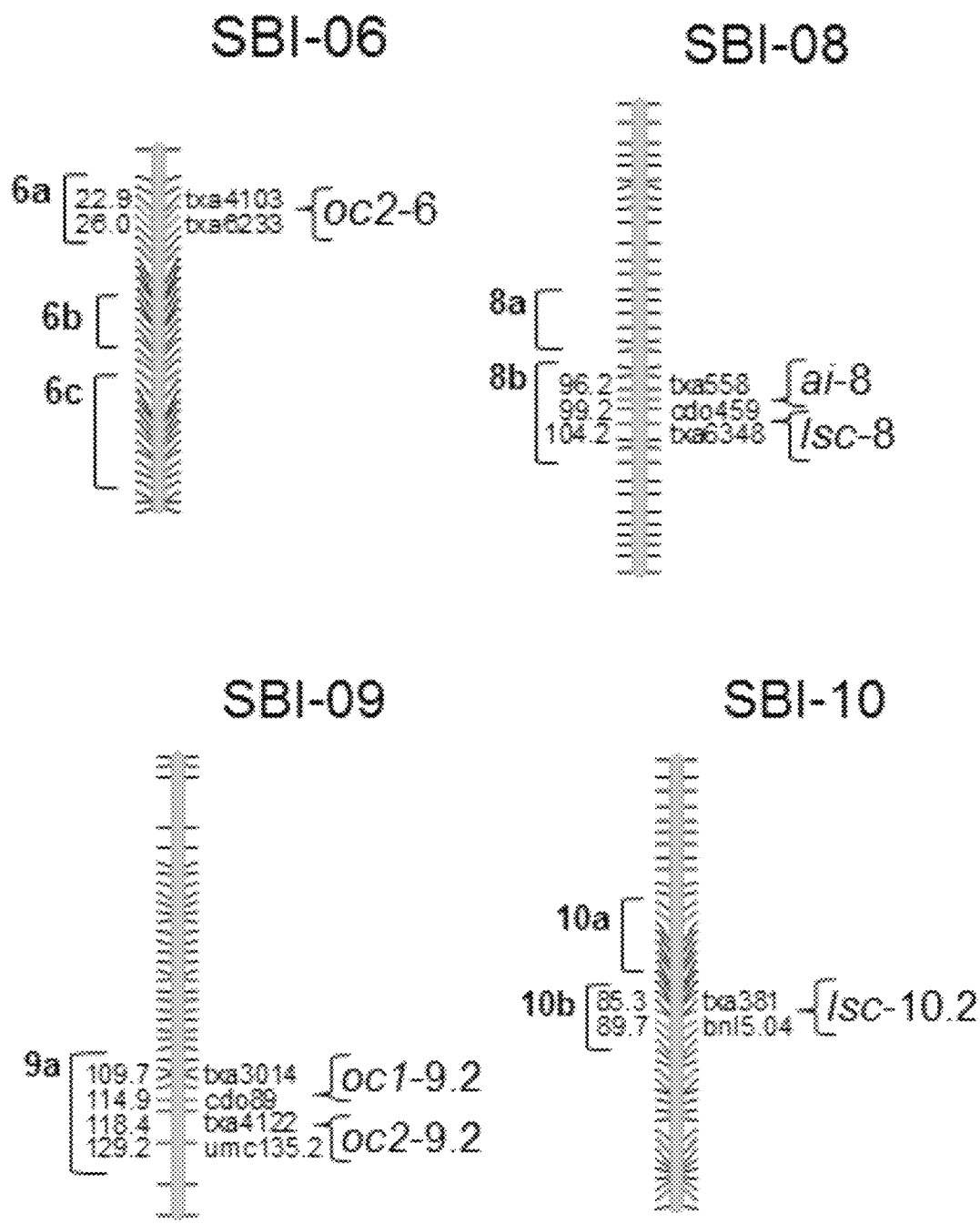

Eighteen apospory associated QTL were identified among the RIL (Table 2). Two of these, Qaes.usu-1.1 and Qaes.usu-1.3, accounted for 8.0 and 49.6% of the AES variation, respectively, and these were closely linked on chromosome 1 (FIG. 54). QTL for three other AES correlated traits, AI (Qai.usu-1), LSC (Qlsc.usu-1.1) and TT (Qtt.usu-1), also occurred in this chromosome region. Meiosis and ES onset timing QTL (Qoc1.usu-3.1, Qoc2.usu-3.1) were linked near the start of chromosome 3. A second AI QTL (Qai.usu-8) was linked to an LSC QTL (Qlsc.usu-8) on chromosome 8 (FIG. 54, Table 2). Additive effects for the low apospory parent (BTx623) allele generally decreased AES, AI, TT and LSC values (negative additive effect values) and increased OC1 and OC2 values (positive additive effect values). Exceptions were Qlsc.usu-10.2, Qoc1.usu-3.1, Qoc1.usu-3.3, Qoc2.usu-3.1, and Qoc2.usu-3.4 (Table 2).

Figure 55:
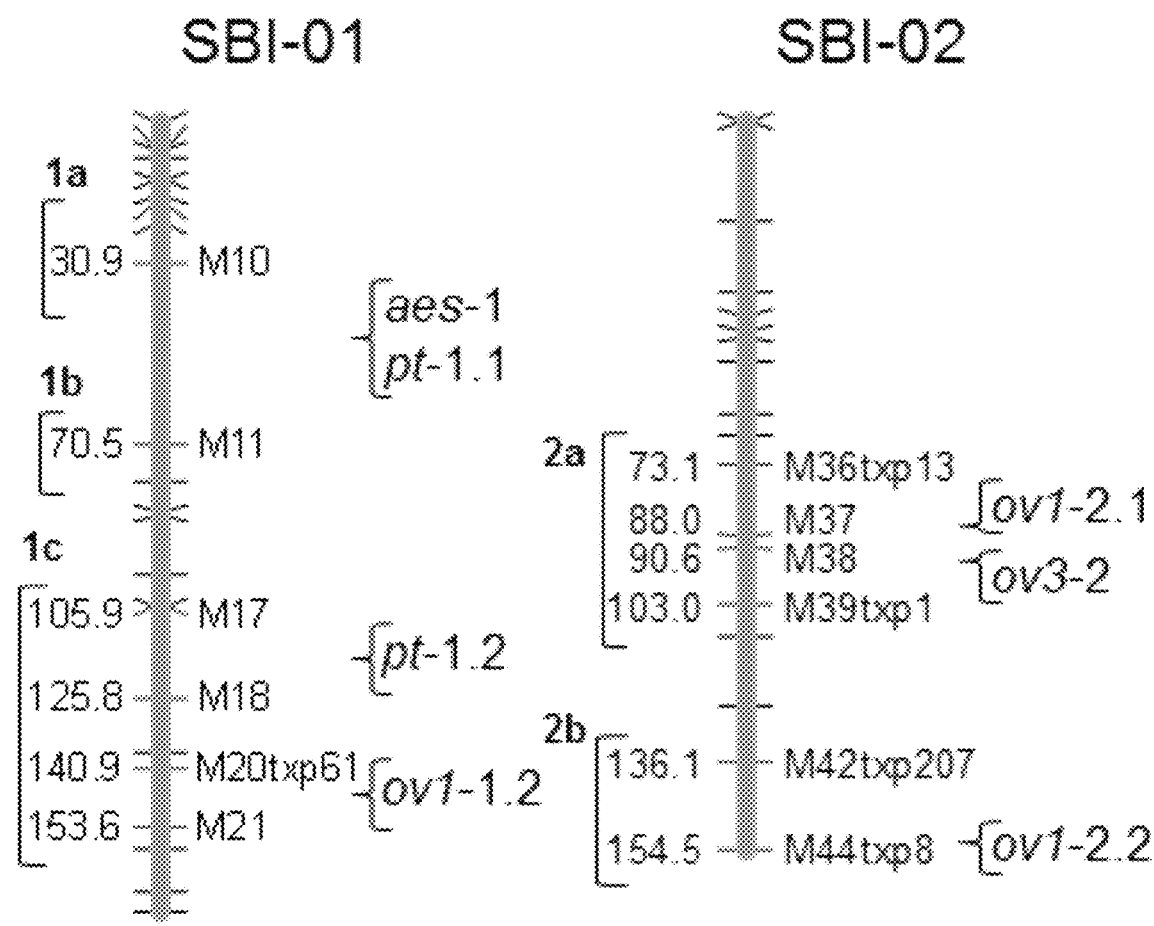
FIG. 55 Apospory associated QTL and nearest flanking markers identified in the $F_2$ mapping population. See Table 3 for full QTL names and marker details. Broad chromosome regions containing QTL are identified alphanumerically. AES, apospory embryo sac; AI, apospory initial; LSC, large stack cell; OC1-2, ovule curvature at the meiocyte and ES1 stages; ovule volumes (estimated from ovule area measurements in sagittal ovule sections) at the meiocyte, ES1 and early ES8 stages (OV1-3); PT, persistent tetrad (delayed degeneration of non-surviving megaspores); TT, twin tetrads.
Figure 55:
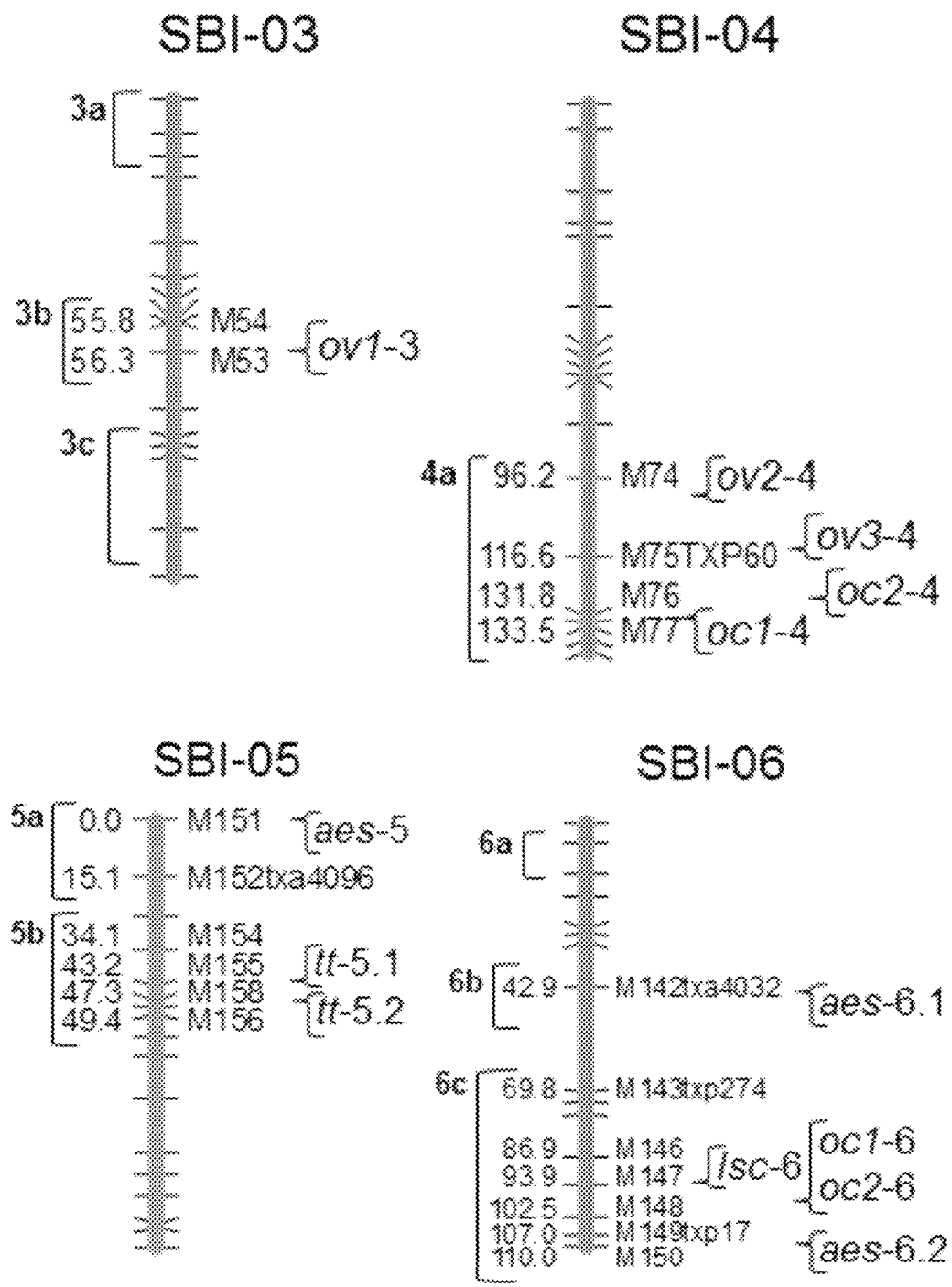
Figure 55:
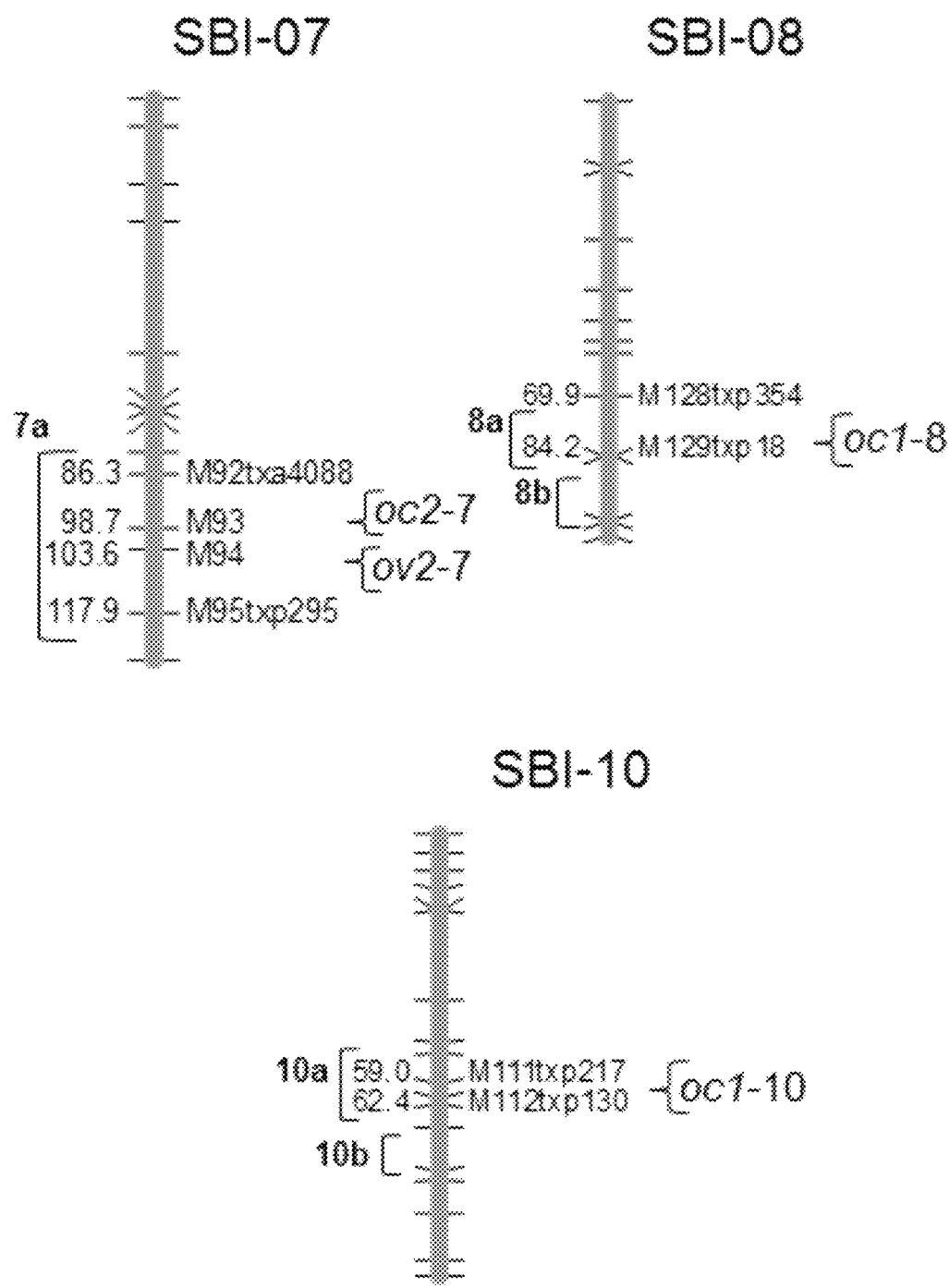

Twenty-four QTL were identified among the $F_2$ (Table 3). Four were AES specific and occurred on chromosomes 1 (Qaes.usu-1), 5 (Qaes.usu-5) and 6 (Qaes.usu-6.1, Qaes.usu-6.2) (FIG. 55). Qaes.usu-1 was tightly linked to Qpt.usu-1.1, and these occurred in the same general region of chromosome 1 that contained Qaes.usu-1.1 and 3 from the RIL population. Likewise, Qpt.usu-1.2 occurred at about the same location as RIL Qoc2.usu-1.2 (compare FIG. 54, 55). The only AES QTL linked to ovule curvature QTL across both mapping populations was Qaes.usu-6.2, which was linked to Qoc1.usu-6 and Qoc2.usu-6. Other QTL important to earliness of meiosis and ES onset (OC1, 2) occurred on chromosomes 4, 6-8 and 10. The low apospory parent allele generally decreased AES, AI, TT and LSC values (negative additive effect values) and increased OC1 and OC2 values (positive additive effect values). However, there were more exceptions in the $F_2$ data (Table 3), which indicates that AES associated traits were enhanced by QTL from both parents. AI QTL were not detected in the $F_2$ population (FIG. 55, Table 3). Twenty broad QTL regions encompassing all 42 QTL were identified (FIG. 54, 55).

Example 13. Expression Profiling

Materials and Methods Two sibs from the $F_2$ population, 151 and 264, with 13.6 and 0.0% AES formation, respectively (50), were selected for gene expression profiling of ovule tissues. Twenty tiller-propagated clones of each were grown as previously described (50). Three germline stages were chosen for profiling: early MMC, early meiocyte, and mid ES stages. Pistil length categories were determined by staging germline development in 240 pistils from sib 151 (170 to 580 μm long), and 257 pistils from sib 264 (250 to 670 μm long). Ovules were excised from pistils in nuclease free water and placed in RNAlater (Qiagen, Germantown, MD, USA). Thirty samples (90-150 ovules each), five for each sib by stage combination, were collected for a total of 601, 699 and 499 ovules and 508, 604 and 499 ovules for the MMC, meiocyte and early ES stages of sexual sib 264 and aposporous sib 151, respectively. Excised ovules were stored at −20° C. To reduce effects of diurnal shifts in gene expression, ovules were excised between 9:00 AM and 1:00 PM. Dissection equipment was cleaned periodically with RNaseZAP (Thermo Fisher, Waltham, Mass.). Ovule samples were transferred to Microcon YM-100 Centrifugal Filter Columns (MilliporeSigma, Burlington, Mass.) containing 200 μL of lysis solution and centrifuged (12,500×g, 10 min, 4° C.). Samples were then rinsed with 100 μL RNase free water, centrifuged again, resuspended in 200 μL of lysis solution plus 20 μL Plant RNA Isolation Aid (Thermo Fisher), ground (on ice) for 2 min using RNAse-free pestles, centrifuged (12,500×g, 2 min, 4° C.), and ground for 1 min. Pestles were rinsed with 100 μL 100% ethanol, which was collected in the grinding tubes. Samples were transferred to Micro Filter Cartridges, and total RNA was isolated using RNAqueous Micro kits (Thermo Fisher). RNA concentrations and quality were checked by Nanodrop-1000 spectrophotometry (Thermo Fisher) and by an Agilent 2100 Bioanalyzer with an RNA 6000 Nano Series II kit (Agilent Technologies, Santa Clara, Calif.). RNA samples were dried in a Vacufuge Concentrator (Eppendorf, Westbury, N.Y.) and amplified using Amino Allyl MessageAmp II kits (Thermo Fisher). Antisense RNA (aRNA) was Nanodrop and Bioanalyzer checked and stored at −80° C. aRNA samples (10 μg each) were Cy3 or Cy5 labeled and purified within 12 h of array hybridization.

Two color microarrays were synthesized from 12,000 35 nt probes by CombiMatrix (Irvine, Calif.) based on unigene EST from sorghum panicles. About 25% of sorghum open reading frames were represented (61). No gap sequences with a ≥94% BLASTN (122) match (≥33 of 35 nt) to the *S. bicolor* V3.1.1 NCBI reference genome (123) were retained (8664 of 12,000 probes). Annotations to *arabidopsis* and *Oryza sativa* L. (rice) were made using Phytozome 12.1.6 (Datafile S1). Labeled 3 μg aRNA samples were fragmented (Thermo Fisher reagents), verified by Nanodrop for concentration and labeling, and applied to 15 two-color arrays. A saturated loop design was used to distribute the 30 sib/stage/replication samples (2:3:5) evenly among the 15 arrays. Arrays were incubated at 45° C. for 16 h and scanned using a ScanArray Express HT (Perkin Elmer, Waltham, Mass.) microarray scanner (5 μm resolution). Median pixel intensities were captured using Imagene software (Biodiscovery, Inc., El Segundo, CA). Median probe intensities were Lowess normalized within arrays and median normalized across arrays. Normalized minimum or maximum values for each set of five replicate values (sib by stage by probe) that differed from the mean of the remaining four values by more than 2.5 times the standard deviation (remaining four values) were removed. Of the 51,984 sets of five replicate values, 89% retained all five values after filtering, and no set had less than four replicate values.

Normalized data were log 2 transformed, and DEG (FDR≤0.05) were identified by class comparison (BRB-ArrayTools 4.6.0, developed by Dr. Richard Simon and the BRB-ArrayTools Development Team). DEG were located to sorghum chromosomes using Phytozome 12.1.6. Overrepresented GO categories (Panther Overrepresentation test, released Nov. 13, 2018) were identified using *arabidopsis* orthologs of up or down regulated DEG (Panther 13.1 release; Panther GO Ontology database, released Nov. 15, 2018). For Panther GO Enrichment analyses, expression data corresponding to *arabidopsis* orthologs were sorted by Log 2 values of fold change ratios. Where multiple probes represented the same *arabidopsis* gene, the most highly up or down regulated probe per gene was retained. Lists of enriched and overrepresented GO categories were produced. Enrichment and overrepresentation tests were performed using Fisher's Exact Test (FDR≤0.05).

qPCR Six DEG were selected for qPCR. Primers were designed, checked for secondary structures (PrimerSelect), and searched by BLAST for similar sequences (word size, 7; expect value, 1000). Sequences unique to sorghum were retained. Sequences predicted to form internal loops or dimers, or those homologous to other genes, were discarded. Primer pairs were tested using gDNA from the aposporous and non-aposporous sibs, and qPCR analyses were performed (Table 10).

Figure 56A:
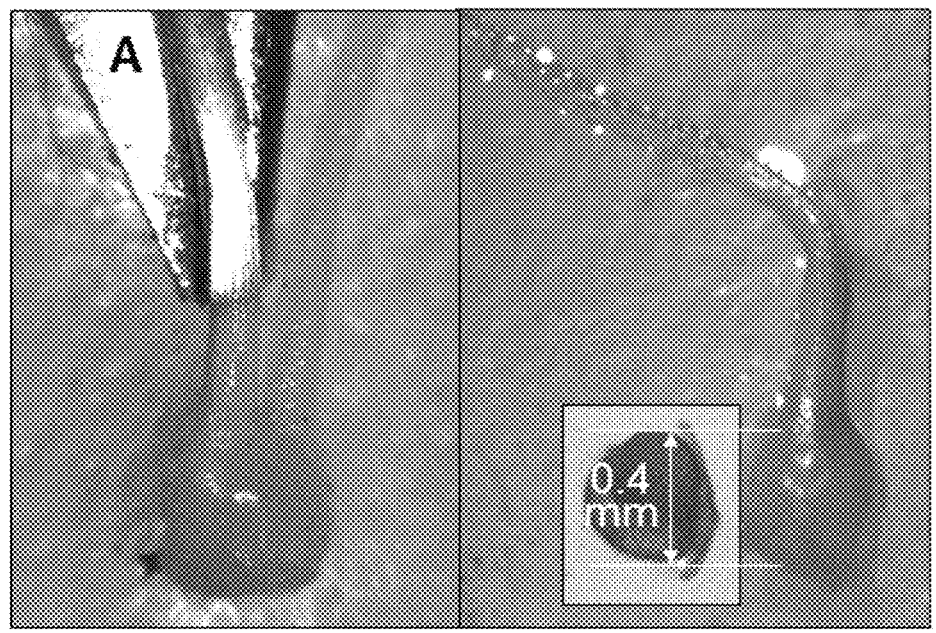
FIGS. 56A-56G Summary of gene expression differences detected between immature ovules excised from an apospory sorghum $F_2$ plant, A151, and those excised from one of its completely sexual full sibs, S264.
Figure 56B:
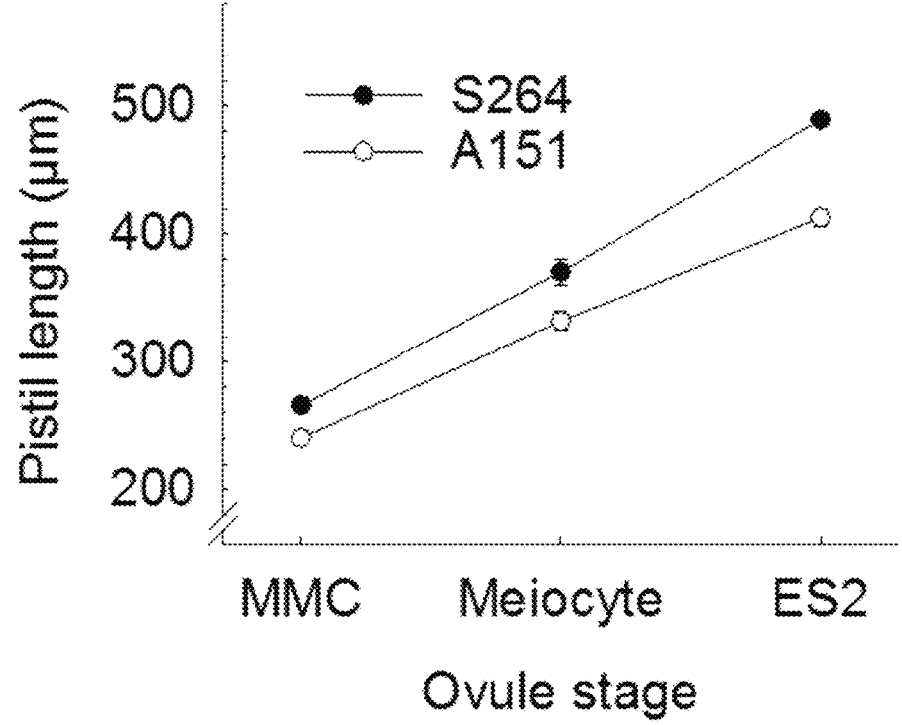
Figure 56C:
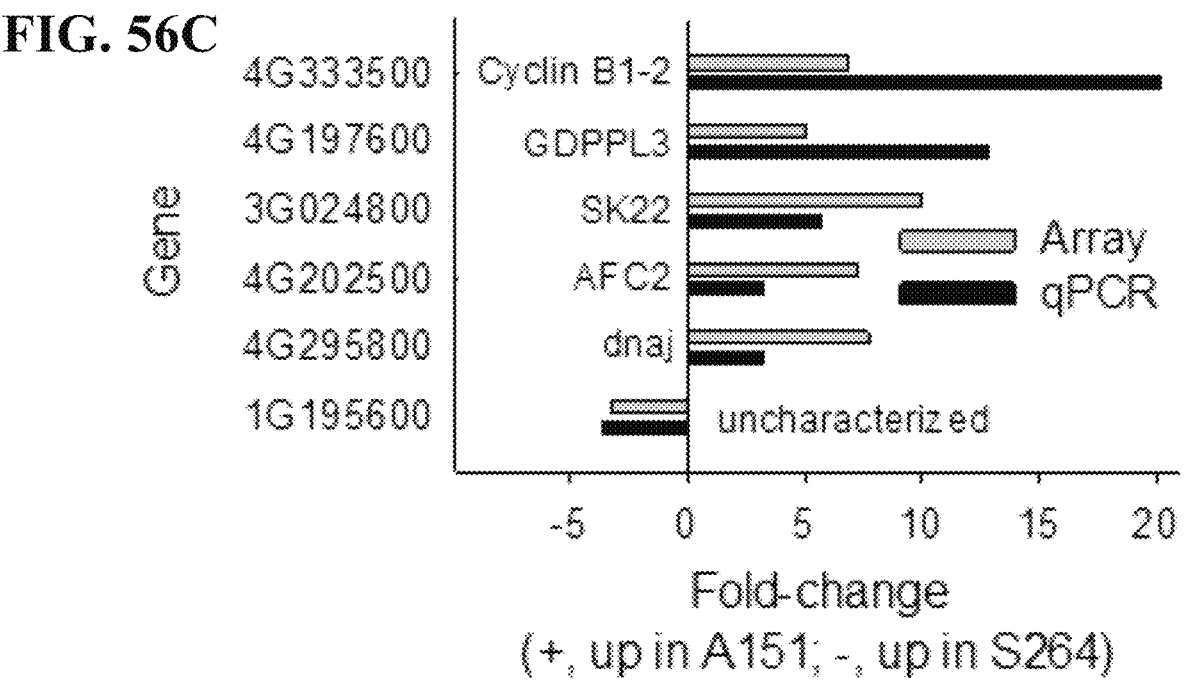
Figure 56D:
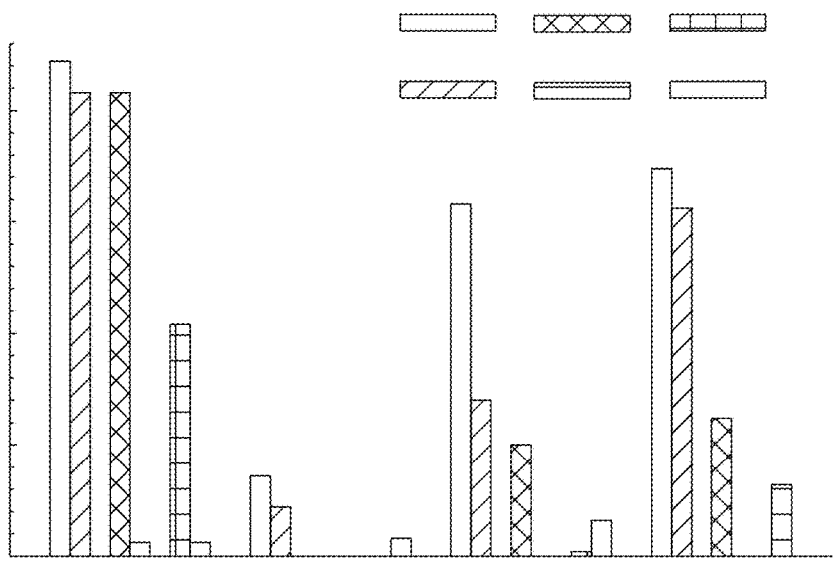
Figure 56E:
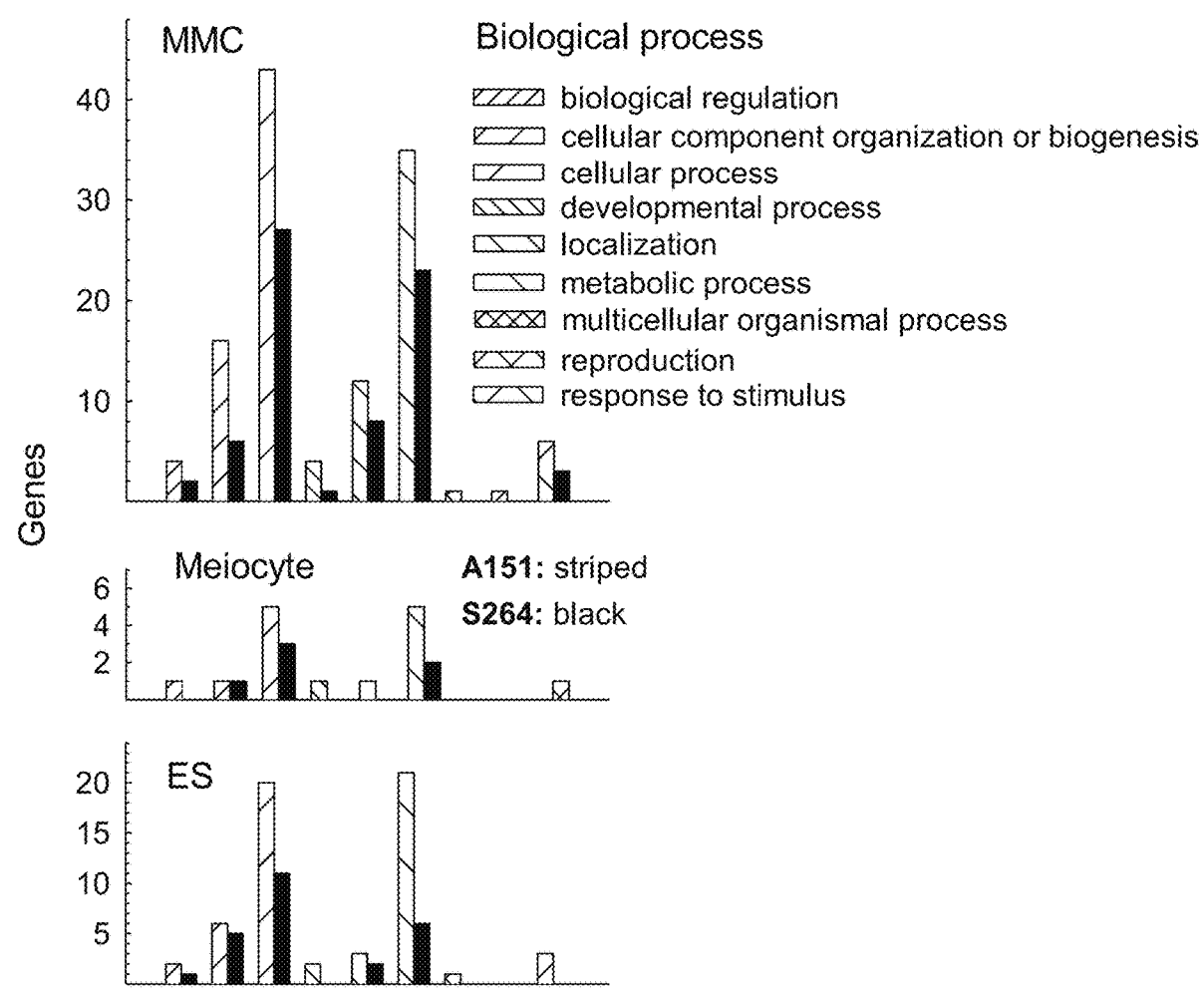
Figure 56F:
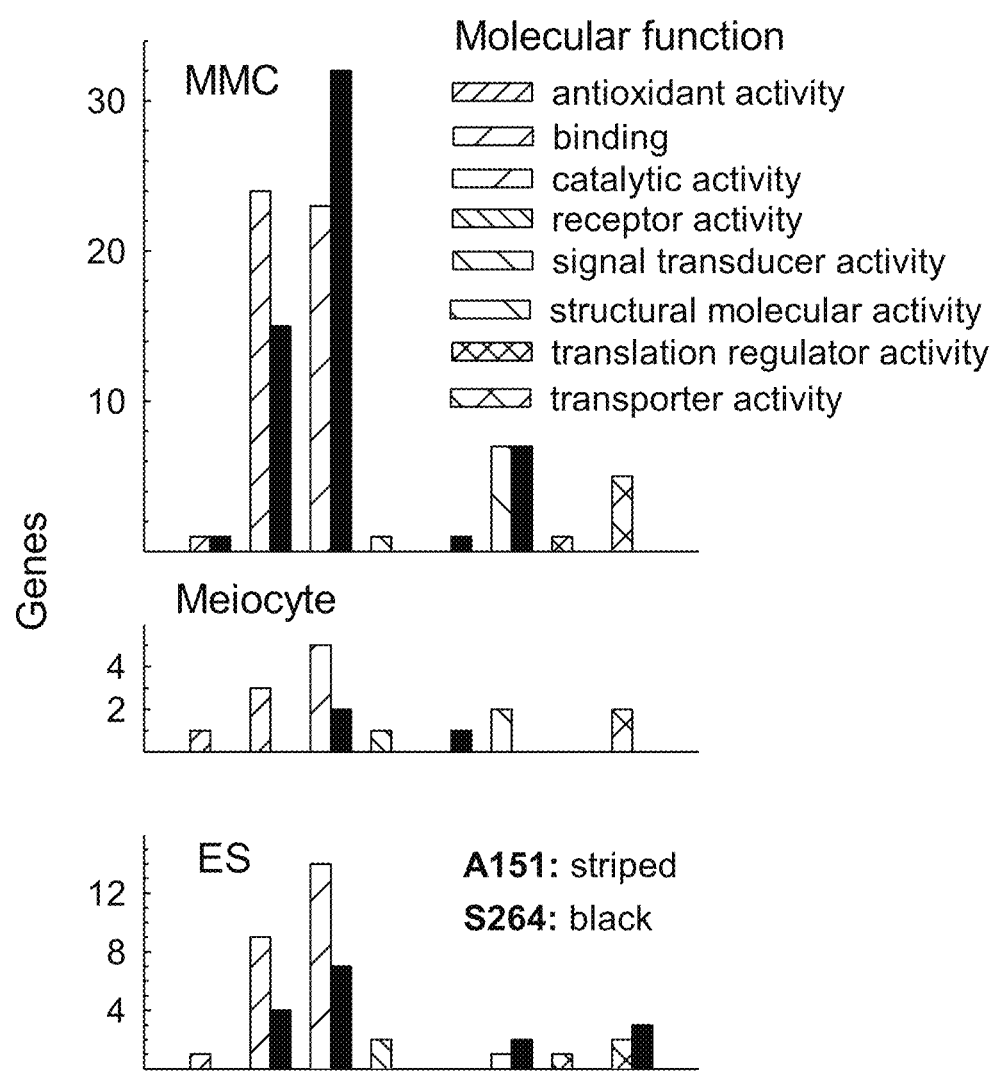
Figure 56G:
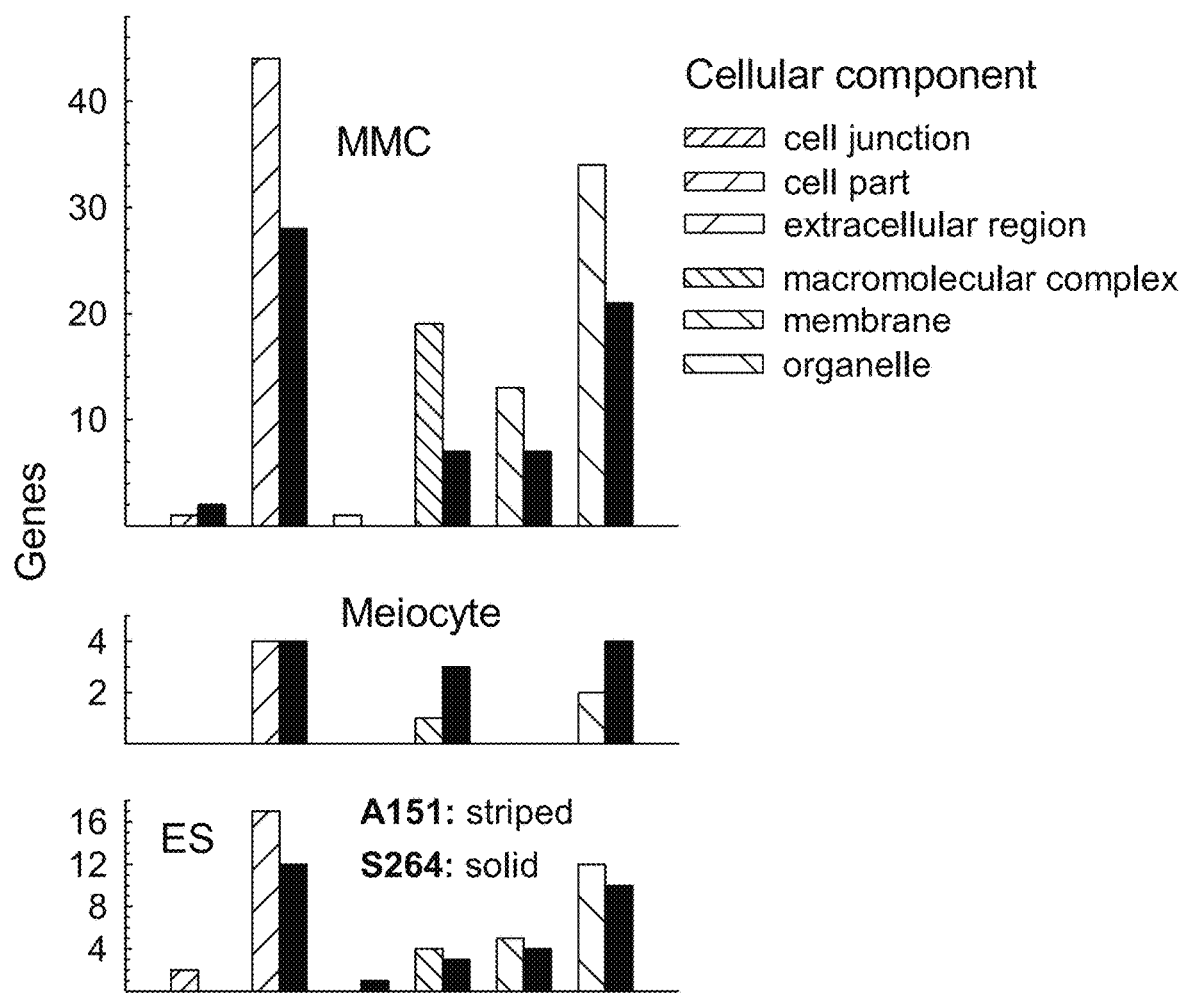

Results Genes putatively influencing AES formation were identified by comparing expression profiles of ovules excised from the highest AES forming $F_2$ sib, A151 (13.6% AES), against those of a completely sexual $F_2$ sib, S264 (FIGS. 56A-56G). Pistils at the MMC, meiocyte (dyad or early tetrad) and ES2 stages of A151 were significantly smaller than those of S264 (FIGS. 56A-56B). This is consistent with AES formation being correlated with precocious onset of meiosis and ES formation (FIG. 53F). Based on averages, pistil length categories were chosen for expression profiling: 170±40, 290±40 and 500±40 μm for early MMC, early meiocyte and mid ES stages of A151, and 170±40, 330±40 and 580±40 μm for the same stages of S264. RNA was extracted from 3410 microexcised ovules (FIG. 56A; 113±14 ovules for each of 30 samples, two sibs by three stages by five replications). Of the 8664 genes probed by the microarrays (Datafile S1), 377 (4.5%) were differentially expressed in one or more of four comparisons made (Table 4). Quantitative RT-PCR (qPCR) analyses were in general agreement with microarray results (FIG. 56C). Of the 377 DEG, 178 occurred within broad QTL regions (Table 4; FIG. 54, 55). On average, apomeiosis (A151) was correlated with higher levels of gene expression (FIG. 56D, DEG bars).

Using *arabidopsis* orthologs, Panther enrichment analyses (65) identified 108 enriched gene ontology (GO) terms, 105 of which were enriched in A151. Like DEG, the highest numbers of enriched GO were detected at the MMC stage (Table 5; FIG. 56D, E-GO bars). Two sets of GO overrepresentation analyses were performed: using *arabidopsis* orthologs of DEG upregulated (Table 6) or downregulated (Table 7) in A151. Here again, more GO terms were identified at the MMC stage (for genes upregulated in A151), with few GO terms being identified by genes upregulated in S264 (FIG. 56D, O-GO). Panther was also used to determine if DEG upregulated in A151 tended to group into different GO categories than DEG upregulated in S264. Partitioning of DEG generally followed the same pattern in both sibs but with more genes upregulated in A151. Eight exceptions were noted. More DEG were upregulated in S264 for 'catalytic activity' at the MMC stage and for 'macromolecular complex' and 'organelle' at the meiocyte stage (FIGS.

56E-56G). Overall, ovules supporting apospory were more bioenergetically active (more DEG and significant GO terms), i.e., they were undergoing more active biological functions and molecular processes and producing more cellular components (Tables 5-7).

Example 14. Pistil Culture Experiments

Material and Methods

Pharmacological Experiments. Plants of *arabidopsis* (Col-0), Drummond's rockcress (Duchesne County, UT, USU Intermountain Herbarium no. UTC00275884) and cowpea (California Blackeye No. 5, W. Atlee Burpee & Co., Warminster, PA) were grown in Sunshine Mix #1 potting soil (Sun Gro Horticulture Canada Ltd, Vancouver, BC) in a walk in growth chamber that maintained 22/16° C. day/night temperatures and a 16/8 h day/night photoperiod. Lighting was supplied by soft white florescent bulbs, incandescent lights, and 1000 W high-pressure sodium-vapor lamps, which provided a photosynthetic photon flux of c. 300 μmol $m^{-2}$ $s^{-1}$ at the canopy surface for *arabidopsis* and rockcress and c. 500 μmol $m^{-2}$ $s^{-1}$ for cowpea. Plants were watered regularly with a dilute solution (250 mg $L^{-1}$) of Peters Professional 20:20:20 fertilizer (Scotts, Maryville, Ohio).

Cytological Analyses. *Arabidopsis*, Drummond's rockcress and cowpea floral buds were fixed in FAA (v/v: 3.7% formaldehyde, 5% acetic acid, 50% ethanol) for 48 h and cleared in 2:1 benzyl benzoate dibutyl phthalate (BBDP) (80): 1) 70% EtOH, 30 min; 95% EtOH, ≥4 h (2×); 95% EtOH:BBDP (2:1), 2 h; 95% EtOH:BBDP (1:2), 4 h; BBDP, 4 h; BBDP, overnight. Cleared pistils were mounted (up to 16 per slide) and measured from the pedicel base to the top of the stigma. Ovule development stages were studied using a BX53 microscope equipped with differential interference contrast optics and a MicroFire 599809 camera (Olympus, Center Valley, Pa., USA). For chromosome staining, pistils were soaked in 95% ethanol that contained 0.1 mg $L^{-1}$ 4',6-diamidino-2-phenylindole (DAPI). Callose was stained by soaking DAPI stained pistils in aqueous aniline blue (Millipore Sigma, Darmstadt, Germany) (124). DAPI fluorescence was detected with a Zeiss LSM 510 confocal microscope with excitation at 408 nm, dichroic reflector at HFT488 nm and detection at 450-650 nm. Callose was distinguished from DAPI by detection at 550-650 nm.

Presence of the following ovule characteristics were recorded: MMCs, Antennaria type diplosporous 1-2 nucleate ES, sexual or *Taraxacum* type diplosporous dyads, sexual tetrads, sexual or *Taraxacum* type diplosporous 1-2 nucleate ES, AI and AES. Developmental stages for the majority of ovules per pistil were recorded, and pistil lengths for the following stages (125) were recorded: 1-II, ovule meristems protruding from placentae (precedes MMC formation); 2-IV, meiosis; 3-III, vacuole in immature ES beginning to appear; 4-VI, nuclear divisions in endosperm underway. To determine average timing of meiosis onset, pistils primarily containing premeiotic (2-III) ovules were located under low light conditions 1 h before the lights came on in the morning. Corresponding sepals were marked with a small point permanent marker. Pistils were then randomly harvested for analysis when the lights came on and 3 h thereafter.

Results

Pistils were aseptically excised, but not disinfested, at the early pre-MMC to MMC stages and incubated in vitro. The basal culture medium for *arabidopsis* and Drummond's rockcress was MS (126) (Caisson Laboratories, Inc., Smithfield, UT USA) with 20 g $L^{-1}$ sucrose or glucose and solidified with 1.45 g $L^{-1}$ Phytogel (MilliporeSigma). Basal medium for cowpea was the same except it contained 60 g $L^{-1}$ sucrose or 30 g $L^{-1}$ glucose, 0.5 μmol $L^{-1}$ naphthalene acetic acid, 5.0 μmol $L^{-1}$ 6-benzylaminopurine, and Gamborg's B5 vitamins. Media were supplemented with 0.5 or 1.0 μmol $L^{-1}$ BR (epibrassinolide); 0.5 or 1.0 μmol $L^{-1}$ DTBA; and/or 0.1 or 0.5 mmol $L^{-1}$ 5-azaC (MilliporeSigma). Media were pH adjusted to 5.75 and autoclaved for 20 min at 121° C. BR was added after autoclaving by filter sterilization. Prior to culturing, pistils were pre-soaked for 60 min in solutions corresponding to their treatment (same concentrations but without basal media components). In another experiment, pistils were presoaked for 7 min in 250 mmol $L^{-1}$ $H_2O_2$. Petri dishes with pistils were incubated for 2-6 d under low light (c. 80 μmol $m^{-2}$ $s^{-1}$) (temperature and photoperiod as above). Ovules that were too young (MMC stage or earlier), too old (ES2 stage or older), or poorly oriented were not scored. Cross-tabulation data were analyzed by Pearson chi-square tests (97).

For topical applications, sepals of floral buds were separated, and pistil lengths were measured using a dissecting microscope. Pistils whose length corresponded to the 2-I (prior to integument budding) or 2-III (active integument budding) stages were identified, and these were treated with a bead of solution containing either 2.0 μmol $L^{-1}$ BR, 50 mmol $L^{-1}$ glucose, or deionized water. The bead was wrapped around the pistil inside the flower bud. After soaking for 60 s, the tip of the inflorescence was inserted into a PCR tube containing the treatment solution. Pistils were soaked for c. 5 h, rinsed with water and air dried. Pistils were harvested for analysis 12-72 h later.

From our profiling results, we derived a model of environment regulated apomixis sex switching (see discussion). Four locations in the model were identified where switching might be induced: 1) antioxidant homeostasis, 2) brassinosteroid (BR) signaling, 3) glucose signaling, and 4) meiosis specific RNA directed DNA methylation (RdDM) (FIG. 57). We then determined average pistil lengths in *arabidopsis*, Drummond's rockcress and cowpea for: i) the pre-MMC to early MMC stage (0.5, 1.5, 1.5 mm, respectively), ii) meiosis (1.4, 2.4, 2.3 mm, respectively), and iii) the mid ES formation stage (1.8, 3.0, 3.7 mm, respectively). Using timed fixations, we determined that meiosis generally occurs in late MMC-staged *arabidopsis* ovules in the morning. Less than 5% of ovules contained active meiocytes just prior to daylight, but after 3 h of daylight, 25% of ovules contained active meiocytes.

Figure 58A:
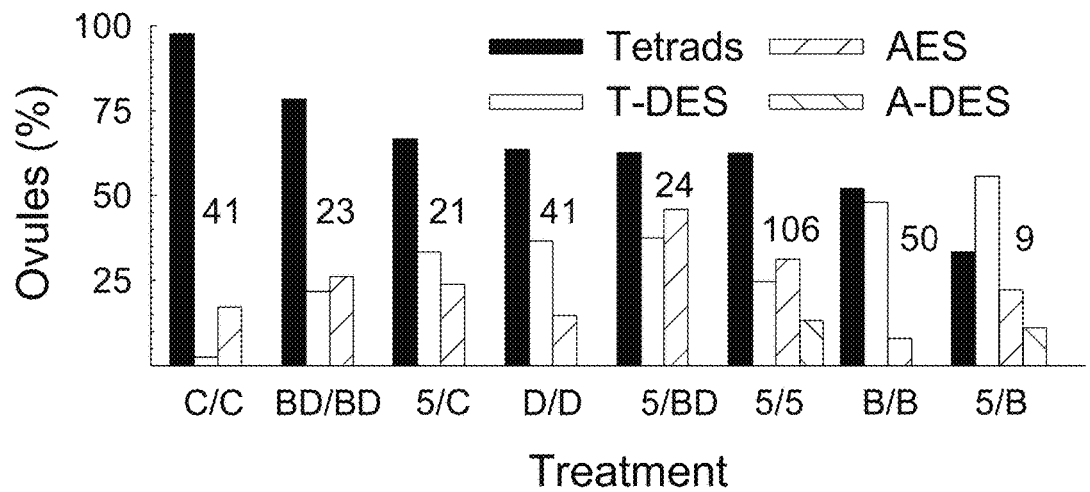
FIGS. 58A-58I Treatment induced *Taraxacum* (T-DES) and Antennaria (A-DES) types of diplosporous ES formation and *Hieracium*-type apospory ES formation (AES) in *Arabidopsis* (FIG. 58A) Percentages of ovules that produced sexual tetrads, T-DES, A-DES and AES. AES ovules also produced a sexual tetrad, which was counted with tetrads. Pretreatment/treatment acronyms: C, control; B, BR; D, DTBA; 5, 5-azaC. Data are sums of four replicates. Sugar type and levels of BR and DTBA did not affect results and were combined. 5-azaC was at 0.5 mmol $L^{-1}$.
Figure 58B:
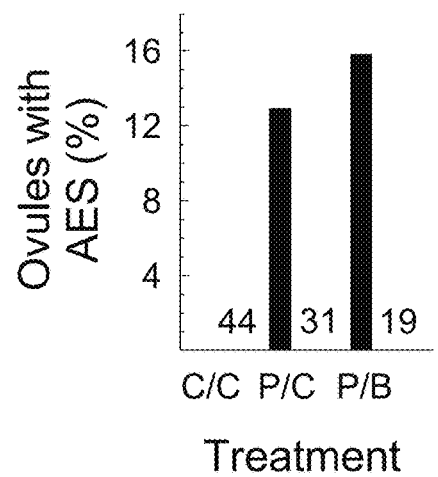
Figure 58C:
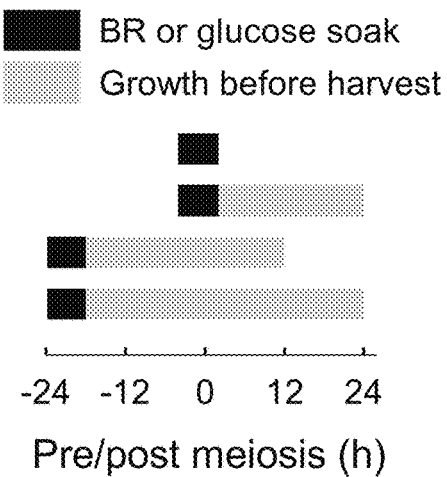
Figure 58D:
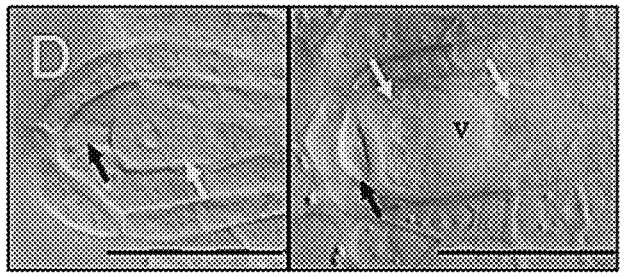
Figure 58E:
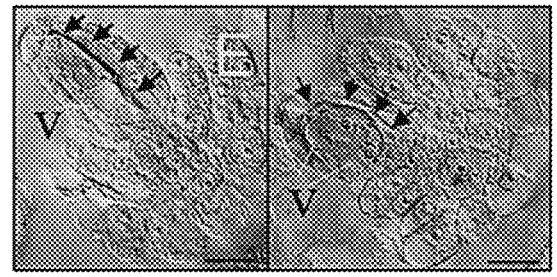

To determine whether apomeiosis is inducible by interrupting peroxide signaling (FIG. 57), we excised early MMC staged *arabidopsis* pistils, soaked them in (S)-2-aminobutane-1,4-dithiol hydrochloride (DTBA, an antioxidant) for 60 min, and cultured them on DTBA containing medium for 4 d (see Materials and Methods). In 40% of ovules, a $1^{st}$ division meiotic restitution (*Taraxacum*-type diplosporous apomeiosis) occurred, which produced a dyad of megaspores (FIG. 58A: D/D). At the time of fixation, some of these had initiated *Taraxacum*-type diplosporous ES, i.e., the micropylar dyad member was degenerating, and the chalazal member was becoming vacuolate and undergoing endomitotic ES formation (FIG. 58D). An additional 18% of ovules completed meiosis, but all four megaspores in these ovules were degenerating and being displaced by one or more AES (FIG. 58E).

Endogenous peroxide is required to activate the transcription factor BRASSINAZOLE-RESISTANT 1 (BZR1) (127). Hence, we tested whether cultured pistils exposed to a 7 min pretreatment in dilute $H_2O_2$ might induce apomeiosis by activating BZR1 (FIG. 57). In 13% of these ovules, surviving megaspores degenerated and were replaced by AES (FIG. 58B: P/C). However, *Taraxacum*-type diplosporous ES formation was absent. This suggests that exogenous $H_2O_2$ reinforced endogenous $H_2O_2$ signaling, thus inducing meiosis, but also stimulated apospory by activating BZR1. Low frequency apospory was also observed when pistils were presoaked in water for 60 min (FIG. 58A: C/C). This may have induced anoxia-associated endogenous $H_2O_2$ production.

Figure 58F:
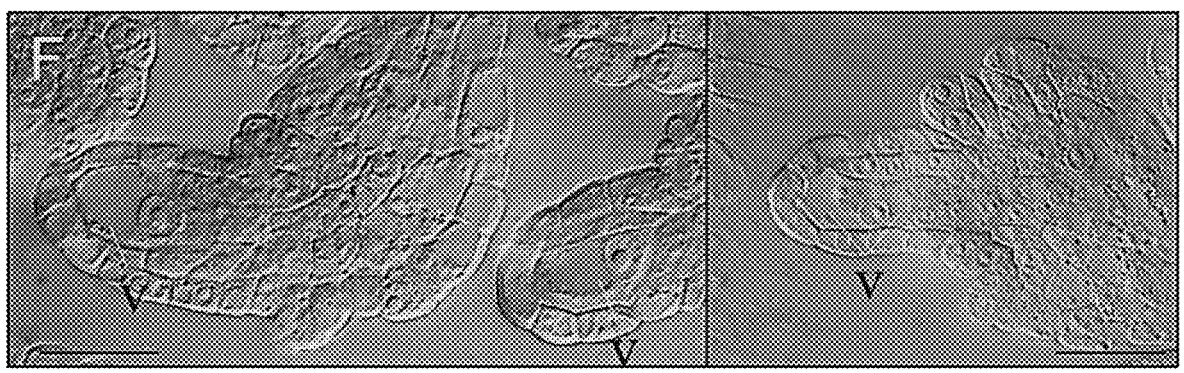
Figures 58G, 58H, 58I:
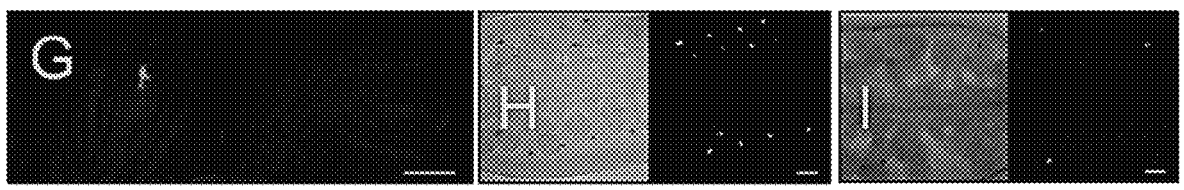

We next asked whether BR alone or in combination with dilute $H_2O_2$ or DTBA would induce apomeiosis. BR alone stopped meiosis early during meiotic prophase in 45% of ovules, and MMC in these ovules were undergoing *Taraxacum* type dyad or ES formation. Low levels of AES formation also occurring (FIG. 58A: B/B). However, adding a $H_2O_2$ pretreatment to BR treated pistils completely prevented *Taraxacum*-type diplospory (FIG. 58B: P/B). Peroxide appeared to reinforce meiosis expression, while the combination of BR and $H_2O_2$ supported apospory (post-meiotic abortion coupled with adventitious ES formation). DTBA and BR increased apospory but suppressed *Taraxacum*-type diplospory (FIG. 58A: BD/BD). Topical applications of BR or glucose to intact pistils induced *Taraxacum*-type diplospory when applications were made 24 h before or immediately before meiosis (FIGS. 58C, 58G). *Taraxacum*-type diplospory was accompanied by an absence of callose deposition in cell walls during megasporogenesis (FIGS. 58H, 58I). Low callose content in meiocyte cell walls is common in *Taraxacum*-type diplosporous apomicts (124, 128). Since meiosis and callose deposition are both induced by oxidative stress (106, 129), the absence of callose may simply reflect a less oxidizing, higher energy (FIG. 57) cellular environment.

In other projects, whole plants of apomictic *Boechera* were chronically stressed by drought (26) and pistils of well-watered apomictic *Boechera* were acutely stressed by $H_2O_2$ applications, sugar starvation, or osmotic stress shortly before apomeiosis (106). In each of these experiments, high frequency shifts from *Taraxacum*-type diplosporous apomeiosis to normal meiosis were observed. Identical switching also occurred when BZR1 was inactivated (106). Also, when pre-MMC staged pistils of triploid *Boechera* cf. *gunnisoniana* were demethylated using 5-azacytidine (5-azaC), 10% of ovules switched from *Taraxacum*-type diplospory (termination of sexual development during meiotic prophase) to Antennaria-type diplospory (termination of sexual development prior to meiosis) (106). Here, demethylation appears to have interrupted the RdDM required for meiosis (130), including the early meiotic events of prophase that characterize *Taraxacum*-type diplospory.

The switch in *B.* cf. *gunnisoniana* from *Taraxacum* to Antennaria-type diplospory in response to 5-azaC (106) suggested that 5-azaC might also switch meiosis to apomeiosis. To test this, we soaked pre-MMC staged *arabidopsis* pistils in 5-azaC for 60 min and then cultured them on either control medium or media containing 5-azaC, BR, or 5-azaC plus BR and DTBA. Greater than 90% of treated ovules developed apomeiotically. At the time of fixation, most ovules were developing by *Taraxacum*-type diplospory or apospory (FIG. 58A: 5/C, 5/BD, 5/5, 5/B). As observed in *Boechera* (106), Antennaria type diplospory occurred in some ovules (FIG. 58A: 5/5, 5/B; 4F). Accordingly, all three major types of apomeiosis in angiosperms were induced in *arabidopsis* simply by modifying the expression of wild type genes. This is consistent with meiosis, but not apomeiosis, requiring meiosis specific RdDM (FIG. 57) (130).

Figure 59A:
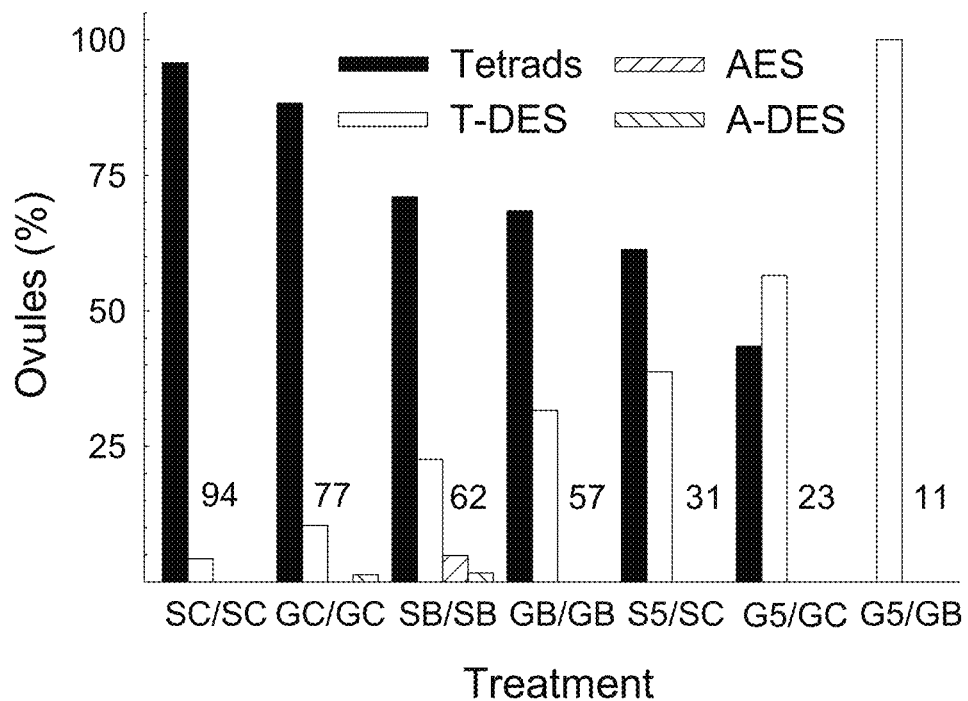
FIGS. 59A-59K Treatment induced *Taraxacum* (T-DES) and Antennaria (A-DES) types of diplosporous ES formation and *Hieracium*-type aposporous ES formation (AES) in Drummond's rockcress and A-DES formation in cowpea.
Figure 59B:
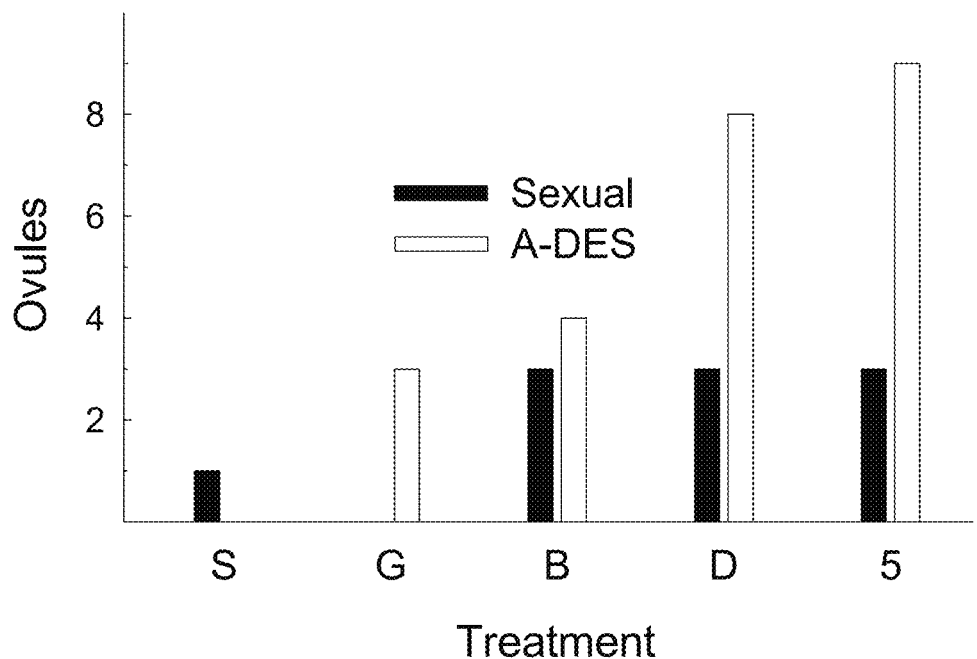
Figures 59C, 59D, 59E:
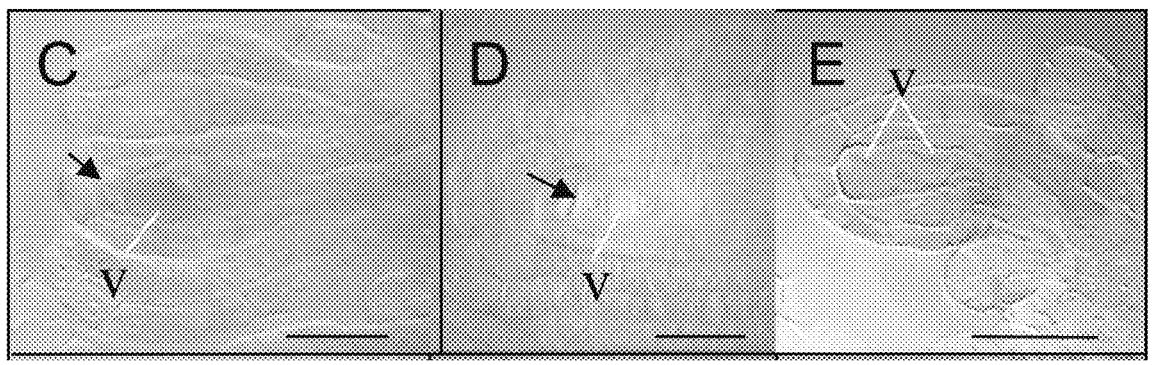
Figures 59F, 59G, 59H:
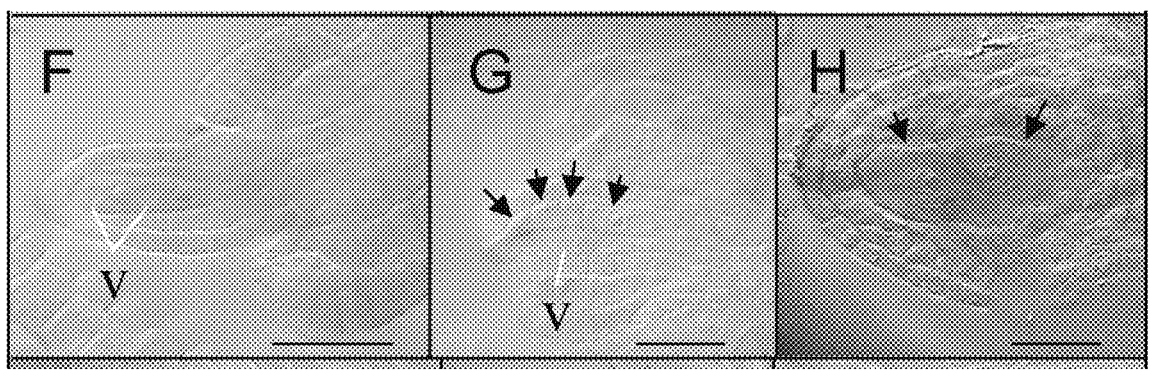

To determine if apomeiosis is inducible in other sexual angiosperms, we exposed pistils of Drummond's rockcress and cowpea to similar treatments (FIGS. 59A-59K). In rockcress, frequencies of meiosis termination followed by *Taraxacum* and *Hieracium* type ES formation (FIGS. 59C-59D, 59G) increased significantly when glucose (38 of 152 ovules) instead of sucrose (26 of 164 ovules) was used (FIG. 59A: SC/SC vs. GC/GC, SB/SB vs. GB/GB, S5/SC vs. G5/GC). BR and 5-azaC appeared to function synergistically in these experiments in inducing dyad formation (FIG. 5: G5/GB). Antennaria type diplospory (pre-meiotic termination of sexual development) was only infrequently observed in rockcress. In contrast, Antennaria type ES formation in cowpea (FIGS. 59H-59K) was induced by multiple treatments (FIG. 59B).

Model Derivation. To identify gene networks putatively responsible for apomixis sex switching, we first evaluated DEG and GO categories that differentiated A151 from S264. A151 ovules experienced high metabolic activity, with many respiration, ribosome biogenesis, and gene expression GO terms being enriched or overrepresented (Tables S5-6). In contrast, S264 ovules were characterized by terms associated with chloroplasts, chemotaxis and mitosis (Tables S5, S7). We initially posited that the high metabolic activity in A151 was caused by efficient energy production or import systems. However, A151 was not characterized by photosynthesis DEG or GO categories, and the immature ovules sampled were generally void of photosynthetic pigments. Likewise, there was no evidence that sugar transport proteins were differentially expressed between sibs. However, cycles of fatty acid synthesis, fatty acid catabolism by beta oxidation, and gluconeogenesis may have occurred to a greater extent in A151 (Table 4: 2-20, 36-41). This suggests that the energy associated differences observed between A151 and S264 involved shifts in carbon usage rather than differences in carbon availability.

In eukaryote cells, switching between metabolic processes responsible for growth (energy usage) and no growth (energy conservation) is regulated by two conserved kinases. Orthologs of these are SUCROSE NONFERMENTING 1 (SNF1) and target of rapamycin (TOR) in yeast, AMP-activated protein kinase (AMPK) and mTOR in animals, and sucrose non-fermenting 1-related kinase (SnRK) and TOR in plants (13, 131). In plants, during high-energy and low-stress conditions, TOR, RAPTOR and LETHAL WITH SEC THIRTEEN 8 (LST8) assemble to form the TORC1 complex. This complex induces rapid growth through enzyme activation, transcriptional reprogramming, and new protein synthesis (13). Included in this high energy metabolic activity is BR synthesis and downstream growth and development processes, which are regulated by the transcription factors BZR1 and BRASSINAZOLE-RESISTANT 2 (BES1, BZR2) (25, 127) (FIG. 57).

Growth cessation and decreased metabolic activity occur when TORC1 is inactivated. In plants, this happens in two ways, by glucose starvation or by accumulation of abscisic acid (ABA). Both processes involve multistep molecular pathways (FIG. 57). Under low energy conditions, glucose signaling is terminated, and this terminates downstream degradation of SnRK1. SnRK1 then accumulates and phosphorylates RAPTOR causing TORC1 to dissociate. Downstream growth promoting processes then cease (13, 17). Under stress conditions, ABA accumulates, and multiple protein phosphatase 2 C proteins (PP2C), including ABA INSENSITIVE 1 and 2 (ABI1, 2) and HIGHLY ABA-INDUCED PP2C GENE 2 (AIP1), are inactivated. SnRK1,2 are then activated by autophosphorylation, and they proceed to inactivate TORC1, again possibly by phosphorylating RAPTOR (59, 60). Active SnRK kinases, which form under low-energy and/or high-stress conditions, activate other enzymes that cause downstream catabolism, autophagy and metabolite recovery through transmembrane transport (16). The upstream sensing and downstream expression phenotypes of SnRK and TOR activation and inactivation, respectively, are well represented among the DEG upregulated in S264 (Table 4: 110-137, 163-185). Conversely, under non-stress or stress-tolerating conditions, as occurs in A151 ovules, CYTOCHROME P450, FAMILY 707, SUBFAMILY A, POLYPEPTIDE 2 (CYP707A2) catabolizes ABA (132). This permits PP2C family proteins to deactivate SnRK1,2 by dephosphorylation. Likewise, under glucose abundant (high energy) conditions, glucose signaling, through the splice variant SPTase13, degrades SnRK1, which allows TORC1 to reform (133). Ovules of A151 were characterized by many DEG and GO terms associated with respiration and high energy processes (Table 4: 2-34; Table 5: 3-20, 33-47, 84-117; Table 6: 6-50). TORC1 functions as a major hub of growth and development in plants (134), and our data suggest that it was active in A151 but suppressed in S264.

The 40 sorghum plants used for ovule collections in this study (20 ramets of each sib) were grown together under ideal conditions. Hence, differences in the expression of stress response genes between these sibs should reflect differences in stress perception processes. Ovules of both sibs were characterized by stress associated DEG and GO terms (Tables 4-7). For A151 ovules, DEG reflect a general perception and tolerance or suppression of drought stress (Table 4: 70-108), which is expected for high energy (glucose containing) tissues (135). In contrast, DEG characterizing S264 ovules included genes associated with inflammatory responses, ABA, and other stress hormone pathways (Table 4: 110-137; 163-185).

The expression levels of two genes (Table 4: 139, 157) could explain the differences in SnRK TOR regulation as observed in our data. The first of these, a LAMMER-type protein kinase gene, sorghum ortholog of *arabidopsis* FUS3-COMPLEMENTING GENE 2 (AFC2), is normally upregulated by ethylene and activates TORC1 by facilitating glucose signaling through spliceosomal activity of protein ARGININE/SERINE-RICH 45 (SR45) (133, 136) (FIG. 57). AFC2 was upregulated in A151 7.0-fold ($2^{nd}$ most highly upregulated gene) and is linked on chromosome four to ovule curvature and volume QTL. The second gene, a sorghum ortholog of the *arabidopsis* PP2C gene AIP1, activates TORC1 by inactivating SnRK (17, 59) (FIG. 57). AIP1 was upregulated 3.0-fold in A151 and is linked on chromosome one to ovule volume QTL.

Two additional genes (Table 4: 70, 141), which regulate downstream processes in the SnRK TOR BR pathway, were also upregulated in A151. These suppress BR signaling downstream of TORC1 (FIG. 57). The first of these, a sorghum ortholog of *arabidopsis* SHAGGY-LIKE PROTEIN KINASE GROUP 2 3 (SK22, ATGSK1), deactivates BZR1 and BES1 by phosphorylation (137). It is linked to ovule curvature QTL on chromosome three and was upregulated in A151 8.9-fold (most highly upregulated gene). The second gene, sorghum ortholog of *arabidopsis* BAK1-INTERACTING RECEPTOR-LIKE KINASE 1 (BIR1), suppresses BZR1 and BES1 at BAK1 (138) (FIG. 57). It was upregulated 2.3-fold and is linked on chromosome five to TT QTL. SK22 and BIR1 may have functioned in A151 ovules as feedback suppressors of BR signaling. As noted above, BR exogenously applied to immature *arabidopsis* pistils induced apomeiosis. Hence, the high levels of SK22 and BIR1 may have prevented AES levels from exceeding 14% in A151.

Apospory in A151 may have been caused by upregulated AFC2 and AIP1. However, the genes for these proteins were not linked to AES QTL. Moreover, ethylene upregulates AFC2 (139), and other ethylene regulated genes were also upregulated in A151 (Table 4: 140-143, 250). This suggests that A151 ovules may have produced more ethylene. In support of this, the stress/pathogen related MAPKKK5 was also upregulated in ovules of A151 (Table 4: 145). This kinase is upregulated by osmotic stress as well as BR signaling (140), both of which are consistent with A151 gene expression. MAPKKK5 increases ethylene biosynthesis by activating ATMAPK3 and ATMAPK6. These in turn activate by phosphorylation the ethylene synthesis enzyme 1-aminocyclopropane-1-carboxylic acid synthase (141). Accordingly, our data suggest that elevated glucose levels (possibly from increased beta oxidation of fatty acids), instead of a variant AFC2 allele, triggered the osmotic stress, glucose signaling, and ethylene signaling that differentiated A151 ovules from those of S264. Ethylene signaling also maintains ROS homeostasis through ethylene response factors. These impart resistances to stress by triggering oxidative bursts that induce ROS scavenger production (142, 143). A comparison of ROS detoxification genes in A151 (Table 4: 71-78) with those in S264 (Table 4: 110-111, 125-126) suggests an enhanced ROS scavenging capability in A151. $H_2O_2$ produced by stress inactivates PP2C (87). This permits SnRK activation (by autophosphorylation) and subsequent silencing of TORC1 (FIG. 57).

Meiosis in plants requires de novo RdDM, which generates a meiosis specific transcriptome in a cell-lineage-specific manner (130). We posited that i) stress or low-energy-activated SnRK are responsible for meiosis-specific RdDM in plant meiocytes and ii) metabolism-regulated stress avoidance in meiocytes stops meiosis and induces apomeiosis. Since our expression profiling data were not restricted to meiocytes, differences between sibs in gene expression associated with RdDM could not be assessed. However, nine DEG associated with small-RNA-regulated gene expression were detected. Three were upregulated in ovules of S264, and these participate in DNA acetylation, methylation and miRNA production (Table 4: 255-257). Two of the six genes upregulated in A151, HEAT INTOLERANT 4 and HISTONE 1.2 (H1.2) (Table 4: 246-247) suppress gene silencing and H1.2 also suppresses recombination (144, 145). These are functions that could reasonably occur as part of an apomeiosis program. The four remaining silencing-associated genes upregulated in A151 participate in DNA methylation or post transcriptional gene silencing (Table 4: 248-251).

Implications. We metabolically induced high frequency apomeiosis in sexual *arabidopsis*, Drummond's rockcress and cowpea. We have used similar procedures to induce parthenogenesis in *arabidopsis* (106, 146). In each case, our approach was to i) silence the sexual pathway and upregulate growth by deactivating SnRK (FIG. 57), and ii) support rapid growth by providing sufficient energy. Our results are consistent with apomixis in eukaryotes being a conserved but rarely expressed alternate phenism of sex ($3^{rd}$ hypothesis in introduction), which is regulated by SnRK (Snf1/AMPK), TOR, and glucose and steroid signaling. These are ancient regulatory pathways that originated during prokaryote or early eukaryote evolution (13, 147). As recently demonstrated for parthenogenesis (148), our research demonstrates that apomeiosis does not require genetic or epigenetic mutations. Instead, wild type genes silence sex and encode the production of ploidy-invariant cells. In contrast, sex involves production of ploidy-reduced cells that require fertilization for life-cycle progression. This apomixis-sex duality, as observed in plants (1), animals (9) and protists (1, 34, 38), fits the definition of a polyphenism (107).

Figures 59I, 59J, 59K:
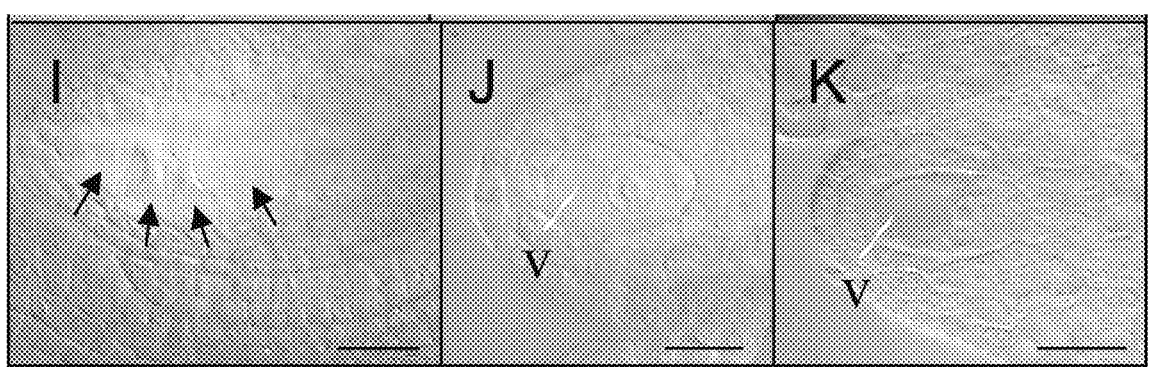

Herein, we associated apomixis sex switching with SnRK activation or silencing and the downstream processes of RdDM, TORC1 activation, and steroid signaling (FIG. 57). Interestingly, Antennaria, *Taraxacum* and *Hieracium* types of apomixis were differentially induced by modifying metabolic activities at different positions in these gene networks. Antennaria type apomeiosis required termination of sex (by inactivating SnRK or by 5-azaC demethylation) before meiosis began. ES formation then occurred precociously while integuments were still budding (FIG. 58F, 59J-K). In contrast, *Taraxacum*-type apomeiosis required termination of sexual development after meiosis had begun but before meiosis-specific recombination and reduction. Induced *Taraxacum* type diplospory in *arabidopsis* and rockcress exhibited the characteristic temporal delay (FIGS. 58D-58E) often observed between sporogenesis and gametogenesis in ovules of sexual plants and natural *Taraxacum*-type diplosporous plants (80). Integument growth proceeded rapidly during this delay (FIGS. 58D-58E). *Hieracium* type apospory was induced primarily by a combination of peroxide and BR signaling. However, crosstalk is extensive between BR, glucose and antioxidant signaling pathways (87), and the extent to which SnRK deactivation occurred in response to this crosstalk is not known. That AES formation occurred early during ovule development in sorghum (A151, FIG. 53D), *arabidopsis* (FIG. 58E), and Drummond's rockcress (FIG. 59G) may simply reflect active TORC1 and BR associated growth responses.

Apomeiosis in A151 was associated with upregulation of bioenergetically active genes and GO categories, whereas meiosis in S264 was associated with gene silencing (Tables S4-7). Likewise, apomeiosis induction in *arabidopsis*, rockcress and cowpea occurred readily when bioenergetics related metabolic processes were activated and/or when DNA methylation was prevented (FIGS. 58A-58I, 59A-59K). That all three types of apomeiosis were readily induced is consistent with apomixis and sex being anciently polyphenic. Polyphenism could explain why apomixis arises in eukaryotes following species hybridization or polyploidization, both of which alter metabolic homeostasis (73, 149). Also, the evolution in plants of a second stress response pathway (SnRK2) may divert metabolic stress away from SnRK1 (150) (FIG. 57). This could explain why apomixis occurs relatively often among plants. Finally, inducing apomeiosis in high yielding hybrids of crop species simply by altering metabolism, as noted recently for parthenogenesis (148), should accelerate R&D programs aimed at relieving food security issues in resource challenged nations.

TABLE 1

Transgressive segregation among RIL for apospory and apospory associated traits (Texas and Utah combined).

| | RIL parents | | RIL | | |
|---|---|---|---|---|---|
| Trait | IS3620C | BTx 623 | Min | Max | Mean |
| AES | 4.8 | 1.7 | 0 | 5.8 | 0.7 |
| AI | 8.0 | 2.0 | 0 | 22.1 | 3.1 |
| LSC | 33.8 | 2.1 | 0 | 39.5 | 7.4 |
| TT | 1.2 | 0.4 | 0 | 1.6 | 0.2 |
| OC1 | 119 | 128 | 110 | 141 | 125 |
| OC2 | 141 | 146 | 121 | 157 | 142 |

TABLE 2

QTL for apospory associated traits in the RIL population grown in Texas and Utah (combined).

| Trait | QTL name | SBI no. | QTL location (cM) | Flanking marker Left | Flanking marker Right | Distance to nearest marker (cM) | LOD | $R^2$ | Additive effect |
|---|---|---|---|---|---|---|---|---|---|
| AI | Qai.usu-1 | 1 | 28.8 | phyC | txa2084* | 0.7 | 3.07 | 11.9 | −1.85 |
| LSC | Qlsc.usu-1.1 | 1 | 28.8 | phyC | txa2084* | 0.7 | 2.9 | 9.0 | −3.75 |
| AES | Qaes.usu-1.1 | 1 | 29.5 | phyC | txa2084* | 0.0 | 2.63 | 8.0 | −0.48 |
| TT | Qtt.usu-1 | 1 | 42.7 | rz474* | umc27 | 2.0 | 11.84 | 51.7 | −0.45 |
| AES | Qaes.usu-1.3 | 1 | 43.7 | rz474 | umc27* | 1.5 | 10.34 | 49.6 | −1.70 |
| OC2 | Qoc2.usu-1.2 | 1 | 166.4 | isu51 | phyB* | 0.0 | 2.51 | 5.6 | 1.56 |
| OC1 | Qoc1.usu-1.4 | 1 | 195.3 | cdo1387 | txp61* | 0.0 | 3.08 | 5.3 | 1.46 |
| OC1 | Qoc1.usu-3.1 | 3 | 8.7 | txa6154 | umc121* | 0.3 | 7.08 | 13.4 | −2.29 |
| OC2 | Qoc2.usu-3.1 | 3 | 9 | txa6154 | umc121* | 0.0 | 4.11 | 9.7 | −2.02 |
| OC1 | Qoc1.usu-3.3 | 3 | 133.3 | isu74.2 | isu121* | 0.0 | 3.15 | 5.4 | −1.54 |
| OC2 | Qoc2.usu-3.4 | 3 | 140 | txa235* | txa422 | 0.0 | 2.57 | 5.9 | −1.67 |
| LSC | Qlsc.usu-3 | 3 | 161.4 | isu166 | txa2027* | 0.0 | 2.24 | 5.5 | −1.99 |
| OC2 | Qoc2.usu-6 | 6 | 23.9 | txa4103* | txa6233 | 1.0 | 3.67 | 8.9 | 1.99 |
| AI | Qai.usu-8 | 8 | 99.2 | txa558 | cdo459* | 0.0 | 2.68 | 8.7 | −1.07 |
| LSC | Qlsc.usu-8 | 8 | 100.2 | cdo459* | txa6348 | 1.0 | 4.95 | 13.5 | −3.11 |
| OC1 | Qoc1.usu-9.2 | 9 | 111.7 | txa3014* | cdo89 | 2.0 | 5.03 | 9.3 | 1.91 |
| OC2 | Qoc2.usu-9.2 | 9 | 126.4 | txa4122 | umc135.2* | 2.8 | 3.42 | 9.3 | 2.00 |
| LSC | Qlsc.usu-10.2 | 10 | 89.7 | txa381 | bnl5.04* | 0.0 | 4.01 | 10.1 | 2.74 |

*Indicates closest marker to QTL $R^2$: percentage of phenotypic variation explained by QTL Additive effect: positive implies that the low apospory parent BTx623 allele increased the phenotypic value, negative implies that the BTx623 allele decreased the phenotypic value

TABLE 3

QTL for apospory associated traits in the F2 population grown in Utah.

| Trait | QTL name | SBI no. | QTL location (cM) | Flanking marker Left | Flanking marker Right | Distance to nearest marker (cM) | LOD | R² | Additive effect |
|---|---|---|---|---|---|---|---|---|---|
| AES | Qaes.usu-1 | 1 | 48.865 | M10* | M11 | 18.0 | 12.8 | 17.8 | 1.02 |
| PT | Qpt.usu-1.1 | 1 | 49.865 | M10* | M11 | 19.0 | 39.1 | 36.7 | 0.31 |
| PT | Qpt.usu-1.2 | 1 | 118.864 | M17 | M18* | 6.9 | 21.6 | 69.0 | 0.36 |
| OV1 | Qov1.usu-1 | 1 | 143.917 | M20txp61 | M21* | 3.0 | 5.2 | 11.4 | 0.50 |
| OV1 | Qov1.usu-2.1 | 2 | 88.042 | M36txp13 | M37* | 0.0 | 4.2 | 8.1 | −0.35 |
| OV3 | Qov3.usu-2 | 2 | 92.587 | M38* | M39txp1 | 2.0 | 4.3 | 9.6 | −2.59 |
| OV1 | Qov1.usu-2.2 | 2 | 152.127 | M42txp207 | M44txp8* | 2.4 | 3.6 | 6.9 | 0.33 |
| OV1 | Qov1.usu-3 | 3 | 56.297 | M54 | M53* | 0.0 | 3.6 | 7.2 | 0.12 |
| OV2 | Qov2.usu-4 | 4 | 101.179 | M74* | M75txp60 | 5.0 | 3.6 | 10.7 | 1.87 |
| OV3 | Qov3.usu-4 | 4 | 116.577 | M74 | M75txp60* | 0.0 | 4.5 | 9.3 | 2.74 |
| OC2 | Qoc2.usu-4 | 4 | 127.577 | M75txp60 | M76* | 4.2 | 6.6 | 15.2 | 1.94 |
| OC1 | Qoc1.usu-4 | 4 | 132.825 | M76 | M77* | 0.7 | 9.1 | 14.7 | 2.66 |
| AES | Qaes.usu-5 | 5 | 0.000 | M151* | M152txa4096 | 0.0 | 12.0 | 17.0 | 0.89 |
| TT | Qtt.usu-5.1 | 5 | 43.052 | M154 | M155* | 0.1 | 16.7 | 45.0 | −1.50 |
| TT | Qtt.usu-5.2 | 5 | 47.341 | M158* | M156 | 0.0 | 17.2 | 44.9 | 1.65 |
| AES | Qaes.usu-6.1 | 6 | 42.86 | M142txa4032* | M143txp274 | 0.0 | 9.3 | 29.1 | −2.35 |
| LSC | Qlsc.usu-6 | 6 | 93.851 | M146 | M147* | 0.1 | 8.6 | 20.4 | −33.44 |
| OC1 | Qoc1.usu-6 | 6 | 98.923 | M147 | M148* | 3.6 | 5.5 | 10.5 | −2.77 |
| OC2 | Qoc22.usu-6 | 6 | 99.923 | M147 | M148* | 2.6 | 4.2 | 10.0 | −1.99 |
| AES | Qaes.usu-6.2 | 6 | 108.006 | M149txp17* | M150 | 1.0 | 4.5 | 5.0 | −1.24 |
| OC2 | Qoc2.usu-7 | 7 | 97.298 | M92txa4088 | M93* | 1.4 | 4.8 | 19.2 | 4.33 |
| OV2 | Qov2.usu-7 | 7 | 104.614 | M94* | M95txp295 | 1.0 | 3.7 | 8.9 | 1.70 |
| OC1 | Qoc1.usu-8 | 8 | 82.929 | M128txp354 | M129txp18* | 1.3 | 6.6 | 10.9 | −2.47 |
| OC1 | Qoc1.usu-10 | 10 | 61.033 | M111txp217 | M112txp130* | 1.3 | 4.6 | 7.4 | 1.92 |

*Indicates closest marker to QTL
R²: percentage of phenotypic variation explained by QTL
Additive effect: positive implies that the low apospory parent allele increased the phenotypic value, negative implies that the low apospory parent allele decreased the phenotypic value

TABLE 4

Chromosomal and functional anotations for differentially expressed genes (DEG) identified by microarrays that compared ovule transcripts of A151 with those of S264 for each stage separately and all stages combined.

| Line no. | DEG | QTL region | Dir | Start | End |
|---|---|---|---|---|---|
| 1 | Bioenergetics and respiration related-A151 up | | | | |
| 2 | Sobic.009G212400 | 9a | + | 55,806,661.00 | 55,810,398.00 |
| 3 | Sobic.002G078300 | | + | 8,140,737.00 | 8,141,673.00 |
| 4 | Sobic.004G161900 | | + | 51,099,644.00 | 51,106,292.00 |
| 5 | Sobic.002G298500 | 2a | + | 67,429,191.00 | 67,431,044.00 |
| 6 | Sobic.009G240700 | | − | 57,799,754.00 | 57,804,273.00 |
| 7 | Sobic.006G216800 | 6c | − | 56,456,307.00 | 56,462,044.00 |
| 8 | Sobic.003G338700 | | − | 66,179,184.00 | 66,180,033.00 |
| 9 | Sobic.006G064600 | 6b | + | 42,451,058.00 | 42,457,085.00 |
| 10 | Sobic.005G181000 | | − | 66,377,840.00 | 66,382,087.00 |
| 11 | Sobic.001G412100 | 1c | + | 69,480,945.00 | 69,485,876.00 |
| 12 | Sobic.007G163100 | 7a | + | 59,730,719.00 | 59,749,288.00 |
| 13 | Sobic.002G005600 | | + | 574,407.00 | 577,863.00 |
| 14 | Sobic.004G207900 | 4a | − | 55,801,519.00 | 55,809,440.00 |
| 15 | Sobic.003G287600 | | + | 62,076,879.00 | 62,080,161.00 |
| 16 | Sobic.002G303300 | 2a | − | 67,925,196.00 | 67,930,951.00 |
| 17 | Sobic.004G056400 | | + | 4,540,873.00 | 4,546,266.00 |
| 18 | LOC110433633 | | | | |
| 19 | Sobic.001G406800 | 1c | + | 69,116,259.00 | 69,120,681.00 |
| 20 | Sobic.001G387200 | 1c | + | 67,450,553.00 | 67,456,023.00 |
| 21 | Sobic.001G047800 | | − | 3,509,307.00 | 3,512,156.00 |
| 22 | Sobic.004G264700 | 4a | + | 60,967,964.00 | 60,971,959.00 |
| 23 | Sobic.001G404800 | 1c | − | 68,947,634.00 | 68,951,155.00 |
| 24 | Sobic.010G032600 | | − | 2,598,096.00 | 2,600,833.00 |
| 25 | Sobic.001G134200 | 1a | − | 10,580,229.00 | 10,583,893.00 |
| 26 | Sobic.001G354600 | 1c | + | 64,446,915.00 | 64,451,924.00 |
| 27 | Sobic.009G162200 | 9a | − | 51,907,742.00 | 51,909,780.00 |
| 28 | Sobic.003G237400 | | − | 57,671,841.00 | 57,676,529.00 |
| 29 | Sobic.009G107200 | | − | 43,052,968.00 | 43,053,868.00 |
| 30 | Sobic.002G189400 | 2a | + | 57,548,771.00 | 57,553,947.00 |
| 31 | Sobic.001G031300 | | + | 2,391,412.00 | 2,395,531.00 |
| 32 | Sobic.010G224700 | | + | 56,679,793.00 | 56,687,091.00 |
| 33 | Sobic.001G235700 | 1b | − | 23,766,207.00 | 23,773,642.00 |
| 34 | Sobic.004G319800 | 4a | − | 65,478,703.00 | 65,482,060.00 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 35 | Bioenergetics and respiration related-A151 down (up in S264) | | | | |
| 36 | Sobic.006G256600 | 6c | + | 59,325,650.00 | 59,330,162.00 |
| 37 | Sobic.002G356000 | | − | 71,896,129.00 | 71,897,303.00 |
| 38 | Sobic.009G031400 | | − | 2,775,343.00 | 2,780,568.00 |
| 39 | Sobic.003G036200 | 3a | + | 3,317,184.00 | 3,322,427.00 |
| 40 | Sobic.002G184600 | 2a | + | 56,856,271.00 | 56,858,640.00 |
| 41 | Sobic.003G049200 | | + | 4,507,218.00 | 4,512,001.00 |
| 42 | Sobic.001G459800 | 1c | − | 73,534,067.00 | 73,537,450.00 |
| 43 | Sobic.001G519700 | | + | 78,556,201.00 | 78,558,727.00 |
| 44 | Sobic.003G370000 | | + | 68,596,291.00 | 68,598,685.00 |
| 45 | Sobic.001G194900 | 1b | − | 17,460,443.00 | 17,466,929.00 |
| 46 | Sobic.001G096800 | 1a | − | 7,442,339.00 | 7,444,186.00 |
| 47 | Sobic.003G258200 | | − | 59,623,226.00 | 59,628,704.00 |
| 48 | Sobic.001G090200 | 1a | + | 6,985,559.00 | 6,988,410.00 |
| 49 | Sobic.002G230100 | 2a | − | 62,133,898.00 | 62,138,981.00 |
| 50 | Sobic.004G068700 | | + | 5,601,968.00 | 5,604,203.00 |
| 51 | Sobic.005G060100 | | − | 6,177,466.00 | 6,183,014.00 |
| 52 | Sobic.003G233000 | | + | 57,206,762.00 | 57,209,171.00 |
| 53 | Sobic.004G207900 | 4a | − | 55,801,519.00 | 55,809,440.00 |
| 54 | Sobic.001G123100 | 1a | + | 9,691,157.00 | 9,697,122.00 |
| 55 | Sobic.007G123500 | 7a | + | 53,008,816.00 | 53,014,660.00 |
| 56 | Sobic.003G327900 | | − | 65,351,362.00 | 65,353,707.00 |
| 57 | LOC110435380 | | | | |
| 58 | Sobic.003G039700 | 3a | + | 3,704,106.00 | 3,706,086.00 |
| 59 | Sobic.006G001000 | | − | 106,708.00 | 108,954.00 |
| 60 | Sobic.006G130300 | 6b | − | 49,461,880.00 | 49,464,336.00 |
| 61 | Sobic.003G292700 | | + | 62,522,638.00 | 62,530,165.00 |
| 62 | Sobic.001G082900 | 1a | + | 6,405,202.00 | 6,408,722.00 |
| 63 | Sobic.007G202800 | | − | 63,368,107.00 | 63,372,640.00 |
| 64 | Sobic.004G206200 | 4a | + | 55,697,535.00 | 55,700,061.00 |
| 65 | Sobic.003G051000 | | + | 4,618,820.00 | 4,623,198.00 |
| 66 | Sobic.007G162600 | 7a | + | 59,667,687.00 | 59,672,991.00 |
| 67 | Sobic.010G092600 | | − | 8,195,416.00 | 8,200,323.00 |
| 68 | Sobic.008G024200 | | + | 2,150,718.00 | 2,153,457.00 |
| 69 | Stress and catabolismo related-A151 up | | | | |
| 70 | Sobic.003G024800 | 3a | + | 2,112,894.00 | 2,117,221.00 |
| 71 | Sobic.004G182800 | | − | 53,660,161.00 | 53,664,134.00 |
| 72 | Sobic.001G371900 | 1c | − | 66,007,310.00 | 66,010,619.00 |
| 73 | Sobic.006G029800 | | + | 6,293,014.00 | 6,306,287.00 |
| 74 | Sobic.001G010800 | | + | 948,055.00 | 950,515.00 |
| 75 | Sobic.010G104100 | | − | 9,788,541.00 | 9,792,566.00 |
| 76 | Sobic.003G140700 | | + | 13,709,403.00 | 13,712,523.00 |
| 77 | Sobic.001G410200 | 1c | − | 69,365,835.00 | 69,369,561.00 |
| 78 | Sobic.004G343200 | 4a | + | 67,364,634.00 | 67,368,957.00 |
| 79 | Sobic.004G333500 | 4a | + | 66,620,626.00 | 66,623,081.00 |
| 80 | Sobic.010G101500 | | + | 9,362,553.00 | 9,369,524.00 |
| 81 | Sobic.004G295800 | 4a | − | 63,558,304.00 | 63,565,377.00 |
| 82 | Sobic.001G293300 | 1c | − | 57,080,138.00 | 57,082,645.00 |
| 83 | Sobic.010G015900 | | − | 1,264,900.00 | 1,272,306.00 |
| 84 | Sobic.006G257900 | 6c | − | 59,420,396.00 | 59,422,685.00 |
| 85 | Sobic.004G057200 | | + | 4,576,127.00 | 4,578,632.00 |
| 86 | Sobic.009G055800 | | + | 5,639,234.00 | 5,640,945.00 |
| 87 | Sobic.001G154100 | | − | 12,370,479.00 | 12,374,638.00 |
| 88 | Sobic.003G338400 | | − | 66,140,464.00 | 66,144,219.00 |
| 89 | Sobic.001G520100 | | + | 78,593,014.00 | 78,598,009.00 |
| 90 | Sobic.010G047400 | | − | 3,668,202.00 | 3,673,695.00 |
| 91 | Sobic.005G208900 | | + | 69,538,522.00 | 69,540,988.00 |
| 92 | Sobic.004G006900 | | − | 588,992.00 | 602,915.00 |
| 93 | Sobic.010G222400 | | − | 56,466,475.00 | 56,468,578.00 |
| 94 | Sobic.001G100900 | 1a | − | 7,684,582.00 | 7,694,636.00 |
| 95 | Sobic.010G001600 | | − | 147,458.00 | 150,483.00 |
| 96 | Sobic.004G177700 | | + | 53,002,892.00 | 53,008,010.00 |
| 97 | Sobic.008G144500 | | + | 57,588,001.00 | 57,590,395.00 |
| 98 | Sobic.006G220900 | 6c | − | 56,767,906.00 | 56,771,340.00 |
| 99 | Sobic.002G243200 | 2a | − | 63,222,508.00 | 63,226,117.00 |
| 100 | Sobic.004G255000 | 4a | − | 60,133,307.00 | 60,135,146.00 |
| 101 | Sobic.001G108900 | 1a | − | 8,442,944.00 | 8,447,886.00 |
| 102 | Sobic.007G029700 | | − | 2,709,378.00 | 2,714,744.00 |
| 103 | Sobic.003G368000 | | + | 68,382,920.00 | 68,386,377.00 |
| 104 | Sobic.003G247000 | | + | 58,587,997.00 | 58,591,669.00 |
| 105 | Sobic.010G181600 | 10b | − | 52,075,764.00 | 52,084,556.00 |
| 106 | Sobic.004G224900 | 4a | + | 57,528,770.00 | 57,533,185.00 |
| 107 | Sobic.004G350400 | 4a | − | 67,916,655.00 | 67,918,352.00 |
| 108 | Sobic.006G252200 | 6c | + | 59,025,016.00 | 59,028,576.00 |
| 109 | Stress and catabolismo related-A151 down | | | | |
| 110 | Sobic.004G171400 | | + | 52,396,486.00 | 52,397,755.00 |
| 111 | Sobic.010G128400 | | + | 16,881,605.00 | 16,882,960.00 |

TABLE 4-continued

Chromosomal and functional anotations for differentially expressed genes (DEG) identified by microarrays that compared ovule transcripts of A151 with those of S264 for each stage separately and all stages combined.

| # | Gene | Stage | +/− | Start | End |
|---|---|---|---|---|---|
| 112 | Sobic.001G483100 | | + | 75,443,322.00 | 75,446,022.00 |
| 113 | Sobic.005G005500 | | + | 427,858.00 | 431,382.00 |
| 114 | Sobic.004G111100 | | + | 10,904,452.00 | 10,908,103.00 |
| 115 | Sobic.006G161300 | 6b | − | 51,920,807.00 | 51,926,017.00 |
| 116 | Sobic.003G317700 | | − | 64,529,397.00 | 64,533,991.00 |
| 117 | Sobic.001G140300 | 1a | − | 11,195,137.00 | 11,198,205.00 |
| 118 | Sobic.004G155600 | | + | 49,232,785.00 | 49,236,916.00 |
| 119 | Sobic.002G031100 | | + | 2,842,055.00 | 2,850,338.00 |
| 120 | Sobic.007G169700 | 7a | + | 60,438,598.00 | 60,447,179.00 |
| 121 | Sobic.007G088300 | | − | 12,259,928.00 | 12,261,363.00 |
| 122 | Sobic.008G004600 | | − | 410,940.00 | 417,101.00 |
| 123 | Sobic.003G221400 | | − | 55,683,202.00 | 55,695,650.00 |
| 124 | Sobic.001G306000 | 1c | + | 59,003,657.00 | 59,006,974.00 |
| 125 | Sobic.002G345700 | | − | 71,147,858.00 | 71,160,490.00 |
| 126 | Sobic.002G157300 | | − | 47,766,918.00 | 47,772,658.00 |
| 127 | Sobic.006G260300 | 6c | − | 59,555,668.00 | 59,559,490.00 |
| 128 | Sobic.005G170100 | | − | 64,933,085.00 | 64,936,631.00 |
| 129 | Sobic.005G167400 | | − | 64,532,937.00 | 64,544,683.00 |
| 130 | Sobic.008G105500 | 8b | − | 49,760,626.00 | 49,764,366.00 |
| 131 | Sobic.001G452100 | 1c | − | 72,881,688.00 | 72,885,057.00 |
| 132 | Sobic.001G441100 | 1c | + | 71,899,741.00 | 71,901,707.00 |
| 133 | Sobic.010G041800 | | + | 3,236,126.00 | 3,241,583.00 |
| 134 | Sobic.003G192400 | | − | 51,421,682.00 | 51,435,088.00 |
| 135 | Sobic.001G317000 | 1c | − | 60,531,076.00 | 60,532,263.00 |
| 136 | Sobic.010G231300 | | + | 57,417,517.00 | 57,425,072.00 |
| 137 | Sobic.004G148600 | | − | 46,677,122.00 | 46,692,976.00 |
| 138 | Hormone and signaling related-A151 up | | | | |
| 139 | Sobic.004G202500 | 4a | − | 55,461,614.00 | 55,464,923.00 |
| 140 | Sobic.002G068900 | | − | 6,826,034.00 | 6,830,569.00 |
| 141 | Sobic.008G181300 | | + | 61,540,335.00 | 61,542,249.00 |
| 142 | Sobic.003G389000 | | + | 69,996,786.00 | 70,004,228.00 |
| 143 | Sobic.010G186200 | 10b | + | 52,679,609.00 | 52,682,635.00 |
| 144 | Sobic.005G084100 | 5b | − | 11,366,416.00 | 11,370,715.00 |
| 145 | Sobic.001G079200 | 1a | + | 6,087,458.00 | 6,095,806.00 |
| 146 | Sobic.005G106600 | 5b | + | 20,000,011.00 | 20,011,951.00 |
| 147 | Sobic.004G162000 | | + | 51,107,526.00 | 51,108,616.00 |
| 148 | Sobic.003G083200 | | − | 7,131,291.00 | 7,133,895.00 |
| 149 | Sobic.010G089700 | | − | 7,785,992.00 | 7,790,247.00 |
| 150 | Sobic.010G005600 | | − | 455,106.00 | 458,342.00 |
| 151 | Sobic.008G163300 | | − | 59,686,853.00 | 59,694,730.00 |
| 152 | Sobic.004G317000 | 4a | − | 65,266,845.00 | 65,268,995.00 |
| 153 | Sobic.003G430400 | 3c | − | 73,313,066.00 | 73,315,829.00 |
| 154 | Sobic.003G279800 | | − | 61,518,335.00 | 61,521,809.00 |
| 155 | Sobic.007G076300 | | + | 8,845,493.00 | 8,848,689.00 |
| 156 | Sobic.002G263100 | 2a | − | 64,804,254.00 | 64,807,107.00 |
| 157 | Sobic.001G424400 | 1c | + | 70,449,095.00 | 70,456,551.00 |
| 158 | Sobic.006G244800 | 6c | + | 58,463,788.00 | 58,467,690.00 |
| 159 | Sobic.007G139600 | 7a | + | 56,795,770.00 | 56,818,088.00 |
| 160 | Sobic.010G210600 | | − | 55,412,773.00 | 55,414,336.00 |
| 161 | Sobic.003G021500 | 3a | − | 1,835,934.00 | 1,839,841.00 |
| 162 | Hormone and signaling related-A151 down | | | | |
| 163 | Sobic.007G105100 | | − | 37,237,894.00 | 37,255,776.00 |
| 164 | Sobic.002G418500 | 2b | − | 76,629,585.00 | 76,632,298.00 |
| 165 | Sobic.003G253600 | | − | 59,222,111.00 | 59,236,014.00 |
| 166 | Sobic.006G187900 | 6c | − | 54,234,445.00 | 54,237,580.00 |
| 167 | Sobic.008G157700 | | − | 59,017,025.00 | 59,021,109.00 |
| 168 | Sobic.001G429700 | 1c | + | 70,889,964.00 | 70,893,347.00 |
| 169 | Sobic.002G393100 | 2b | − | 74,592,120.00 | 74,594,652.00 |
| 170 | Sobic.004G209900 | 4a | − | 55,960,660.00 | 55,965,540.00 |
| 171 | Sobic.002G181800 | 2a | − | 56,299,329.00 | 56,304,699.00 |
| 172 | Sobic.004G132900 | | + | 20,672,482.00 | 20,691,277.00 |
| 173 | Sobic.009G237600 | | + | 57,581,046.00 | 57,585,953.00 |
| 174 | Sobic.001G449700 | 1c | − | 72,675,652.00 | 72,677,546.00 |
| 175 | Sobic.001G125700 | 1a | − | 9,896,488.00 | 9,900,431.00 |
| 176 | Sobic.003G037000 | 3a | + | 3,459,184.00 | 3,466,465.00 |
| 177 | Sobic.009G116500 | 9a | + | 45,901,652.00 | 45,903,700.00 |
| 178 | Sobic.004G038300 | | + | 3,151,419.00 | 3,161,122.00 |
| 179 | Sobic.009G005700 | | − | 511,754.00 | 518,321.00 |
| 180 | Sobic.009G104600 | | + | 42,251,527.00 | 42,253,047.00 |
| 181 | Sobic.002G265800 | 2a | + | 65,074,582.00 | 65,076,415.00 |
| 182 | Sobic.004G349300 | 4a | − | 67,820,227.00 | 67,823,186.00 |
| 183 | Sobic.001G331200 | 1c | − | 61,899,347.00 | 61,901,912.00 |
| 184 | Sobic.009G229200 | 9a | − | 56,991,373.00 | 56,996,042.00 |
| 185 | Sobic.008G039800 | | − | 3,848,579.00 | 3,853,000.00 |
| 186 | Gene expression related-A151 up | | | | |
| 187 | Sobic.004G211400 | 4a | − | 56,110,439.00 | 56,118,269.00 |
| 188 | Sobic.004G155700 | | − | 49,237,038.00 | 49,239,769.00 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 189 | Sobic.004G211400 | 4a | − | 56,110,439.00 | 56,118,269.00 |
| 190 | Sobic.003G038100 | 3a | + | 3,574,836.00 | 3,580,910.00 |
| 191 | Sobic.004G211100 | 4a | − | 56,089,565.00 | 56,095,813.00 |
| 192 | Sobic.001G041200 | | + | 3,057,449.00 | 3,061,041.00 |
| 193 | Sobic.001G369000 | 1c | + | 65,750,487.00 | 65,757,894.00 |
| 194 | Sobic.002G046100 | | − | 4,347,013.00 | 4,349,948.00 |
| 195 | Sobic.001G122400 | 1a | − | 9,629,736.00 | 9,633,723.00 |
| 196 | Sobic.004G045400 | | + | 3,734,132.00 | 3,736,141.00 |
| 197 | Sobic.003G322400 | | + | 64,940,491.00 | 64,942,268.00 |
| 198 | Sobic.004G339200 | 4a | − | 67,109,556.00 | 67,113,760.00 |
| 199 | Sobic.001G147100 | 1a | − | 11,823,321.00 | 11,827,257.00 |
| 200 | Sobic.006G098500 | 6b | + | 46,795,404.00 | 46,801,286.00 |
| 201 | Sobic.004G271400 | 4a | − | 61,533,213.00 | 61,535,083.00 |
| 202 | Sobic.002G081600 | | − | 8,663,170.00 | 8,665,337.00 |
| 203 | Sobic.002G355300 | | + | 71,848,813.00 | 71,854,809.00 |
| 204 | Sobic.010G005300 | | − | 437,432.00 | 439,264.00 |
| 205 | Sobic.001G105100 | 1a | − | 8,047,924.00 | 8,052,102.00 |
| 206 | Sobic.001G281900 | 1c | − | 55,295,759.00 | 55,299,089.00 |
| 207 | Sobic.008G098800 | 8a | + | 46,900,059.00 | 46,902,765.00 |
| 208 | Sobic.001G541100 | | + | 80,382,343.00 | 80,387,475.00 |
| 209 | Sobic.006G138100 | 6b | − | 50,028,162.00 | 50,030,586.00 |
| 210 | Sobic.010G173100 | 10b | − | 50,836,164.00 | 50,840,275.00 |
| 211 | Sobic.009G182600 | 9a | + | 53,609,100.00 | 53,618,974.00 |
| 212 | Sobic.004G323700 | 4a | + | 65,841,267.00 | 65,845,629.00 |
| 213 | Sobic.006G160200 | 6b | − | 51,828,572.00 | 51,832,182.00 |
| 214 | Sobic.003G332401 | | + | 65,682,270.00 | 65,687,556.00 |
| 215 | Sobic.010G206200 | 10b | + | 54,918,479.00 | 54,920,768.00 |
| 216 | Sobic.004G145801 | | + | 45,028,987.00 | 45,031,184.00 |
| 217 | Sobic.008G128600 | | − | 55,481,164.00 | 55,485,537.00 |
| 218 | Sobic.006G252100 | 6c | − | 59,021,146.00 | 59,024,787.00 |
| 219 | Sobic.010G065400 | | − | 5,194,398.00 | 5,196,431.00 |
| 220 | Sobic.003G109600 | | − | 9,889,177.00 | 9,891,530.00 |
| 221 | Sobic.004G185600 | | − | 53,837,495.00 | 53,841,559.00 |
| 222 | Sobic.006G147000 | 6b | − | 50,855,833.00 | 50,858,144.00 |
| 223 | Sobic.001G016500 | | + | 1,432,980.00 | 1,435,566.00 |
| 224 | Sobic.001G011000 | | + | 955,066.00 | 959,328.00 |
| 225 | Sobic.001G386700 | 1c | − | 67,431,733.00 | 67,434,257.00 |
| 226 | Sobic.003G422900 | 3c | − | 72,761,769.00 | 72,768,462.00 |
| 227 | Sobic.001G447300 | 1c | − | 72,434,772.00 | 72,440,788.00 |
| 228 | Sobic.010G251100 | | − | 59,035,964.00 | 59,040,060.00 |
| 229 | Sobic.007G067700 | | − | 7,538,860.00 | 7,544,108.00 |
| 230 | Sobic.007G188900 | | − | 62,164,561.00 | 62,168,253.00 |
| 231 | Sobic.004G040900 | | + | 3,365,451.00 | 3,368,808.00 |
| 232 | Gene expression related-A151 down | | | | |
| 233 | Sobic.003G439900 | 3c | + | 73,930,707.00 | 73,932,390.00 |
| 234 | Sobic.008G108601 | 8b | + | 50,678,830.00 | 50,681,996.00 |
| 235 | Sobic.007G102800 | | + | 28,109,724.00 | 28,115,479.00 |
| 236 | Sobic.009G072200 | | − | 8,808,799.00 | 8,810,778.00 |
| 237 | Sobic.010G269600 | | + | 60,376,184.00 | 60,381,115.00 |
| 238 | Sobic.002G389600 | 2b | + | 74,293,692.00 | 74,298,572.00 |
| 239 | Sobic.001G175300 | | + | 14,732,032.00 | 14,734,480.00 |
| 240 | Sobic.009G244300 | | − | 58,029,456.00 | 58,032,033.00 |
| 241 | Sobic.001G008500 | | + | 815,311.00 | 818,496.00 |
| 242 | Sobic.007G011600 | | + | 1,078,165.00 | 1,083,465.00 |
| 243 | Sobic.006G126900 | 6b | + | 49,201,758.00 | 49,207,749.00 |
| 244 | Sobic.009G135600 | 9a | − | 49,063,509.00 | 49,069,038.00 |
| 245 | sRNA regulation of gene expression related-A151 up | | | | |
| 246 | Sobic.002G041400 | | + | 3,982,568.00 | 3,988,803.00 |
| 247 | Sobic.001G054800 | | − | 4,083,841.00 | 4,085,256.00 |
| 248 | Sobic.009G216700 | 9a | + | 56,101,914.00 | 56,104,511.00 |
| 249 | Sobic.001G289800 | 1c | + | 56,625,147.00 | 56,632,184.00 |
| 250 | Sobic.001G536400 | | − | 79,968,301.00 | 79,976,378.00 |
| 251 | Sobic.001G094500 | 1a | − | 7,251,832.00 | 7,257,471.00 |
| 252 | sRNA regulation of gene expression related-A151 down | | | | |
| 253 | Sobic.003G350100 | | − | 66,983,843.00 | 66,984,520.00 |
| 254 | Sobic.003G347900 | | + | 66,843,808.00 | 66,844,475.00 |
| 255 | Sobic.001G522600 | | − | 78,750,598.00 | 78,763,175.00 |
| 256 | Sobic.003G330900 | | + | 65,571,917.00 | 65,576,344.00 |
| 257 | Sobic.003G104000 | | − | 9,320,871.00 | 9,325,420.00 |
| 258 | Growth and development related-A151 up | | | | |
| 259 | Sobic.004G093700 | | + | 8,026,516.00 | 8,029,406.00 |
| 260 | Sobic.004G197600 | | + | 54,869,063.00 | 54,874,521.00 |
| 261 | Sobic.010G172400 | 10b | − | 50,682,130.00 | 50,686,559.00 |
| 262 | Sobic.006G152600 | 6b | + | 51,306,815.00 | 51,310,968.00 |
| 263 | Sobic.002G148100 | | + | 37,812,109.00 | 37,835,896.00 |
| 264 | Sobic.004G025900 | | + | 2,068,232.00 | 2,070,112.00 |
| 265 | Sobic.003G049600 | | + | 4,541,987.00 | 4,548,948.00 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 266 | Sobic.001G046400 | | − | 3,414,553.00 | 3,416,917.00 |
| 267 | Sobic.009G259200 | | − | 59,268,214.00 | 59,273,174.00 |
| 268 | Sobic.004G187900 | | − | 53,982,411.00 | 53,987,262.00 |
| 269 | Sobic.010G266300 | | + | 60,153,893.00 | 60,157,793.00 |
| 270 | Sobic.002G113800 | | − | 13,873,467.00 | 13,877,355.00 |
| 271 | Sobic.008G160400 | | − | 59,364,648.00 | 59,372,381.00 |
| 272 | Sobic.004G190600 | | − | 54,238,547.00 | 54,242,928.00 |
| 273 | Sobic.001G086600 | 1a | − | 6,708,365.00 | 6,712,052.00 |
| 274 | Sobic.010G097600 | | − | 8,834,293.00 | 8,842,412.00 |
| 275 | Sobic.003G250700 | | − | 58,912,369.00 | 58,916,372.00 |
| 276 | Sobic.004G350300 | 4a | + | 67,909,245.00 | 67,913,847.00 |
| 277 | Sobic.006G050600 | 6a | + | 37,902,059.00 | 37,905,264.00 |
| 278 | Sobic.001G398500 | 1c | − | 68,430,187.00 | 68,435,279.00 |
| 279 | Sobic.003G334700 | | − | 65,800,311.00 | 65,817,128.00 |
| 280 | Sobic.002G201900 | 2a | + | 59,174,209.00 | 59,182,754.00 |
| 281 | Sobic.001G119900 | 1a | + | 9,323,804.00 | 9,328,062.00 |
| 282 | Sobic.005G187500 | | − | 67,236,800.00 | 67,240,653.00 |
| 283 | Sobic.004G243800 | 4a | + | 59,138,508.00 | 59,142,210.00 |
| 284 | Sobic.002G175400 | 2a | + | 55,392,886.00 | 55,396,332.00 |
| 285 | Sobic.007G019300 | | + | 1,815,408.00 | 1,821,577.00 |
| 286 | Growth and development related-A151 down | | | | |
| 287 | Sobic.009G132400 | 9a | + | 48,658,015.00 | 48,663,505.00 |
| 288 | Sobic.006G221300 | 6c | − | 56,801,263.00 | 56,805,484.00 |
| 289 | Sobic.001G195600 | 1b | − | 17,559,339.00 | 17,570,228.00 |
| 290 | Sobic.008G034400 | | + | 3,170,967.00 | 3,177,019.00 |
| 291 | Sobic.007G011300 | | + | 1,015,277.00 | 1,024,534.00 |
| 292 | Sobic.004G351200 | 4a | + | 67,979,891.00 | 67,983,213.00 |
| 293 | Sobic.004G215700 | 4a | + | 56,560,203.00 | 56,563,749.00 |
| 294 | Sobic.003G228900 | | + | 56,711,355.00 | 56,715,010.00 |
| 295 | Sobic.010G108600 | | − | 10,801,407.00 | 10,803,603.00 |
| 296 | Sobic.003G371100 | | + | 68,700,072.00 | 68,702,793.00 |
| 297 | Sobic.003G445300 | 3c | − | 74,316,138.00 | 74,319,335.00 |
| 298 | Sobic.001G091300 | 1a | − | 7,061,979.00 | 7,065,251.00 |
| 299 | Sobic.010G248200 | | + | 58,827,900.00 | 58,830,677.00 |
| 300 | LOC110433098 | | | | |
| 301 | Sobic.004G134600 | | + | 23,730,325.00 | 23,731,465.00 |
| 302 | Sobic.002G220600 | 2a | + | 61,218,206.00 | 61,224,916.00 |
| 303 | LOC8078215 | | | | |
| 304 | Sobic.001G363700 | 1c | − | 65,296,362.00 | 65,298,761.00 |
| 305 | Sobic.001G497700 | | + | 76,754,067.00 | 76,755,663.00 |
| 306 | Sobic.001G088100 | 1a | + | 6,849,743.00 | 6,857,801.00 |
| 307 | Sobic.003G334700 | | − | 65,800,311.00 | 65,817,128.00 |
| 308 | Sobic.001G281600 | 1c | + | 55,224,357.00 | 55,229,298.00 |
| 309 | Sobic.002G143300 | | + | 23,996,491.00 | 23,997,147.00 |
| 310 | Sobic.003G173800 | 3b | + | 40,590,216.00 | 40,592,214.00 |
| 311 | Sobic.010G134400 | 10a | + | 19,611,856.00 | 19,615,565.00 |
| 312 | Sobic.003G427600 | 3c | + | 73,106,229.00 | 73,116,438.00 |
| 313 | Sobic.003G403500 | 3c | + | 71,135,507.00 | 71,139,196.00 |
| 314 | Other-A151 up | | | | |
| 315 | Sobic.010G094301 | | − | 8,392,412.00 | 8,393,275.00 |
| 316 | Sobic.003G048500 | | + | 4,469,847.00 | 4,473,953.00 |
| 317 | Sobic.004G208100 | 4a | − | 55,815,801.00 | 55,819,196.00 |
| 318 | Sobic.005G112632 | | − | 38,945,695.00 | 38,947,112.00 |
| 319 | LOC110435809 | | | | |
| 320 | LOC110431211 | | | | |
| 321 | Sobic.002G254100 | 2a | + | 64,052,061.00 | 64,057,021.00 |
| 322 | Sobic.004G136500 | | − | 35,597,222.00 | 35,601,506.00 |
| 323 | Sobic.004G331800 | 4a | + | 66,488,126.00 | 66,488,764.00 |
| 324 | Sobic.004G007300 | | + | 646,027.00 | 651,065.00 |
| 325 | Sobic.001G541400 | | − | 80,446,007.00 | 80,446,534.00 |
| 326 | Sobic.001G442200 | 1c | − | 71,974,109.00 | 71,977,005.00 |
| 327 | LOC110431017 | | | | |
| 328 | MultiHit5375 | | | | |
| 329 | Sobic.003G029200 | 3a | − | 2,570,016.00 | 2,571,927.00 |
| 330 | Sobic.001G381900 | 1c | − | 66,987,709.00 | 66,992,513.00 |
| 331 | MultiHit7742 | | | | |
| 332 | Sobic.003G140900 | | − | 13,720,240.00 | 13,722,426.00 |
| 333 | Sobic.001G121100 | 1a | − | 9,416,143.00 | 9,419,471.00 |
| 334 | Sobic.001G143300 | 1a | − | 11,487,034.00 | 11,491,162.00 |
| 335 | Sobic.002G364800 | 2b | + | 72,539,353.00 | 72,549,086.00 |
| 336 | Sobic.003G088400 | | − | 7,689,356.00 | 7,690,085.00 |
| 337 | Sobic.001G154400 | | + | 12,398,998.00 | 12,404,024.00 |
| 338 | MultiHit5916 | | | | |
| 339 | MultiHit3601 | | | | |
| 340 | Sobic.003G113500 | | − | 10,197,758.00 | 10,198,740.00 |
| 341 | Sobic.001G087700 | 1a | + | 6,829,749.00 | 6,834,430.00 |
| 342 | LOC8081614 | | | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 343 | LOC110429578 | | | | |
| 344 | Sobic.005G228700 | | + | 71,599,142.00 | 71,600,181.00 |
| 345 | Sobic.004G134900 | | − | 25,798,505.00 | 25,813,769.00 |
| 346 | Sobic.001G012200 | | − | 1,048,825.00 | 1,050,688.00 |
| 347 | Sobic.001G193100 | 1b | − | 17,194,950.00 | 17,201,000.00 |
| 348 | Other-A151 down | | | | |
| 349 | Sobic.002G200900 | 2a | + | 59,072,224.00 | 59,081,085.00 |
| 350 | Sobic.001G455600 | 1c | − | 73,156,146.00 | 73,161,755.00 |
| 351 | Sobic.008G026200 | | + | 2,374,545.00 | 2,378,981.00 |
| 352 | Sobic.009G003300 | | − | 281,759.00 | 284,401.00 |
| 353 | Sobic.004G105500 | | − | 9,943,886.00 | 9,950,013.00 |
| 354 | Sobic.004G324800 | 4a | + | 66,019,388.00 | 66,021,561.00 |
| 355 | Sobic.002G191800 | 2a | − | 57,813,088.00 | 57,821,201.00 |
| 356 | Sobic.002G171300 | 2a | − | 54,284,767.00 | 54,286,113.00 |
| 357 | Sobic.001G298700 | 1c | + | 57,952,711.00 | 57,959,561.00 |
| 358 | Sobic.006G206200 | 6c | + | 55,583,866.00 | 55,587,925.00 |
| 359 | Sobic.010G016500 | | + | 1,315,565.00 | 1,316,314.00 |
| 360 | Sobic.006G052800 | | + | 38,516,836.00 | 38,527,925.00 |
| 361 | Sobic.001G536800 | | − | 79,991,887.00 | 79,994,910.00 |
| 362 | Sobic.001G146301 | 1a | + | 11,761,695.00 | 11,761,976.00 |
| 363 | Sobic.002G151300 | | − | 45,071,634.00 | 45,075,710.00 |
| 364 | Sobic.001G098600 | 1a | − | 7,564,826.00 | 7,566,576.00 |
| 365 | Sobic.001G072700 | 1a | − | 5,531,321.00 | 5,535,715.00 |
| 366 | MultiHit113 | | | | |
| 367 | Sobic.001G204700 | 1b | + | 18,682,956.00 | 18,687,507.00 |
| 368 | Sobic.001G051800 | | − | 3,819,287.00 | 3,820,358.00 |
| 369 | Sobic.006G122500 | 6b | + | 48,857,920.00 | 48,859,019.00 |
| 370 | Sobic.009G224400 | 9a | − | 56,652,597.00 | 56,656,038.00 |
| 371 | Sobic.005G021200 | 5a | − | 1,962,720.00 | 1,967,001.00 |
| 372 | Sobic.005G084300 | 5b | + | 11,464,730.00 | 11,467,848.00 |
| 373 | Sobic.004G162200 | | − | 51,111,914.00 | 51,121,956.00 |
| 374 | Sobic.003G018000 | 3a | − | 1,595,535.00 | 1,598,853.00 |
| 375 | Sobic.006G258800 | 6c | − | 59,470,927.00 | 59,474,298.00 |
| 376 | Sobic.001G103600 | 1a | + | 7,951,939.00 | 7,954,166.00 |
| 377 | Sobic.009G252100 | | + | 58,682,087.00 | 58,684,835.00 |
| 378 | Sobic.004G019400 | | + | 1,548,120.00 | 1,551,366.00 |
| 379 | Sobic.002G330800 | | + | 69,944,334.00 | 69,948,618.00 |
| 380 | MultiHit10711 | | | | |
| 381 | Sobic.005G143200 | | − | 60,675,665.00 | 60,681,004.00 |
| 382 | Sobic.006G219500 | 6c | + | 56,670,879.00 | 56,674,646.00 |
| 383 | Sobic.002G365550 | 2b | − | 72,580,073.00 | 72,580,967.00 |
| 384 | Sobic.006G066600 | 6b | − | 42,692,211.00 | 42,697,583.00 |
| 385 | Sobic.010G109600 | | − | 10,900,233.00 | 10,904,247.00 |
| 386 | Sobic.009G007700 | | − | 712,811.00 | 715,485.00 |
| 387 | Sobic.003G206300 | | − | 53,671,219.00 | 53,672,149.00 |
| 388 | Sobic.004G272700 | 4a | + | 61,636,902.00 | 61,641,337.00 |
| 389 | Sobic.001G182850 | 1b | + | 15,495,162.00 | 15,498,334.00 |
| 390 | Sobic.009G186400 | 9a | − | 53,925,415.00 | 53,925,993.00 |

| Line no. | DEG | *Arabidopsis* ortholog | General functions summarized from TAIR | *Oryza sativa* ortholog | USU ref. |
|---|---|---|---|---|---|
| 1 | Bioenergetics and respiration related-A151 up | | | | |
| 2 | Sobic.009G212400 | AT5G15090 | respiratory metabolite exchange between mitochondria and cytosol | LOC_Os05g45950.1 | 3975 |
| 3 | Sobic.002G078300 | AT2G44620 | MITOCHONDRIAL ACYL CARRIER PROTEIN 1, MTACP1, fatty acid biosynthesis | LOC_Os07g12150.1 | 228 |
| 4 | Sobic.004G161900 | AT5G36880 | ACETYL-COA SYNTHASE, ethanol & acetaldehyde detoxification | LOC_Os02g32490.1 | 6831 |
| 5 | Sobic.002G298500 | AT1G36150 | lipid transport | LOC_Os07g29230.1 | 7373 |
| 6 | Sobic.009G240700 | AT1G53240 | MITOCHONDRIAL MALATE DEHYDROGENASE 1, MMDH1, TCA, response to salt stress | LOC_Os01g46070.1 | 5478 |
| 7 | Sobic.006G216800 | AT1G03000 | PEX6, involved in fatty acid beta-oxidation | LOC_Os04g52690.2 | 3789 |
| 8 | Sobic.003G338700 | AT5G01870 | lipid transport | LOC_Os01g60740.1 | 1214 |

TABLE 4-continued

Chromosomal and functional anotations for differentially expressed genes (DEG) identified by microarrays that compared ovule transcripts of A151 with those of S264 for each stage separately and all stages combined.

| # | | | | | |
|---|---|---|---|---|---|
| 9 | Sobic.006G064600 | AT5G36880 | ACETYL-COA SYNTHASE, ACS detoxification | LOC_Os04g33190.1 | 11473 |
| 10 | Sobic.005G181000 | AT5G65110 | acyl-CoA oxidase, long chain fatty acid biosynthesis | LOC_Os11g39220.1 | 11879 |
| 11 | Sobic.001G412100 | AT2G39290 | glycerophospholipid biosynthetic process in chloroplasts | LOC_Os03g17520.1 | 7640 |
| 12 | Sobic.007G163100 | AT1G15780 | MED15A, positive regulation of fatty acid biosynthetic process | LOC_Os08g45080.1 | 8073 |
| 13 | Sobic.002G005600 | AT5G01410 | PDX1, response to lipid hydroperoxide, non-ionic osmotic stress, oxidative stress, salt stress, vitamin B6 biosynthetic process | LOC_Os07g01020.1 | 4270 |
| 14 | Sobic.004G207900 | AT2G43240 | nucleotide-sugar transporter | LOC_Os02g39200.1 | 1995 |
| 15 | Sobic.003G287600 | AT3G16520 | UDP-GLUCOSYL TRANSFERASE 88A1, UGT88A1, UDP-glycosyltransferase activity | LOC_Os01g53350.1 | 9615 |
| 16 | Sobic.002G303300 | AT4G11610 | glycosyl transfer | LOC_Os07g30020.1 | 4095 |
| 17 | Sobic.004G056400 | AT1G16300 | GAPCP-2, chloroplast glucose metabolism | LOC_Os02g07490.1 | 5420 |
| 18 | LOC110433633 | AT1G78800 | glycosyl transfer | | 7036 |
| 19 | Sobic.001G406800 | AT3G47340 | ASN1, GLUTAMINE-DEPENDENT ASPARAGINE SYNTHASE 1, sugar inducible asparagine synthase | LOC_Os03g18130.1 | 7048 |
| 20 | Sobic.001G387200 | AT4G26410 | RHIP1, RGS1-HXK1 INTERACTING PROTEIN, required for certain glucose-regulated gene expression | LOC_Os03g20860.1 | 755 |
| 21 | Sobic.001G047800 | AT4G32470 | Mitochondrial ETC | LOC_Os03g59220.1 | 7903 |
| 22 | Sobic.004G264700 | AT5G13450 | ATP synthase subunit | LOC_Os06g43850.1 | 8240 |
| 23 | Sobic.001G404800 | AT5G18800 | mitochondrial ETC protein | LOC_Os03g18420.1 | 8002 |
| 24 | Sobic.010G032600 | AT1G80230 | mitochondrial ETC | LOC_Os06g05080.1 | 9727 |
| 25 | Sobic.001G134200 | AT1G67350 | photorespiration, mitochondrial ETC | LOC_Os03g48110.1 | 3421 |
| 26 | Sobic.001G354600 | AT4G39680 | chloroplast DNA binding | LOC_Os03g26630.2 | 1852 |
| 27 | Sobic.009G162200 | AT3G55520 | chloroplast protein folding | LOC_Os05g38370.1 | 9304 |
| 28 | Sobic.003G237400 | AT1G80300 | ATP/ADP transporter | LOC_Os01g45910.1 | 6988 |
| 29 | Sobic.009G107200 | AT2G47480 | mitochondrial protein | LOC_Os05g28840.1 | 6232 |
| 30 | Sobic.002G189400 | AT5G23050 | chloropast ligase | LOC_Os09g21230.1 | 9855 |
| 31 | Sobic.001G031300 | AT1G74850 | plastid transcription | LOC_Os03g60910.1 | 2478 |
| 32 | Sobic.010G224700 | AT1G30680 | plastid DNA replication and RNA primer formation | LOC_Os06g45980.1 | 432 |
| 33 | Sobic.001G235700 | AT2G37020 | chloroplast DNA binding | LOC_Os10g30640.1 | 1467 |
| 34 | Sobic.004G319800 | AT5G20720 | chloroplast chaperonin | LOC_Os06g09679.1 | 5162 |
| 35 | Bioenergetics and respiration related-A151 down (up in S264) | | | | |
| 36 | Sobic.006G256600 | AT3G58010 | plastoglobulin | LOC_Os04g57020.1 | 10016 |
| 37 | Sobic.002G356000 | AT1G03103 | lipid transport | LOC_Os06g46870.1 | 7259 |
| 38 | Sobic.009G031400 | AT2G47240 | acyl-CoA synthetase, long-chain and very-long-chain fatty acid, cuticular wax and cutin biosynthesis | LOC_Os05g04170.3 | 2974 |
| 39 | Sobic.003G036200 | AT1G79750 | NADP-ME4, fatty acid biosynthesis | LOC_Os01g09320.1 | 5214 |
| 40 | Sobic.002G184600 | AT5G10100 | TPP1, TREHALOSE-6-PHOSPHATE PHOSPHATASE | LOC_Os08g31630.1 | 8135 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 41 | Sobic.003G049200 | AT5G20080 | FAD/NAD(P)-binding oxidoreductase, response to salt stress | LOC_Os01g07910.1 | 3333 |
| 42 | Sobic.001G459800 | AT5G15490 | UDP-glucose dehydrogenase | LOC_Os12g25690.1 | 5949 |
| 43 | Sobic.001G519700 | AT1G14590 | chloroplast nucleotide-sugar transferase | LOC_Os03g03730.1 | 11444 |
| 44 | Sobic.003G370000 | AT1G44575 | CP22, PS II light harvesting | LOC_Os01g64960.1 | 9064 |
| 45 | Sobic.001G194900 | AT2G43400 | mitochondrial ETC protein | LOC_Os10g37210.1 | 532 |
| 46 | Sobic.001G096800 | AT4G19390 | chloroplast protein | LOC_Os03g52910.1 | 8200 |
| 47 | Sobic.003G258200 | AT4G23850 | fatty acid biosynthesis | LOC_Os01g48910.1 | 208 |
| 48 | Sobic.001G090200 | AT1G55370 | PS ETC | LOC_Os03g53710.1 | 4306 |
| 49 | Sobic.002G230100 | AT4G33580 | chloroplast CO2 regulator | LOC_Os09g28910.1 | 9616 |
| 50 | Sobic.004G068700 | AT5G25140 | CYP71B13, oxygen binding in chloroplast | LOC_Os02g09220.1 | 10519 |
| 51 | Sobic.005G060100 | AT1G35510 | chloroplast glycosyl transferase | LOC_Os12g07540.1 | 2873 |
| 52 | Sobic.003G233000 | AT2G15480 | UDP-GLUCOSYL TRANSFERASE 73B5 | LOC_Os01g45110.1 | 4228 |
| 53 | Sobic.004G207900 | AT2G43240 | nucleotide-sugar transporter | LOC_Os02g39200.1 | 3180 |
| 54 | Sobic.001G123100 | AT3G18080 | carbohydrate metabolic process | LOC_Os03g49610.1 | 8301 |
| 55 | Sobic.007G123500 | AT1G22150 | cloroplast sulfate transporter | LOC_Os08g31410.1 | 3921 |
| 56 | Sobic.003G327900 | AT5G07050 | chloroplast transmembrane transporter activity | LOC_Os01g58910.1 | 11252 |
| 57 | LOC110435380 | AT1G13230 | chloroplast signal transduction | | 8689 |
| 58 | Sobic.003G039700 | AT5G59530 | oxidation reduction | LOC_Os06g14400.1 | 7843 |
| 59 | Sobic.006G001000 | AT5G06900 | CYTOCHROME P450 | LOC_Os04g01140.1 | 11296 |
| 60 | Sobic.006G130300 | AT5G36700 | cloroplast phosphatase | LOC_Os04g41340.1 | 10638 |
| 61 | Sobic.003G292700 | AT1G63640 | kinesin complex | LOC_Os01g54080.1 | 6879 |
| 62 | Sobic.001G082900 | AT1G13970 | mitochondrial protein | LOC_Os03g55180.1 | 8307 |
| 63 | Sobic.007G202800 | AT3G20240 | Mitochondrial substrate carrier | LOC_Os08g40850.1 | 11421 |
| 64 | Sobic.004G206200 | AT4G14605 | mitochondrial transcription termination factor | LOC_Os02g39040.1 | 8613 |
| 65 | Sobic.003G051000 | AT5G62960 | chloroplast membrane | LOC_Os01g07700.1 | 3153 |
| 66 | Sobic.007G162600 | AT1G04620 | chlorophyll metabolic process | LOC_Os04g25400.2 | 4218 |
| 67 | Sobic.010G092600 | AT5G37820 | chloroplast transmembrane transporter activity | LOC_Os06g12310.1 | 3447 |
| 68 | Sobic.008G024200 | AT4G35490 | MITOCHONDRIAL RIBOSOMAL PROTEIN L11 | LOC_Os10g32870.1 | 7805 |
| 69 | Stress and catabolismo related-A151 up | | | | |
| 70 | Sobic.003G024800 | AT1G06390 | SK22 osmotic stress suppression | LOC_Os01g10840.1 | 9199 |
| 71 | Sobic.004G182800 | AT2G02380 | ATGSTZ2, GLUTATHIONE S-TRANSFERASE (CLASS ZETA) 2, toxin catabolism | LOC_Os02g35590.2 | 9577 |
| 72 | Sobic.001G371900 | AT1G08830 | SOD1, salt stress, sucrose stimulus response | LOC_Os03g22810.1 | 8019 |
| 73 | Sobic.006G029800 | AT1G08110 | glyoxalase metabolism | LOC_Os05g22970.1 | 10772 |
| 74 | Sobic.001G010800 | AT3G54900 | GRXCP, GLUTAREDOXIN, glutathione disulfide oxidoreductase activity, cellular stress responses | LOC_Os03g63420.1 | 8803 |

TABLE 4-continued

Chromosomal and functional annotations for differentially expressed genes (DEG) identified by microarrays that compared ovule transcripts of A151 with those of S264 for each stage separately and all stages combined.

| | | | | | |
|---|---|---|---|---|---|
| 75 | Sobic.010G104100 | AT1G10170 | NFXL1, protein ubiquitination, hydrogen peroxide metabolism, regulation of transcription, DNA-templated, response to light intensity, microbial phytotoxin, salt stress, salicylic acid biosynthetic process | LOC_Os06g14190.1 | 9082 |
| 76 | Sobic.003G140700 | AT4G33420 | PRX47, hydrogen peroxide catabolic process, oxidation-reduction process, response to oxidative stress | LOC_Os01g19020.1 | 3404 |
| 77 | Sobic.001G410200 | AT1G07890 | cytosolic APX1 | LOC_Os03g17690.1 | 5593 |
| 78 | Sobic.004G343200 | AT5G43940 | ADH2, glutathione-dependent formaldehyde dehydrogenase, involved in NO detoxification | LOC_Os02g57040.1 | 5701 |
| 79 | Sobic.004G333500 | AT1G67250 | proteasome | LOC_Os02g55640.1 | 11201 |
| 80 | Sobic.010G101500 | AT5G59140 | ubiquitination | LOC_Os11g48030.1 | 10361 |
| 81 | Sobic.004G295800 | AT5G22060 | ATJ2, protein folding, response to heat | LOC_Os02g43930.1 | 5541 |
| 82 | Sobic.001G293300 | AT3G60210 | refolding in chloroplast and mitochondria | LOC_Os10g41710.1 | 4433 |
| 83 | Sobic.010G015900 | AT5G62090 | SLK2, regulation of response to osmotic stress | LOC_Os06g03600.1 | 11590 |
| 84 | Sobic.006G257900 | AT1G64230 | ubiquitination | LOC_Os04g57220.2 | 8030 |
| 85 | Sobic.004G057200 | AT1G33490 | ubiquitination | LOC_Os05g01510.1 | 8835 |
| 86 | Sobic.009G055800 | AT4G34190 | SEP1, STRESS ENHANCED PROTEIN 1, stress enhanced protein that localizes to the thylakoid | LOC_Os10g25570.2 | 3840 |
| 87 | Sobic.001G154100 | AT5G22060 | protein folding, response to heat | LOC_Os03g44620.2 | 9513 |
| 88 | Sobic.003G338400 | AT3G08760 | SIK, osmotic stress-inducible kinase that functions as a negative regulator of osmotic stress signaling in plants | LOC_Os01g60700.1 | 11194 |
| 89 | Sobic.001G520100 | AT1G11310 | defense response to fungus | LOC_Os03g03700.1 | 4646 |
| 90 | Sobic.010G047400 | AT5G53330 | ubiquitination | LOC_Os06g06530.1 | 8017 |
| 91 | Sobic.005G208900 | AT2G31510 | ubiquitination | LOC_Os09g38630.1 | 231 |
| 92 | Sobic.004G006900 | AT3G06240 | F-box protein | LOC_Os10g41650.1 | 10587 |
| 93 | Sobic.010G222400 | AT3G06190 | BPM2, cellular response to salt stress, cellular response to water deprivation, protein ubiquitination, response to osmotic stress | LOC_Os06g14060.1 | 4515 |
| 94 | Sobic.001G100900 | AT5G27660 | misfolded protein degradation | LOC_Os12g04750.1 | 6312 |
| 95 | Sobic.010G001600 | AT5G54080 | tyrosine catabolism | LOC_Os06g01360.1 | 4437 |
| 96 | Sobic.004G177700 | AT1G33970 | defense response protein | LOC_Os02g35130.2 | 4786 |
| 97 | Sobic.008G144500 | AT1G27730 | SALT TOLERANCE ZINC FINGER, STZ, response to cold, high light intensity, oxidative stress, salt stress, water deprivation | LOC_Os12g39400.1 | 10517 |
| 98 | Sobic.006G220900 | AT1G62040 | ubiquitin protein | LOC_Os08g09240.1 | 6770 |
| 99 | Sobic.002G243200 | AT5G56000 | HSP90.4 | LOC_Os09g30412.1 | 8370 |
| 100 | Sobic.004G255000 | AT5G10770 | protease | LOC_Os02g48870.1 | 1641 |
| 101 | Sobic.001G108900 | AT1G63850 | ubiquitination | LOC_Os03g51380.1 | 11402 |
| 102 | Sobic.007G029700 | AT1G30440 | ubiquitination | LOC_Os08g03650.1 | 3037 |
| 103 | Sobic.003G368000 | AT1G25280 | ubiquitination | LOC_Os01g64700.2 | 10215 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 104 | Sobic.003G247000 | AT1G11910 | APA1, protein catabolic process, response to cytokinin and salt stress | LOC_Os01g47410.1 | 5603 |
| 105 | Sobic.010G181600 | AT1G52730 | ubiquitination | LOC_Os06g39760.1 | 7570 |
| 106 | Sobic.004G224900 | AT1G16470 | ubiquitination | LOC_Os03g26970.1 | 7842 |
| 107 | Sobic.004G350400 | AT5G55590 | pectin catabolic process | LOC_Os11g45730.1 | 7584 |
| 108 | Sobic.006G252200 | AT5G05780 | ubiquitination | LOC_Os04g56646.1 | 4572 |
| 109 | Stress and catabolismo related-A151 down | | | | |
| 110 | Sobic.004G171400 | AT3G62760 | GSTF13, glutathione transferase, toxin catabolism | LOC_Os01g27360.1 | 1730 |
| 111 | Sobic.010G128400 | AT3G21770 | Peroxidase superfamily protein, hydrogen peroxide catabolic process, response to oxidative stress | LOC_Os06g29470.1 | 11029 |
| 112 | Sobic.001G483100 | AT5G35590 | ubiquitination | LOC_Os03g08280.1 | 5572 |
| 113 | Sobic.005G005500 | AT5G01650 | chloroplast inflamitory response | LOC_Os12g01680.1 | 7751 |
| 114 | Sobic.004G111100 | AT5G45910 | lipid catabolism | LOC_Os02g15230.1 | 5889 |
| 115 | Sobic.006G161300 | AT1G62710 | protease | LOC_Os04g45470.1 | 3467 |
| 116 | Sobic.003G317700 | AT5G54250 | hypersensitive response gene | LOC_Os01g57370.1 | 927 |
| 117 | Sobic.001G140300 | AT1G58370 | xylanase | LOC_Os03g47010.1 | 10646 |
| 118 | Sobic.004G155600 | AT5G53150 | protein folding, heat shock | LOC_Os02g30620.3 | 2754 |
| 119 | Sobic.002G031100 | AT3G07040 | HR defense response | LOC_Os07g27370.1 | 8655 |
| 120 | Sobic.007G169700 | AT2G36310 | purine and pyrimidine catabolism | LOC_Os08g44370.1 | 7696 |
| 121 | Sobic.007G088300 | AT5G06760 | LEA4-5, response to osmotic stress, response to water deprivation | LOC_Os08g23870.1 | 8733 |
| 122 | Sobic.008G004600 | AT5G06460 | UBA 2, ubiquitination, cellular response to DNA damage stimulus | LOC_Os11g01510.3 | 6482 |
| 123 | Sobic.003G221400 | AT1G80410 | EMB2753, response to water deprivation | LOC_Os01g43030.1 | 396 |
| 124 | Sobic.001G306000 | AT2G45910 | protein phosphorylation, protein ubiquitination | LOC_Os10g40100.2 | 6309 |
| 125 | Sobic.002G345700 | AT2G41790 | peroxisome | LOC_Os07g38270.1 | 5725 |
| 126 | Sobic.002G157300 | AT5G55260 | PPX2, protein phosphatase | LOC_Os09g11230.1 | 10019 |
| 127 | Sobic.006G260300 | AT5G43060 | protease | LOC_Os04g57440.1 | 5072 |
| 128 | Sobic.005G170100 | AT3G03530 | NPC4, NON-SPECIFIC PHOSPHOLIPASE C4, induced by phosphate starvation to increase phosphate supplies | LOC_Os11g38050.1 | 6708 |
| 129 | Sobic.005G167400 | AT3G07040 | HR defense response | LOC_Os08g42670.2 | 8186 |
| 130 | Sobic.008G105500 | AT2G03530 | uracil salvage | LOC_Os12g31860.3 | 1463 |
| 131 | Sobic.001G452100 | AT2G33380 | CLO3, calcium binding protein induced by ABA, salt, desiccation | LOC_Os03g12230.1 | 9693 |
| 132 | Sobic.001G441100 | AT1G66160 | ubiquitination | LOC_Os03g13740.1 | 1771 |
| 133 | Sobic.010G041800 | AT2G30920 | ubiquinone biosynthetic process | LOC_Os06g05900.1 | 6836 |
| 134 | Sobic.003G192400 | AT1G70250 | Protease inhibitor | LOC_Os01g02810.1 | 6050 |
| 135 | Sobic.001G317000 | AT1G10370 | GSTU17, EARLY-RESPONSIVE TO DEHYDRATION 9 (ERD9, suppresses drought and salt stress signal transduction pathways | LOC_Os10g38740.1 | 936 |
| 136 | Sobic.010G231300 | AT1G05200 | GLR3.4, calcium-mediated signaling, cellular calcium ion homeostasis | LOC_Os06g46670.2 | 90 |
| 137 | Sobic.004G148600 | AT3G04710 | TPR10, may interact with Hsp90/Hsp70 as co-chaperones | LOC_Os02g29140.1 | 258 |
| 138 | Hormone and signaling related-A151 up | | | | |
| 139 | Sobic.004G202500 | AT4G24740 | AFC2 degrades SnRK1 (TOR activation) | LOC_Os12g27520.1 | 3685 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 140 | Sobic.002G068900 | AT3G46060 | ARA-3, RAB GTPASE HOMOLOG 8A, ethylene-activated signal transduction | LOC_Os07g09680.1 | 3515 |
| 141 | Sobic.008G181300 | AT4G20880 | ERT2, ethylene regulated nuclear protein | LOC_Os12g43350.1 | 245 |
| 142 | Sobic.003G389000 | AT5G36890 | BETA GLUCOSIDASE 42, BGLU42, cellular response to ethylene stimulus, cellular response to iron ion, cellular response to nitric oxide | LOC_Os01g67220.2 | 5266 |
| 143 | Sobic.010G186200 | AT2G25490 | EBF1, EIN3-BINDING F BOX PROTEIN 1, negative regulation of ethylene-activated signaling | LOC_Os06g40360.1 | 152 |
| 144 | Sobic.005G084100 | AT5G48380 | BIR (BAK1-INTERACTING RECEPTOR-LIKE KINASE 1) negatively regulates multiple plant resistance signaling pathways | LOC_Os11g14420.1 | 11998 |
| 145 | Sobic.001G079200 | AT5G66850 | MAPKKK5 stress activated signaling | LOC_Os03g55560.1 | 6504 |
| 146 | Sobic.005G106600 | AT5G19010 | MPK16 signal transduction | LOC_Os05g05160.1 | 1540 |
| 147 | Sobic.004G162000 | AT2G16600 | protein refolding, signal transduction | LOC_Os02g02890.1 | 5711 |
| 148 | Sobic.003G083200 | AT5G57580 | calmodulin binding, regulation of salicylic acid biosynthetic process | LOC_Os01g04280.1 | 6361 |
| 149 | Sobic.010G089700 | AT1G78080 | RAP2.4, cellular response to salt stress, cytokinin-activated signaling pathway, ethylene-activated signaling pathway, red or far-red light signaling pathway | LOC_Os06g11860.1 | 10893 |
| 150 | Sobic.010G005600 | AT5G63060 | phosphatidylinositol transfer family protein | LOC_Os02g21630.1 | 10385 |
| 151 | Sobic.008G163300 | AT4G14350 | intracellular signal transduction | LOC_Os12g19290.1 | 2600 |
| 152 | Sobic.004G317000 | AT3G13960 | GRF5 GROWTH-REGULATING FACTOR 5 transcription activation | LOC_Os02g53690.1 | 6115 |
| 153 | Sobic.003G430400 | AT1G76640 | calmodulin like 39 | LOC_Os01g72530.1 | 8848 |
| 154 | Sobic.003G279800 | AT4G17520 | response to cytokinin | LOC_Os01g52390.1 | 5388 |
| 155 | Sobic.007G076300 | AT1G64520 | RPN12A, cytokinin-activated signaling pathway, protein catabolic process, response to heat, misfolded protein, | LOC_Os07g25420.1 | 5456 |
| 156 | Sobic.002G263100 | AT3G07480 | 2Fe-2S, ferredoxin, response to cytokinin | LOC_Os09g33950.1 | 5924 |
| 157 | Sobic.001G424400 | AT1G07430 | PP2C GENE 2 | LOC_Os03g16170.1 | 5315 |
| 158 | Sobic.006G244800 | AT5G20900 | JAZ12, regulation of JA signaling | LOC_Os04g55520.2 | 3916 |
| 159 | Sobic.007G139600 | AT5G35180 | signal transduction protein, disease resistance | LOC_Os08g34060.1 | 9068 |
| 160 | Sobic.010G210600 | AT1G80920 | TOC12, protein folding, response to light | LOC_Os06g44160.1 | 10370 |
| 161 | Sobic.003G021500 | AT1G53210 | NCL, Ca homeostasis | LOC_Os01g11414.1 | 5324 |
| 162 | Hormone and signaling related-A151 down | | | | |
| 163 | Sobic.007G105100 | AT5G40440 | ATMKK3, ABA-activated signaling | LOC_Os06g27890.2 | 9812 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 164 | Sobic.002G418500 | AT2G46400 | WRKY46 TF feedforward inhibition of osmotic stress-dependent LR inhibition via reg. of ABA signaling, BR mediated signaling pathway | LOC_Os07g48260.1 | 8624 |
| 165 | Sobic.003G253600 | AT3G58640 | Mitogen activated protein kinase kinase kinase-like protein | LOC_Os01g48330.1 | 10354 |
| 166 | Sobic.006G187900 | AT1G01480 | ACC2 ethylene biosynthesis | LOC_Os04g48850.1 | 4405 |
| 167 | Sobic.008G157700 | AT5G25610 | RD22, response to abscisic acid, response to desiccation, response to salt stress mediated by ABA | LOC_Os08g38810.1 | 251 |
| 168 | Sobic.001G429700 | AT5G22090 | EAR1, ENHANCER OF ABA CO-RECEPTOR 1 negative regulator of ABA signaling that enhances the activity of all six clade A PP2Cs | LOC_Os03g15530.1 | 672 |
| 169 | Sobic.002G393100 | AT5G50600 | HSD2, steroid biosynthetic process | LOC_Os12g27830.1 | 2101 |
| 170 | Sobic.004G209900 | AT2G31800 | signal transduction | LOC_Os02g39560.1 | 6923 |
| 171 | Sobic.002G181800 | AT1G72970 | HOTHEAD EMBRYO SAC DEVELOPMENT ARREST 17 cell cell signaling, ES formation | LOC_Os09g19930.1 | 1420 |
| 172 | Sobic.004G132900 | AT3G49260 | calmodulin binding | LOC_Os02g19640.1 | 10513 |
| 173 | Sobic.009G237600 | AT2G46270 | G-BOX BINDING FACTOR 3, GBF3, ABA-induced transcription regulator | LOC_Os05g49420.1 | 763 |
| 174 | Sobic.001G449700 | AT5G42650 | JA biosynthesis | LOC_Os03g12500.1 | 7876 |
| 175 | Sobic.001G125700 | AT1G55020 | JA biosynthesis | LOC_Os03g49380.1 | 603 |
| 176 | Sobic.003G037000 | AT4G33080 | signal transduction kinase | LOC_Os01g09200.1 | 9543 |
| 177 | Sobic.009G116500 | AT2G23610 | JA metabolism | LOC_Os05g30760.1 | 243 |
| 178 | Sobic.004G038300 | AT2G07050 | CAS1, BR biosynthesis | LOC_Os11g35710.1 | 5067 |
| 179 | Sobic.009G005700 | AT5G42140 | RCC1, regulator of chromosome condensation, signal transduction | LOC_Os01g73410.1 | 3006 |
| 180 | Sobic.009G104600 | AT3G51810 | AT3, ARABIDOPSIS THALIANA LATE EMBRYOGENESIS ABUNDANT 1, ABA inducible | LOC_Os05g28210.1 | 820 |
| 181 | Sobic.002G265800 | AT2G43820 | salicylic acid metabolism | LOC_Os09g34250.1 | 11446 |
| 182 | Sobic.004G349300 | AT4G00330 | CRCK2, calmodulin binding receptor-like cytoplasmic kinase, chloroplast and cytoplasm | LOC_Os02g57560.1 | 4828 |
| 183 | Sobic.001G331200 | AT4G37390 | negative component of auxin signaling | LOC_Os07g40290.1 | 6209 |
| 184 | Sobic.009G229200 | AT2G22670 | IAA8, IAA inducible transcriptional repressor | LOC_Os05g48590.1 | 3163 |
| 185 | Sobic.008G039800 | AT5G22400 | Rho GTPase activating protein, signal transduction | LOC_Os11g05540.1 | 6301 |
| 186 | Gene expression related-A151 up | | | | |
| 187 | Sobic.004G211400 | AT4G31580 | RSZ22 mRNA splicing regulator | LOC_Os02g39720.2 | 6275 |
| 188 | Sobic.004G155700 | AT2G43810 | LSM6B, mRNA splicing, spliceosome | LOC_Os02g30624.2 | 9682 |
| 189 | Sobic.004G211400 | AT4G31580 | RSZ22 duplicate array probe, splicing regulator | LOC_Os02g39720.2 | 760 |
| 190 | Sobic.003G038100 | AT1G25350 | OVA9 glutaminyl-tRNA translation | LOC_Os01g09000.1 | 9528 |
| 191 | Sobic.004G211100 | AT4G32720 | LA1 ribsome biogenesis & embryogenesis | LOC_Os02g39700.1 | 6828 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 192 | Sobic.001G041200 | AT2G38730 | protein folding | LOC_Os03g59700.1 | 8929 |
| 193 | Sobic.001G369000 | AT4G23460 | protein vesicle transport | LOC_Os03g23950.1 | 5691 |
| 194 | Sobic.002G046100 | AT2G36320 | zinc finger protein | LOC_Os07g07350.3 | 8838 |
| 195 | Sobic.001G122400 | AT5G14320 | EMB3137 ribosomal protein | LOC_Os03g49710.1 | 10986 |
| 196 | Sobic.004G045400 | AT3G10950 | ribosome protein | LOC_Os05g48320.1 | 4696 |
| 197 | Sobic.003G322400 | AT4G39200 | ribosomal protein | LOC_Os08g44480.1 | 2809 |
| 198 | Sobic.004G339200 | AT5G43320 | protein phosphorylation | LOC_Os02g56560.1 | 11542 |
| 199 | Sobic.001G147100 | AT5G27990 | ribosome protein | LOC_Os08g39820.1 | 235 |
| 200 | Sobic.006G098500 | AT1G47500 | RNA binding protein | LOC_Os04g37690.1 | 5851 |
| 201 | Sobic.004G271400 | AT2G37190 | ribosome large subunit protein | LOC_Os02g47140.2 | 8911 |
| 202 | Sobic.002G081600 | AT2G32060 | ribosome protein | LOC_Os07g05580.1 | 10781 |
| 203 | Sobic.002G355300 | AT3G07810 | mRNA binding | LOC_Os07g39560.3 | 2077 |
| 204 | Sobic.010G005300 | AT1G33140 | ribosome protein | LOC_Os09g31180.1 | 6512 |
| 205 | Sobic.001G105100 | AT5G55940 | ER protein | LOC_Os04g20230.1 | 10155 |
| 206 | Sobic.001G281900 | AT5G17060 | vesicle-mediated transport | LOC_Os10g42940.1 | 7360 |
| 207 | Sobic.008G098800 | AT5G10360 | ribosomal small subunit protein | LOC_Os03g27260.1 | 9770 |
| 208 | Sobic.001G541100 | AT4G30600 | ER targeting protein | LOC_Os08g37444.3 | 5382 |
| 209 | Sobic.006G138100 | AT3G48930 | ribosome protein | LOC_Os04g42380.1 | 1943 |
| 210 | Sobic.010G173100 | AT1G09640 | translation elongation | LOC_Os06g37440.1 | 6002 |
| 211 | Sobic.009G182600 | AT1G65440 | transcriptional regulator | LOC_Os05g41510.1 | 9546 |
| 212 | Sobic.004G323700 | AT4G32600 | zinc finger protein | LOC_Os02g54624.1 | 2806 |
| 213 | Sobic.006G160200 | AT2G45140 | ER protein | LOC_Os08g06020.1 | 2788 |
| 214 | Sobic.003G332401 | AT3G62290 | vesicle-mediated transport | LOC_Os05g41060.1 | 10064 |
| 215 | Sobic.010G206200 | AT3G52580 | ribosomal protein | LOC_Os02g06700.2 | 9585 |
| 216 | Sobic.004G145801 | AT3G61110 | ribosomal protein | LOC_Os04g27860.1 | 1876 |
| 217 | Sobic.008G128600 | AT4G02080 | ER vesicle mediated transport | LOC_Os12g37360.1 | 10021 |
| 218 | Sobic.006G252100 | AT5G03500 | transcriptional regulator | LOC_Os04g56640.1 | 2097 |
| 219 | Sobic.010G065400 | AT5G58020 | RTF2, regulation of pre-mRNA splicing | LOC_Os06g08490.1 | 4294 |
| 220 | Sobic.003G109600 | AT2G37270 | RPS5B, ribosomal protein, response to cytokinin | LOC_Os11g29190.2 | 8863 |
| 221 | Sobic.004G185600 | AT1G68140 | zinc finger protein | LOC_Os02g35840.1 | 4556 |
| 222 | Sobic.006G147000 | AT2G20450 | ribosomal protein | LOC_Os02g40880.1 | 6262 |
| 223 | Sobic.001G016500 | AT1G27400 | ribosomal protein | LOC_Os09g08430.1 | 6322 |
| 224 | Sobic.001G011000 | AT4G02930 | translation elongation | LOC_Os03g63410.1 | 3702 |
| 225 | Sobic.001G386700 | AT3G04030 | MYR2, homeodomain-like TF protein | LOC_Os03g20900.1 | 10677 |
| 226 | Sobic.003G422900 | AT4G36960 | mRNA binding, splice variant | LOC_Os01g71770.1 | 3469 |
| 227 | Sobic.001G447300 | AT4G19210 | ribosomal subunit export from nucleas | LOC_Os11g34350.1 | 8970 |
| 228 | Sobic.010G251100 | AT3G13920 | EIF4A1, translation initiation factor | LOC_Os02g05330.1 | 10502 |
| 229 | Sobic.007G067700 | AT1G11650 | mRNA binding | LOC_Os04g53440.2 | 6450 |
| 230 | Sobic.007G188900 | AT1G52630 | protein glycosylation | LOC_Os08g42550.6 | 9490 |
| 231 | Sobic.004G040900 | AT1G36730 | translation initiation factor | LOC_Os06g48350.1 | 9942 |
| 232 | Gene expression related-A151 down | | | | |
| 233 | Sobic.003G439900 | AT1G04270 | ribosome protein | LOC_Os07g08660.1 | 3892 |
| 234 | Sobic.008G108601 | AT3G43980 | ribosomal protein | LOC_Os11g41610.1 | 6064 |
| 235 | Sobic.007G102800 | AT4G22320 | golgin protein | LOC_Os08g25080.1 | 7392 |
| 236 | Sobic.009G072200 | AT5G56840 | myb-like transcription factor | LOC_Os05g10690.1 | 8879 |
| 237 | Sobic.010G269600 | AT4G35785 | RNA-binding (RRM/RBD/RNP motifs) family protein, mRNA splicing | LOC_Os06g50890.1 | 6642 |
| 238 | Sobic.002G389600 | AT3G04930 | transcriptional regulator | LOC_Os03g25430.1 | 7401 |
| 239 | Sobic.001G175300 | AT2G36620 | ribosomal protein | LOC_Os05g40820.2 | 9569 |
| 240 | Sobic.009G244300 | AT1G75250 | RAD-LIKE 6, TF | LOC_Os05g50340.1 | 1289 |
| 241 | Sobic.001G008500 | AT1G61010 | mRNA processing and splicing | LOC_Os03g63590.1 | 1574 |
| 242 | Sobic.007G011600 | AT4G10070 | KH domain protein | LOC_Os08g01930.1 | 388 |
| 243 | Sobic.006G126900 | AT1G10390 | nucleoporin | LOC_Os12g06890.1 | 3412 |
| 244 | Sobic.009G135600 | AT2G26920 | translation elongation | LOC_Os05g33850.1 | 1310 |
| 245 | sRNA regulation of gene expression related-A151 up | | | | |

TABLE 4-continued

Chromosomal and functional anotations for differentially expressed genes (DEG) identified by microarrays
that compared ovule transcripts of A151 with those of S264 for each stage separately and all stages combined.

| | | | | | |
|---|---|---|---|---|---|
| 246 | Sobic.002G041400 | AT5G10010 | HEAT INTOLERANT 4, HIT4, negative regulation of gene silencing | LOC_Os04g56590.1 | 11309 |
| 247 | Sobic.001G054800 | AT2G30620 | H1.2, HISTONE 1.2, negative regulation of chromatin silencing | LOC_Os07g08710.1 | 5961 |
| 248 | Sobic.009G216700 | AT5G14530 | ANTHESIS PROMOTING FACTOR 1 (APRF1) H3-K4 trimethylation | LOC_Os05g46570.1 | 8501 |
| 249 | Sobic.001G289800 | AT3G48050 | SUO, miRNA inhibition of translation | LOC_Os02g50840.2 | 11578 |
| 250 | Sobic.001G536400 | AT5G09860 | THO1, RNA splicing, ethylene-activated signaling, gene silencing by RNA, production of ta-siRNAs involved in RNA interference | LOC_Os03g01970.1 | 11830 |
| 251 | Sobic.001G094500 | AT3G54560 | HTA11, HISTONE H2A 11, histone methylation in response to developmental and environmental ques | LOC_Os03g53190.1 | 3887 |
| 252 | sRNA regulation of gene expression related-A151 down | | | | |
| 253 | Sobic.003G350100 | AT3G45980 | H2B, HISTONE H2B | LOC_Os08g38300.1 | 10923 |
| 254 | Sobic.003G347900 | AT3G53730 | Histone superfamily protein | LOC_Os01g61920.1 | 9255 |
| 255 | Sobic.001G522600 | AT2G19260 | RING/FYVE/PHD zinc finger superfamily protein, histone acetyltransferase complex | LOC_Os04g34720.2 | 9393 |
| 256 | Sobic.003G330900 | AT5G04940 | SUVH1, histone lysine methylation, epigenetic regulation | LOC_Os01g59620.1 | 2956 |
| 257 | Sobic.003G104000 | AT5G20170 | MED17, production of miRNAs involved in gene silencing | LOC_Os12g44140.1 | 316 |
| 258 | Growth and development related-A151 up | | | | |
| 259 | Sobic.004G093700 | AT2G19580 | aging related | LOC_Os02g12750.1 | 4538 |
| 260 | Sobic.004G197600 | AT4G26690 | cell wall related | LOC_Os02g37590.1 | 6592 |
| 261 | Sobic.010G172400 | AT3G13772 | cell adhesion | LOC_Os06g37160.1 | 2174 |
| 262 | Sobic.006G152600 | AT1G65730 | oligopeptide transport | LOC_Os04g44320.1 | 2506 |
| 263 | Sobic.002G148100 | AT1G55840 | transporter activity | LOC_Os09g08390.1 | 7599 |
| 264 | Sobic.004G025900 | AT1G32170 | cell wall biogenesis | LOC_Os02g03550.1 | 7850 |
| 265 | Sobic.003G049600 | AT4G32410 | cell wall organization | LOC_Os05g08370.1 | 3830 |
| 266 | Sobic.001G046400 | AT3G08030 | cell wall protein | LOC_Os03g59300.1 | 3452 |
| 267 | Sobic.009G259200 | AT4G23900 | nucleoside diphosphate phosphorylation | LOC_Os05g51700.1 | 6127 |
| 268 | Sobic.004G187900 | AT5G64300 | riboflavin biosynthesis | LOC_Os02g36340.1 | 6342 |
| 269 | Sobic.010G266300 | AT2G21160 | translocon membrane protein | LOC_Os06g50154.1 | 7594 |
| 270 | Sobic.002G113800 | AT1G23820 | polyamine biosynthesis | LOC_Os07g22600.1 | 7750 |
| 271 | Sobic.008G160400 | AT4G02710 | actin filiment binding | LOC_Os12g41200.1 | 10186 |
| 272 | Sobic.004G190600 | AT1G18800 | NRP2, NAP1-RELATED PROTEIN 2, cell differentiation, cell proliferation, homologous recombination, lateral root formation, nucleosome assembly | LOC_Os02g36710.1 | 7569 |
| 273 | Sobic.001G086600 | AT1G69060 | vacuolar membrane | LOC_Os03g54150.1 | 3270 |
| 274 | Sobic.010G097600 | AT1G10200 | cytoskeleton | LOC_Os06g13030.1 | 2899 |
| 275 | Sobic.003G250700 | AT5G03170 | cell wall biogenesis | LOC_Os01g47780.1 | 5229 |
| 276 | Sobic.004G350300 | AT5G04410 | NAC2 flavinoid biosynthesis | LOC_Os02g57650.1 | 7939 |
| 277 | Sobic.006G050600 | AT1G27990 | transmembrane protein | LOC_Os04g31710.1 | 5283 |
| 278 | Sobic.001G398500 | AT4G02170 | fiber protein | LOC_Os03g19070.1 | 2371 |
| 279 | Sobic.003G334700 | AT2G35630 | cytoskeleton | LOC_Os01g60050.1 | 11517 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 280 | Sobic.002G201900 | AT4G02050 | STP7, SUGAR TRANSPORTER PROTEIN 7, transports arabinose and xylose | LOC_Os09g24924.1 | 7999 |
| 281 | Sobic.001G119900 | AT1G28180 | helicase | LOC_Os03g50090.3 | 1835 |
| 282 | Sobic.005G187500 | AT4G00850 | GIF3, GRF1-INTERACTING FACTOR 3, cell proliferation | LOC_Os11g40100.3 | 9999 |
| 283 | Sobic.004G243800 | AT5G62580 | microtubule protein | LOC_Os02g50640.1 | 3012 |
| 284 | Sobic.002G175400 | AT2G46210 | sphingolipid biosynthetic process | LOC_Os09g16920.1 | 4647 |
| 285 | Sobic.007G019300 | AT3G55480 | vacuole transport | LOC_Os01g74180.1 | 2962 |
| 286 | Growth and development related-A151 down | | | | |
| 287 | Sobic.009G132400 | AT5G51600 | syncytium formation | LOC_Os01g49200.1 | 7441 |
| 288 | Sobic.006G221300 | AT1G50660 | cytoskeleton | LOC_Os04g53350.1 | 4271 |
| 289 | Sobic.001G195600 | AT4G00690 | AA metabolism | LOC_Os08g20480.1 | 5265 |
| 290 | Sobic.008G034400 | AT2G28600 | helicase | LOC_Os12g05230.1 | 10183 |
| 291 | Sobic.007G011300 | AT1G31480 | SGR2, SHOOT GRAVITROPISM 2, amyloplast organization, gravity sensing | LOC_Os08g01920.1 | 2657 |
| 292 | Sobic.004G351200 | AT4G00430 | water transport | LOC_Os02g57720.1 | 945 |
| 293 | Sobic.004G215700 | AT3G63130 | mitosis | LOC_Os05g46560.2 | 2686 |
| 294 | Sobic.003G228900 | AT3G14680 | membrane protein | LOC_Os01g43844.1 | 6941 |
| 295 | Sobic.010G108600 | AT1G68530 | very long chain fatty acid biosynthesis | LOC_Os02g49920.1 | 11886 |
| 296 | Sobic.003G371100 | AT1G22540 | membrane component | LOC_Os01g65110.1 | 3385 |
| 297 | Sobic.003G445300 | AT4G01470 | water channel | LOC_Os01g74450.1 | 11168 |
| 298 | Sobic.001G091300 | AT5G47420 | membrane function | LOC_Os03g53600.1 | 8921 |
| 299 | Sobic.010G248200 | AT2G24550 | centromere protein | LOC_Os09g32330.1 | 1847 |
| 300 | LOC110433098 | AT3G53320 | mitotic spindle microtubule | | 9038 |
| 301 | Sobic.004G134600 | AT2G24450 | membrane protein | LOC_Os02g26290.1 | 7303 |
| 302 | Sobic.002G220600 | AT2G30070 | potassium transporter | LOC_Os09g27580.3 | 11987 |
| 303 | LOC8078215 | AT5G12010 | nuclease | | 11116 |
| 304 | Sobic.001G363700 | AT5G07990 | flavenoid biosynthesis | LOC_Os09g26960.1 | 6058 |
| 305 | Sobic.001G497700 | AT3G22490 | RAB28, ion cell balance during late embryogenesis | LOC_Os03g06360.1 | 4862 |
| 306 | Sobic.001G088100 | AT4G16420 | ADA2B, controls switch from cell proliferation to cell differentiation | LOC_Os03g53960.1 | 10379 |
| 307 | Sobic.003G334700 | AT2G35630 | cytoskeleton | LOC_Os01g60050.1 | 3060 |
| 308 | Sobic.001G281600 | AT5G63610 | CDKE;1, CYCLIN-DEPENDENT KINASE E-1, cell division | LOC_Os10g42950.1 | 8016 |
| 309 | Sobic.002G143300 | AT4G31830 | transmembrane protein | LOC_Os09g04100.1 | 4557 |
| 310 | Sobic.003G173800 | AT2G15450 | pectin metabolism | LOC_Os01g33300.1 | 2383 |
| 311 | Sobic.010G134400 | AT3G51520 | triglyceride biosynthetic process | LOC_Os06g22080.1 | 3550 |
| 312 | Sobic.003G427600 | AT2G41740 | cytoskeleton | LOC_Os03g24220.1 | 1215 |
| 313 | Sobic.003G403500 | AT4G12840 | membrane component | LOC_Os01g69050.1 | 5823 |
| 314 | Other-A151 up | | | | |
| 315 | Sobic.010G094301 | | | | 9768 |
| 316 | Sobic.003G048500 | AT5G20060 | hydrolase | LOC_Os01g07960.2 | 3963 |
| 317 | Sobic.004G208100 | | | | 8182 |
| 318 | Sobic.005G112632 | | | | 188 |
| 319 | LOC110435809 | | | | 4312 |
| 320 | LOC110431211 | AT5G39710 | Tetratricopeptide repeat protein | | 9700 |
| 321 | Sobic.002G254100 | | | | 7470 |
| 322 | Sobic.004G136500 | | | | 5377 |
| 323 | Sobic.004G331800 | | | | 1483 |
| 324 | Sobic.004G007300 | AT5G17160 | aspartic acid rich protein | LOC_Os02g47130.1 | 7510 |
| 325 | Sobic.001G541400 | | | | 6445 |
| 326 | Sobic.001G442200 | AT1G14700 | dephosphorylation | LOC_Os03g13540.1 | 5805 |
| 327 | LOC110431017 | | | | 7532 |
| 328 | MultiHit5375 | | | | 5375 |
| 329 | Sobic.003G029200 | AT1G27480 | hydrolase | LOC_Os10g08026.1 | 4664 |
| 330 | Sobic.001G381900 | AT2G38570 | hypothetical protein | LOC_Os03g21630.1 | 4308 |
| 331 | MultiHit7742 | | | | 7742 |
| 332 | Sobic.003G140900 | | | | 6244 |
| 333 | Sobic.001G121100 | | | | 8308 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 334 | Sobic.001G143300 | AT4G19640 | intracellular protein transport | LOC_Os12g43550.2 | 5267 |
| 335 | Sobic.002G364800 | AT1G26520 | cobalamin synthesis | LOC_Os07g40790.2 | 5796 |
| 336 | Sobic.003G088400 | | | | 9321 |
| 337 | Sobic.001G154400 | AT3G44150 | Expp1 protein | LOC_Os03g44560.1 | 6558 |
| 338 | MultiHit5916 | | | | 5916 |
| 339 | MultiHit3601 | | | | 3601 |
| 340 | Sobic.003G113500 | | | | 6284 |
| 341 | Sobic.001G087700 | AT4G16370 | iron transporter | LOC_Os03g54000.1 | 3749 |
| 342 | LOC8081614 | AT2G23090 | uncharacterized protein | | 9526 |
| 343 | LOC110429578 | | | | 7886 |
| 344 | Sobic.005G228700 | AT5G02380 | METALLOTHIONEIN 2B | LOC_Os03g17870.1 | 9792 |
| 345 | Sobic.004G134900 | | | | 2016 |
| 346 | Sobic.001G012200 | | | | 8090 |
| 347 | Sobic.001G193100 | AT5G41950 | Tetratricopeptide repeat protein | LOC_Os10g37430.1 | 7540 |
| 348 | Other-A151 down | | | | |
| 349 | Sobic.002G200900 | AT1G74640 | CP hydrolase | LOC_Os09g24710.1 | 4127 |
| 350 | Sobic.001G455600 | AT1G55880 | CP hydrolase | LOC_Os03g11660.1 | 2447 |
| 351 | Sobic.008G026200 | | | | 10705 |
| 352 | Sobic.009G003300 | | | | 1767 |
| 353 | Sobic.004G105500 | AT3G58110 | hypothetical protein | LOC_Os06g34710.1 | 11648 |
| 354 | Sobic.004G324800 | | | | 1225 |
| 355 | Sobic.002G191800 | | | | 9559 |
| 356 | Sobic.002G171300 | | | | 3991 |
| 357 | Sobic.001G298700 | | | | 9405 |
| 358 | Sobic.006G206200 | | | | 10943 |
| 359 | Sobic.010G016500 | | | | 9888 |
| 360 | Sobic.006G052800 | AT5G65750 | TCA protein | LOC_Os04g32020.1 | 928 |
| 361 | Sobic.001G536800 | | | | 10343 |
| 362 | Sobic.001G146301 | | | | 284 |
| 363 | Sobic.002G151300 | | | | 6112 |
| 364 | Sobic.001G098600 | AT5G05250 | hypothetical protein | LOC_Os03g52680.1 | 6308 |
| 365 | Sobic.001G072700 | AT1G19400 | dehydrogenase | LOC_Os03g56420.1 | 1341 |
| 366 | MultiHit113 | | | | 113 |
| 367 | Sobic.001G204700 | AT3G63390 | hypothetical protein | LOC_Os11g40200.1 | 11182 |
| 368 | Sobic.001G051800 | | | | 3539 |
| 369 | Sobic.006G122500 | AT3G01660 | methyltransferase activity | LOC_Os04g40530.1 | 3874 |
| 370 | Sobic.009G224400 | | | | 9599 |
| 371 | Sobic.005G021200 | AT5G50350 | hypothetical protein | LOC_Os11g03550.1 | 4728 |
| 372 | Sobic.005G084300 | | | | 8998 |
| 373 | Sobic.004G162200 | AT5G47900 | acyl transferase | LOC_Os02g32504.1 | 8773 |
| 374 | Sobic.003G018000 | | | | 7164 |
| 375 | Sobic.006G258800 | AT4G22260 | carotenoid biosynthesis in chloroplasts | LOC_Os04g57320.1 | 4366 |
| 376 | Sobic.001G103600 | AT5G43400 | uncharacterized protein | LOC_Os09g32360.1 | 7415 |
| 377 | Sobic.009G252100 | | | | 3089 |
| 378 | Sobic.004G019400 | AT1G61680 | terpene synthase | LOC_Os02g02930.1 | 9780 |
| 379 | Sobic.002G330800 | | | | 1389 |
| 380 | MultiHit10711 | | | | 10711 |
| 381 | Sobic.005G143200 | | | | 1849 |
| 382 | Sobic.006G219500 | AT1G30320 | remorin protein | LOC_Os04g52920.1 | 11620 |
| 383 | Sobic.002G365550 | AT5G09530 | proline rich protein | LOC_Os07g40860.2 | 7972 |
| 384 | Sobic.006G066600 | | | | 4632 |
| 385 | Sobic.010G109600 | AT3G18500 | Dnase | LOC_Os06g15410.1 | 8804 |
| 386 | Sobic.009G007700 | | | | 5935 |
| 387 | Sobic.003G206300 | | | | 11635 |
| 388 | Sobic.004G272700 | AT1G65060 | phenylpropanoid metabolic process | LOC_Os02g46970.1 | 3328 |
| 389 | Sobic.001G182850 | | | | 7983 |
| 390 | Sobic.009G186400 | | | | 2366 |

| Line | | Early MMC | | Early meiocyte | |
|---|---|---|---|---|---|
| no. | DEG | Fold | FDR | Fold | FDR |
| 1 | Bioenergetics and respiration related-A151 up | | | | |
| 2 | Sobic.009G212400 | 2.27 | 1.72E−02 | 2.49 | 1.91E−02 |
| 3 | Sobic.002G078300 | 2.26 | 3.02E−02 | 2.61 | 3.35E−02 |
| 4 | Sobic.004G161900 | 3.2 | 2.04E−03 | 2.66 | 3.64E−03 |
| 5 | Sobic.002G298500 | 2.45 | 2.96E−03 | | |
| 6 | Sobic.009G240700 | | | | |
| 7 | Sobic.006G216800 | 2.15 | 7.32E−03 | | |
| 8 | Sobic.003G338700 | | | | |
| 9 | Sobic.006G064600 | 2.02 | 1.62E−02 | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 10 | Sobic.005G181000 | 2.82 | 2.88E-02 | | |
| 11 | Sobic.001G412100 | 2.28 | 3.68E-02 | | |
| 12 | Sobic.007G163100 | | | | |
| 13 | Sobic.002G005600 | 1.92 | 1.82E-02 | | |
| 14 | Sobic.004G207900 | 2.48 | 1.61E-02 | | |
| 15 | Sobic.003G287600 | | | | |
| 16 | Sobic.002G303300 | | | 2.58 | 7.59E-03 |
| 17 | Sobic.004G056400 | | | | |
| 18 | LOC110433633 | 1.69 | 2.06E-02 | | |
| 19 | Sobic.001G406800 | 3.79 | 3.91E-02 | | |
| 20 | Sobic.001G387200 | 2.06 | 4.20E-02 | | |
| 21 | Sobic.001G047800 | 3.34 | 5.47E-03 | | |
| 22 | Sobic.004G264700 | 2.13 | 1.39E-02 | | |
| 23 | Sobic.001G404800 | 2.15 | 1.77E-02 | | |
| 24 | Sobic.010G032600 | 2.43 | 9.71E-03 | | |
| 25 | Sobic.001G134200 | 2.58 | 3.88E-02 | | |
| 26 | Sobic.001G354600 | 2.48 | 1.61E-03 | | |
| 27 | Sobic.009G162200 | | | | |
| 28 | Sobic.003G237400 | | | | |
| 29 | Sobic.009G107200 | | | | |
| 30 | Sobic.002G189400 | | | | |
| 31 | Sobic.001G031300 | | | | |
| 32 | Sobic.010G224700 | | | | |
| 33 | Sobic.001G235700 | 2.61 | 3.14E-02 | | |
| 34 | Sobic.004G319800 | | | | |
| 35 | Bioenergetics and respiration related-A151 down (up in S264) | | | | |
| 36 | Sobic.006G256600 | 0.43 | 6.58E-03 | | |
| 37 | Sobic.002G356000 | | | | |
| 38 | Sobic.009G031400 | | | | |
| 39 | Sobic.003G036200 | 0.52 | 1.38E-02 | | |
| 40 | Sobic.002G184600 | 0.51 | 1.50E-02 | | |
| 41 | Sobic.003G049200 | | | | |
| 42 | Sobic.001G459800 | 0.47 | 4.18E-03 | 0.38 | 8.62E-03 |
| 43 | Sobic.001G519700 | | | | |
| 44 | Sobic.003G370000 | | | | |
| 45 | Sobic.001G194900 | | | | |
| 46 | Sobic.001G096800 | 0.54 | 1.53E-02 | | |
| 47 | Sobic.003G258200 | | | | |
| 48 | Sobic.001G090200 | 0.48 | 2.46E-02 | | |
| 49 | Sobic.002G230100 | 0.55 | 3.04E-02 | | |
| 50 | Sobic.004G068700 | 0.58 | 3.45E-02 | | |
| 51 | Sobic.005G060100 | 0.5 | 2.41E-02 | | |
| 52 | Sobic.003G233000 | 0.56 | 2.79E-02 | | |
| 53 | Sobic.004G207900 | 0.54 | 3.51E-02 | | |
| 54 | Sobic.001G123100 | 0.56 | 4.45E-02 | | |
| 55 | Sobic.007G123500 | 0.51 | 1.67E-02 | | |
| 56 | Sobic.003G327900 | | | | |
| 57 | LOC110435380 | | | | |
| 58 | Sobic.003G039700 | | | | |
| 59 | Sobic.006G001000 | 0.38 | 6.03E-03 | | |
| 60 | Sobic.006G130300 | | | | |
| 61 | Sobic.003G292700 | 0.53 | 1.85E-02 | | |
| 62 | Sobic.001G082900 | 0.46 | 2.78E-02 | | |
| 63 | Sobic.007G202800 | | | | |
| 64 | Sobic.004G206200 | 0.55 | 4.11E-02 | | |
| 65 | Sobic.003G051000 | 0.58 | 4.31E-02 | | |
| 66 | Sobic.007G162600 | 0.48 | 4.43E-02 | | |
| 67 | Sobic.010G092600 | 0.54 | 4.64E-02 | | |
| 68 | Sobic.008G024200 | 0.55 | 4.70E-02 | | |
| 69 | Stress and catabolismo related-A151 up | | | | |
| 70 | Sobic.003G024800 | 9.41 | 7.00E-05 | 7.52 | 5.51E-04 |
| 71 | Sobic.004G182800 | | | | |
| 72 | Sobic.001G371900 | 1.74 | 4.57E-02 | | |
| 73 | Sobic.006G029800 | | | | |
| 74 | Sobic.001G010800 | | | | |
| 75 | Sobic.010G104100 | | | | |
| 76 | Sobic.003G140700 | | | | |
| 77 | Sobic.001G410200 | | | 2.25 | 3.29E-02 |
| 78 | Sobic.004G343200 | 3.03 | 3.39E-02 | | |
| 79 | Sobic.004G333500 | 5.97 | 3.97E-04 | | |
| 80 | Sobic.010G101500 | 1.91 | 1.02E-02 | | |
| 81 | Sobic.004G295800 | 2.67 | 6.88E-04 | 3.52 | 8.06E-03 |
| 82 | Sobic.001G293300 | 2.08 | 2.01E-02 | | |
| 83 | Sobic.010G015900 | | | | |
| 84 | Sobic.006G257900 | 10.51 | 2.27E-03 | | |
| 85 | Sobic.004G057200 | 2.34 | 7.53E-03 | | |
| 86 | Sobic.009G055800 | | | | |

TABLE 4-continued

Chromosomal and functional anotations for differentially expressed genes (DEG) identified by microarrays that compared ovule transcripts of A151 with those of S264 for each stage separately and all stages combined.

| # | Gene | | | | |
|---|---|---|---|---|---|
| 87 | Sobic.001G154100 | 1.99 | 2.52E−02 | | |
| 88 | Sobic.003G338400 | 2.53 | 4.74E−03 | | |
| 89 | Sobic.001G520100 | | | | |
| 90 | Sobic.010G047400 | | | | |
| 91 | Sobic.005G208900 | | | | |
| 92 | Sobic.004G006900 | 3.12 | 1.55E−02 | | |
| 93 | Sobic.010G222400 | 1.95 | 1.16E−02 | | |
| 94 | Sobic.001G100900 | | | | |
| 95 | Sobic.010G001600 | | | | |
| 96 | Sobic.004G177700 | | | | |
| 97 | Sobic.008G144500 | | | | |
| 98 | Sobic.006G220900 | 2.43 | 1.71E−02 | | |
| 99 | Sobic.002G243200 | 3.2 | 2.02E−02 | | |
| 100 | Sobic.004G255000 | 2.19 | 2.05E−02 | | |
| 101 | Sobic.001G108900 | | | | |
| 102 | Sobic.007G029700 | 2.03 | 3.17E−02 | | |
| 103 | Sobic.003G368000 | 1.76 | 3.18E−02 | | |
| 104 | Sobic.003G247000 | | | | |
| 105 | Sobic.010G181600 | | | | |
| 106 | Sobic.004G224900 | 2.05 | 4.46E−02 | | |
| 107 | Sobic.004G350400 | | | | |
| 108 | Sobic.006G252200 | 2.8 | 4.95E−02 | | |
| 109 | Stress and catabolismo related-A151 down | | | | |
| 110 | Sobic.004G171400 | 0.47 | 6.00E−03 | | |
| 111 | Sobic.010G128400 | 0.55 | 4.55E−02 | | |
| 112 | Sobic.001G483100 | | | 0.46 | 3.19E−02 |
| 113 | Sobic.005G005500 | | | | |
| 114 | Sobic.004G111100 | | | 0.34 | 4.17E−02 |
| 115 | Sobic.006G161300 | | | | |
| 116 | Sobic.003G317700 | | | | |
| 117 | Sobic.001G140300 | 0.57 | 2.38E−02 | | |
| 118 | Sobic.004G155600 | | | | |
| 119 | Sobic.002G031100 | | | | |
| 120 | Sobic.007G169700 | | | | |
| 121 | Sobic.007G088300 | | | | |
| 122 | Sobic.008G004600 | | | | |
| 123 | Sobic.003G221400 | | | | |
| 124 | Sobic.001G306000 | 0.53 | 3.37E−02 | | |
| 125 | Sobic.002G345700 | 0.5 | 1.73E−02 | | |
| 126 | Sobic.002G157300 | 0.57 | 1.25E−02 | | |
| 127 | Sobic.006G260300 | | | | |
| 128 | Sobic.005G170100 | 0.47 | 1.65E−02 | | |
| 129 | Sobic.005G167400 | 0.54 | 1.66E−02 | | |
| 130 | Sobic.008G105500 | 0.5 | 1.89E−02 | | |
| 131 | Sobic.001G452100 | 0.52 | 2.23E−02 | | |
| 132 | Sobic.001G441100 | 0.6 | 2.48E−02 | | |
| 133 | Sobic.010G041800 | 0.57 | 2.49E−02 | | |
| 134 | Sobic.003G192400 | 0.56 | 3.02E−02 | | |
| 135 | Sobic.001G317000 | 0.63 | 3.20E−02 | | |
| 136 | Sobic.010G231300 | 0.58 | 3.61E−02 | | |
| 137 | Sobic.004G148600 | 0.61 | 4.59E−02 | | |
| 138 | Hormone and signaling related-A151 up | | | | |
| 139 | Sobic.004G202500 | 6.13 | 7.00E−05 | 7.7 | 1.91E−03 |
| 140 | Sobic.002G068900 | 3.14 | 9.75E−03 | | |
| 141 | Sobic.008G181300 | 2.52 | 1.87E−02 | | |
| 142 | Sobic.003G389000 | | | | |
| 143 | Sobic.010G186200 | 2.84 | 4.91E−02 | | |
| 144 | Sobic.005G084100 | | | | |
| 145 | Sobic.001G079200 | | | | |
| 146 | Sobic.005G106600 | | | | |
| 147 | Sobic.004G162000 | 3.82 | 7.00E−03 | | |
| 148 | Sobic.003G083200 | 2.23 | 3.24E−02 | | |
| 149 | Sobic.010G089700 | 2.07 | 8.37E−03 | | |
| 150 | Sobic.010G005600 | | | | |
| 151 | Sobic.008G163300 | | | | |
| 152 | Sobic.004G317000 | 3.05 | 1.23E−02 | | |
| 153 | Sobic.003G430400 | | | | |
| 154 | Sobic.003G279800 | 3.06 | 2.22E−02 | | |
| 155 | Sobic.007G076300 | 1.85 | 2.78E−02 | | |
| 156 | Sobic.002G263100 | 1.96 | 2.86E−02 | | |
| 157 | Sobic.001G424400 | 2.84 | 3.10E−02 | | |
| 158 | Sobic.006G244800 | 2.49 | 3.21E−02 | | |
| 159 | Sobic.007G139600 | 2.56 | 3.22E−02 | | |
| 160 | Sobic.010G210600 | | | | |
| 161 | Sobic.003G021500 | | | 2.26 | 4.91E−02 |
| 162 | Hormone and signaling related-A151 down | | | | |
| 163 | Sobic.007G105100 | 0.5 | 4.48E−02 | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 164 | Sobic.002G418500 | 0.43 | 4.70E−03 | | |
| 165 | Sobic.003G253600 | 0.47 | 6.26E−03 | | |
| 166 | Sobic.006G187900 | 0.57 | 3.06E−02 | | |
| 167 | Sobic.008G157700 | 0.43 | 9.68E−03 | | |
| 168 | Sobic.001G429700 | 0.42 | 3.13E−02 | | |
| 169 | Sobic.002G393100 | 0.51 | 4.16E−02 | | |
| 170 | Sobic.004G209900 | | | | |
| 171 | Sobic.002G181800 | 0.41 | 5.87E−03 | | |
| 172 | Sobic.004G132900 | | | | |
| 173 | Sobic.009G237600 | | | | |
| 174 | Sobic.001G449700 | 0.46 | 2.46E−02 | | |
| 175 | Sobic.001G125700 | 0.48 | 9.16E−03 | | |
| 176 | Sobic.003G037000 | | | | |
| 177 | Sobic.009G116500 | | | | |
| 178 | Sobic.004G038300 | | | | |
| 179 | Sobic.009G005700 | 0.55 | 2.39E−02 | | |
| 180 | Sobic.009G104600 | 0.61 | 2.49E−02 | | |
| 181 | Sobic.002G265800 | 0.57 | 2.49E−02 | | |
| 182 | Sobic.004G349300 | 0.5 | 3.43E−02 | | |
| 183 | Sobic.001G331200 | 0.51 | 3.63E−02 | | |
| 184 | Sobic.009G229200 | | | | |
| 185 | Sobic.008G039800 | 0.58 | 4.95E−02 | | |
| 186 | Gene expression related-A151 up | | | | |
| 187 | Sobic.004G211400 | | | 2.84 | 2.33E−02 |
| 188 | Sobic.004G155700 | | | | |
| 189 | Sobic.004G211400 | 2.21 | 2.77E−03 | | |
| 190 | Sobic.003G038100 | 1.83 | 4.37E−02 | | |
| 191 | Sobic.004G211100 | | | | |
| 192 | Sobic.001G041200 | 2.06 | 2.64E−02 | | |
| 193 | Sobic.001G369000 | 3.49 | 1.82E−02 | | |
| 194 | Sobic.002G046100 | | | | |
| 195 | Sobic.001G122400 | 2.74 | 8.67E−03 | | |
| 196 | Sobic.004G045400 | | | | |
| 197 | Sobic.003G322400 | 3.18 | 3.18E−03 | | |
| 198 | Sobic.004G339200 | | | | |
| 199 | Sobic.001G147100 | 2.18 | 3.83E−02 | | |
| 200 | Sobic.006G098500 | | | | |
| 201 | Sobic.004G271400 | | | | |
| 202 | Sobic.002G081600 | 8.33 | 1.02E−02 | | |
| 203 | Sobic.002G355300 | | | | |
| 204 | Sobic.010G005300 | | | | |
| 205 | Sobic.001G105100 | | | | |
| 206 | Sobic.001G281900 | | | | |
| 207 | Sobic.008G098800 | | | | |
| 208 | Sobic.001G541100 | 2.49 | 1.44E−02 | | |
| 209 | Sobic.006G138100 | 3.86 | 1.60E−02 | | |
| 210 | Sobic.010G173100 | 4.26 | 1.74E−02 | | |
| 211 | Sobic.009G182600 | 2.34 | 1.82E−02 | | |
| 212 | Sobic.004G323700 | 2.47 | 1.92E−02 | | |
| 213 | Sobic.006G160200 | 1.94 | 1.94E−02 | | |
| 214 | Sobic.003G332401 | 2.37 | 2.47E−02 | | |
| 215 | Sobic.010G206200 | 3.04 | 2.60E−02 | | |
| 216 | Sobic.004G145801 | 2.78 | 2.60E−02 | | |
| 217 | Sobic.008G128600 | 2.14 | 2.69E−02 | | |
| 218 | Sobic.006G252100 | 2.1 | 2.97E−02 | | |
| 219 | Sobic.010G065400 | 2.26 | 3.18E−02 | | |
| 220 | Sobic.003G109600 | 2.36 | 3.20E−02 | | |
| 221 | Sobic.004G185600 | | | | |
| 222 | Sobic.006G147000 | 2.42 | 3.33E−02 | | |
| 223 | Sobic.001G016500 | 2.7 | 3.44E−02 | | |
| 224 | Sobic.001G011000 | | | | |
| 225 | Sobic.001G386700 | | | | |
| 226 | Sobic.003G422900 | 1.88 | 4.11E−02 | | |
| 227 | Sobic.001G447300 | 1.84 | 4.51E−02 | | |
| 228 | Sobic.010G251100 | 2.02 | 4.56E−02 | | |
| 229 | Sobic.007G067700 | 1.99 | 4.61E−02 | | |
| 230 | Sobic.007G188900 | | | | |
| 231 | Sobic.004G040900 | 2.07 | 4.96E−02 | | |
| 232 | Gene expression related-A151 down | | | | |
| 233 | Sobic.003G439900 | 0.34 | 4.81E−03 | 0.28 | 4.71E−03 |
| 234 | Sobic.008G108601 | | | | |
| 235 | Sobic.007G102800 | | | | |
| 236 | Sobic.009G072200 | 0.53 | 1.16E−02 | | |
| 237 | Sobic.010G269600 | | | | |
| 238 | Sobic.002G389600 | 0.53 | 1.93E−02 | | |
| 239 | Sobic.001G175300 | 0.53 | 1.40E−02 | | |
| 240 | Sobic.009G244300 | 0.52 | 1.40E−02 | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 241 | Sobic.001G008500 | 0.55 | 1.71E−02 | | |
| 242 | Sobic.007G011600 | 0.47 | 1.98E−02 | | |
| 243 | Sobic.006G126900 | 0.53 | 3.46E−02 | | |
| 244 | Sobic.009G135600 | | | | |
| 245 | sRNA regulation of gene expression related-A151 up | | | | |
| 246 | Sobic.002G041400 | 3.34 | 1.87E−02 | | |
| 247 | Sobic.001G054800 | | | | |
| 248 | Sobic.009G216700 | | | 2.24 | 1.92E−02 |
| 249 | Sobic.001G289800 | | | | |
| 250 | Sobic.001G536400 | | | | |
| 251 | Sobic.001G094500 | | | | |
| 252 | sRNA regulation of gene expression related-A151 down | | | | |
| 253 | Sobic.003G350100 | 0.18 | 5.98E−04 | 0.15 | 2.24E−04 |
| 254 | Sobic.003G347900 | | | 0.42 | 3.00E−02 |
| 255 | Sobic.001G522600 | | | | |
| 256 | Sobic.003G330900 | 0.54 | 3.98E−02 | | |
| 257 | Sobic.003G104000 | 0.5 | 4.48E−02 | | |
| 258 | Growth and development related-A151 up | | | | |
| 259 | Sobic.004G093700 | 5.32 | 3.45E−04 | | |
| 260 | Sobic.004G197600 | 3.34 | 3.97E−04 | 4.32 | 5.51E−04 |
| 261 | Sobic.010G172400 | 2.09 | 1.83E−02 | | |
| 262 | Sobic.006G152600 | | | | |
| 263 | Sobic.002G148100 | | | 2.12 | 2.20E−02 |
| 264 | Sobic.004G025900 | | | | |
| 265 | Sobic.003G049600 | | | | |
| 266 | Sobic.001G046400 | | | | |
| 267 | Sobic.009G259200 | | | | |
| 268 | Sobic.004G187900 | | | | |
| 269 | Sobic.010G266300 | 2.05 | 1.58E−02 | | |
| 270 | Sobic.002G113800 | 2.18 | 2.89E−02 | | |
| 271 | Sobic.008G160400 | 2.76 | 1.57E−02 | | |
| 272 | Sobic.004G190600 | 3.25 | 1.69E−02 | | |
| 273 | Sobic.001G086600 | 1.85 | 1.69E−02 | | |
| 274 | Sobic.010G097600 | | | | |
| 275 | Sobic.003G250700 | 1.79 | 2.20E−02 | | |
| 276 | Sobic.004G350300 | 3.48 | 2.48E−02 | | |
| 277 | Sobic.006G050600 | | | | |
| 278 | Sobic.001G398500 | | | | |
| 279 | Sobic.003G334700 | 1.99 | 2.84E−02 | | |
| 280 | Sobic.002G201900 | 1.67 | 3.21E−02 | | |
| 281 | Sobic.001G119900 | | | | |
| 282 | Sobic.005G187500 | 1.76 | 3.26E−02 | | |
| 283 | Sobic.004G243800 | 1.96 | 3.39E−02 | | |
| 284 | Sobic.002G175400 | | | | |
| 285 | Sobic.007G019300 | | | | |
| 286 | Growth and development related-A151 down | | | | |
| 287 | Sobic.009G132400 | 0.48 | 9.47E−03 | | |
| 288 | Sobic.006G221300 | 0.34 | 7.13E−03 | 0.22 | 2.10E−03 |
| 289 | Sobic.001G195600 | 0.19 | 2.99E−03 | 0.15 | 2.24E−04 |
| 290 | Sobic.008G034400 | | | | |
| 291 | Sobic.007G011300 | | | | |
| 292 | Sobic.004G351200 | 0.45 | 1.00E−02 | | |
| 293 | Sobic.004G215700 | | | | |
| 294 | Sobic.003G228900 | | | | |
| 295 | Sobic.010G108600 | 0.47 | 1.20E−02 | | |
| 296 | Sobic.003G371100 | 0.55 | 2.95E−02 | | |
| 297 | Sobic.003G445300 | | | | |
| 298 | Sobic.001G091300 | | | | |
| 299 | Sobic.010G248200 | 0.47 | 1.39E−02 | | |
| 300 | LOC110433098 | | | | |
| 301 | Sobic.004G134600 | 0.52 | 1.94E−02 | | |
| 302 | Sobic.002G220600 | | | | |
| 303 | LOC8078215 | | | 0.38 | 2.16E−02 |
| 304 | Sobic.001G363700 | 0.46 | 2.78E−02 | | |
| 305 | Sobic.001G497700 | 0.49 | 3.41E−02 | | |
| 306 | Sobic.001G088100 | | | | |
| 307 | Sobic.003G334700 | | | | |
| 308 | Sobic.001G281600 | | | | |
| 309 | Sobic.002G143300 | 0.49 | 3.67E−02 | | |
| 310 | Sobic.003G173800 | 0.54 | 3.76E−02 | | |
| 311 | Sobic.010G134400 | 0.64 | 4.03E−02 | | |
| 312 | Sobic.003G427600 | 0.5 | 4.09E−02 | | |
| 313 | Sobic.003G403500 | 0.56 | 4.31E−02 | | |
| 314 | Other-A151 up | | | | |
| 315 | Sobic.010G094301 | 2.7 | 8.95E−04 | 3.34 | 1.09E−03 |
| 316 | Sobic.003G048500 | 3.1 | 6.88E−04 | | |
| 317 | Sobic.004G208100 | 2.54 | 1.88E−02 | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 318 | Sobic.005G112632 | | | 2.85 | 2.13E−03 |
| 319 | LOC110435809 | 1.59 | 3.53E−02 | 2.05 | 4.59E−02 |
| 320 | LOC110431211 | 1.6 | 4.72E−02 | 1.95 | 1.60E−02 |
| 321 | Sobic.002G254100 | | | 2.11 | 4.44E−02 |
| 322 | Sobic.004G136500 | 1.78 | 4.71E−02 | | |
| 323 | Sobic.004G331800 | 4.48 | 4.25E−03 | | |
| 324 | Sobic.004G007300 | | | | |
| 325 | Sobic.001G541400 | 2.14 | 5.72E−03 | | |
| 326 | Sobic.001G442200 | 2.91 | 6.28E−03 | | |
| 327 | LOC110431017 | | | | |
| 328 | MultiHit5375 | 1.9 | 1.09E−02 | | |
| 329 | Sobic.003G029200 | | | | |
| 330 | Sobic.001G381900 | | | | |
| 331 | MultiHit7742 | | | | |
| 332 | Sobic.003G140900 | | | | |
| 333 | Sobic.001G121100 | | | | |
| 334 | Sobic.001G143300 | | | | |
| 335 | Sobic.002G364800 | | | | |
| 336 | Sobic.003G088400 | | | 2.25 | 2.49E−02 |
| 337 | Sobic.001G154400 | 2.06 | 2.60E−02 | | |
| 338 | MultiHit5916 | 3.69 | 2.69E−02 | | |
| 339 | MultiHit3601 | 3.48 | 2.77E−02 | | |
| 340 | Sobic.003G113500 | | | | |
| 341 | Sobic.001G087700 | | | | |
| 342 | LOC8081614 | 2.07 | 3.10E−02 | | |
| 343 | LOC110429578 | | | | |
| 344 | Sobic.005G228700 | | | | |
| 345 | Sobic.004G134900 | | | | |
| 346 | Sobic.001G012200 | | | | |
| 347 | Sobic.001G193100 | | | | |
| 348 | Other-A151 down | | | | |
| 349 | Sobic.002G200900 | 0.51 | 1.02E−02 | | |
| 350 | Sobic.001G455600 | 0.44 | 5.31E−03 | | |
| 351 | Sobic.008G026200 | 0.5 | 1.25E−02 | | |
| 352 | Sobic.009G003300 | 0.49 | 9.54E−03 | | |
| 353 | Sobic.004G105500 | 0.44 | 6.06E−03 | | |
| 354 | Sobic.004G324800 | | | | |
| 355 | Sobic.002G191800 | | | | |
| 356 | Sobic.002G171300 | | | | |
| 357 | Sobic.001G298700 | | | | |
| 358 | Sobic.006G206200 | | | | |
| 359 | Sobic.010G016500 | 0.57 | 3.70E−02 | | |
| 360 | Sobic.006G052800 | | | | |
| 361 | Sobic.001G536800 | | | | |
| 362 | Sobic.001G146301 | | | | |
| 363 | Sobic.002G151300 | | | | |
| 364 | Sobic.001G098600 | | | 0.27 | 3.40E−03 |
| 365 | Sobic.001G072700 | | | | |
| 366 | MultiHit113 | 0.39 | 6.62E−03 | | |
| 367 | Sobic.001G204700 | | | | |
| 368 | Sobic.001G051800 | 0.47 | 8.45E−03 | | |
| 369 | Sobic.006G122500 | | | | |
| 370 | Sobic.009G224400 | 0.57 | 1.21E−02 | | |
| 371 | Sobic.005G021200 | | | | |
| 372 | Sobic.005G084300 | 0.51 | 1.49E−02 | | |
| 373 | Sobic.004G162200 | 0.56 | 1.56E−02 | | |
| 374 | Sobic.003G018000 | | | | |
| 375 | Sobic.006G258800 | 0.52 | 1.76E−02 | | |
| 376 | Sobic.001G103600 | 0.48 | 2.10E−02 | | |
| 377 | Sobic.009G252100 | 0.55 | 2.24E−02 | | |
| 378 | Sobic.004G019400 | 0.46 | 2.26E−02 | | |
| 379 | Sobic.002G330800 | 0.54 | 2.34E−02 | | |
| 380 | MultiHit10711 | | | | |
| 381 | Sobic.005G143200 | | | | |
| 382 | Sobic.006G219500 | 0.54 | 3.21E−02 | | |
| 383 | Sobic.002G365550 | 0.54 | 3.30E−02 | | |
| 384 | Sobic.006G066600 | 0.59 | 3.79E−02 | | |
| 385 | Sobic.010G109600 | 0.52 | 4.17E−02 | | |
| 386 | Sobic.009G007700 | | | 0.39 | 4.25E−02 |
| 387 | Sobic.003G206300 | 0.56 | 4.57E−02 | | |
| 388 | Sobic.004G272700 | 0.52 | 4.77E−02 | | |
| 389 | Sobic.001G182850 | 0.55 | 4.79E−02 | | |
| 390 | Sobic.009G186400 | 0.57 | 4.89E−02 | | |

TABLE 4-continued

Chromosomal and functional anotations for differentially expressed genes (DEG) identified by microarrays that compared ovule transcripts of A151 with those of S264 for each stage separately and all stages combined.

| Line no. | DEG | Mid ES Fold | Mid ES FDR | All stages combined Fold | All stages combined FDR |
|---|---|---|---|---|---|
| 1 | Bioenergetics and respiration related-A151 up | | | | |
| 2 | Sobic.009G212400 | | | 2.3 | 1.00E−07 |
| 3 | Sobic.002G078300 | 2.84 | 1.17E−02 | 2.58 | 1.00E−07 |
| 4 | Sobic.004G161900 | 2.85 | 3.77E−02 | 2.88 | 1.00E−07 |
| 5 | Sobic.002G298500 | | | | |
| 6 | Sobic.009G240700 | | | 2.37 | 3.57E−03 |
| 7 | Sobic.006G216800 | | | | |
| 8 | Sobic.003G338700 | | | 1.68 | 9.74E−03 |
| 9 | Sobic.006G064600 | 3 | 1.20E−02 | | |
| 10 | Sobic.005G181000 | | | 1.58 | 1.32E−02 |
| 11 | Sobic.001G412100 | | | | |
| 12 | Sobic.007G163100 | 1.88 | 4.39E−02 | | |
| 13 | Sobic.002G005600 | | | | |
| 14 | Sobic.004G207900 | | | 2.21 | 1.12E−03 |
| 15 | Sobic.003G287600 | 4.39 | 2.54E−03 | | |
| 16 | Sobic.002G303300 | | | | |
| 17 | Sobic.004G056400 | | | 1.65 | 1.16E−02 |
| 18 | LOC110433633 | | | | |
| 19 | Sobic.001G406800 | | | | |
| 20 | Sobic.001G387200 | | | | |
| 21 | Sobic.001G047800 | | | | |
| 22 | Sobic.004G264700 | | | 1.67 | 7.60E−03 |
| 23 | Sobic.001G404800 | | | 1.64 | 8.18E−03 |
| 24 | Sobic.010G032600 | | | | |
| 25 | Sobic.001G134200 | | | | |
| 26 | Sobic.001G354600 | | | | |
| 27 | Sobic.009G162200 | | | 1.5 | 6.00E−03 |
| 28 | Sobic.003G237400 | | | 1.59 | 9.74E−03 |
| 29 | Sobic.009G107200 | 3.16 | 2.65E−02 | 1.97 | 1.18E−02 |
| 30 | Sobic.002G189400 | | | 1.79 | 1.27E−02 |
| 31 | Sobic.001G031300 | 2.24 | 1.80E−02 | | |
| 32 | Sobic.010G224700 | 2.16 | 2.78E−02 | | |
| 33 | Sobic.001G235700 | | | | |
| 34 | Sobic.004G319800 | 1.84 | 3.93E−02 | | |
| 35 | Bioenergetics and respiration related-A151 down (up in S264) | | | | |
| 36 | Sobic.006G256600 | 0.36 | 4.82E−03 | 0.41 | 1.00E−07 |
| 37 | Sobic.002G356000 | | | 0.64 | 6.65E−03 |
| 38 | Sobic.009G031400 | 0.49 | 1.37E−02 | | |
| 39 | Sobic.003G036200 | | | | |
| 40 | Sobic.002G184600 | | | | |
| 41 | Sobic.003G049200 | 0.44 | 3.39E−02 | | |
| 42 | Sobic.001G459800 | | | 0.5 | 8.47E−06 |
| 43 | Sobic.001G519700 | | | 0.57 | 1.15E−03 |
| 44 | Sobic.003G370000 | 0.42 | 1.37E−02 | 0.64 | 9.74E−03 |
| 45 | Sobic.001G194900 | | | 0.62 | 1.10E−02 |
| 46 | Sobic.001G096800 | | | | |
| 47 | Sobic.003G258200 | | | 0.66 | 8.52E−03 |
| 48 | Sobic.001G090200 | | | | |
| 49 | Sobic.002G230100 | | | | |
| 50 | Sobic.004G068700 | | | | |
| 51 | Sobic.005G060100 | | | | |
| 52 | Sobic.003G233000 | | | | |
| 53 | Sobic.004G207900 | | | | |
| 54 | Sobic.001G123100 | | | | |
| 55 | Sobic.007G123500 | | | 0.58 | 8.77E−05 |
| 56 | Sobic.003G327900 | | | 0.64 | 1.56E−03 |
| 57 | LOC110435380 | | | 0.65 | 1.58E−03 |
| 58 | Sobic.003G039700 | | | 0.65 | 5.20E−03 |
| 59 | Sobic.006G001000 | | | | |
| 60 | Sobic.006G130300 | | | 0.65 | 8.52E−03 |
| 61 | Sobic.003G292700 | | | 0.63 | 1.20E−02 |
| 62 | Sobic.001G082900 | | | | |
| 63 | Sobic.007G202800 | 0.51 | 3.33E−02 | | |
| 64 | Sobic.004G206200 | | | | |
| 65 | Sobic.003G051000 | | | | |
| 66 | Sobic.007G162600 | | | | |
| 67 | Sobic.010G092600 | | | | |
| 68 | Sobic.008G024200 | | | | |
| 69 | Stress and catabolismo related-A151 up | | | | |
| 70 | Sobic.003G024800 | 9.97 | 3.26E−04 | 8.87 | 1.00E−07 |
| 71 | Sobic.004G182800 | 3.03 | 1.41E−02 | 2.25 | 2.07E−03 |
| 72 | Sobic.001G371900 | | | 1.75 | 1.27E−02 |
| 73 | Sobic.006G029800 | | | 1.65 | 1.27E−02 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 74 | Sobic.001G010800 | | | 1.42 | 1.48E−02 |
| 75 | Sobic.010G104100 | 2.23 | 1.85E−02 | | |
| 76 | Sobic.003G140700 | 3.41 | 1.87E−02 | | |
| 77 | Sobic.001G410200 | | | | |
| 78 | Sobic.004G343200 | | | | |
| 79 | Sobic.004G333500 | 6.88 | 3.26E−04 | 5.33 | 1.00E−07 |
| 80 | Sobic.010G101500 | 2.2 | 2.05E−02 | 2.1 | 1.00E−07 |
| 81 | Sobic.004G295800 | 4.06 | 7.67E−03 | 3.33 | 1.00E−07 |
| 82 | Sobic.001G293300 | | | 1.8 | 6.66E−04 |
| 83 | Sobic.010G015900 | 2.44 | 3.98E−02 | 2.12 | 7.09E−04 |
| 84 | Sobic.006G257900 | | | 3.64 | 1.15E−02 |
| 85 | Sobic.004G057200 | | | 1.81 | 2.40E−03 |
| 86 | Sobic.009G055800 | 2.08 | 2.93E−02 | 1.75 | 2.55E−03 |
| 87 | Sobic.001G154100 | 2.27 | 3.50E−02 | 1.71 | 4.29E−03 |
| 88 | Sobic.003G338400 | | | | |
| 89 | Sobic.001G520100 | 3.69 | 7.89E−03 | | |
| 90 | Sobic.010G047400 | | | 1.52 | 9.74E−03 |
| 91 | Sobic.005G208900 | | | 1.51 | 1.10E−02 |
| 92 | Sobic.004G006900 | | | 2.25 | 1.15E−02 |
| 93 | Sobic.010G222400 | 1.94 | 4.43E−02 | | |
| 94 | Sobic.001G100900 | | | 2.22 | 1.23E−02 |
| 95 | Sobic.010G001600 | | | 2.17 | 1.29E−02 |
| 96 | Sobic.004G177700 | | | 2.41 | 1.33E−02 |
| 97 | Sobic.008G144500 | | | 2.25 | 1.38E−02 |
| 98 | Sobic.006G220900 | | | | |
| 99 | Sobic.002G243200 | | | | |
| 100 | Sobic.004G255000 | | | | |
| 101 | Sobic.001G108900 | | | 2.52 | 2.53E−02 |
| 102 | Sobic.007G029700 | | | | |
| 103 | Sobic.003G368000 | | | | |
| 104 | Sobic.003G247000 | | | 3.2 | 3.39E−02 |
| 105 | Sobic.010G181600 | | | 3.3 | 3.69E−02 |
| 106 | Sobic.004G224900 | | | | |
| 107 | Sobic.004G350400 | | | 2.47 | 4.66E−02 |
| 108 | Sobic.006G252200 | | | | |
| 109 | Stress and catabolismo related-A151 down | | | | |
| 110 | Sobic.004G171400 | | | 0.58 | 2.10E−05 |
| 111 | Sobic.010G128400 | | | 0.61 | 2.48E−03 |
| 112 | Sobic.001G483100 | | | 0.52 | 2.10E−05 |
| 113 | Sobic.005G005500 | 0.54 | 3.45E−02 | 0.57 | 6.46E−05 |
| 114 | Sobic.004G111100 | | | 0.48 | 7.78E−05 |
| 115 | Sobic.006G161300 | | | 0.6 | 3.98E−04 |
| 116 | Sobic.003G317700 | 0.37 | 3.47E−03 | | |
| 117 | Sobic.001G140300 | | | 0.61 | 4.38E−03 |
| 118 | Sobic.004G155600 | | | 0.67 | 4.46E−03 |
| 119 | Sobic.002G031100 | | | 0.57 | 7.60E−03 |
| 120 | Sobic.007G169700 | | | 0.66 | 8.34E−03 |
| 121 | Sobic.007G088300 | | | 0.67 | 9.74E−03 |
| 122 | Sobic.008G004600 | | | 0.66 | 9.74E−03 |
| 123 | Sobic.003G221400 | | | 0.63 | 1.14E−02 |
| 124 | Sobic.001G306000 | | | 0.62 | 1.21E−02 |
| 125 | Sobic.002G345700 | | | 0.67 | 1.22E−02 |
| 126 | Sobic.002G157300 | | | | |
| 127 | Sobic.006G260300 | 0.42 | 2.31E−02 | 0.66 | 1.27E−02 |
| 128 | Sobic.005G170100 | | | | |
| 129 | Sobic.005G167400 | | | | |
| 130 | Sobic.008G105500 | | | | |
| 131 | Sobic.001G452100 | | | | |
| 132 | Sobic.001G441100 | | | | |
| 133 | Sobic.010G041800 | | | | |
| 134 | Sobic.003G192400 | | | | |
| 135 | Sobic.001G317000 | | | | |
| 136 | Sobic.010G231300 | | | | |
| 137 | Sobic.004G148600 | | | | |
| 138 | Hormone and signaling related-A151 up | | | | |
| 139 | Sobic.004G202500 | 7.31 | 1.11E−03 | 6.99 | 1.00E−07 |
| 140 | Sobic.002G068900 | | | 2.31 | 1.17E−04 |
| 141 | Sobic.008G181300 | | | 2.13 | 8.69E−03 |
| 142 | Sobic.003G389000 | 2.23 | 9.57E−03 | | |
| 143 | Sobic.010G186200 | | | | |
| 144 | Sobic.005G084100 | 2.71 | 5.95E−03 | 1.94 | 7.09E−04 |
| 145 | Sobic.001G079200 | | | 1.68 | 3.11E−03 |
| 146 | Sobic.005G106600 | | | 1.48 | 3.86E−03 |
| 147 | Sobic.004G162000 | | | 2.02 | 4.47E−03 |
| 148 | Sobic.003G083200 | 3.13 | 6.94E−03 | 1.9 | 6.20E−03 |
| 149 | Sobic.010G089700 | | | | |
| 150 | Sobic.010G005600 | | | 1.53 | 8.94E−03 |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 151 | Sobic.008G163300 | | | 1.83 | 1.18E−02 |
| 152 | Sobic.004G317000 | | | | |
| 153 | Sobic.003G430400 | 2 | 2.16E−02 | | |
| 154 | Sobic.003G279800 | | | | |
| 155 | Sobic.007G076300 | | | | |
| 156 | Sobic.002G263100 | | | | |
| 157 | Sobic.001G424400 | 3.16 | 4.76E−02 | | |
| 158 | Sobic.006G244800 | | | | |
| 159 | Sobic.007G139600 | | | | |
| 160 | Sobic.010G210600 | 1.8 | 4.68E−02 | | |
| 161 | Sobic.003G021500 | | | | |
| 162 | Hormone and signaling related-A151 down | | | | |
| 163 | Sobic.007G105100 | | | 0.55 | 6.92E−05 |
| 164 | Sobic.002G418500 | | | | |
| 165 | Sobic.003G253600 | | | | |
| 166 | Sobic.006G187900 | | | 0.68 | 6.56E−03 |
| 167 | Sobic.008G157700 | | | | |
| 168 | Sobic.001G429700 | | | | |
| 169 | Sobic.002G393100 | | | | |
| 170 | Sobic.004G209900 | 0.54 | 2.73E−02 | 0.62 | 9.00E−04 |
| 171 | Sobic.002G181800 | | | 0.49 | 1.65E−03 |
| 172 | Sobic.004G132900 | | | 0.65 | 4.58E−03 |
| 173 | Sobic.009G237600 | | | 0.66 | 7.60E−03 |
| 174 | Sobic.001G449700 | | | 0.59 | 7.60E−03 |
| 175 | Sobic.001G125700 | | | | |
| 176 | Sobic.003G037000 | | | 0.67 | 1.18E−02 |
| 177 | Sobic.009G116500 | | | 0.63 | 1.27E−02 |
| 178 | Sobic.004G038300 | | | 0.68 | 1.14E−02 |
| 179 | Sobic.009G005700 | | | | |
| 180 | Sobic.009G104600 | | | | |
| 181 | Sobic.002G265800 | | | | |
| 182 | Sobic.004G349300 | | | | |
| 183 | Sobic.001G331200 | | | | |
| 184 | Sobic.009G229200 | 0.58 | 3.72E−02 | | |
| 185 | Sobic.008G039800 | | | | |
| 186 | Gene expression related-A151 up | | | | |
| 187 | Sobic.004G211400 | | | 2.01 | 8.47E−06 |
| 188 | Sobic.004G155700 | 1.74 | 4.20E−02 | 1.68 | 1.53E−05 |
| 189 | Sobic.004G211400 | | | 2 | 1.53E−05 |
| 190 | Sobic.003G038100 | | | 2 | 1.53E−05 |
| 191 | Sobic.004G211100 | 1.77 | 4.41E−02 | 1.73 | 7.78E−05 |
| 192 | Sobic.001G041200 | 1.82 | 4.71E−02 | 1.78 | 1.15E−04 |
| 193 | Sobic.001G369000 | | | 2.59 | 7.74E−04 |
| 194 | Sobic.002G046100 | | | 2 | 1.14E−03 |
| 195 | Sobic.001G122400 | | | 1.97 | 1.54E−03 |
| 196 | Sobic.004G045400 | 2.22 | 3.33E−02 | 1.71 | 2.07E−03 |
| 197 | Sobic.003G322400 | | | | |
| 198 | Sobic.004G339200 | 3.19 | 7.54E−03 | | |
| 199 | Sobic.001G147100 | | | 2.12 | 9.23E−03 |
| 200 | Sobic.006G098500 | 2.26 | 9.50E−03 | | |
| 201 | Sobic.004G271400 | | | 2.85 | 9.74E−03 |
| 202 | Sobic.002G081600 | | | | |
| 203 | Sobic.002G355300 | 2.39 | 1.04E−02 | | |
| 204 | Sobic.010G005300 | | | 2.13 | 1.25E−02 |
| 205 | Sobic.001G105100 | | | 1.96 | 1.27E−02 |
| 206 | Sobic.001G281900 | | | 1.93 | 1.27E−02 |
| 207 | Sobic.008G098800 | | | 1.96 | 1.30E−02 |
| 208 | Sobic.001G541100 | | | | |
| 209 | Sobic.006G138100 | | | | |
| 210 | Sobic.010G173100 | | | | |
| 211 | Sobic.009G182600 | | | | |
| 212 | Sobic.004G323700 | | | | |
| 213 | Sobic.006G160200 | | | | |
| 214 | Sobic.003G332401 | | | | |
| 215 | Sobic.010G206200 | | | | |
| 216 | Sobic.004G145801 | | | | |
| 217 | Sobic.008G128600 | | | | |
| 218 | Sobic.006G252100 | | | | |
| 219 | Sobic.010G065400 | | | | |
| 220 | Sobic.003G109600 | | | | |
| 221 | Sobic.004G185600 | 2.13 | 3.28E−02 | | |
| 222 | Sobic.006G147000 | | | | |
| 223 | Sobic.001G016500 | | | | |
| 224 | Sobic.001G011000 | 2.12 | 3.65E−02 | | |
| 225 | Sobic.001G386700 | 5.2 | 4.05E−02 | | |
| 226 | Sobic.003G422900 | | | | |
| 227 | Sobic.001G447300 | | | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 228 | Sobic.010G251100 | | | | |
| 229 | Sobic.007G067700 | | | | |
| 230 | Sobic.007G188900 | 2.22 | 4.65E−02 | | |
| 231 | Sobic.004G040900 | | | | |
| 232 | Gene expression related-A151 down | | | | |
| 233 | Sobic.003G439900 | 0.23 | 1.59E−03 | 0.28 | 1.00E−07 |
| 234 | Sobic.008G108601 | | | 0.46 | 6.65E−04 |
| 235 | Sobic.007G102800 | | | 0.59 | 7.25E−04 |
| 236 | Sobic.009G072200 | | | | |
| 237 | Sobic.010G269600 | | | 0.68 | 1.27E−02 |
| 238 | Sobic.002G389600 | | | 0.65 | 1.27E−02 |
| 239 | Sobic.001G175300 | | | | |
| 240 | Sobic.009G244300 | | | | |
| 241 | Sobic.001G008500 | | | | |
| 242 | Sobic.007G011600 | | | | |
| 243 | Sobic.006G126900 | | | | |
| 244 | Sobic.009G135600 | 0.57 | 3.96E−02 | | |
| 245 | sRNA regulation of gene expression related-A151 up | | | | |
| 246 | Sobic.002G041400 | 6.17 | 2.19E−03 | 3.32 | 3.41E−05 |
| 247 | Sobic.001G054800 | | | 2.7 | 7.68E−03 |
| 248 | Sobic.009G216700 | | | 1.71 | 1.19E−03 |
| 249 | Sobic.001G289800 | 3 | 2.36E−02 | | |
| 250 | Sobic.001G536400 | 2.42 | 3.35E−02 | | |
| 251 | Sobic.001G094500 | 2.79 | 3.86E−02 | | |
| 252 | sRNA regulation of gene expression related-A151 down | | | | |
| 253 | Sobic.003G350100 | 0.15 | 2.91E−03 | 0.16 | 1.00E−07 |
| 254 | Sobic.003G347900 | | | 0.59 | 2.45E−04 |
| 255 | Sobic.001G522600 | | | 0.65 | 4.42E−04 |
| 256 | Sobic.003G330900 | | | | |
| 257 | Sobic.003G104000 | | | | |
| 258 | Growth and development related-A151 up | | | | |
| 259 | Sobic.004G093700 | 5.41 | 3.26E−04 | 4.58 | 1.00E−07 |
| 260 | Sobic.004G197600 | 5.11 | 9.05E−04 | 4.21 | 1.00E−07 |
| 261 | Sobic.010G172400 | 1.95 | 3.39E−02 | 1.86 | 1.14E−04 |
| 262 | Sobic.006G152600 | 2.09 | 7.45E−03 | 1.6 | 1.99E−04 |
| 263 | Sobic.002G148100 | | | 1.68 | 7.09E−04 |
| 264 | Sobic.004G025900 | | | 1.7 | 2.09E−03 |
| 265 | Sobic.003G049600 | | | 1.75 | 3.86E−03 |
| 266 | Sobic.001G046400 | 3.16 | 2.31E−02 | 2.06 | 9.15E−03 |
| 267 | Sobic.009G259200 | | | 1.95 | 9.74E−03 |
| 268 | Sobic.004G187900 | | | 1.46 | 1.15E−02 |
| 269 | Sobic.010G266300 | | | 1.61 | 1.36E−02 |
| 270 | Sobic.002G113800 | | | 1.63 | 1.48E−02 |
| 271 | Sobic.008G160400 | | | | |
| 272 | Sobic.004G190600 | | | | |
| 273 | Sobic.001G086600 | | | | |
| 274 | Sobic.010G097600 | 3.5 | 1.87E−02 | | |
| 275 | Sobic.003G250700 | | | | |
| 276 | Sobic.004G350300 | | | | |
| 277 | Sobic.006G050600 | 3.55 | 2.55E−02 | | |
| 278 | Sobic.001G398500 | 2.83 | 2.69E−02 | | |
| 279 | Sobic.003G334700 | | | | |
| 280 | Sobic.002G201900 | | | | |
| 281 | Sobic.001G119900 | 2.19 | 3.22E−02 | | |
| 282 | Sobic.005G187500 | | | | |
| 283 | Sobic.004G243800 | | | | |
| 284 | Sobic.002G175400 | 2.23 | 3.98E−02 | | |
| 285 | Sobic.007G019300 | 1.95 | 4.90E−02 | | |
| 286 | Growth and development related-A151 down | | | | |
| 287 | Sobic.009G132400 | 0.37 | 5.67E−03 | 0.45 | 1.00E−07 |
| 288 | Sobic.006G221300 | 0.19 | 3.84E−03 | 0.24 | 1.00E−07 |
| 289 | Sobic.001G195600 | 0.31 | 6.14E−03 | 0.21 | 1.00E−07 |
| 290 | Sobic.008G034400 | 0.46 | 1.84E−02 | 0.6 | 6.46E−05 |
| 291 | Sobic.007G011300 | | | 0.64 | 4.65E−04 |
| 292 | Sobic.004G351200 | | | 0.6 | 2.85E−03 |
| 293 | Sobic.004G215700 | 0.54 | 4.60E−02 | 0.65 | 3.57E−03 |
| 294 | Sobic.003G228900 | | | 0.67 | 1.15E−02 |
| 295 | Sobic.010G108600 | | | | |
| 296 | Sobic.003G371100 | | | 0.64 | 1.25E−02 |
| 297 | Sobic.003G445300 | | | 0.59 | 1.25E−02 |
| 298 | Sobic.001G091300 | 0.52 | 3.72E−02 | 0.67 | 1.27E−02 |
| 299 | Sobic.010G248200 | | | | |
| 300 | LOC110433098 | 0.5 | 1.92E−02 | | |
| 301 | Sobic.004G134600 | | | | |
| 302 | Sobic.002G220600 | 0.47 | 1.98E−02 | | |
| 303 | LOC8078215 | | | | |
| 304 | Sobic.001G363700 | | | | |

TABLE 4-continued

Chromosomal and functional anotations for differentially expressed genes (DEG) identified by microarrays that compared ovule transcripts of A151 with those of S264 for each stage separately and all stages combined.

| | | | | | |
|---|---|---|---|---|---|
| 305 | Sobic.001G497700 | | | | |
| 306 | Sobic.001G088100 | 0.52 | 3.58E−02 | | |
| 307 | Sobic.003G334700 | 0.58 | 3.66E−02 | | |
| 308 | Sobic.001G281600 | 0.55 | 3.66E−02 | | |
| 309 | Sobic.002G143300 | | | | |
| 310 | Sobic.003G173800 | | | | |
| 311 | Sobic.010G134400 | | | | |
| 312 | Sobic.003G427600 | | | | |
| 313 | Sobic.003G403500 | | | | |
| 314 | Other-A151 up | | | | |
| 315 | Sobic.010G094301 | 3.89 | 3.26E−04 | 3.27 | 1.00E−07 |
| 316 | Sobic.003G048500 | 3.26 | 6.78E−03 | 2.88 | 1.00E−07 |
| 317 | Sobic.004G208100 | 3.02 | 1.46E−02 | 2.55 | 1.00E−07 |
| 318 | Sobic.005G112632 | 2.12 | 1.86E−02 | 2.16 | 1.00E−07 |
| 319 | LOC110435809 | 2.46 | 5.03E−03 | 1.99 | 1.00E−07 |
| 320 | LOC110431211 | 2.02 | 2.26E−02 | 1.82 | 1.00E−07 |
| 321 | Sobic.002G254100 | | | 1.77 | 2.10E−05 |
| 322 | Sobic.004G136500 | | | 1.69 | 1.15E−04 |
| 323 | Sobic.004G331800 | | | 2.93 | 4.42E−04 |
| 324 | Sobic.004G007300 | | | 1.55 | 1.88E−03 |
| 325 | Sobic.001G541400 | | | | |
| 326 | Sobic.001G442200 | | | | |
| 327 | LOC110431017 | | | 1.5 | 8.52E−03 |
| 328 | MultiHit5375 | | | | |
| 329 | Sobic.003G029200 | 2.85 | 1.12E−02 | | |
| 330 | Sobic.001G381900 | | | 1.73 | 1.14E−02 |
| 331 | MultiHit7742 | | | 1.63 | 1.22E−02 |
| 332 | Sobic.003G140900 | | | 2.31 | 1.25E−02 |
| 333 | Sobic.001G121100 | 2.19 | 1.38E−02 | | |
| 334 | Sobic.001G143300 | | | 2.18 | 1.38E−02 |
| 335 | Sobic.002G364800 | 2.35 | 1.51E−02 | | |
| 336 | Sobic.003G088400 | | | | |
| 337 | Sobic.001G154400 | | | | |
| 338 | MultiHit5916 | | | | |
| 339 | MultiHit3601 | | | | |
| 340 | Sobic.003G113500 | 3.12 | 2.91E−02 | | |
| 341 | Sobic.001G087700 | 1.8 | 2.93E−02 | | |
| 342 | LOC8081614 | | | | |
| 343 | LOC110429578 | 1.99 | 4.21E−02 | | |
| 344 | Sobic.005G228700 | 2.26 | 4.46E−02 | | |
| 345 | Sobic.004G134900 | 1.75 | 4.72E−02 | | |
| 346 | Sobic.001G012200 | 2.26 | 4.79E−02 | | |
| 347 | Sobic.001G193100 | 3.71 | 4.83E−02 | | |
| 348 | Other-A151 down | | | | |
| 349 | Sobic.002G200900 | 0.47 | 2.43E−02 | 0.54 | 1.00E−07 |
| 350 | Sobic.001G455600 | 0.5 | 4.85E−02 | 0.49 | 1.00E−07 |
| 351 | Sobic.008G026200 | 0.43 | 1.63E−02 | 0.47 | 1.00E−07 |
| 352 | Sobic.009G003300 | 0.39 | 1.50E−02 | 0.45 | 1.00E−07 |
| 353 | Sobic.004G105500 | 0.36 | 4.67E−03 | 0.39 | 1.00E−07 |
| 354 | Sobic.004G324800 | | | 0.54 | 1.51E−04 |
| 355 | Sobic.002G191800 | | | 0.48 | 2.65E−04 |
| 356 | Sobic.002G171300 | 0.39 | 7.02E−03 | 0.51 | 2.79E−04 |
| 357 | Sobic.001G298700 | | | 0.66 | 3.68E−04 |
| 358 | Sobic.006G206200 | 0.5 | 2.71E−02 | 0.62 | 6.16E−04 |
| 359 | Sobic.010G016500 | | | 0.63 | 7.52E−04 |
| 360 | Sobic.006G052800 | | | 0.64 | 1.14E−03 |
| 361 | Sobic.001G536800 | | | 0.61 | 1.73E−03 |
| 362 | Sobic.001G146301 | | | 0.61 | 1.79E−03 |
| 363 | Sobic.002G151300 | 0.51 | 3.88E−02 | 0.6 | 2.85E−03 |
| 364 | Sobic.001G098600 | | | 0.47 | 6.07E−03 |
| 365 | Sobic.001G072700 | | | 0.58 | 6.56E−03 |
| 366 | MultiHit113 | | | | |
| 367 | Sobic.001G204700 | | | 0.65 | 8.18E−03 |
| 368 | Sobic.001G051800 | | | | |
| 369 | Sobic.006G122500 | | | 0.68 | 8.52E−03 |
| 370 | Sobic.009G224400 | | | | |
| 371 | Sobic.005G021200 | | | 0.68 | 1.36E−02 |
| 372 | Sobic.005G084300 | | | | |
| 373 | Sobic.004G162200 | | | | |
| 374 | Sobic.003G018000 | 0.35 | 1.56E−02 | | |
| 375 | Sobic.006G258800 | | | | |
| 376 | Sobic.001G103600 | | | | |
| 377 | Sobic.009G252100 | | | | |
| 378 | Sobic.004G019400 | | | | |
| 379 | Sobic.002G330800 | | | | |
| 380 | MultiHit10711 | 0.45 | 2.60E−02 | | |
| 381 | Sobic.005G143200 | 0.45 | 3.16E−02 | | |

TABLE 4-continued

Chromosomal and functional anotations for differentially expressed genes (DEG) identified by microarrays that compared ovule transcripts of A151 with those of S264 for each stage separately and all stages combined.

| | |
|---|---|
| 382 | Sobic.006G219500 |
| 383 | Sobic.002G365550 |
| 384 | Sobic.006G066600 |
| 385 | Sobic.010G109600 |
| 386 | Sobic.009G007700 |
| 387 | Sobic.003G206300 |
| 388 | Sobic.004G272700 |
| 389 | Sobic.001G182850 |
| 390 | Sobic.009G186400 |

TABLE 5

Enriched GO terms (FDR ≤ 0.05) based on average A151 to S264 expression ratios (all detected genes per GO category) for each stage separately and for all stages combined. Significant GO terms were not detected at the meiocyte stage.

| Line no. | GO term | Genes | Early MMC Up (+) or down (−) in A151 | Early MMC P value | Early MMC FDR | Mid ES Up (+) or down (−) in A151 | Mid ES P value | Mid ES FDR | All stages combined Up (+) or down (−) in A151 | All stages combined P value | All stages combined FDR |
|---|---|---|---|---|---|---|---|---|---|---|---|
| 1 | Biological Process | | | | | | | | | | |
| 2 | Cellular protein and macromolecule processes | | | | | | | | | | |
| 3 | cellular protein metabolic process (GO: 0044267) | 884 | + | 7.24E-06 | 1.51E-03 | | | | + | 1.96E-04 | 2.84E-02 |
| 4 | cellular macromolecule metabolic process (GO: 0044260) | 1157 | + | 2.94E-05 | 4.26E-03 | | | | + | 1.86E-04 | 2.98E-02 |
| 5 | macromolecule metabolic process (GO: 0043170) | 1477 | + | 5.50E-05 | 6.93E-03 | | | | | | |
| 6 | protein metabolic process (GO: 0019538) | 974 | + | 1.01E-05 | 1.87E-03 | | | | + | 1.14E-04 | 2.27E-02 |
| 7 | organonitrogen compound metabolic process (GO: 1901564) | 1363 | + | 1.11E-04 | 1.26E-02 | | | | + | 1.19E-04 | 2.27E-02 |
| 8 | nitrogen compound metabolic process | 1790 | + | 1.93E-04 | 1.97E-02 | | | | | | |
| 9 | cellular macromolecule biosynthetic process (GO: 0034645) | 404 | + | 3.29E-08 | 2.62E-05 | + | 3.99E-06 | 3.18E-03 | + | 1.21E-08 | 9.62E-06 |
| 10 | macromolecule biosynthetic process | 416 | + | 6.31E-08 | 3.36E-05 | + | 1.90E-05 | 1.01E-02 | + | 6.39E-08 | 4.37E-05 |
| 11 | peptide biosynthetic process (GO: 0043043) | 204 | + | 1.84E-12 | 8.82E-09 | + | 4.50E-08 | 2.16E-04 | + | 2.09E-11 | 9.99E-08 |
| 12 | peptide metabolic process (GO: 0006518) | 228 | + | 5.00E-12 | 7.98E-09 | + | 4.03E-07 | 4.82E-04 | + | 5.94E-11 | 9.49E-08 |
| 13 | cellular amide metabolic process (GO: 0043603) | 277 | + | 5.88E-10 | 5.63E-07 | + | 1.69E-06 | 1.62E-03 | + | 1.86E-09 | 1.78E-06 |
| 14 | cellular nitrogen compound metabolic process (GO: 0034641) | 942 | + | 4.22E-06 | 9.62E-04 | | | | + | 1.06E-05 | 4.63E-03 |
| 15 | organonitrogen compound biosynthetic process (GO: 1901566) | 510 | + | 2.47E-06 | 6.96E-04 | + | 2.69E-05 | 1.29E-02 | + | 4.22E-07 | 2.25E-04 |
| 16 | amide biosynthetic process (GO: 0043604) | 232 | + | 8.70E-11 | 1.04E-07 | + | 1.19E-07 | 1.90E-04 | + | 3.75E-10 | 4.49E-07 |
| 17 | cellular nitrogen compound biosynthetic process (GO: 0044271) | 449 | + | 4.85E-07 | 2.32E-04 | + | 1.88E-05 | 1.12E-02 | + | 8.44E-08 | 5.05E-05 |
| 18 | Gene expression | | | | | | | | | | |
| 19 | gene expression (GO: 0010467) | 531 | + | 5.32E-08 | 3.18E-05 | + | 4.50E-08 | 1.08E-04 | + | 2.05E-06 | 9.81E-04 |
| 20 | translation (GO: 0006412) | | | | | | | | | + | 2.09E-11 | 4.99E-08 |
| 21 | Intracellular transport and localization | | | | | | | | | | |
| 22 | cellular protein localization (GO: 0034613) | 246 | + | 2.76E-05 | 4.13E-03 | | | | + | 1.77E-04 | 2.93E-02 |
| 23 | protein localization (GO: 0008104) | 290 | + | 1.44E-05 | 2.46E-03 | | | | + | 1.03E-04 | 2.23E-02 |
| 24 | macromolecule localization (GO: 0033036) | 355 | + | 2.26E-04 | 2.25E-02 | | | | | | |
| 25 | cellular macromolecule localization (GO: 0070727) | 255 | + | 3.96E-05 | 5.42E-03 | | | | + | 2.23E-04 | 3.14E-02 |
| 26 | intracellular transport (GO: 0046907) | 259 | + | 2.56E-04 | 2.40E-02 | | | | | | |
| 27 | establishment of localization in cell (GO: 0051649) | 272 | + | 2.27E-04 | 2.21E-02 | | | | | | |
| 28 | protein transport (GO: 0015031) | 258 | + | 2.95E-06 | 7.85E-04 | | | | + | 2.98E-05 | 9.51E-03 |
| 29 | establishment of protein localization (GO: 0045184) | 260 | + | 3.67E-06 | 8.77E-04 | | | | + | 3.69E-05 | 1.10E-02 |
| 30 | peptide transport (GO: 0015833) | 277 | + | 1.84E-04 | 1.92E-02 | | | | | | |
| 31 | amide transport (GO: 0042886) | 285 | + | 5.19E-04 | 4.28E-02 | | | | | | |
| 32 | Ribosome complex processes | | | | | | | | | | |
| 33 | ribonucleoprotein complex assembly | 64 | + | 9.84E-07 | 3.62E-04 | | | | + | 1.35E-04 | 2.40E-02 |
| 34 | ribonucleoprotein complex subunit organization (GO: 0071826) | 66 | + | 4.52E-06 | 9.84E-04 | | | | | | |
| 35 | protein-containing complex subunit organization (GO: 0043933) | 202 | + | 2.04E-06 | 6.51E-04 | | | | | | |

TABLE 5-continued

Enriched GO terms (FDR ≤ 0.05) based on average A151 to S264 expression ratios (all detected genes per GO category) for each stage separately and for all stages combined. Significant GO terms were not detected at the meiocyte stage.

| Line no. | GO term | Genes | Early MMC Up (+) or down (−) in A151 | Early MMC P value | Early MMC FDR | Mid ES Up (+) or down (−) in A151 | Mid ES P value | Mid ES FDR | All stages combined Up (+) or down (−) in A151 | All stages combined P value | All stages combined FDR |
|---|---|---|---|---|---|---|---|---|---|---|---|
| 36 | cellular component organization (GO: 0016043) | 808 | + | 1.15E−04 | 1.28E−02 | | | | | | |
| 37 | cellular component organization or biogenesis (GO: 0071840) | 923 | + | 4.39E−05 | 5.84E−03 | | | | | | |
| 38 | ribonucleoprotein complex biogenesis | 170 | + | 1.37E−06 | 4.68E−04 | | | | | | |
| 39 | cellular component biogenesis (GO: 0044085) | 408 | + | 9.69E−06 | 1.85E−03 | | | | + | 1.80E−05 | 6.17E−03 |
| 40 | cellular protein-containing complex assembly (GO: 0034622) | 147 | + | 3.51E−08 | 2.40E−05 | | | | + | 1.44E−05 | 5.75E−03 |
| 41 | protein-containing complex assembly | 172 | + | 8.69E−07 | 3.46E−04 | | | | + | 9.29E−05 | 2.22E−02 |
| 42 | cellular component assembly (GO: 0022607) | 243 | + | 3.03E−05 | 4.27E−03 | | | | + | 9.88E−05 | 2.25E−02 |
| 43 | ribosomal large subunit biogenesis (GO: 0042273) | 31 | + | 2.13E−05 | 3.28E−03 | | | | | | |
| 44 | ribosome biogenesis (GO: 0042254) | 133 | + | 1.87E−05 | 2.98E−03 | | | | | | |
| 45 | ribosome assembly (GO: 0042255) | 25 | + | 5.37E−07 | 2.34E−04 | | | | | | |
| 46 | organelle assembly (GO: 0070925) | 52 | + | 2.52E−04 | 2.41E−02 | | | | | | |
| 47 | organelle organization (GO: 0006996) | 530 | + | 4.10E−04 | 3.57E−02 | | | | | | |
| 48 | Proteasomal processes | | | | | | | | | | |
| 49 | proteasomal protein catabolic process (GO: 0010498) | 82 | + | 1.58E−04 | 1.68E−02 | | | | | | |
| 50 | proteolysis involved in cellular protein catabolic process (GO: 0051603) | 193 | + | 8.41E−05 | 1.01E−02 | | | | + | 3.53E−04 | 4.69E−02 |
| 51 | proteolysis (GO: 0006508) | 318 | + | 3.56E−04 | 3.21E−02 | | | | | | |
| 52 | cellular protein catabolic process (GO: 0044257) | 198 | + | 5.10E−05 | 6.60E−03 | | | | + | 1.94E−04 | 2.90E−02 |
| 53 | cellular macromolecule catabolic process (GO: 0044265) | 248 | + | 4.97E−04 | 4.18E−02 | | | | | | |
| 54 | macromolecule catabolic process (GO: 0009057) | 291 | + | 4.26E−04 | 3.64E−02 | | | | + | 1.71E−05 | 6.29E−03 |
| 55 | protein catabolic process (GO: 0030163) | 218 | + | 1.28E−05 | 2.26E−03 | | | | + | 7.58E−05 | 1.91E−02 |
| 56 | organonitrogen compound catabolic process (GO: 1901565) | 291 | + | 1.25E−04 | 1.37E−02 | | | | | | |
| 57 | ubiquitin-dependent protein catabolic process (GO: 0006511) | 156 | + | 1.76E−05 | 2.91E−03 | | | | | | |
| 58 | modification-dependent protein catabolic process (GO: 0019941) | 162 | + | 2.23E−06 | 6.67E−04 | | | | + | 5.23E−05 | 1.39E−02 |
| 59 | modification-dependent macromolecule catabolic process (GO: 0043632) | 165 | + | 8.00E−06 | 1.60E−03 | | | | + | 1.14E−04 | 2.37E−02 |
| 60 | Chemotaxis processes | | | | | | | | | | |
| 61 | positive chemotaxis (GO: 0050918) | 9 | − | 6.44E−04 | 5.06E−02 | | | | | | |
| 62 | chemotaxis (GO: 0006935) | 9 | − | 6.44E−04 | 4.90E−02 | | | | | | |
| 63 | taxis (GO: 0042330) | 9 | − | 6.44E−04 | 5.14E−02 | | | | | | |
| 64 | Molecular Function | | | | | | | | | | |
| 65 | Structural molecule activity | | | | | | | | | | |
| 66 | structural molecule activity (GO: 0005198) | 162 | + | 0.00E+00 | 0.00E+00 | + | 1.54E−09 | 3.56E−06 | | | |
| 67 | Nucleic acid binding | | | | | | | | | | |
| 68 | RNA binding (GO: 0003723) | 433 | + | 5.51E−07 | 3.18E−04 | | | | | | |
| 69 | nucleic acid binding (GO: 0003676) | 859 | + | 8.84E−05 | 1.70E−02 | | | | | | |
| 70 | organic cyclic compound binding (GO: 0097159) | 1559 | + | 1.35E−05 | 6.21E−03 | | | | | | |
| 71 | binding (GO: 0005488) | 2792 | + | 3.65E−04 | 4.21E−02 | | | | | | |

TABLE 5-continued

Enriched GO terms (FDR ≤ 0.05) based on average A151 to S264 expression ratios (all detected genes per GO category) for each stage separately and for all stages combined. Significant GO terms were not detected at the meiocyte stage.

| Line no. | GO term | Genes | Early MMC Up (+) or down (−) in A151 | Early MMC P value | Early MMC FDR | Mid ES Up (+) or down (−) in A151 | Mid ES P value | Mid ES FDR | All stages combined Up (+) or down (−) in A151 | All stages combined P value | All stages combined FDR |
|---|---|---|---|---|---|---|---|---|---|---|---|
| 72 | heterocyclic compound binding (GO: 1901363) | 1554 | + | 1.79E-05 | 6.90E-03 | | | | | | |
| 73 | guanyl ribonucleotide binding (GO: 0032561) | 87 | + | 9.00E-05 | 1.60E-02 | | | | | | |
| 74 | guanyl nucleotide binding (GO: 0019001) | 87 | + | 9.00E-05 | 1.22E-02 | | | | | | |
| 75 | purine ribonucleoside binding (GO: 0032550) | 87 | + | 9.00E-05 | 1.48E-02 | | | | | | |
| 76 | purine nucleoside binding (GO: 0001883) | 87 | + | 9.00E-05 | 1.39E-02 | | | | | | |
| 77 | nucleoside binding (GO: 0001882) | 89 | + | 8.46E-05 | 1.78E-02 | | | | | | |
| 78 | ribonucleoside binding (GO: 0032549) | 89 | + | 8.46E-05 | 1.95E-02 | | | | | | |
| 79 | Cellular Component | | | | | | | | | | |
| 80 | Cytosole components | | | | | | | | | | |
| 81 | cytosolic part (GO: 0044445) | 133 | + | 1.11E-16 | 3.29E-14 | | 2.38E-10 | 2.11E-07 | | | |
| 82 | cytosol (GO: 0005829) | 981 | + | 4.52E-10 | 3.35E-08 | | 3.02E-06 | 4.47E-04 | | | |
| 83 | Ribosome components | | | | | | | | | | |
| 84 | large ribosomal subunit (GO: 0015934) | 58 | + | 7.72E-10 | 4.90E-08 | | 4.70E-06 | 5.96E-04 | | | |
| 85 | ribosomal subunit (GO: 0044391) | 99 | + | 2.22E-16 | 4.93E-14 | | 2.12E-09 | 6.28E-07 | | | |
| 86 | ribonucleoprotein complex (GO: 1990904) | 331 | + | 2.13E-13 | 3.15E-11 | | 2.99E-04 | 1.66E-02 | | | |
| 87 | protein-containing complex (GO: 0032991) | 1089 | + | 0.00E+00 | 0.00E+00 | | 8.43E-06 | 9.35E-04 | | | |
| 88 | intracellular organelle part (GO: 0044446) | 1964 | + | 1.59E-07 | 7.04E-06 | | | | | | |
| 89 | organelle part (GO: 0044422) | 1966 | + | 1.27E-07 | 6.26E-06 | | | | | | |
| 90 | ribosome (GO: 0005840) | 155 | + | 1.55E-15 | 2.76E-13 | | 7.61E-09 | 1.69E-06 | | | |
| 91 | intracellular non-membrane-bounded organelle (GO: 0043232) | 537 | + | 2.36E-11 | 2.99E-09 | | 4.63E-05 | 4.56E-03 | | | |
| 92 | non-membrane-bounded organelle (GO: 0043228) | 537 | + | 2.36E-11 | 2.62E-09 | | 4.63E-05 | 4.11E-03 | | | |
| 93 | cytosolic ribosome (GO: 0022626) | 112 | + | 1.11E-16 | 4.93E-14 | | 4.14E-10 | 1.84E-07 | | | |
| 94 | small ribosomal subunit (GO: 0015935) | 41 | + | 3.10E-08 | 1.84E-06 | | 9.68E-05 | 7.16E-03 | | | |
| 95 | Nuclear components | | | | | | | | | | |
| 96 | nuclear lumen (GO: 0031981) | 351 | + | 2.41E-07 | 1.02E-05 | | | | | | |
| 97 | intracellular organelle lumen (GO: 0070013) | 441 | + | 1.38E-10 | 1.36E-08 | | 2.18E-04 | 1.49E-02 | | | |
| 98 | organelle lumen (GO: 0043233) | 441 | + | 1.38E-10 | 1.12E-08 | | 2.18E-04 | 1.29E-02 | | | |
| 99 | membrane-enclosed lumen (GO: 0031974) | 441 | + | 1.38E-10 | 1.23E-08 | | 2.18E-04 | 1.38E-02 | | | |
| 100 | nuclear part (GO: 0044428) | 470 | + | 4.40E-07 | 1.50E-05 | | | | | | |
| 101 | Mitochondrial components | | | | | | | | | | |
| 102 | mitochondrial respirasome (GO: 0005746) | 43 | + | 2.85E-07 | 1.15E-05 | | | | | | |
| 103 | mitochondrial inner membrane (GO: 0005743) | 118 | + | 4.56E-04 | 1.01E-02 | | | | | | |
| 104 | mitochondrial membrane (GO: 0031966) | 136 | + | 2.19E-04 | 5.56E-03 | | | | | | |
| 105 | organelle membrane (GO: 0031090) | 700 | + | 1.62E-03 | 2.94E-02 | | | | | | |
| 106 | mitochondrial envelope (GO: 0005740) | 145 | + | 3.31E-04 | 7.95E-03 | | | | | | |
| 107 | mitochondrial part (GO: 0044429) | 209 | + | 2.92E-07 | 1.08E-05 | + | 4.81E-04 | 2.51E-02 | | | |
| 108 | respirasome (GO: 0070469) | 50 | + | 5.51E-06 | 1.75E-04 | | | | | | |
| 109 | mitochondrial membrane part (GO: 0044455) | 90 | + | 4.81E-06 | 1.58E-04 | | | | | | |
| 110 | respiratory chain complex I (GO: 0045271) | 32 | + | 8.61E-06 | 2.47E-04 | | | | | | |
| 111 | respiratory chain complex (GO: 0098803) | 43 | + | 2.85E-07 | 1.10E-05 | | | | | | |
| 112 | membrane protein complex (GO: 0098796) | 258 | + | 2.82E-05 | 7.36E-04 | | | | | | |
| 113 | NADH dehydrogenase complex (GO: 0030964) | 32 | + | 8.61E-06 | 2.64E-04 | | | | | | |
| 114 | catalytic complex (GO: 1902494) | 370 | + | 9.12E-06 | 2.53E-04 | | | | | | |

TABLE 5-continued

Enriched GO terms (FDR ≤ 0.05) based on average A151 to S264 expression ratios (all detected genes per GO category) for each stage separately and for all stages combined. Significant GO terms were not detected at the meiocyte stage.

| Line no. | GO term | Genes | Early MMC | | | Mid ES | | | All stages combined | | |
|---|---|---|---|---|---|---|---|---|---|---|---|
| | | | Up (+) or down (−) in A151 | P value | FDR | Up (+) or down (−) in A151 | P value | FDR | Up (+) or down (−) in A151 | P value | FDR |
| 115 | inner mitochondrial membrane protein complex (GO: 0098800) | 66 | + | 3.31E-07 | 1.18E-05 | | | | | | |
| 116 | mitochondrial protein complex (GO: 0098798) | 86 | + | 1.27E-07 | 5.94E-06 | | | | | | |
| 117 | oxidoreductase complex (GO: 1990204) | 60 | + | 4.38E-04 | 9.98E-03 | | | | | | |
| 118 | Symplast components | | | | | | | | | | |
| 119 | symplast (GO: 0055044) | 338 | + | 5.23E-04 | 1.08E-02 | | | | | | |
| 120 | Cell junction components | | | | | | | | | | |
| 121 | cell-cell junction (GO: 0005911) | 338 | + | 5.23E-04 | 1.11E-02 | | | | | | |
| 122 | cell junction (GO: 0030054) | 338 | + | 5.23E-04 | 1.06E-02 | | | | | | |
| 123 | Proteasome components | | | | | | | | | | |
| 124 | endopeptidase complex (GO: 1905369) | 39 | + | 7.40E-04 | 1.43E-02 | | | | | | |
| 125 | peptidase complex (GO: 1905368) | 45 | + | 4.19E-04 | 9.79E-03 | | | | | | |
| 126 | Endomembrane components | | | | | | | | | | |
| 127 | endomembrane system (GO: 0012505) | 792 | + | 3.30E-04 | 8.13E-03 | | | | | | |

TABLE 6

GO terms overrepresented (FDR ≤ 0.05) by DEG upregulated in A151
for each stage separately and for all stages combined.
Significant GO terms were not detected at the meiocyte stage.

| | | Early MMC | | | |
|---|---|---|---|---|---|
| Line no. | GO term | Obs. | Exp. | Raw P value | FDR |
| 1 | Biological Process | | | | |
| 2 | Response to Stimuli | | | | |
| 3 | response to cytokinin | 8 | 0.9 | 2.78E−06 | 3.29E−03 |
| 4 | negative regulation of response to stimulus | | | | |
| 5 | Gene expression | | | | |
| 6 | translation | 12 | 2.0 | 1.09E−06 | 3.21E−03 |
| 7 | cellular protein metabolic process | 25 | 10.5 | 4.42E−05 | 2.01E−02 |
| 8 | cellular macromolecule metabolic process | 29 | 14.0 | 1.21E−04 | 3.77E−02 |
| 9 | cellular metabolic process | 48 | 26.1 | 3.24E−06 | 3.20E−03 |
| 10 | cellular process | 61 | 37.5 | 2.46E−06 | 3.64E−03 |
| 11 | metabolic process | 49 | 30.0 | 7.47E−05 | 2.45E−02 |
| 12 | protein metabolic process | 26 | 11.6 | 6.57E−05 | 2.29E−02 |
| 13 | organonitrogen compound metabolic process | 32 | 15.7 | 4.72E−05 | 1.99E−02 |
| 14 | cellular macromolecule biosynthetic process | 15 | 4.4 | 3.82E−05 | 1.88E−02 |
| 15 | macromolecule biosynthetic process | 15 | 4.6 | 5.45E−05 | 2.15E−02 |
| 16 | peptide biosynthetic process | 12 | 2.1 | 1.19E−06 | 2.34E−03 |
| 17 | peptide metabolic process | 12 | 2.3 | 4.30E−06 | 3.18E−03 |
| 18 | cellular amide metabolic process | 13 | 2.8 | 4.57E−06 | 3.00E−03 |
| 19 | cellular nitrogen compound metabolic process | 25 | 10.8 | 6.12E−05 | 2.26E−02 |
| 20 | organonitrogen compound biosynthetic process | 17 | 5.0 | 1.12E−05 | 6.00E−03 |
| 21 | amide biosynthetic process | 13 | 2.3 | 5.07E−07 | 3.00E−03 |
| 22 | cellular nitrogen compound biosynthetic process | 17 | 4.6 | 3.67E−06 | 3.10E−03 |
| 23 | gene expression | 18 | 5.5 | 9.78E−06 | 5.78E−03 |
| 24 | Molecular Function | | | | |
| 25 | Ribosome function | | | | |
| 26 | structural constituent of ribosome | 9 | 1.3 | 8.20E−06 | 1.26E−02 |
| 27 | structural molecule activity | 10 | 1.8 | 1.77E−05 | 1.81E−02 |
| 28 | Binding | | | | |
| 29 | binding | 63 | 36.3 | 1.03E−07 | 3.15E−04 |
| 30 | Cellular Component | | | | |
| 31 | Ribosome components | | | | |
| 32 | cytosolic small ribosomal subunit | 6 | 0.4 | 3.20E−06 | 5.72E−04 |
| 33 | small ribosomal subunit | 7 | 0.5 | 6.93E−07 | 3.71E−04 |
| 34 | ribosomal subunit | 9 | 1.2 | 3.31E−06 | 5.07E−04 |
| 35 | ribonucleoprotein complex | 13 | 3.3 | 2.97E−05 | 2.12E−03 |
| 36 | protein-containing complex | 28 | 11.5 | 5.58E−06 | 7.48E−04 |
| 37 | cytoplasmic part | 64 | 44.9 | 1.76E−04 | 7.27E−03 |
| 38 | cytoplasm | 70 | 53.2 | 8.99E−04 | 3.44E−02 |
| 39 | intracellular organelle part | 41 | 19.6 | 8.84E−07 | 3.16E−04 |
| 40 | organelle part | 41 | 19.6 | 9.02E−07 | 2.42E−04 |
| 41 | ribosome | 10 | 1.7 | 9.60E−06 | 9.36E−04 |
| 42 | intracellular non-membrane-bounded organelle | 17 | 6.1 | 1.13E−04 | 5.03E−03 |
| 43 | non-membrane-bounded organelle | 17 | 6.1 | 1.13E−04 | 4.83E−03 |
| 44 | cytosolic ribosome | 9 | 1.1 | 2.57E−06 | 5.52E−04 |
| 45 | cytosolic part | 9 | 1.3 | 7.03E−06 | 8.37E−04 |
| 46 | cytosol | 35 | 8.4 | 1.12E−13 | 1.20E−10 |
| 47 | Mitochondrial components | | | | |
| 48 | respirasome | 4 | 0.5 | 1.30E−03 | 4.63E−02 |
| 49 | membrane | 46 | 28.4 | 2.15E−04 | 8.54E−03 |
| 50 | mitochondrial part | 8 | 2.0 | 9.26E−04 | 3.42E−02 |
| 51 | Vacuole components | | | | |
| 52 | vacuolar membrane | 10 | 2.3 | 1.08E−04 | 5.27E−03 |
| 53 | whole membrane | 13 | 3.5 | 5.40E−05 | 2.89E−03 |
| 54 | vacuolar part | 10 | 2.3 | 1.12E−04 | 5.24E−03 |
| 55 | vacuole | 15 | 4.0 | 1.13E−05 | 9.34E−04 |
| 56 | bounding membrane of organelle | 15 | 4.6 | 5.40E−05 | 2.76E−03 |
| 57 | organelle membrane | 19 | 6.6 | 2.71E−05 | 2.07E−03 |
| 58 | Plasma membrane components | | | | |
| 59 | plasmodesma | 13 | 3.5 | 4.81E−05 | 3.22E−03 |
| 60 | symplast | 13 | 3.5 | 4.81E−05 | 3.03E−03 |
| 61 | cell-cell junction | 13 | 3.5 | 4.91E−05 | 2.92E−03 |
| 62 | cell junction | 13 | 3.5 | 4.91E−05 | 2.77E−03 |
| 63 | plasma membrane | 30 | 13.0 | 8.41E−06 | 9.01E−04 |
| 64 | cell periphery | 33 | 15.4 | 1.06E−05 | 9.48E−04 |
| 65 | Nuclear components | | | | |
| 66 | nucleolus | | | | |
| 67 | nuclear lumen | | | | |
| 68 | intracellular organelle lumen | | | | |
| 69 | organelle lumen | | | | |
| 70 | membrane-enclosed lumen | | | | |
| 71 | organelle part | | | | |

TABLE 6-continued

GO terms overrepresented (FDR ≤ 0.05) by DEG upregulated in A151
for each stage separately and for all stages combined.
Significant GO terms were not detected at the meiocyte stage.

| | |
|---|---|
| 72 | Chloroplast components |
| 73 | chloroplast part |
| 74 | plastid part |

| Line no. | Mid ES | | | | All stages combined | | | |
|---|---|---|---|---|---|---|---|---|
| | Obs. | Exp. | Raw P value | FDR | Obs. | Exp. | Raw P value | FDR |
| 1 | | | | | | | | |
| 2 | | | | | | | | |
| 3 | | | | | | | | |
| 4 | 6 | 0.5 | 1.52E−05 | 4.48E−02 | | | | |
| 5 | | | | | | | | |
| 6 | | | | | | | | |
| 7 | | | | | | | | |
| 8 | | | | | | | | |
| 9 | | | | | | | | |
| 10 | | | | | | | | |
| 11 | | | | | | | | |
| 12 | | | | | | | | |
| 13 | | | | | | | | |
| 14 | | | | | | | | |
| 15 | | | | | | | | |
| 16 | | | | | | | | |
| 17 | | | | | | | | |
| 18 | | | | | | | | |
| 19 | | | | | | | | |
| 20 | | | | | | | | |
| 21 | | | | | | | | |
| 22 | | | | | | | | |
| 23 | | | | | | | | |
| 24 | | | | | | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| 31 | | | | | | | | |
| 32 | | | | | | | | |
| 33 | | | | | | | | |
| 34 | | | | | | | | |
| 35 | | | | | | | | |
| 36 | | | | | 20 | 8.4 | 1.67E−04 | 1.63E−02 |
| 37 | | | | | 52 | 32.9 | 9.76E−06 | 1.74E−03 |
| 38 | | | | | 55 | 39.0 | 1.63E−04 | 1.74E−02 |
| 39 | | | | | 36 | 14.3 | 1.44E−08 | 1.54E−05 |
| 40 | | | | | | | | |
| 41 | | | | | | | | |
| 42 | | | | | | | | |
| 43 | | | | | | | | |
| 44 | | | | | | | | |
| 45 | | | | | | | | |
| 46 | | | | | 18 | 6.1 | 2.75E−05 | 4.21E−03 |
| 47 | | | | | | | | |
| 48 | | | | | | | | |
| 49 | | | | | | | | |
| 50 | | | | | 7 | 1.5 | 6.67E−04 | 4.47E−02 |
| 51 | | | | | | | | |
| 52 | | | | | | | | |
| 53 | | | | | | | | |
| 54 | | | | | | | | |
| 55 | | | | | | | | |
| 56 | | | | | | | | |
| 57 | | | | | | | | |
| 58 | | | | | | | | |
| 59 | | | | | | | | |
| 60 | | | | | | | | |
| 61 | | | | | | | | |
| 62 | | | | | | | | |
| 63 | | | | | 22 | 9.6 | 1.50E−04 | 1.79E−02 |
| 64 | | | | | 24 | 11.3 | 2.36E−04 | 2.11E−02 |
| 65 | | | | | | | | |
| 66 | | | | | 8 | 1.2 | 3.43E−05 | 4.60E−03 |
| 67 | | | | | 10 | 2.7 | 3.85E−04 | 3.18E−02 |

TABLE 6-continued

GO terms overrepresented (FDR ≤ 0.05) by DEG upregulated in A151
for each stage separately and for all stages combined.
Significant GO terms were not detected at the meiocyte stage.

| | | | | |
|---|---|---|---|---|
| 68 | 15 | 3.3 | 9.43E−07 | 3.37E−04 |
| 69 | 15 | 3.3 | 9.43E−07 | 2.02E−04 |
| 70 | 15 | 3.3 | 9.43E−07 | 2.53E−04 |
| 71 | 36 | 14.4 | 1.48E−08 | 7.92E−06 |
| 72 | | | | |
| 73 | 12 | 3.8 | 4.26E−04 | 3.26E−02 |
| 74 | 12 | 3.9 | 5.00E−04 | 3.57E−02 |

TABLE 7

GO terms overrepresented (FDR ≤ 0.05) by DEG downregulated in A151 for each stage separately and for all stages combined.
Significant GO terms were not detected across stages.

| Line no. | GO term | Early MMC | | | | Meiocyte | | | | Mid ES | | | |
|---|---|---|---|---|---|---|---|---|---|---|---|---|---|
| | | Obs. | Exp. | Raw P value | FDR | Obs. | Exp. | Raw P value | FDR | Obs. | Exp. | Raw P value | FDR |
| 1 | Cellular Component | | | | | | | | | | | | |
| 2 | Chloroplast component | | | | | | | | | | | | |
| 3 | chloroplast | 36 | 17.3 | 5.71E−06 | 3.06E−03 | | | | | | | | |
| 4 | plastid | 37 | 17.5 | 2.85E−06 | 3.05E−03 | | | | | | | | |
| 5 | cytoplasm | 66 | 47.9 | 1.32E−04 | 4.72E−02 | | | | | | | | |
| 6 | Vacuole component | | | | | | | | | | | | |
| 7 | vacuolar membrane | | | | | 4 | 0.2 | 4.97E−05 | 5.33E−02 | | | | |
| 8 | vacuolar part | | | | | 4 | 0.2 | 5.07E−05 | 2.72E−02 | | | | |
| 9 | Mitosis components | | | | | | | | | | | | |
| 10 | nucleosome | | | | | 2 | 0.0 | 1.38E−04 | 4.92E−02 | | | | |
| 11 | DNA packaging complex | | | | | 2 | 0.0 | 1.67E−04 | 4.49E−02 | | | | |
| 12 | preprophase band | | | | | | | | | 2 | 0.0 | 1.68E−04 | 4.50E−02 |
| 13 | microtubule cytoskeleton | | | | | | | | | 4 | 0.3 | 1.46E−04 | 5.21E−02 |
| 14 | cytoskeletal part | | | | | | | | | 4 | 0.3 | 2.46E−04 | 5.27E−02 |
| 15 | intracellular organelle part | | | | | | | | | 14 | 5.4 | 2.65E−04 | 4.74E−02 |
| 16 | organelle part | | | | | | | | | 14 | 5.4 | 2.68E−04 | 4.11E−02 |
| 17 | cortical microtubule cytoskeleton | | | | | | | | | 2 | 0.0 | 3.69E−04 | 4.94E−02 |
| 18 | phragmoplast | | | | | | | | | 4 | 0.1 | 1.78E−06 | 1.91E−03 |
| 19 | spindle | | | | | | | | | 3 | 0.1 | 7.28E−05 | 3.90E−02 |

TABLE 8

RIL framework markers.

| CS | Name | LOD | cM | CS | Name | LOD | cM |
|---|---|---|---|---|---|---|---|
| LG-01 | txa3383 | 22.5 | 0.0 | LG-01 | txa4031 | 27.56 | 61.7 |
| LG-01 | txa2704 | 29.6 | 2.6 | LG-01 | txa2615 | 23.12 | 66.1 |
| LG-01 | isu63.2 | 9.17 | 7.6 | LG-01 | umc166 | 22.71 | 70.1 |
| LG-01 | txa6198 | 30 | 8.4 | LG-01 | txa2655 | 24.07 | 73.9 |
| LG-01 | txa6003 | 36.93 | 8.4 | LG-01 | txa2217 | 32.18 | 75.5 |
| LG-01 | umc84 | 20.94 | 11.9 | LG-01 | txa6133 | 40.23 | 75.5 |
| LG-01 | cdo457 | 28.14 | 13.2 | LG-01 | umc124.3 | 28.35 | 78.2 |
| LG-01 | txa3632 | 36.33 | 13.2 | LG-01 | txa6014 | 37.13 | 78.6 |
| LG-01 | isu70 | 26.42 | 16.1 | LG-01 | txa440 | 31.72 | 80.4 |
| LG-01 | txa6286 | 25.59 | 19.0 | LG-01 | umc115 | 29.9 | 81.6 |
| LG-01 | txa3257 | 32.83 | 19.8 | LG-01 | txa3411 | 36.33 | 83.5 |
| LG-01 | txp208 | 24.76 | 23.4 | LG-01 | txa2847 | 29.03 | 86.1 |
| LG-01 | txs1082 | 31.95 | 24.4 | LG-01 | txa3334 | 37.42 | 86.5 |
| LG-01 | phyC | 32.37 | 24.8 | LG-01 | umc167 | — | 89.4 |
| LG-01 | txp325 | 28.46 | 26.5 | LG-01 | txs361.1 | 22.77 | 93.7 |
| LG-01 | txa2084 | 32.3 | 29.5 | LG-01 | txa2091 | 26.75 | 95.5 |
| LG-01 | txa3488 | 32.01 | 30.6 | LG-01 | txa42 | 25.65 | 97.5 |
| LG-01 | txp302 | 31.9 | 31.7 | LG-01 | txa2285 | 26.01 | 100.6 |
| LG-01 | cdo121 | 31.32 | 33.3 | LG-01 | isu73 | 25.45 | 103.4 |
| LG-01 | txa357 | 23.31 | 38.2 | LG-01 | txa148 | 23.23 | 107.8 |
| LG-01 | rz474 | 23.9 | 40.7 | LG-01 | txa2623 | 27.09 | 109.6 |
| LG-01 | txs1075.1 | 28.53 | 42.4 | LG-01 | txa6185 | 30.78 | 110.5 |
| LG-01 | isu76 | 28.18 | 45.2 | LG-01 | txa6297 | 37.53 | 110.5 |
| LG-01 | umc27 | 37.23 | 45.2 | LG-01 | cdo20 | 27.67 | 112.4 |
| LG-01 | txa3953 | 29.03 | 48.5 | LG-01 | txa216 | 26.23 | 114.3 |
| LG-01 | txa3126 | 19.05 | 54.8 | LG-01 | txa494 | 21.85 | 117.4 |

TABLE 8-continued

RIL framework markers.

| CS | Name | LOD | cM |
|---|---|---|---|
| LG-01 | isu165 | — | 120.0 |
| LG-01 | txa2059 | 21.13 | 124.3 |
| LG-01 | txa243 | 24.67 | 127.8 |
| LG-01 | txa2355 | 38.43 | 127.8 |
| LG-01 | txa2644 | 36.83 | 128.2 |
| LG-01 | txa2609 | 28.25 | 130.0 |
| LG-01 | txa6334 | 25.89 | 132.6 |
| LG-01 | txa6277 | 24.49 | 136.6 |
| LG-01 | txa2658 | 28.17 | 138.6 |
| LG-01 | rz251 | 28.53 | 139.9 |
| LG-01 | txa3812 | 29.69 | 141.3 |
| LG-01 | txa6088 | 32.54 | 144.9 |
| LG-01 | txs1225 | 21.66 | 149.7 |
| LG-01 | umc95 | 21.13 | 153.8 |
| LG-01 | txp58 | 25.73 | 156.3 |
| LG-01 | txa4021 | 23.27 | 160.1 |
| LG-01 | txa3826 | 24.52 | 163.4 |
| LG-01 | cdo938 | 33.03 | 163.4 |
| LG-01 | isu51 | 27.05 | 165.5 |
| LG-01 | phyB | 31.66 | 166.4 |
| LG-01 | txp75 | 28.24 | 168.8 |
| LG-01 | txp279 | 26.03 | 172.3 |
| LG-01 | txa2837 | 26.42 | 175.4 |
| LG-01 | txa3660 | 25.86 | 178.4 |
| LG-01 | txa4101 | 27.89 | 180.3 |
| LG-01 | txa6208 | 28.46 | 182.3 |
| LG-01 | txa2304 | 31.72 | 183.6 |
| LG-01 | txa203 | 38.73 | 183.6 |
| LG-01 | txa3580 | 26.97 | 186.4 |
| LG-01 | txa3795 | 25.86 | 189.2 |
| LG-01 | cdo1387 | 25.36 | 190.6 |
| LG-01 | txa6057 | 23.96 | 193.3 |
| LG-01 | txa4241 | 32.54 | 194.1 |
| LG-01 | txp61 | 31.43 | 195.3 |
| LG-01 | txa4149 | 33.12 | 196.0 |
| LG-01 | txa6215 | 18.96 | 203.7 |
| LG-01 | txa200 | 29.69 | 205.5 |
| LG-01 | txa3629 | 35.73 | 205.5 |
| LG-01 | txa298 | 23.9 | 209.8 |
| LG-01 | txp319 | 31.14 | 211.3 |
| LG-01 | rz329 | 29.6 | 213.0 |
| LG-01 | txa3958 | 31.95 | 213.9 |
| LG-01 | umc157 | — | 217.7 |
| LG-01 | txa2945 | 31.07 | 218.4 |
| LG-01 | txp340 | 29.98 | 219.6 |
| LG-01 | txa6274 | 27.12 | 223.7 |
| LG-01 | rz273 | 21.48 | 228.1 |
| LG-01 | txa3303 | 22.68 | 231.6 |
| LG-02 | txa2851 | 25.49 | 0.0 |
| LG-02 | txs1267 | 32.88 | 5.3 |
| LG-02 | txs1573.2 | 33.93 | 5.3 |
| LG-02 | txp63 | 7.46 | 7.5 |
| LG-02 | txa3726 | 34.75 | 7.9 |
| LG-02 | txa472 | 25.04 | 11.1 |
| LG-02 | txa3341 | 20.93 | 16.4 |
| LG-02 | txa591 | 25.21 | 20.4 |
| LG-02 | txa3329 | 28.18 | 23.1 |
| LG-02 | isu67 | — | 25.5 |
| LG-02 | txa6150 | 23.39 | 30.0 |
| LG-02 | txp211 | 35.13 | 30.0 |
| LG-02 | txa6355 | 26.57 | 32.9 |
| LG-02 | txa3547 | 30.16 | 34.8 |
| LG-02 | txa2501 | 28.18 | 36.7 |
| LG-02 | txa55 | 25.73 | 39.1 |
| LG-02 | txa2142 | 34.75 | 39.5 |
| LG-02 | txa2717 | 26.97 | 42.6 |
| LG-02 | txa3604 | 29.88 | 44.5 |
| LG-02 | txa3451 | 27.9 | 48.5 |
| LG-02 | txs1891 | — | 50.8 |
| LG-02 | txa280 | 25.61 | 52.6 |
| LG-02 | txa2792 | 20.87 | 56.9 |
| LG-02 | txa414 | 33.46 | 58.0 |
| LG-02 | isu97.2 | 26.49 | 60.3 |
| LG-02 | isu71 | 32.67 | 60.8 |
| LG-02 | txa426 | 30.85 | 62.4 |
| LG-02 | txa172 | 32.59 | 63.6 |
| LG-02 | txa609 | 32.01 | 64.8 |
| LG-02 | txa251 | 23.12 | 68.3 |
| LG-02 | isu151 | — | 71.0 |
| LG-02 | txa4071 | 24.8 | 73.3 |
| LG-02 | txa3358 | 26.57 | 75.7 |
| LG-02 | txa2724 | 39.03 | 75.7 |
| LG-02 | txa3648 | 39.33 | 75.7 |
| LG-02 | txa602 | 29.6 | 77.3 |
| LG-02 | txa2832 | 37.23 | 77.3 |
| LG-02 | txa211 | 39.03 | 77.3 |
| LG-02 | txa3697 | 30.75 | 78.9 |
| LG-02 | txp13 | 26.39 | 79.7 |
| LG-02 | isu94 | 27.33 | 82.2 |
| LG-02 | txa6074 | 16.58 | 89.7 |
| LG-02 | umc88.1 | 33.93 | 90.0 |
| LG-02 | txa2201 | 34.75 | 90.4 |
| LG-02 | txa2008 | 32.54 | 91.7 |
| LG-02 | txa2159 | 33.42 | 92.5 |
| LG-02 | txa3763 | 28.18 | 94.9 |
| LG-02 | umc139 | 26.49 | 97.6 |
| LG-02 | txa6138 | 24.13 | 101.1 |
| LG-02 | txa3420 | 34.59 | 101.9 |
| LG-02 | txa2616 | 28.8 | 104.3 |
| LG-02 | txa2514 | 39.33 | 104.3 |
| LG-02 | txa3397 | 39.63 | 104.3 |
| LG-02 | txa3153 | 25.21 | 107.8 |
| LG-02 | txa409 | 25.73 | 110.4 |
| LG-02 | txs1111 | 24.52 | 113.9 |
| LG-02 | umc5 | 32.24 | 114.8 |
| LG-02 | txp56 | 23.53 | 118.5 |
| LG-02 | txa481 | 24.8 | 121.0 |
| LG-02 | txa612 | 22.03 | 124.6 |
| LG-02 | txa6165 | 32.97 | 125.0 |
| LG-02 | txa3866 | 30.78 | 126.1 |
| LG-02 | txa6164 | 30.48 | 127.2 |
| LG-02 | isu117 | — | 129.3 |
| LG-02 | isu43 | 27.89 | 131.9 |
| LG-02 | txs645.1 | 37.23 | 131.9 |
| LG-02 | umc22.1 | 30.27 | 134.1 |
| LG-02 | txa6076 | 36.63 | 134.1 |
| LG-02 | umc88.2 | 31.48 | 134.5 |
| LG-02 | txa264 | 30.78 | 137.1 |
| LG-02 | txa598 | 23.39 | 141.1 |
| LG-02 | cdo385 | 23.31 | 145.2 |
| LG-02 | txa6045 | 27.4 | 148.0 |
| LG-02 | umc4 | 24.9 | 151.2 |
| LG-02 | txa313 | 25.08 | 153.8 |
| LG-02 | txa6115 | 33.12 | 154.6 |
| LG-02 | umc149 | — | 157.5 |
| LG-02 | txp207 | 28.17 | 159.9 |
| LG-02 | txa6338 | 33.26 | 160.4 |
| LG-02 | txs1845 | 34.15 | 160.8 |
| LG-02 | umc125 | 17.62 | 168.3 |
| LG-02 | umc122 | 22.96 | 171.2 |
| LG-02 | bnl8.37 | 30.89 | 171.7 |
| LG-02 | rz395 | 25.17 | 175.4 |
| LG-02 | isu75.2 | 27.05 | 178.2 |
| LG-02 | txs283 | — | 180.5 |
| LG-02 | txa6117 | 23.04 | 184.2 |
| LG-02 | isu123.2 | 23.04 | 187.5 |
| LG-02 | bnl16.06 | 24.34 | 189.9 |
| LG-02 | txp8 | 21.43 | 193.4 |
| LG-02 | txa311 | 22.5 | 196.9 |
| LG-02 | txa493 | 20.63 | 201.5 |
| LG-02 | txa6044 | 28.53 | 202.9 |
| LG-02 | txs1610 | 26.46 | 205.0 |
| LG-03 | txa3395 | 25.21 | 0.0 |
| LG-03 | txa2580 | 30.85 | 1.9 |
| LG-03 | txa3461 | 28.8 | 4.3 |
| LG-03 | txa6154 | 36.53 | 4.7 |
| LG-03 | txa2105 | 7.32 | 6.6 |
| LG-03 | umc121 | 25.45 | 9.0 |
| LG-03 | txs1178 | 28.17 | 11.9 |
| LG-03 | txa4134 | 22.77 | 15.2 |
| LG-03 | txa376 | 26.8 | 16.7 |
| LG-03 | umc124.1 | 23.67 | 20.3 |

TABLE 8-continued

RIL framework markers.

| CS | Name | LOD | cM |
|---|---|---|---|
| LG-03 | txa3498 | 32.67 | 20.8 |
| LG-03 | txa6160 | 29.89 | 22.4 |
| LG-03 | txa6272 | 27.8 | 25.2 |
| LG-03 | txa2734 | 26.01 | 28.6 |
| LG-03 | txa2614 | 29.32 | 31.6 |
| LG-03 | txs1092 | — | 33.3 |
| LG-03 | txa3003 | 21.66 | 37.4 |
| LG-03 | txa2096 | 29.03 | 39.4 |
| LG-03 | txa2714 | 29.59 | 41.4 |
| LG-03 | txa3848 | 29.88 | 43.4 |
| LG-03 | txa3552 | 19.8 | 49.4 |
| LG-03 | txa2546 | 28.52 | 51.8 |
| LG-03 | txa267 | 28.53 | 53.3 |
| LG-03 | txa29 | 27.03 | 55.3 |
| LG-03 | txa30 | 36.83 | 55.7 |
| LG-03 | txa3021 | 28.24 | 58.1 |
| LG-03 | txa2260 | 39.33 | 58.1 |
| LG-03 | txa3837 | 25.21 | 61.6 |
| LG-03 | txa2899 | 24.13 | 65.1 |
| LG-03 | txs578 | — | 68.3 |
| LG-03 | isu148 | 24.13 | 71.8 |
| LG-03 | txa2171 | 25.17 | 74.4 |
| LG-03 | umc152.1 | 26.75 | 76.1 |
| LG-03 | rz244 | 23.67 | 79.5 |
| LG-03 | cdo920 | 25.36 | 81.9 |
| LG-03 | isu114 | 25.08 | 84.3 |
| LG-03 | txa3261 | 24.21 | 88.2 |
| LG-03 | txa4054 | 28.18 | 90.6 |
| LG-03 | txp183 | 21.03 | 94.0 |
| LG-03 | txa2735 | 18.96 | 98.8 |
| LG-03 | txa2607 | 25.31 | 102.6 |
| LG-03 | txa4106 | 28.14 | 104.8 |
| LG-03 | txa6309 | 32.54 | 105.9 |
| LG-03 | umc93 | 27.61 | 108.2 |
| LG-03 | umc63 | 36.33 | 108.2 |
| LG-03 | txp120 | 27.68 | 110.9 |
| LG-03 | txa2595 | 37.53 | 111.6 |
| LG-03 | txa2074 | 34.59 | 111.6 |
| LG-03 | cdo1160 | 15.62 | 118.4 |
| LG-03 | txa2110 | 20.35 | 125.2 |
| LG-03 | txa389 | 35.43 | 125.2 |
| LG-03 | txs1175 | 28.17 | 127.5 |
| LG-03 | isu74.2 | 30.19 | 128.6 |
| LG-03 | cdo470 | 26.51 | 130.1 |
| LG-03 | txa4019 | 28.25 | 133.3 |
| LG-03 | isu121 | 34.53 | 133.3 |
| LG-03 | umc17 | 36.33 | 134.7 |
| LG-03 | txa2984 | 32.08 | 135.6 |
| LG-03 | txa235 | 20.87 | 140.0 |
| LG-03 | txa2961 | 26.01 | 142.5 |
| LG-03 | txa2877 | 30.85 | 144.4 |
| LG-03 | txs422 | 31.66 | 145.5 |
| LG-03 | txs1927 | 38.13 | 145.5 |
| LG-03 | bnl15.20 | 29.03 | 147.3 |
| LG-03 | bcd738 | 21.73 | 149.1 |
| LG-03 | txa4063 | 28.17 | 149.1 |
| LG-03 | txa2986 | 32.59 | 150.3 |
| LG-03 | txa2937 | 28.17 | 151.9 |
| LG-03 | isu166 | — | 156.1 |
| LG-03 | txa2271 | 22.77 | 158.3 |
| LG-03 | txa2027 | 20.76 | 161.4 |
| LG-03 | txa6283 | 23.58 | 165.1 |
| LG-03 | txa2051 | 28.74 | 166.9 |
| LG-03 | txa3448 | 28.18 | 169.0 |
| LG-03 | isu68 | — | 174.5 |
| LG-03 | txa3891 | 23.39 | 177.4 |
| LG-03 | txa3610 | 27.4 | 179.8 |
| LG-03 | txa2056 | 24.67 | 183.0 |
| LG-03 | txa3904 | 31.36 | 183.8 |
| LG-03 | txa4073 | 31.95 | 184.6 |
| LG-03 | txa341 | 18.41 | 190.0 |
| LG-03 | txa3859 | 24.9 | 192.5 |
| LG-03 | isu52.1 | 16.71 | 198.5 |
| LG-03 | txa4138 | 22.2 | 202.4 |
| LG-03 | txi5 | 35.43 | 202.4 |
| LG-04 | txa2353 | 14.17 | 0.0 |
| LG-04 | isu61.3 | 21.97 | 5.0 |
| LG-04 | txs754 | 22.2 | 9.7 |
| LG-04 | txa50 | 25.17 | 12.5 |
| LG-04 | txa2605 | 29.32 | 14.2 |
| LG-04 | txa3921 | 30.56 | 15.5 |
| LG-04 | txa3997 | 31.19 | 17.5 |
| LG-04 | txa3882 | 29.03 | 19.1 |
| LG-04 | txa6 | 25.92 | 22.3 |
| LG-04 | txa2348 | 30.27 | 24.0 |
| LG-04 | txa6339 | 30.45 | 25.9 |
| LG-04 | umc40.2 | 16.45 | 33.8 |
| LG-04 | txa4132 | 25.92 | 36.4 |
| LG-04 | isu56 | — | 43.1 |
| LG-04 | txa3854 | 33.63 | 43.1 |
| LG-04 | txa495 | 16.41 | 48.6 |
| LG-04 | txa2669 | 31.23 | 48.6 |
| LG-04 | txa4212 | 28.25 | 50.5 |
| LG-04 | txa6268 | 29.03 | 52.7 |
| LG-04 | txa4036 | 37.23 | 52.7 |
| LG-04 | txa257 | 20.63 | 57.7 |
| LG-04 | txa2204 | 18.96 | 63.7 |
| LG-04 | txa2178 | 24.4 | 67.3 |
| LG-04 | txa3537 | 20.37 | 72.5 |
| LG-04 | txa345 | 24.67 | 75.8 |
| LG-04 | txa548 | 15.62 | 82.9 |
| LG-04 | txa2577 | 34.45 | 83.3 |
| LG-04 | txa3796 | 32.3 | 84.4 |
| LG-04 | txa3955 | 29.32 | 85.9 |
| LG-04 | txa2029 | 27.12 | 88.2 |
| LG-04 | txa6172 | 36.93 | 88.2 |
| LG-04 | txa6285 | 38.13 | 88.2 |
| LG-04 | txa6166 | 39.33 | 88.2 |
| LG-04 | txs1146.2 | 38.43 | 88.2 |
| LG-04 | txa4011 | 34.45 | 88.6 |
| LG-04 | txa6189 | 35.94 | 89.7 |
| LG-04 | txa6258 | 30.75 | 91.6 |
| LG-04 | txa2085 | 30.73 | 93.5 |
| LG-04 | txp12 | — | 94.1 |
| LG-04 | txa218 | 18.55 | 100.5 |
| LG-04 | txa2095 | 13.37 | 110.4 |
| LG-04 | isu42 | 26.49 | 112.4 |
| LG-04 | txa2017 | 24.52 | 117.9 |
| LG-04 | umc54 | — | 120.6 |
| LG-04 | isu132 | 25.73 | 123.8 |
| LG-04 | txp24 | 31.78 | 124.4 |
| LG-04 | isu35 | 28.46 | 126.9 |
| LG-04 | txs604 | 26.01 | 129.9 |
| LG-04 | txa516 | 26.14 | 133.5 |
| LG-04 | txa2068 | 35.77 | 134.2 |
| LG-04 | txa6013 | 26.97 | 137.8 |
| LG-04 | txa4016 | 29.98 | 139.4 |
| LG-04 | txp51 | 25.86 | 142.4 |
| LG-04 | txa2706 | 26.29 | 147.2 |
| LG-04 | txa6257 | 38.43 | 147.2 |
| LG-04 | txa6269 | 27.4 | 150.1 |
| LG-04 | bec1427 | 26.46 | 152.6 |
| LG-04 | cdo516.1 | 25.61 | 155.0 |
| LG-04 | txs1103 | — | 157.6 |
| LG-04 | txp21 | 18.03 | 165.4 |
| LG-04 | txa2633 | 27.9 | 167.6 |
| LG-04 | umc104 | 16.71 | 174.4 |
| LG-05 | txa3948 | 26.77 | 0.0 |
| LG-05 | isu84.2 | 20.89 | 2.9 |
| LG-05 | txa160 | 34.45 | 4.1 |
| LG-05 | txa518 | 27.9 | 5.7 |
| LG-05 | txa4199 | 27.33 | 8.4 |
| LG-05 | txa6065 | 35.64 | 10.8 |
| LG-05 | txp65 | — | 11.2 |
| LG-05 | txa2037 | 18.16 | 18.7 |
| LG-05 | txp94 | 20.48 | 24.0 |
| LG-05 | txa2893 | 26.42 | 26.7 |
| LG-05 | txs722 | 37.53 | 26.7 |
| LG-05 | txa350 | 25.51 | 29.2 |
| LG-05 | txa6047 | 30.18 | 31.3 |
| LG-05 | txa3190 | 33.17 | 32.4 |
| LG-05 | txa6284 | 32.01 | 33.5 |

TABLE 8-continued

RIL framework markers.

| CS | Name | LOD | cM |
|---|---|---|---|
| LG-05 | txa4135 | 32.83 | 34.2 |
| LG-05 | txa2284 | 28.74 | 35.8 |
| LG-05 | umc52 | 9.9 | 41.0 |
| LG-05 | txa2256 | 11.71 | 50.1 |
| LG-05 | txa2545 | 37.23 | 50.1 |
| LG-05 | isu120 | 22.57 | 53.6 |
| LG-05 | txp225 | 18.03 | 56.9 |
| LG-05 | txa3429 | 25.36 | 58.2 |
| LG-05 | txa2038 | 27.24 | 61.1 |
| LG-05 | txa169 | 23.04 | 64.8 |
| LG-05 | txa507 | 29.03 | 67.0 |
| LG-05 | isu36.2 | 34.75 | 68.2 |
| LG-05 | isu59 | 37.23 | 68.2 |
| LG-05 | txa6216 | 38.13 | 68.2 |
| LG-05 | txa6278 | 39.93 | 68.2 |
| LG-05 | txa68 | 34.89 | 68.9 |
| LG-05 | txa2141 | 26.42 | 71.8 |
| LG-05 | txa290 | 20.42 | 77.0 |
| LG-05 | txa3444 | 34 | 77.8 |
| LG-05 | txa324 | 32.54 | 78.6 |
| LG-05 | txa2152 | 29.02 | 79.5 |
| LG-05 | txa4081 | 22.73 | 83.7 |
| LG-05 | txa2071 | 33.71 | 84.5 |
| LG-05 | txa3452 | 39.63 | 84.5 |
| LG-05 | txa3886 | 31.04 | 86.1 |
| LG-05 | txp23 | 24.07 | 90.0 |
| LG-05 | txa3109 | 24.88 | 93.7 |
| LG-05 | txa3398 | 22.5 | 98.1 |
| LG-05 | txa2093 | 34.53 | 98.1 |
| LG-05 | txa2323 | 18.12 | 106.7 |
| LG-05 | txa221 | 36.93 | 106.7 |
| LG-05 | txa2836 | 27.05 | 113.9 |
| LG-05 | txp123 | — | 115.8 |
| LG-05 | txa6092 | 33.42 | 116.2 |
| LG-05 | txp136 | 25.64 | 118.1 |
| LG-05 | txa2902 | 22.5 | 121.3 |
| LG-05 | txa312 | 20.16 | 130.0 |
| LG-05 | txa4048 | 23.53 | 138.2 |
| LG-06 | txp6 | 10.35 | 0.0 |
| LG-06 | cdo718 | — | 11.6 |
| LG-06 | txa7 | 26.29 | 13.5 |
| LG-06 | txa462 | 23.18 | 15.9 |
| LG-06 | txa2124 | 29.6 | 21.1 |
| LG-06 | txa2926 | 24.94 | 24.5 |
| LG-06 | txa4103 | 29.6 | 27.7 |
| LG-06 | txa3407 | 30.75 | 29.2 |
| LG-06 | txa6233 | 27.05 | 32.2 |
| LG-06 | isu142 | 24.9 | 35.8 |
| LG-06 | txa445 | 29.03 | 38.0 |
| LG-06 | txa2568 | 31.61 | 39.6 |
| LG-06 | umc119 | 23.94 | 43.0 |
| LG-06 | txa202 | 25.36 | 49.3 |
| LG-06 | txa3011 | 28.46 | 51.4 |
| LG-06 | txa2221 | 31.95 | 53.4 |
| LG-06 | txa410 | 35.94 | 53.8 |
| LG-06 | isu138 | — | 54.8 |
| LG-06 | txa238 | 32.83 | 55.3 |
| LG-06 | txa605 | 28.74 | 56.8 |
| LG-06 | txa6281 | 33.33 | 58.4 |
| LG-06 | txa294 | 27.09 | 58.4 |
| LG-06 | txa176 | 35.43 | 62.2 |
| LG-06 | txa2530 | 24.34 | 62.2 |
| LG-06 | txa2150 | 34.53 | 62.2 |
| LG-06 | umc53 | 32.37 | 63.1 |
| LG-06 | txp274 | 27.61 | 65.5 |
| LG-06 | isu58 | 34.15 | 66.4 |
| LG-06 | txa33 | 36.63 | 66.4 |
| LG-06 | txa4009 | 31.61 | 67.9 |
| LG-06 | umc34 | 25.92 | 70.1 |
| LG-06 | txa278 | 23.62 | 72.0 |
| LG-06 | txa555 | 24.24 | 74.4 |
| LG-06 | txa4052 | 28.25 | 75.6 |
| LG-06 | txs1906 | — | 77.9 |
| LG-06 | txa6313 | 22.78 | 79.6 |
| LG-06 | bnl10.13 | 29.98 | 81.4 |
| LG-06 | umc44 | 37.83 | 81.4 |
| LG-06 | txa3110 | 29.03 | 83.7 |
| LG-06 | txp176 | 17.99 | 86.5 |
| LG-06 | txa3496 | 21.13 | 88.5 |
| LG-06 | txa2039 | 24.13 | 92.3 |
| LG-06 | txa6222 | 32.47 | 93.9 |
| LG-06 | txa4062 | 26.03 | 97.2 |
| LG-06 | txs2063 | 27.33 | 99.6 |
| LG-06 | txa6140 | 35.05 | 100.0 |
| LG-06 | isu147 | 29.89 | 102.0 |
| LG-06 | txp17 | — | 105.4 |
| LG-06 | txa3457 | 31.43 | 106.5 |
| LG-06 | txa587 | 37.53 | 106.5 |
| LG-06 | txa2549 | 31.95 | 107.3 |
| LG-06 | txa528 | 33.03 | 107.3 |
| LG-06 | txa3926 | 30.19 | 108.6 |
| LG-06 | txa6261 | 28.74 | 110.3 |
| LG-06 | txa6062 | 36.53 | 110.8 |
| LG-06 | umc58.2 | 26.8 | 112.5 |
| LG-06 | txa2721 | 23.24 | 115.9 |
| LG-06 | txa6061 | 34.59 | 118.6 |
| LG-06 | txa6322 | 25.49 | 119.4 |
| LG-06 | txa6026 | 39.93 | 120.2 |
| LG-06 | txa342 | 31.01 | 122.1 |
| LG-07 | txp40 | 14.29 | 0.0 |
| LG-07 | txa3944 | 27.32 | 6.5 |
| LG-07 | isu139 | — | 8.4 |
| LG-07 | txa4023 | 25.32 | 10.9 |
| LG-07 | txa2650 | 24.62 | 14.3 |
| LG-07 | txa3692 | 36.83 | 14.7 |
| LG-07 | txa2844 | 39.03 | 14.7 |
| LG-07 | rz143.2 | 17.75 | 21.0 |
| LG-07 | txs1931 | 29.7 | 21.6 |
| LG-07 | txa3336 | 27.89 | 23.7 |
| LG-07 | txa3146 | 24.4 | 27.7 |
| LG-07 | txa2286 | 25.49 | 31.0 |
| LG-07 | txa2896 | 27.52 | 35.2 |
| LG-07 | txp159 | — | 37.9 |
| LG-07 | txs1096 | 19.97 | 43.5 |
| LG-07 | txp312 | 27.12 | 45.9 |
| LG-07 | txa3935 | 25.86 | 48.6 |
| LG-07 | txa2708 | 27.12 | 50.9 |
| LG-07 | txa2624 | 24.4 | 54.6 |
| LG-07 | txa3017 | 31.14 | 55.9 |
| LG-07 | txa219 | 31.36 | 57.2 |
| LG-07 | txa16 | 32.73 | 57.2 |
| LG-07 | isu38 | — | 58.2 |
| LG-07 | txa3888 | 16.24 | 66.4 |
| LG-07 | bec147 | 20.87 | 71.8 |
| LG-07 | txa307 | 25.89 | 73.8 |
| LG-07 | txa358 | 22.68 | 76.4 |
| LG-07 | txa2578 | 28.17 | 77.9 |
| LG-07 | txa2333 | 36.33 | 78.1 |
| LG-07 | txs2014.2 | 36.33 | 78.3 |
| LG-07 | txa2076 | 36.93 | 79.0 |
| LG-07 | txa3901 | 37.53 | 79.4 |
| LG-07 | isu98.2 | 36.63 | 79.4 |
| LG-07 | txa166 | 38.43 | 79.4 |
| LG-07 | umc47.2 | 35.64 | 79.8 |
| LG-07 | txa13 | 24.06 | 83.1 |
| LG-07 | txa604 | 24.62 | 85.6 |
| LG-07 | txa4088 | 25.64 | 87.7 |
| LG-07 | umc23 | 27.32 | 89.4 |
| LG-07 | txa11 | 24.9 | 91.9 |
| LG-07 | txp92 | 20.37 | 96.9 |
| LG-07 | txa79 | 30.18 | 98.6 |
| LG-07 | txa6362 | 29.31 | 100.6 |
| LG-07 | txa3581 | 16.96 | 108.4 |
| LG-07 | txa584 | 25.04 | 112.2 |
| LG-07 | txa2796 | 29.89 | 114.2 |
| LG-07 | txa2053 | 20.07 | 119.1 |
| LG-07 | isu116 | 29.36 | 121.7 |
| LG-07 | txs1579 | — | 124.0 |
| LG-07 | txa487 | 21.16 | 128.8 |
| LG-07 | txa486 | 32.73 | 128.8 |
| LG-07 | txa601 | 20.89 | 134.4 |
| LG-07 | txa2007 | 25.59 | 137.5 |

TABLE 8-continued

RIL framework markers.

| CS | Name | LOD | cM |
|---|---|---|---|
| LG-07 | txa419 | 30.75 | 139.2 |
| LG-07 | txa354 | 21.4 | 143.7 |
| LG-07 | txa2639 | 26.49 | 146.1 |
| LG-07 | txa3228 | 31.72 | 147.7 |
| LG-07 | txa406 | 30.27 | 149.3 |
| LG-07 | txa2548 | 32.67 | 149.7 |
| LG-07 | txs1554 | — | 150.9 |
| LG-07 | txa6102 | 23.04 | 155.6 |
| LG-08 | txp273 | 18.38 | 0.0 |
| LG-08 | txa4058 | 11.49 | 6.1 |
| LG-08 | txa2317 | 23.04 | 13.1 |
| LG-08 | txa3517 | 23.27 | 16.8 |
| LG-08 | txa3513 | 24.67 | 20.1 |
| LG-08 | txa4214 | 23.79 | 22.9 |
| LG-08 | txa3855 | 25.36 | 25.2 |
| LG-08 | txa6029 | 31.19 | 26.3 |
| LG-08 | bnl3.04 | 32.13 | 26.3 |
| LG-08 | txa2780 | 26.2 | 30.1 |
| LG-08 | txa3386 | 24.67 | 33.2 |
| LG-08 | txa2117 | 32.97 | 33.6 |
| LG-08 | txp47 | — | 38.7 |
| LG-08 | txa4117 | 17.31 | 45.5 |
| LG-08 | txa2866 | 20.23 | 51.0 |
| LG-08 | txa416 | 23.24 | 55.3 |
| LG-08 | txa2612 | 26.69 | 58.2 |
| LG-08 | txa3650 | 26.29 | 60.5 |
| LG-08 | txa3861 | 29.9 | 61.4 |
| LG-08 | isu54 | — | 63.8 |
| LG-08 | txa348 | 21.66 | 68.1 |
| LG-08 | txa6174 | 29.88 | 70.0 |
| LG-08 | txa6211 | 27.52 | 72.7 |
| LG-08 | umc18 | 25.04 | 76.4 |
| LG-08 | umc130 | 28.43 | 77.5 |
| LG-08 | rz261 | 25.36 | 80.2 |
| LG-08 | txp294 | 28.17 | 82.5 |
| LG-08 | txa3856 | 24.21 | 86.0 |
| LG-08 | txs645.2 | 27.05 | 88.2 |
| LG-08 | txa3853 | 25.73 | 90.7 |
| LG-08 | isu145.2 | 26.14 | 92.7 |
| LG-08 | txa3130 | 27.33 | 94.7 |
| LG-08 | txa3771 | 27.32 | 96.2 |
| LG-08 | txa558 | 32.13 | 96.2 |
| LG-08 | cdo459 | — | 99.2 |
| LG-08 | txa6348 | 21.15 | 104.2 |
| LG-08 | txa6347 | 26.57 | 109.5 |
| LG-08 | txs560 | 30.85 | 111.2 |
| LG-08 | txa6090 | 34.75 | 111.6 |
| LG-08 | txp250 | 27.32 | 113.4 |
| LG-08 | txa4084 | 24.9 | 116.6 |
| LG-08 | txa4112 | 19.65 | 122.7 |
| LG-08 | txp105 | 24.9 | 126.1 |
| LG-08 | txa2778 | 31.78 | 126.6 |
| LG-08 | txa3709 | 28.82 | 128.0 |
| LG-08 | txa2789 | 29.11 | 129.4 |
| LG-08 | txa4014 | 28.25 | 132.9 |
| LG-08 | txa588 | 23.79 | 136.8 |
| LG-08 | txa3876 | 23.27 | 140.4 |
| LG-08 | isu146 | 26.01 | 143.3 |
| LG-08 | txa6304 | 26.01 | 146.3 |
| LG-08 | txa2332 | 33.71 | 147.1 |
| LG-08 | txa189 | 28.17 | 149.4 |
| LG-08 | txa2948 | 26.29 | 152.3 |
| LG-09 | txs2148.1 | 31.43 | 0.0 |
| LG-09 | rz390 | 24.06 | 3.0 |
| LG-09 | txs1703 | 6.47 | 6.6 |
| LG-09 | cdo580 | — | 23.5 |
| LG-09 | txs1150 | 27.92 | 24.1 |
| LG-09 | umc64 | — | 30.2 |
| LG-09 | txa4137 | 18.52 | 36.6 |
| LG-09 | txa3845 | 25.86 | 39.4 |
| LG-09 | txa4213 | 37.23 | 39.4 |
| LG-09 | txa6214 | 29.31 | 41.7 |
| LG-09 | txa6132 | 35.13 | 41.7 |
| LG-09 | txp287 | 27.03 | 43.6 |
| LG-09 | txa2326 | 26.58 | 45.5 |
| LG-09 | txa3526 | 28.52 | 47.8 |
| LG-09 | txa4184 | 26.85 | 50.1 |
| LG-09 | txp67 | 25.92 | 52.5 |
| LG-09 | txa2542 | 27.89 | 54.4 |
| LG-09 | txa567 | 38.13 | 54.4 |
| LG-09 | txa2600 | 22.98 | 58.8 |
| LG-09 | txa3160 | 22.71 | 62.8 |
| LG-09 | txa2011 | 27.68 | 65.1 |
| LG-09 | txa3379 | 36.53 | 65.5 |
| LG-09 | sBAC120 | — | 68.8 |
| LG-09 | txa393 | 26.77 | 71.0 |
| LG-09 | txa2098 | 35.64 | 71.4 |
| LG-09 | txa3248 | 32.01 | 72.8 |
| LG-09 | txa2517 | 27.09 | 74.5 |
| LG-09 | txa21 | 33.33 | 74.5 |
| LG-09 | txa3716 | 34.83 | 74.5 |
| LG-09 | txa2063 | 29.69 | 75.9 |
| LG-09 | txa3380 | 35.64 | 76.3 |
| LG-09 | txa3315 | 39.03 | 76.3 |
| LG-09 | txa3733 | 36.83 | 76.7 |
| LG-09 | txa2933 | 35.18 | 77.5 |
| LG-09 | txs943 | 33.56 | 78.5 |
| LG-09 | txs1383 | 26.29 | 81.6 |
| LG-09 | txa4113 | 24.52 | 85.0 |
| LG-09 | bcd454 | — | 87.7 |
| LG-09 | txa6308 | 23.39 | 91.7 |
| LG-09 | txa2599 | 27.4 | 94.0 |
| LG-09 | txa509 | 28.46 | 95.5 |
| LG-09 | txa66 | 33.56 | 96.1 |
| LG-09 | txa590 | 35.64 | 96.7 |
| LG-09 | txa2135 | 37.83 | 97.1 |
| LG-09 | txa415 | 29.59 | 99.4 |
| LG-09 | txa2351 | 29.08 | 101.7 |
| LG-09 | txa547 | 23.27 | 105.3 |
| LG-09 | txa411 | 32.24 | 106.1 |
| LG-09 | txa3772 | 21.16 | 109.7 |
| LG-09 | txa3014 | 34.53 | 109.7 |
| LG-09 | cdo89 | — | 114.9 |
| LG-09 | txa4122 | 23.86 | 118.4 |
| LG-09 | umc135.2 | 36.63 | 129.2 |
| LG-09 | umc132 | — | 129.2 |
| LG-09 | cdo393 | 8.81 | 143.1 |
| LG-09 | cdo542 | 36.03 | 143.1 |
| LG-09 | isu140 | 12.92 | 153.0 |
| LG-10 | txa2678 | 15.92 | 0.0 |
| LG-10 | txs1146.1 | 24.4 | 5.9 |
| LG-10 | txa385 | 27.85 | 8.4 |
| LG-10 | txa6105 | 36.03 | 10.2 |
| LG-10 | txa6066 | 37.83 | 10.2 |
| LG-10 | cdo590 | 6.15 | 10.2 |
| LG-10 | txa3245 | 23.67 | 13.3 |
| LG-10 | txa6210 | 25.73 | 15.6 |
| LG-10 | txs1078 | 27.09 | 17.2 |
| LG-10 | cdo475 | 24.24 | 20.5 |
| LG-10 | txa2968 | 23.39 | 24.0 |
| LG-10 | txa4225 | 28.46 | 26.0 |
| LG-10 | txa2720 | 29.03 | 28.0 |
| LG-10 | txa3924 | 28.74 | 30.4 |
| LG-10 | txa3872 | 36.63 | 30.4 |
| LG-10 | txa3961 | 28.74 | 32.4 |
| LG-10 | txa6009 | 22.71 | 36.5 |
| LG-10 | txa3503 | 30.75 | 38.2 |
| LG-10 | isu136 | — | 41.4 |
| LG-10 | txa6327 | 29.89 | 43.2 |
| LG-10 | umc113 | 29.59 | 45.1 |
| LG-10 | txa453 | 29.59 | 47.0 |
| LG-10 | txa2556 | 38.13 | 47.0 |
| LG-10 | txa398 | 26.42 | 49.7 |
| LG-10 | cdo516.2 | 20.87 | 54.1 |
| LG-10 | txa4156 | 17.62 | 59.9 |
| LG-10 | txs558 | 30.48 | 60.7 |
| LG-10 | txa2343 | 26.77 | 62.8 |
| LG-10 | txa3607 | 29.4 | 64.3 |
| LG-10 | txp20 | 22.56 | 68.1 |
| LG-10 | cdo17 | 30.59 | 70.0 |
| LG-10 | txa156 | 26.75 | 72.0 |
| LG-10 | txa2786 | 38.73 | 72.0 |

TABLE 8-continued

RIL framework markers.

| CS | Name | LOD | cM |
|---|---|---|---|
| LG-10 | txa452 | 26.03 | 75.1 |
| LG-10 | txa2555 | 38.43 | 75.1 |
| LG-10 | txa4064 | 35.94 | 75.8 |
| LG-10 | umc61.2 | 22.89 | 77.4 |
| LG-10 | txa3998 | 31.07 | 77.9 |
| LG-10 | txa2148 | 24.49 | 80.3 |
| LG-10 | rz476 | 25.89 | 81.1 |
| LG-10 | txa3821 | 28.82 | 82.5 |
| LG-10 | txs443 | 32.24 | 83.4 |
| LG-10 | txa2104 | 32.01 | 84.9 |
| LG-10 | isu128.1 | 36.93 | 84.9 |
| LG-10 | txa381 | 36.63 | 85.3 |
| LG-10 | bnl5.04 | — | 89.7 |
| LG-10 | umc114.3 | 25.04 | 93.1 |
| LG-10 | txa2522 | 35.13 | 93.1 |
| LG-10 | txa309 | 21.66 | 97.8 |
| LG-10 | txa6098 | 28.17 | 99.8 |
| LG-10 | cdo400 | 27.03 | 101.8 |
| LG-10 | txa3881 | 18.38 | 106.7 |
| LG-10 | umc150 | 25.49 | 110.7 |
| LG-10 | txa2005 | 32.08 | 111.1 |
| LG-10 | umc218 | — | 114.0 |
| LG-10 | txs1684 | 31.36 | 114.9 |
| LG-10 | txa4040 | 26.75 | 117.0 |
| LG-10 | txa2537 | 31.66 | 118.0 |
| LG-10 | txa3376 | 31.43 | 119.2 |
| LG-10 | txa2156 | 18.55 | 126.2 |
| LG-10 | txa37 | 38.43 | 126.2 |
| LG-10 | txa259 | 28.18 | 128.5 |
| LG-10 | txs758 | 25.92 | 130.8 |
| LG-10 | txa3596 | 24.49 | 133.5 |
| LG-10 | txa2069 | 34 | 134.2 |
| LG-10 | txa3601 | 29.89 | 135.7 |
| LG-10 | txa6251 | 31.14 | 136.8 |
| LG-10 | txa413 | 29.4 | 138.3 |
| LG-10 | isu45 | 26.97 | 139.7 |
| LG-10 | txa2727 | 28.46 | 142.3 |
| LG-10 | rz143.1 | 16.36 | 148.4 |

TABLE 9

Placed F$_2$ framework markers.

| cS | Name | cM |
|---|---|---|
| LG-01 | M1txa3905a | 0.0 |
| LG-01 | M2TS068a | 5.6 |
| LG-01 | M3a | 6.1 |
| LG-01 | M4a | 8.2 |
| LG-01 | M5CS004Na | 12.6 |
| LG-01 | M6a | 13.1 |
| LG-01 | M7txp302a | 16.6 |
| LG-01 | M8txp482a | 18.3 |
| LG-01 | M9txa6387a | 22.7 |
| LG-01 | M10a | 30.9 |
| LG-01 | M11a | 70.5 |
| LG-01 | M12a | 78.5 |
| LG-01 | M13a | 84.7 |
| LG-01 | M14a | 86.2 |
| LG-01 | M15a | 98.7 |
| LG-01 | M16a | 105.8 |
| LG-01 | M17a | 105.9 |
| LG-01 | M18a | 125.8 |
| LG-01 | M19a | 137.4 |
| LG-01 | M20txp61a | 140.9 |
| LG-01 | M21a | 153.6 |
| LG-01 | M22a | 158.4 |
| LG-01 | M23txp46a | 167.8 |
| LG-01 | M24a | 172.3 |
| LG-02 | M25txp96b | 0.0 |
| LG-02 | M26txp197b | 0.6 |
| LG-02 | M27txp211b | 21.3 |
| LG-02 | M28b | 36.3 |
| LG-02 | M29b | 41.2 |
| LG-02 | M30b | 44.4 |
| LG-02 | M31b | 46.1 |
| LG-02 | M32b | 51.2 |
| LG-02 | M33b | 62.3 |
| LG-02 | M34txp72b | 66.8 |
| LG-02 | M36txp13b | 73.1 |
| LG-02 | M37b | 88.0 |
| LG-02 | M38b | 90.6 |
| LG-02 | M39txp1b | 103.0 |
| LG-02 | M40b | 109.6 |
| LG-02 | M41b | 124.2 |
| LG-02 | M42txp207b | 136.1 |
| LG-02 | M44txp8b | 154.5 |
| LG-03 | M45c | 0.0 |
| LG-03 | M46txp492c | 8.9 |
| LG-03 | M47c | 14.4 |
| LG-03 | M48c | 19.7 |
| LG-03 | M49txp500c | 35.9 |
| LG-03 | M50c | 45.3 |
| LG-03 | M51txp461c | 49.5 |
| LG-03 | M52c | 54.4 |
| LG-03 | M54c | 55.8 |
| LG-03 | M53c | 56.3 |
| LG-03 | M55txp336c | 63.6 |
| LG-03 | M56c | 77.7 |
| LG-03 | M57c | 84.4 |
| LG-03 | M58c | 86.3 |
| LG-03 | M59txa4107c | 89.5 |
| LG-03 | M60txa3390c | 107.7 |
| LG-03 | M61txi7c | 119.7 |
| LG-04 | M62txp506d | 0.0 |
| LG-04 | M63d | 6.5 |
| LG-04 | M64d | 22.6 |
| LG-04 | M65d | 30.7 |
| LG-04 | M66d | 34.2 |
| LG-04 | M67txa3635d | 52.0 |
| LG-04 | M68d | 62.1 |
| LG-04 | M69txp12d | 65.3 |
| LG-04 | M70d | 68.1 |
| LG-04 | M71txa4091d | 69.9 |
| LG-04 | M72txa4231d | 70.5 |
| LG-04 | M73d | 82.3 |
| LG-04 | M74d | 96.2 |
| LG-04 | M75TXP60d | 116.6 |
| LG-04 | M76d | 131.8 |
| LG-04 | M77d | 133.5 |
| LG-04 | M78d | 134.8 |
| LG-04 | M79d | 137.8 |
| LG-04 | M80d | 140.9 |
| LG-05 | M151j | 0.0 |
| LG-05 | M152txa4096j | 15.1 |
| LG-05 | M153txp303j | 25.0 |
| LG-05 | M154j | 34.1 |
| LG-05 | M155j | 43.2 |
| LG-05 | M158j | 47.3 |
| LG-05 | M156j | 49.4 |
| LG-05 | M157j | 51.3 |
| LG-05 | M159j | 57.0 |
| LG-05 | M161j | 61.7 |
| LG-05 | M162txp23j | 72.9 |
| LG-05 | M163j | 87.3 |
| LG-05 | M164txp123j | 93.0 |
| LG-05 | M165j | 98.5 |
| LG-05 | M166txa4048j | 105.4 |
| LG-05 | M167j | 107.1 |
| LG-05 | M168j | 112.1 |
| LG-06 | M135i | 0.0 |
| LG-06 | M136i | 5.3 |
| LG-06 | M137i | 13.3 |
| LG-06 | M138TXP6i | 19.1 |
| LG-06 | M139i | 27.2 |
| LG-06 | M140i | 28.8 |
| LG-06 | M141i | 31.4 |
| LG-06 | M142txa4032i | 42.9 |
| LG-06 | M143txp274i | 69.8 |

TABLE 9-continued

Placed F$_2$ framework markers.

| cS | Name | cM |
|---|---|---|
| LG-06 | M144txa3860i | 72.6 |
| LG-06 | M145txa4090i | 75.7 |
| LG-06 | M146i | 86.9 |
| LG-06 | M147i | 93.9 |
| LG-06 | M148i | 102.5 |
| LG-06 | M149txp17i | 107.0 |
| LG-06 | M150i | 110.0 |
| LG-07 | M81e | 0.0 |
| LG-07 | M82txp36e | 6.2 |
| LG-07 | M83txp40e | 6.2 |
| LG-07 | M84e | 19.7 |
| LG-07 | M85txp159e | 28.2 |
| LG-07 | M86e | 58.3 |
| LG-07 | M87txa4110e | 69.2 |
| LG-07 | M88e | 71.4 |
| LG-07 | M89txp278e | 71.8 |
| LG-07 | M90e | 73.9 |
| LG-07 | M91txa4046e | 81.0 |
| LG-07 | M92txa4088e | 86.3 |
| LG-07 | M93e | 98.7 |
| LG-07 | M94e | 103.6 |
| LG-07 | M95txp295e | 117.9 |
| LG-07 | M96e | 129.0 |
| LG-08 | M120txp273h | 0.0 |
| LG-08 | M121h | 15.4 |
| LG-08 | M122txp47h | 16.5 |
| LG-08 | M123txa3861h | 33.0 |
| LG-08 | M124h | 44.9 |
| LG-08 | M125h | 52.3 |
| LG-08 | M126txa4109h | 56.9 |
| LG-08 | M127h | 60.2 |
| LG-08 | M128txp354h | 69.9 |
| LG-08 | M129txp18h | 84.2 |
| LG-08 | M130txp321h | 84.6 |
| LG-08 | M132h | 99.5 |
| LG-08 | M133txa4014h | 100.2 |
| LG-08 | M134h | 103.6 |
| LG-09 | M97f | 0.0 |
| LG-09 | M98f | 5.4 |
| LG-09 | M99txp258f | 8.4 |
| LG-09 | M100f | 22.4 |
| LG-09 | M101txa4113f | 41.4 |
| LG-10 | M102g | 0.0 |
| LG-10 | M103g | 4.7 |
| LG-10 | M104g | 9.0 |
| LG-10 | M105g | 13.0 |
| LG-10 | M106g | 17.6 |
| LG-10 | M107g | 18.2 |
| LG-10 | M108g | 39.5 |
| LG-10 | M109txa4049g | 49.3 |
| LG-10 | M110g | 52.1 |
| LG-10 | M111txp217g | 59.0 |
| LG-10 | M112txp130g | 62.4 |
| LG-10 | M113g | 64.2 |
| LG-10 | M114g | 69.8 |
| LG-10 | M115g | 79.6 |
| LG-10 | M116txa4236g | 82.1 |
| LG-10 | M117txa4040g | 90.1 |
| LG-10 | M118g | 101.1 |
| LG-10 | M119g | 104.8 |

TABLE 10

Forward and reverse primers used for qPCR.

| Primer name | Gene (Sobic.3) | Sequence | SEQ ID NO. |
|---|---|---|---|
| 3004G202500 F | 4G202500 | CAGATCGGCACTCTGACAAA | 39 |
| 3004G202500 R | | TGCTGTTAAACGGTCTGCTG | 40 |
| 3003G024800 F | 3G024800 | GGGATGTAAAGCCCCAAAAT | 41 |
| 3003G024800 R | | GGGATGTAAAGCCCCAAAAT | 42 |
| 3004G197600 F | 4G197600 | AGAACGCACCACCCTTTATG | 43 |
| 3004G197600 R | | GGAAGCACATAGCATCAGCA | 44 |
| 3004G295800 F | 4G295800 | GGGTCAAGCTGATGAAGCTC | 45 |
| 3004G295800 R | | GCCTTGTGTTGACCTGGTTT | 46 |
| 3004G333500 F | 4G333500 | GCATGAAGAGGGAGATCAGC | 47 |
| 3004G333500 R | | CATCCAGGGAACCTGTCAGT | 48 |
| 3001G195600 F | 1G195600 | TGGAGCTATGGGACAGGAAC | 49 |
| 3001G195600 R | | CGAGAGATTTGTCGATGCAA | 50 |

Total RNA was isolated using TRIzol ® Reagent (Thermo Fisher). RNA was digested with RNase-free DNase I (Thermo Fisher), and cDNA synthesis was performed using Superscript III First-Strand Synthesis System for RT-PCR (Thermo Fisher).
qPCR reactions were performed using a DNA Engine, Opticon 2, Continuous Florescence Detection System (Bio-Rad, Hercules, CA) in MicroAmp Optical 96-well 12 reaction plates with optical covers.
The Real Time PCR volume of 25 µL contained 12.5 µL 2X SYBR GreenER qPCR SuperMix Universal (Thermo Fisher), 200 nM each of forward and reverse primers, and 5 µL of diluted DNA sample. Reaction conditions were as follows: 50° C. for 2 min, 95° C. for 10 min, 40 cycles of 95° C. for 30 sec, 54° C. for 30 sec, and 72° C. for 30 sec.
Reactions were performed in triplicate, and melting curve analyses were performed.
Relative quantification values and standard deviations were calculated using the comparative CT method.
Values were normalized to the expression of the reference. Differences in expression were identified by Student's t-tests.

TABLE 11

| | | Concentration range | | Duration of pre-treatment (minutes) | |
|---|---|---|---|---|---|
| | Method | preferred | most preferred | preferred | most preferred |
| Inducing sex in apomictic plants | | | | | |
| sugar starvation (mmol sucrose equivalents in media per liter) | Culture pistils on sugar free media | <6 | 0 | <10 | 0 |
| hydrogen peroxide (mmol per liter) | Directly expose pistils, in vitro or in situ, to solution prior to megasporogenesis | 80-150 | 100 | 5-25 | 15 |

TABLE 11-continued

| | | preferred | most preferred | preferred | most preferred |
|---|---|---|---|---|---|
| PEG 6000 (g per liter) | Directly expose pistils, in vitro and/or in situ, to solution prior to megasporogenesis | 20-30 | 25 | 5-25 | 15 |
| brassinazole (μmol per liter) | Directly expose pistils, in vitro and/or in situ, to solution prior to megasporogenesis | 0.5-5 | 1 | <20 | 10 |
| *Inducing apomeiosis in sexual plants* | | | | | |
| epibrassinolide (epiBL) (μmol per liter) | Directly expose pistils, in vitro and/or in situ, to solution prior to megasporogenesis | 0.05-15 | 0.1-10 | <20 | 10 |
| fluridone (μmol per liter) | Directly expose pistils, in vitro and/or in situ, to solution prior to megasporogenesis | 2-20 | 10 | <20 | 10 |
| 5-azacytidine (μmol per liter) | Directly expose pistils, in vitro and/or in situ, to solution prior to megasporogenesis | 50-1000 | 500 | <20 | 10 |
| DTBA (μmol per liter) | Directly expose pistils, in vitro and/or in situ, to solution prior to megasporogenesis | 0.5-2 | 1 | <20 | 10 |
| Glucose (mmol per liter) | Directly expose pistils in situ to solution prior to megasporogenesis | 30-90 | 70 | 180-480 | 360 |
| Glucose (mmol per liter) | Directly expose pistils in vitro to solution prior to megasporogenesis | 30-90 | 70 | 4-120 | 10 |
| Sucrose (mmol per liter) | Directly expose pistils, in vitro and/or in situ, to solution prior to megasporogenesis | 30-70 | 50 | <20 | 10 |
| *Inducing parthenogenesis in sexual plants* | | | | | |
| fluridone (μmol per liter) | Directly expose pistils, in vitro and/or in situ, to solution prior to megasporogenesis | 2-20 | 10 | <20 | 10 |
| epiBL (μmol per liter) | Directly expose pistils in situ to solution prior to anthesis or fertilization | 0.5-4 | 2 | 180-480 | 360 |
| glucose (mmol per liter) | | 50-140 | 110 | | |
| DTBA (μmol per liter) | Directly expose pistils in vitro and/or in situ to solution prior to anthesis or fertilization | 0.05-0.5 | 0.1 | <20 | 10 |
| glucose (mmol per liter) | | 50-140 | 110 | | |

| | | Begin application (hours before megasporogenesis onset) | | Begin application to harvest (days) | |
|---|---|---|---|---|---|
| | Method | preferred | most preferred | preferred | most preferred |
| *Inducing sex in apomictic plants* | | | | | |
| sugar starvation (mmol sucrose equivalents in media per liter) | Culture pistils on sugar free media | 48-18 | 36 | 1-3 | 2 |
| hydrogen peroxide (mmol per liter) | Directly expose pistils, in vitro or in situ, to solution prior to megasporogenesis | 24-1 | 12 | Pretreatment only 1-3 | 2 |
| PEG 6000 (g per liter) | Directly expose pistils, in vitro and/or in situ, to solution prior to megasporogenesis | 24-1 | 12 | 1-3 | 1 |
| brassinazole (μmol per liter) | Directly expose pistils, in vitro and/or in situ, to solution prior to megasporogenesis | 24-1 | 12 | 1-3 | 1 |
| *Inducing apomeiosis in sexual plants* | | | | | |
| epibrassinolide (epiBL) (μmol per liter) | Directly expose pistils, in vitro and/or in situ, to solution prior to megasporogenesis | 24-6 | 12 | 1-3 | 1 |
| fluridone (μmol per liter) | Directly expose pistils, in vitro and/or in situ, to solution prior to megasporogenesis | 24-6 | 12 | 1-3 | 1 |
| 5-azacytidine (μmol per liter) | Directly expose pistils, in vitro and/or in situ, to solution prior to megasporogenesis | 24-6 | 12 | 1-3 | 1 |
| DTBA (μmol per liter) | Directly expose pistils, in vitro and/or in situ, to solution prior to megasporogenesis | 24-6 | 12 | 1-3 | 1 |
| Glucose (mmol per liter) | Directly expose pistils in situ to solution prior to megasporogenesis | 24-6 | 12 | Pretreatment only 1-3 | 1 |
| Glucose (mmol per liter) | Directly expose pistils in vitro to solution prior to megasporogenesis | 24-6 | 12 | 1-3 | 1 |
| Sucrose (mmol per liter) | Directly expose pistils, in vitro and/or in situ, to solution prior to megasporogenesis | 24-6 | 12 | 1-3 | 1 |
| *Inducing parthenogenesis in sexual plants* | | | | | |
| fluridone (μmol per liter) | Directly expose pistils, in vitro and/or in situ, to solution prior to megasporogenesis | 24-6 | 12 | 1-3 | |
| epiBL (μmol per liter) | Directly expose pistils in situ to solution prior to anthesis or fertilization | 24-48 | 36 | Pretreatment only | |
| glucose (mmol per liter) | | | | 2-5 | 4 |

TABLE 11-continued

| | | | | | |
|---|---|---|---|---|---|
| DTBA (μmol per liter) glucose (mmol per liter) | Directly expose pistils in vitro and/or in situ to solution prior to anthesis or fertilization | 24-48 | 36 | 2-5 | 4 |

REFERENCES

1. Asker S E & Jerling L (1992) Apomixis in Plants (CRC Press, Inc., Boca Raton, Fla.) p 298.
2. Matzk F, Meister A, & Schubert I (2000) An efficient screen for reproductive pathways using mature seeds of monocots and dicots. Plant Journal 21(1):97-108.
3. Naumova T N, et al. (2001) Reproductive development in apomictic populations of Arabis holboellii (Brassicaceae). Sex Plant Reprod 14(4):195-200.
4. Taskin K M, Turgut K, & Scott R J (2004) Apomictic development in Arabis gunnisoniana. Israel Journal of Plant Sciences 52(2):155-160.
5. Aliyu O M, Schranz M E, & Sharbel T F (2010) Quantitative variation for apomictic reproduction in the genus Boechera (Brassicaceae). Am J Bot 97(10):1719-1731.
6. Dobes C, Koch M, & Sharbel T F (2006) Embryology, karyology, and modes of reproduction in the North American genus Boechera (Brassicaceae): A compilation of seven decades of research. Annals of the Missouri Botanical Garden 93(3):517-534.
7 Hand M L & Koltunow A M (2014) The genetic control of apomixis: asexual seed formation. Genetics 197(2):441-450.
8. Hojsgaard D, Klatt S, Baier R, Carman J G, & Horandl E (2014) Taxonomy and Biogeography of Apomixis in Angiosperms and Associated Biodiversity Characteristics. Critical Reviews in Plant Sciences 33(5):414-427.
9. Suomalainen E, Saura A, & Lokki J (1987) Cytology and Evolution in Parthenogenesis (CRC Press, Inc., Boca Raton, Fla., USA) p 216.
10. Carman J G (1997) Asynchronous expression of duplicate genes in angiosperms may cause apomixis, bispory, tetraspory, and polyembryony. Biological Journal of the Linnean Society 61(1):51-94.
11. Yuan L P (1993) Progress of two-line system in hybrid rice breeding. New Frontiers in Rice Research, eds Muralidhoran K & Siddig E A (Directorate of Rice Research, Hyderabad, India), pp 86-93.
12. Toenniessen G H (2001) Feeding the world in the 21st century: plant breeding, biotechnology and the potential role of apomixis. The flowering of apomixis: from mechanisms to genetic engineering, eds Savidan Y, Carman J G, & Dresselhaus T (CIMMYT, IRD, European Commission DG VI (FAIR), Mexico, D.F.).
13. Broeckx T, Hulsmans S, & Rolland F (2016) The plant energy sensor: evolutionary conservation and divergence of SnRK1 structure, regulation, and function. J Exp Bot 67(22):6215-6252.
14. Mittler R & Blumwald E (2015) The roles of ROS and ABA in systemic acquired acclimation. Plant Cell 27(1):64-70.
15. Dong Y, et al. (2017) Sulfur availability regulates plant growth via glucose-TOR signaling. Nat Commun 8(1):1174.
16. Soto-Burgos J & Bassham D C (2017) SnRK1 activates autophagy via the TOR signaling pathway in Arabidopsis thaliana. PLoS One 12(8):e0182591.
17. Nukarinen E, et al. (2016) Quantitative phosphoproteomics reveals the role of the AMPK plant ortholog SnRK1 as a metabolic master regulator under energy deprivation. Sci Rep 6:31697.
18. Xiong Y, et al. (2013) Glucose-TOR signalling reprograms the transcriptome and activates meristems. Nature 496(7444):181-186.
19. Xiong Y & Sheen J (2015) Novel links in the plant TOR kinase signaling network. Curr Opin Plant Biol 28:83-91.
20. Paul M J, Oszvald M, Jesus C, Rajulu C, & Griffiths C A (2017) Increasing crop yield and resilience with trehalose 6-phosphate: targeting a feast-famine mechanism in cereals for better source-sink optimization. J Exp Bot 68(16):4455-4462.
21. Li X, et al. (2017) Differential TOR activation and cell proliferation in Arabidopsis root and shoot apexes. Proc Natl Acad Sci USA 114(10):2765-2770.
22. Rahikainen M, Pascual J, Alegre S, Durian G, & Kangasjarvi S (2016) PP2A Phosphatase as a Regulator of ROS Signaling in Plants. Antioxidants (Basel) 5(1).
23. Tsai A Y & Gazzarrini S (2014) Trehalose-6-phosphate and SnRK1 kinases in plant development and signaling: the emerging picture. Front Plant Sci 5:119.
24. Iordachescu M & Imai R (2011) Trehalose and abiotic stress in biological systems. Abiotic Stress in Plants—Mechanisms and Adaptations, ed Shanker A (INTECH, Rijeka, Croatia).
25. Zhang Z, et al. (2016) TOR Signaling Promotes Accumulation of BZR1 to Balance Growth with Carbon Availability in Arabidopsis. Curr Biol 26(14):1854-1860.
26. Mateo de Arias M (2015) Effects of plant stress on facultative apomixis in Boechera (Brassicaceae). PhD Dissertation (Utah State University, Logan, Utah, USA).
27. Shilling M P (2016) Hybridization, population genetic structure and gene expression in the genus Boechera. PhD (Utah State University, All Graduate Theses and Dissertations. 5192).
28. Sailer C, Schmid B, & Grossniklaus U (2016) Apomixis Allows the Transgenerational Fixation of Phenotypes in Hybrid Plants. Curr Biol 26(3):331-337.
29. Mangelsdorf P C & Reeves R G (1931) Hybridisation of maize, Tripsacum and Euchlaena. Journal of Heredity 22:329-343.
30. Rao N G P & Narayana L L (1968) Apomixis in grain sorghums. Indian Journal of Genetics and Plant Breeding 28:121-127.
31. Asker S (1979) Progress in apomixis research. Hereditas 91:231-240.
32. Hanna W W & Bashaw E C (1987) Apomixis—Its Identification and Use in Plant-Breeding. Crop Science 27(6):1136-1139.
33. Barcaccia G & Albertini E (2013) Apomixis in plant reproduction: a novel perspective on an old dilemma. Plant Reprod 26(3):159-179.
34. Bilinski C A, Marmiroli N, & Miller J J (1989) Apomixis in Saccharomyces cerevisiae and other eukaryotic microorganisms. Adv Microb Physiol 30:23-52.

35. Grimanelli D (2012) Epigenetic regulation of reproductive development and the emergence of apomixis in angiosperms. Curr Opin Plant Biol 15(1):57-62.
36. Neiman M, Sharbel T F, & Schwander T (2014) Genetic causes of transitions from sexual reproduction to asexuality in plants and animals. J Evol Biol 27(7):1346-1359.
37. Nogler G A (1984) Gametophytic apomixis. Embryology of angiosperms, ed John B M (Springer-Verlag, New York), pp 475-518.
38. Mogie M (1992) The evolution of asexual reproduction in plants (Chapman & Hall, London) p 276.
39. Savidan Y (2000) Apomixis: Genetics and Breeding. Plant Breeding Reviews, ed Janick J (John Wiley & Sons, Inc., New York), Vol 18, pp 13-86.
40. Crevillen P, et al. (2014) Epigenetic reprogramming that prevents transgenerational inheritance of the vernalized state. Nature 515(7528):587-590.
41. Crisp P A, Ganguly D, Eichten S R, Borovitz J O, & Pogson B J (2016) Reconsidering plant memory: intersections between stress recovery, RNA turnover, and epigenetics. Science Advances 2(2):e1501733
42. Bonasio R (2015) The expanding epigenetic landscape of non-model organisms. J Exp Biol 218(Pt 1):114-122.
43. Cavalier-Smith T (2010) Origin of the cell nucleus, mitosis and sex: roles of intracellular coevolution. Biol Direct 5:7.
44. Bernstein H & Bernstein C (2013) Evolutionary Origin and Adaptive Function of Meiosis. Meiosis, eds Bernstein H & Bernstein C (InTech, Rijeka, Croatia), p 123.
45. Adl S M, et al. (2012) The revised classification of eukaryotes. J Eukaryot Microbiol 59(5):429-493.
46. Speijer D, Lukes J, & Elias M (2015) Sex is a ubiquitous, ancient, and inherent attribute of eukaryotic life. P Natl Acad Sci USA 112(29):8827-8834.
47. McKenney P T, Driks A, & Eichenberger P (2013) The *Bacillus subtilis* endospore: assembly and functions of the multilayered coat. Nat Rev Microbiol 11(1):33-44.
48. Horandl E & Hadacek F (2013) The oxidative damage initiation hypothesis for meiosis. Plant Reprod 26(4):351-367.
49. Shimkets L J (2013) Prokaryotic life cycles. The Prokaryotes, ed Rosenberg E (Springer-Verlag, Berlin Heidelberg), pp 318-336.
50. Carman J G, Jamison M, Elliott E, Dwivedi K K, & Naumova T N (2011) Apospory appears to accelerate onset of meiosis and sexual embryo sac formation in sorghum ovules. BMC Plant Biol 11:9.
51. Tashiro T, et al. (2017) Early trace of life from 3.95 Ga sedimentary rocks in Labrador, Canada. Nature 549 (7673):516-518.
52. Brukhin V (2017) Molecular and genetic regulation of apomixis. Russian Journal of Genetics 53(9):943-964.
53. Nedelcu A M (2005) Sex as a response to oxidative stress: stress genes co-opted for sex. P Roy Soc B-Biol Sci 272(1575):1935-1940.
54. Sabbe K, Chepurnov V A, Vyverman W, & Mann D G (2004) Apomixis in *Achnanthes* (Bacillariophyceae); development of a model system for diatom reproductive biology. European Journal of Phycology 39(3):327-341.
55. Liu Q, Yu R-C, Yan T, Zhang Q-C, & Zhou M-J (2014) Laboratory study on the life history of bloom-forming Ulva prolifera in the Yellow Sea. Estuarine, Coastal and Shelf Science 163:82-88.
56. Hanson S J, et al. (2013) Inventory and phylogenetic analysis of meiotic genes in monogonont rotifers. J Hered 104(3):357-370.
57. Schurko A M & Logsdon J M, Jr. (2008) Using a meiosis detection toolkit to investigate ancient asexual "scandals" and the evolution of sex. BioEssays 30:579-589.
58. Patil S, et al. (2015) Identification of the meiotic toolkit in diatoms and exploration of meiosis-specific SPO11 and RAD51 homologs in the sexual species *Pseudo-nitzschia multistriata* and *Seminavis robusta*. BMC Genomics 16:930.
59. Wang P, et al. (2018) Reciprocal Regulation of the TOR Kinase and ABA Receptor Balances Plant Growth and Stress Response. Mol Cell 69(1):100-112 e106.
60. Jamsheer K M, et al. (2018) FCS-like zinc finger 6 and 10 repress SnRK1 signalling in *Arabidopsis*. Plant J 94(2):232-245.
61. Kim J S, et al. (2005) Comprehensive molecular cytogenetic analysis of sorghum genome architecture: distribution of euchromatin, heterochromatin, genes and recombination in comparison to rice. Genetics 171(4):1963-1976.
62. Woo Y, et al. (2004) A comparison of cDNA, oligonucleotide, and Affymetrix GeneChip gene expression microarray platforms. J Biomol Tech 15(4):276-284.
63. Wu H, Kerr K, & Chruchill G (2002) The Analysis of Gene Expression Data: Methods and Software, eds Parmigiani ESGG, Irizarry R A, & Seger S L (Springer, New York), pp 313-431.
64. Altschul S F, et al. (1997) Gapped BLAST and PSI-BLAST: a new generation of protein database search programs. Nucleic Acids Research 25(17):3389-3402.
65. Mi H, et al. (2017) PANTHER version 11: expanded annotation data from Gene Ontology and Reactome pathways, and data analysis tool enhancements. Nucleic Acids Res 45(D1):D183-D189.
66. Bailey C D, et al. (2006) Toward a global phylogeny of the Brassicaceae. Mol Biol Evol 23(11):2142-2160.
67. Mandakova T, Schranz M E, Sharbel T F, de Jong H, & Lysak M A (2015) Karyotype evolution in apomictic *Boechera* and the origin of the aberrant chromosomes. Plant J 82(5):785-793.
68. Windham M D & Al-Shehbaz I A (2006) New and noteworth species of *Boechera* (Brassicaceae) I: sexual diploids. Harvard Papers in Botany 11(1):61-88.
69. Alexander P J, et al. (2013) Molecular Phylogenetics and Taxonomy of the Genus <I>Boechera</I> and Related Genera (Brassicaceae: Boechereae). Systematic Botany 38(1):192-209.
70. Alexander P J, et al. (2015) Weaving a Tangled Web: Divergent and Reticulate Speciation in *Boechera fendleri* sensu lato (Brassicaceae: Boechereae). Systematic Botany 40(2):572-596.
71. Windham M D, et al. (2015) Searching for Diamonds in the Apomictic Rough: A Case Study Involving *Boechera lignifera* (Brassicaceae). Systematic Botany 40(4):1031-1044.
72. Mau M, et al. (2015) Hybrid apomicts trapped in the ecological niches of their sexual ancestors. Proc Natl Acad Sci USA 112(18):E2357-2365.
73. Shah J N, et al. (2016) Depletion of Key Meiotic Genes and Transcriptome-Wide Abiotic Stress Reprogramming Mark Early Preparatory Events Ahead of Apomeiotic Transition. Front Plant Sci 7:1539.
74. Li F W, Rushworth C A, Beck J B, & Windham M D (2017) *Boechera* microsatellite website: an online portal for species identification and determination of hybrid parentage. Database (Oxford) 2017(1).

75. Al-Shehbaz I A & Windham M D (2010) *Boechera*. Flora of North America North of Mexico, ed Committee FoNA (Oxford University Press, Oxford), pp 347-412.
76. Bocher T W (1951) Cytological and embryological studies in the amphi-apomictic *Arabis holboellii* complex. KongelDanske Vidensk-SelskabBiolSkr 6:1-59.
77. Carman J G (2007) Do duplicate genes cause apomixis. Apomixis: Evolution, Mechanisms and Perspectives, eds Horandl E, Grossniklaus U, van Dijk P J, & Sharbel T F (A. R. G. Gantner Verlag K. G., Liechtenstein), pp 63-91.
78. Sharbel T F, et al. (2010) Apomictic and sexual ovules of *Boechera* display heterochronic global gene expression patterns. Plant Cell 22(3):655-671.
79. Schmidt A, et al. (2014) Apomictic and sexual germline development differ with respect to cell cycle, transcriptional, hormonal and epigenetic regulation. PLoS Genet 10(7):e1004476.
80. Crane C F & Carman J G (1987) Mechanisms of Apomixis in Elymus-Rectisetus from Eastern Australia and New-Zealand. American Journal of Botany 74(4):477-496.
81. Michelakis E D, et al. (2002) Diversity in mitochondrial function explains differences in vascular oxygen sensing. Circ Res 90(12):1307-1315.
82. Metallo C M & Vander Heiden M G (2013) Understanding metabolic regulation and its influence on cell physiology. Mol Cell 49(3):388-398.
83. Bertero T, Rezzonico R, Pottier N, & Mari B (2017) Impact of MicroRNAs in the Cellular Response to Hypoxia. Int Rev Cell Mol Biol 333:91-158.
84. Herr J M J (1995) The origin of the ovule. American Journal of Botany 82(4):547-564.
85. Goldberg R B, Beals T P, & Sanders P M (1993) Anther development: basic principles and practical applications. Plant Cell 5(10):1217-1229.
86. Suttangkakul A, Li F, Chung T, & Vierstra R D (2011) The ATG1/ATG13 protein kinase complex is both a regulator and a target of autophagic recycling in *Arabidopsis*. Plant Cell 23(10):3761-3779.
87. Vardhini B V & Anjum N A (2015) Brassinosteroids make plant life easier under abiotic stresses mainly by modulating major components of antioxidant defense system. Frontiers in Environmental Science 2.
88. Knox R B & Heslop-Harrison J (1963) Experimental control of aposporous apomixis in a grass of the Andropogoneae. Bot Not 116:127-141.
89. Knox R B (1967) Apomixis: seasonal and population differences in a grass. Science 157(3786):325-326.
90. Saran S & Dewet J M J (1976) Environmental-Control of Reproduction in Dichanthium-Intermedium. J Cytol Genet 11:22-28.
91. Evans L T & Knox R B (1969) Environmental control of reproduction in Themeda *australis*. Australian Journal of Botany 17:375-389.
92. Langmead B, Trapnell C, Pop M, & Salzberg S L (2009) Ultrafast and memory-efficient alignment of short DNA sequences to the human genome. Genome Biol 10(3):R25.
93. Trapnell C, Pachter L, & Salzberg S L (2009) TopHat: discovering splice junctions with RNA-Seq. Bioinformatics 25(9):1105-1111.
94. Li H, et al. (2009) The Sequence Alignment/Map format and SAMtools. Bioinformatics 25(16):2078-2079.
95. Anders S & Huber W (2010) Differential expression analysis for sequence count data. Genome Biol 11(10):R106.
96. Pellino M, Sharbel T F, Mau M, Amiteye S, & Corral J M (2011) Selection of reference genes for quantitative real-time PCR expression studies of microdissected reproductive tissues in apomictic and sexual *Boechera*. BMC Res Notes 4:303.
97. SYSTAT (2004) SYSTAT for Windows (SYSTAT Software, Inc 2004, Ver. No. 11.00.01).
98. Sheen J (2014) Master Regulators in Plant Glucose Signaling Networks. Journal of Plant Biology 57(2):67-79.
99. Stresemann C & Lyko F (2008) Modes of action of the DNA methyltransferase inhibitors azacytidine and decitabine. Int J Cancer 123(1):8-13.
100. Schmid Hempel P (2011) Evolutionary parasitology. The integrated study of infections, immunology, ecology, and genetics. (Oxford University Press, Oxford).
101. Mora C, Tittensor D P, Adl S, Simpson A G, & Worm B (2011) How many species are there on Earth and in the ocean? PLoS Biol 9(8):e1001127.
102. Johri B M, Ambegaokar K B, & Srivastava P S (1992) Comparative Embryology of Angiosperms (Springer-Verlag, New York).
103. Carman J G (2000) The evolution of gametophytic apomixis. Embryology of Flowering Plants, Vol. 3: The Systems of Reproduction, ed Batygina T B (Russian Academy of Sciences, St. Petersburg), pp 218-245.
104. Klatt S, et al. (2016) Photoperiod Extension Enhances Sexual Megaspore Formation and Triggers Metabolic Reprogramming in Facultative Apomictic *Ranunculus auricomus*. Frontiers in Plant Science 7.
105. Rodrigo J M, et al. (2017) Apomixis frequency under stress conditions in weeping lovegrass (*Eragrostis curvula*). PLoS One 12(4):e0175852.
106. Gao L (2018) Pharmacologically Induced Meiosis Apomeiosis Interconversions in *Boechera, Arabidopsis* and *Vigna*. Ph.D. (Utah State University, https://digitalcommons.usu.edu/etd/7222).
107. Projecto-Garcia J, Biddle J F, & Ragsdale E J (2017) Decoding the architecture and origins of mechanisms for developmental polyphenism. Curr Opin Genet Dev 47:1-8.
108. Ogawa K & Miura T (2014) Aphid polyphenisms: trans-generational developmental regulation through viviparity. Front Physiol 5:1.
109. Zhang Y N, et al. (2016) Reproductive switching analysis of *Daphnia* similoides between sexual female and parthenogenetic female by transcriptome comparison. Sci Rep 6:34241.
110. Simon J-C, Delmotte F, Rispe C, & Crease T (2003) Phylogenetic relationships between parthenogens and their sexual relatives: the possible routes to parthenogenesis in animals. Biological Journal of the Linnean Society 79:151-163.
111. Hoj sgaard D, et al. (2014) Emergence of apospory and bypass of meiosis via apomixis after sexual hybridisation and polyploidisation. New Phytol 204(4):1000-1012.
112. Barke B H, Daubert M, & Horandl E (2018) Establishment of Apomixis in Diploid F2 Hybrids and Inheritance of Apospory From F1 to F2 Hybrids of the *Ranunculus auricomus* Complex. Front Plant Sci 9:1111.
113. Burow G B, et al. (2011) Registration of the BTx623/IS3620C recombinant inbred mapping population of sorghum. Journal of Plant Registrations 5(1):141-145.
114. Menz M A, et al. (2002) A high-density genetic map of *Sorghum bicolor* (L.) Moench based on 2926 AFLP, RFLP and SSR markers. Plant Mol Biol 48(5-6):483-499.

115. Van Ooij en J W (2009) MapQTL 6, Software for the mapping of quantitative trait loci in experimental populations of diploid speciesKyazma B V, Wageningen, Netherlands).
116. Lander E S & Botstein D (1989) Mapping Mendelian factors underlying quantitative traits using RFLP linkage maps. Genetics 121:185-199.
117. Lander E & Kruglyak L (1995) Genetic dissection of complex traits: guidelines for interpreting and reporting linkage results. Nat Genet 11(3):241-247.
118. Van Ooijen J W (1999) LOD significance thresholds for QTL analysis in experimental populations of diploid species. Heredity (Edinb) 83 (Pt 5):613-624.
119. Jansen R C & Stam P (1994) High resolution of quantitative traits into multiple loci via interval mapping. Genetics 136:1447-1455.
120. Churchill G A & Doerge R W (1994) Empirical threshold values for quantitative trait mapping. Genetics 138:963-971.
121. Voorrips R E (2002) MapChart: Software for the Graphical Presentation of Linkage Maps and QTLs. Journal of Heredity 93(1):77-78.
122. Johnson M, et al. (2008) NCBI BLAST: a better web interface. Nucleic Acids Res 36(Web Server issue):W5-9.
123. McCormick R F, et al. (2018) The *Sorghum bicolor* reference genome: improved assembly, gene annotations, a transcriptome atlas, and signatures of genome organization. Plant J 93(2):338-354.
124. Peel M, Carman J G, & Leblanc 0 (1997) Megasporocyte callose in apomictic buffelgrass, Kentucky bluegrass, *Pennisetum squamulatum* Fresen, *Tripsacum* L. and weeping lovegrass. Crop Science 37:724-732.
125. Schneitz K, Hulskamp M, & Pruitt R E (1995) Wild-type ovule development in *Arabidopsis thaliana*: a light microscope study of cleared whole-mount tissue. The Plant Journal 7(5):731-749.
126. Murashige T & Skoog F (1962) A revised medium for rapid growth and bio assays with tobacco tissue cultures. Phsiologia *Plantarum* 15:473-497.
127. Tian Y, et al. (2018) Hydrogen peroxide positively regulates brassinosteroid signaling through oxidation of the BRASSINAZOLE-RESISTANT1 transcription factor. Nat Commun 9(1):1063.
128. Musial K & Koscinska-Pajak M (2017) Pattern of callose deposition during the course of meiotic diplospory in *Chondrilla juncea* (Asteraceae, Cichorioideae). Protoplasma 254(4):1499-1505.
129. Luna E, et al. (2011) Callose deposition: a multifaceted plant defense response. Mol Plant Microbe Interact 24(2):183-193.
130. Walker J, et al. (2018) Sexual-lineage-specific DNA methylation regulates meiosis in *Arabidopsis*. Nat Genet 50(1):130-137.
131. Siqueira J A, Hardoim P, Ferreira P C G, Nunes-Nesi A, & Hemerly A S (2018) Unraveling Interfaces between Energy Metabolism and Cell Cycle in Plants. Trends Plant Sci 23 (8):731-747.
132. Arve L E, et al. (2015) Growth in continuous high air humidity increases the expression of CYP707A-genes and inhibits stomatal closure. Environmental and Experimental Botany 115:11-19.
133. Carvalho R F, et al. (2016) The *Arabidopsis* SR45 Splicing Factor, a Negative Regulator of Sugar Signaling, Modulates SNF1-Related Protein Kinase 1 Stability. Plant Cell 28(8):1910-1925.
134. Li Q F, et al. (2018) The brassinosteroid-regulated transcription factors BZR1/BES1 function as a coordinator in multisignal-regulated plant growth. Biochim Biophys Acta Gene Regul Mech 1861(6):561-571.
135. Mittler R (2017) ROS Are Good. Trends Plant Sci 22(1):11-19.
136. Xing D, Wang Y, Hamilton M, Ben-Hur A, & Reddy A S (2015) Transcriptome-Wide Identification of RNA Targets of *Arabidopsis* SERINE/ARGININE-RICH45 Uncovers the Unexpected Roles of This RNA Binding Protein in RNA Processing. Plant Cell 27(12):3294-3308.
137. Youn J H & Kim T W (2015) Functional insights of plant GSK3-like kinases: multi-taskers in diverse cellular signal transduction pathways. Mol Plant 8(4):552-565.
138. Liu Y, Huang X, Li M, He P, & Zhang Y (2016) Loss-of-function of *Arabidopsis* receptor-like kinase BIR1 activates cell death and defense responses mediated by BAK1 and SOBIR1. New Phytol 212(3):637-645.
139. Sessa G, Raz V, Savaldi S, & Fluhr R (1996) PK12, a plant dual-specificity protein kinase of the LAMMER family, is regulated by the hormone ethylene. The Plant Cell 8:2223-2234.
140. Yan H, et al. (2018) BRASSINOSTEROID-SIGNALING KINASE1 Phosphorylates MAPKKK5 to Regulate Immunity in *Arabidopsis*. Plant Physiol 176(4):2991-3002.
141. Liu Y & Zhang S (2004) Phosphorylation of 1-aminocyclopropane-1-carboxylic acid synthase by MPK6, a stress-responsive mitogen-activated protein kinase, induces ethylene biosynthesis in *Arabidopsis*. Plant Cell 16(12):3386-3399.
142. Yao Y, et al. (2017) ETHYLENE RESPONSE FACTOR 74 (ERF74) plays an essential role in controlling a respiratory burst oxidase homolog D (RbohD)-dependent mechanism in response to different stresses in *Arabidopsis*. New Phytol 213(4):1667-1681.
143. Muller M & Munne-Bosch S (2015) Ethylene Response Factors: A Key Regulatory Hub in Hormone and Stress Signaling. Plant Physiol 169(1):32-41.
144. Wang L C, Wu J R, Hsu Y J, & Wu S J (2015) *Arabidopsis* HIT4, a regulator involved in heat-triggered reorganization of chromatin and release of transcriptional gene silencing, relocates from chromocenters to the nucleolus in response to heat stress. New Phytol 205(2):544-554.
145. Downs J A, Kosmidou E, Morgan A, & Jackson S P (2003) Suppression of homologous recombination by the *Saccharomyces cerevisiae* linker histone. Molecular Cell 11:1685-1692.
146. Sherwood D A (2018) A simple metabolic switch may activate apomixis in *Arabidopsis thaliana*. Ph.D. (Utah State University, Logan, Utah).
147. Narula J, Fujita M, & Igoshin O A (2016) Functional requirements of cellular differentiation: lessons from *Bacillus subtilis*. Curr Opin Microbiol 34:38-46.
148. Khanday I, Skinner D, Yang B, Mercier R, & Sundaresan V (2018) A male-expressed rice embryogenic trigger redirected for asexual propagation through seeds. Nature.
149. Kirk H, Choi Y H, Kim H K, Verpoorte R, & van der Meij den E (2005) Comparing metabolomes: the chemical consequences of hybridization in plants. New Phytol 167(2):613-622.
150. Rosenberger C L & Chen J (2018) To Grow or Not to Grow: TOR and SnRK2 Coordinate Growth and Stress Response in *Arabidopsis*. Mol Cell 69(1):3-4.

What is claimed is:

1. A method of inducing gametophytic apomixis in a sexual angiosperm, comprising applying a chemical to the sexual angiosperm that increases glucose signaling, decreases osmotic stress, decreases oxidative stress, decreases perceived oxidative stress, or a combination thereof in a female germline cell and/or a female germline-associated tissue in the sexual angiosperm, wherein applying the chemical to the sexual angiosperm comprises applying the chemical within 24 to 6 hours before megasporogenesis onset, anthesis, or fertilization in an amount and time sufficient to induce gametophytic apomixis and gametophytic apomixis comprises apomeiosis and parthenogenesis and sexual reproduction comprises meiosis and syngamy.

2. The method of claim 1, wherein the chemical applied to the sexual angiosperm decrease oxidative stress in the female germline cell and/or the female germline-associated tissue in the sexual angiosperm, the sexual angiosperm being selected from the group consisting of: alfalfa, amaranth, asparagus, barley, beans, beets, buckwheat, canary grass, cacao, carob, carrots, castor beans, chickpeas, chilis, clover, coffee, cotton, cowpea, cucumbers, kaniwa, lentils, lettuce, lupin beans, maize (corn), melons, mesquite, millet, oat, onions, peanuts, peas, peppers, pitseed goosefoot, *quinoa*, rapeseed, rice, rye, sorghum, soybeans, spelt, squashes, sunflowers, tamarind, tomatoes, triticale, turnips, wheat, and wild rice.

3. The method of claim 2, applying fluridone, ABA, or a combination thereof to the sexual angiosperm in an amount and time sufficient to induce gametophytic apomixis.

4. The method of claim 1, wherein the female germline cell and/or female germline-associated tissue comprises a megaspore mother cell, adjacent cells of the ovule nucellus, or integuments and fluridone is applied.

5. The method of claim 2, wherein the sexual angiosperm is selected from the sexual group consisting of: alfalfa, barley, beans, cotton, maize (corn), millet, oat, *quinoa*, rapeseed, rice, rye, sorghum, soybeans, wheat, and wild rice.

6. The method of claim 1, comprising applying 30-90 mmol/L glucose, 30-70 mmol/L sucrose, or both to a pistil of the sexual angiosperm.

7. The method of claim 1 comprising applying 1-1,000 µM 5-azaC to a pistil of the sexual angiosperm.

8. The method of claim 1, comprising applying 0.05-15 μM epiBL to a pistil of the sexual angiosperm.

9. The method of claim 6, wherein the sexual angiosperm is selected from the sexual group consisting of: alfalfa, amaranth, asparagus, barley, beans, beets, buckwheat, canary grass, cacao, carob, carrots, castor beans, chickpeas, chilis, clover, coffee, cotton, cowpea, cucumbers, kaniwa, lentils, lettuce, lupin beans, maize (corn), melons, mesquite, millet, oat, onions, peanuts, peas, peppers, pitseed goosefoot, *quinoa*, rapeseed, rice, rye, sorghum, soybeans, spelt, squashes, sunflowers, tamarind, tomatoes, triticale, turnips, wheat, and wild rice.

10. A method of inducing gametophytic apomixis in a sexual angiosperm, comprising applying a chemical to the sexual angiosperm that decreases oxidative stress in a female germline cell and/or a female germline-associated tissue in the sexual angiosperm at least within 24 to 6 hours before megasporogenesis onset, the chemical being applied in an amount and time sufficient to induce gametophytic apomixis, wherein the sexual angiosperm is selected from the sexual group consisting of: alfalfa, amaranth, asparagus, barley, beans, beets, buckwheat, canary grass, cacao, carob, carrots, castor beans, chickpeas, chilis, clover, coffee, cotton, cowpea, cucumbers, kaniwa, lentils, lettuce, lupin beans, maize (corn), melons, mesquite, millet, oat, onions, peanuts, peas, peppers, pitseed goosefoot, *quinoa*, rapeseed, rice, rye, sorghum, soybeans, spelt, squashes, sunflowers, tamarind, tomatoes, triticale, turnips, wheat, and wild rice; and gametophytic apomixis comprises apomeiosis and parthenogenesis and sexual reproduction comprises meiosis and syngamy.

11. The method of claim 10, comprising applying fluridone, abscisic acid (ABA) or both to a pistil of the sexual angiosperm.

12. The method of claim 11, wherein fluridone is applied to a pistil of the sexual angiosperm.

13. The method of claim 11, wherein ABA is applied to a pistil of the sexual angiosperm.

14. A method of inducing gametophytic apomixis in a sexual angiosperm, comprising applying a chemical to the sexual angiosperm that increases glucose signaling, decreases osmotic stress, decreases oxidative stress, decreases perceived oxidative stress, or a combination thereof in a female germline cell and/or a female germline-associated tissue in the sexual angiosperm, wherein the chemical is applied at least within 24 to 6 hours before megasporogenesis onset, anthesis, or fertilization in an amount and time sufficient to induce gametophytic apomixis.

15. The method of claim 14, wherein the chemical applied to the sexual angiosperm decrease oxidative stress in the female germline cell and/or the female germline-associated tissue in the sexual angiosperm, the sexual angiosperm being selected from the group consisting of: alfalfa, amaranth, asparagus, barley, beans, beets, buckwheat, canary grass, cacao, carob, carrots, castor beans, chickpeas, chills, clover, coffee, cotton, cowpea, cucumbers, kaniwa, lentils, lettuce, lupin beans, maize (corn), melons, mesquite, millet, oat, onions, peanuts, peas, peppers, pitseed goosefoot, *quinoa*, rapeseed, rice, rye, sorghum, soybeans, spelt, squashes, sunflowers, tamarind, tomatoes, triticale, turnips, wheat, and wild rice.

16. The method of claim 14, applying fluridone, ABA, or a combination thereof to the sexual angiosperm in an amount and time sufficient to induce gametophytic apomixis.

17. The method of claim 14, wherein the sexual angiosperm is selected from the sexual group consisting of: alfalfa, barley, beans, cotton, maize (corn), millet, oat, *quinoa*, rapeseed, rice, rye, sorghum, soybeans, wheat, and wild rice.

18. The method of claim 14, wherein ABA or epiBL is applied directly to the pistils of the sexual angiosperm.

19. The method of claim 14, wherein fluridone, or 5-azaC is applied directly to the pistils of the sexual angiosperm.

20. The method of claim 14, wherein fluridone or DTBA is applied directly to the pistils of the sexual angiosperm.

* * * * *

SEQUENCE LISTING

<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cgacgacaac gcttctatga                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ccaaccttcg tgtgttcctt                    20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cttccatgga tcttggtgct                    20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
atctccatct ggtggtctcg                    20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcaagcaatg agccctaaag                    20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
actgctcctg ttgagccta                    20

<210> SEQ ID NO 7
<211> LENGTH: 20
<212> TYPE: DNA
<213> ORGANISM: Artificial Sequence

```
<220> FEATURE:
<223> OTHER INFORMATION: Primer

<400> SEQUENCE: 7
cctgaaattt ccgttggaga                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gccaaagcca ccatcattag                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgccgcgtac tatcaacaag                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgcttcttgg acctgatcct                                               20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
atctttgcgg gagactctga                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gttttgctgg ctcgtactcc                                               20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
cgtttctcct aagcctgtcg                                               20
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gatcctgatt ttgcctccaa                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tgttactggg cgaagttcct                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ggaaccatcc tgcacacttt                                               20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gttcaagaaa gcctgccaag                                               20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ggcatttcgt cgaacacttt                                               20

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gatctcccaa tggctaagg                                                19

<210> SEQ ID NO 20
<211> LENGTH: 20
<212> TYPE: DNA
<213> ORGANISM: Artificial Sequence
<220> FEATURE:
<223> OTHER INFORMATION: Primer
```

```
<400> SEQUENCE: 20
catgcgtctt cttctccaca                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
caacggccag cttcttactc                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tcatcccaag tggatccttc                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tggaggaaaa ccatcaggag                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggattcacag cattgggagt                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tcatctgcgt tgaggatctg                                              20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gatgaagttc tcgcggtttc                                              20
```

```
<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aacatgggat ccatggaaaa                                        20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
attgtctcgt cgctggttct                                        20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cagatgtgtc gtgggtgaac                                        20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tatgccacaa tctgctgctc                                        20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tcgcattaca cttgctctgc                                        20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
atcgtctcat cgaacgatcc                                        20

<210> SEQ ID NO 33
<211> LENGTH: 20
<212> TYPE: DNA
<213> ORGANISM: Artificial Sequence
<220> FEATURE:
<223> OTHER INFORMATION: Primer
```

<400> SEQUENCE: 33
ttcaggctat tgggaattg                                                 20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tcgaacctcg tctcttcgtt                                                20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tcatctgcgt tgaggatctg                                                20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gatgaagttc tcgcggtttc                                                20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
agttgacaga gccggaagaa                                                20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
ccattcctgc tgaaaacgat                                                20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
cagatcggca ctctgacaaa                                                20

```
<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tgctgttaaa cggtctgctg                                              20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
gggatgtaaa gccccaaaat                                              20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gggatgtaaa gccccaaaat                                              20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
agaacgcacc acccttatg                                               20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ggaagcacat agcatcagca                                              20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gggtcaagct gatgaagctc                                              20

<210> SEQ ID NO 46
<211> LENGTH: 20
<212> TYPE: DNA
<213> ORGANISM: Artificial Sequence
<220> FEATURE:
<223> OTHER INFORMATION: Primer
```

```
<400> SEQUENCE: 46
gccttgtgtt gacctggttt                                               20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gcatgaagag ggagatcagc                                               20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
catccaggga acctgtcagt                                               20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
tggagctatg ggacaggaac                                               20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cgagagattt gtcgatgcaa                                               20
```